US011840559B2

(12) United States Patent
Blackwell et al.

(10) Patent No.: US 11,840,559 B2
(45) Date of Patent: *Dec. 12, 2023

(54) GLUCAGON-RECEPTOR SELECTIVE POLYPEPTIDES AND METHODS OF USE THEREOF

(71) Applicant: Intarcia Therapeutics Inc., Boston, MA (US)

(72) Inventors: William Blackwell, Research Triangle Park, NC (US); Ved P. Srivastava, Research Triangle Park, NC (US); Mark A. Paulik, Research Triangle Park, NC (US); Andrew Young, Research Triangle Park, NC (US); Robert Neil Hunter, III, Boston, MA (US); Steven Thomas Dock, Boston, MA (US)

(73) Assignee: i2o Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/538,507

(22) Filed: Nov. 30, 2021

(65) Prior Publication Data

US 2022/0332781 A1 Oct. 20, 2022

Related U.S. Application Data

(63) Continuation of application No. 16/667,502, filed on Oct. 29, 2019, now Pat. No. 11,214,607, which is a continuation of application No. 15/595,809, filed on May 15, 2017, now Pat. No. 10,501,517.

(60) Provisional application No. 62/420,937, filed on Nov. 11, 2016, provisional application No. 62/414,146, filed on Oct. 28, 2016, provisional application No. 62/337,005, filed on May 16, 2016.

(51) Int. Cl.
| | |
|---|---|
| *C07K 14/605* | (2006.01) |
| *C07K 14/00* | (2006.01) |
| *A61K 38/26* | (2006.01) |
| *A61K 9/00* | (2006.01) |
| *A61M 5/142* | (2006.01) |
| *A61M 31/00* | (2006.01) |
| *A61M 5/145* | (2006.01) |

(52) U.S. Cl.
CPC .......... *C07K 14/605* (2013.01); *A61K 9/0004* (2013.01); *A61K 38/26* (2013.01); *C07K 14/00* (2013.01); *A61M 5/14276* (2013.01); *A61M 31/002* (2013.01); *A61M 2005/14513* (2013.01)

(58) Field of Classification Search
CPC .............................. A61K 38/26; C07K 14/605
See application file for complete search history.

(56) References Cited

U.S. PATENT DOCUMENTS

| | | | |
|---|---|---|---|
| 2,110,208 | A | 3/1938 | Eggert |
| 2,168,437 | A | 8/1939 | Buercklin |
| 2,531,724 | A | 11/1950 | Cevasco |
| D179,537 | S | 1/1957 | Floyd et al. |
| 3,025,991 | A | 3/1962 | Gillon |
| 3,122,162 | A | 2/1964 | Sands |
| 3,523,906 | A | 8/1970 | Vrancken et al. |
| 3,625,214 | A | 12/1971 | Higuchi |
| 3,632,768 | A | 1/1972 | Bergy et al. |
| 3,691,090 | A | 9/1972 | Kitajima et al. |
| 3,713,919 | A | 1/1973 | Tomic |
| D226,915 | S | 5/1973 | Huggins |
| 3,732,865 | A | 5/1973 | Higuchi et al. |
| 3,737,337 | A | 6/1973 | Schnoring et al. |
| 3,773,919 | A | 11/1973 | Boswell et al. |
| 3,797,492 | A | 3/1974 | Place |
| 3,869,549 | A | 3/1975 | Geller |
| 3,891,570 | A | 6/1975 | Fukushima et al. |
| D236,035 | S | 7/1975 | Ciencewicki |
| 3,960,757 | A | 6/1976 | Morishita et al. |
| 3,987,790 | A | 10/1976 | Eckenhoff et al. |
| 3,995,631 | A | 12/1976 | Higuchi et al. |
| 3,995,632 | A | 12/1976 | Nakano et al. |
| 4,008,719 | A | 2/1977 | Theeuwes et al. |

(Continued)

FOREIGN PATENT DOCUMENTS

| | | |
|---|---|---|
| CN | 102459325 A | 5/2012 |
| CN | 104447980 A | 3/2015 |

(Continued)

OTHER PUBLICATIONS

Du et al. "Drug Carriers for the Delivery of Therapeutic Peptides", Biomacromolecules, 2014, 1097-1114 (Year: 2014).*

(Continued)

*Primary Examiner* — Lianko G Garyu

(74) *Attorney, Agent, or Firm* — Brian C. Trinque; Lathrop GPM LLP

(57) ABSTRACT

This invention relates to isolated polypeptides that are glucagon-receptor selective analogs and peptide derivatives thereof. These analogs are selective for human glucagon receptor with improved solubility, thermal stability, and physicochemical properties as compared to native endogenous glucagon. This invention also relates to methods of using such polypeptides in a variety of therapeutic and diagnostic indications, as well as methods of producing such polypeptides. These analogs are useful, alone or in combination with other therapeutic peptides, in methods of treating obesity, diabetes, metabolic disorders, and other disorders or disease.

19 Claims, 21 Drawing Sheets

Specification includes a Sequence Listing.

(56) References Cited

U.S. PATENT DOCUMENTS

| | | | |
|---|---|---|---|
| 4,034,756 | A | 7/1977 | Higuchi et al. |
| 4,078,060 | A | 3/1978 | Benson et al. |
| 4,111,201 | A | 9/1978 | Theeuwes |
| 4,111,202 | A | 9/1978 | Theeuwes |
| 4,111,203 | A | 9/1978 | Theeuwes |
| 4,203,439 | A | 5/1980 | Theeuwes |
| 4,211,771 | A | 7/1980 | Witkowski et al. |
| 4,221,862 | A | 9/1980 | Naito et al. |
| 4,243,030 | A | 1/1981 | Lynch et al. |
| D258,837 | S | 4/1981 | Spranger et al. |
| D259,458 | S | 6/1981 | Fuller et al. |
| 4,305,927 | A | 12/1981 | Theeuwes et al. |
| 4,310,516 | A | 1/1982 | Chang et al. |
| 4,340,054 | A | 7/1982 | Michaels |
| 4,350,271 | A | 9/1982 | Eckenhoff |
| 4,373,527 | A | 2/1983 | Fischell |
| 4,376,118 | A | 3/1983 | Daher et al. |
| 4,384,975 | A | 5/1983 | Fong |
| 4,389,330 | A | 6/1983 | Tice et al. |
| 4,439,196 | A | 3/1984 | Higuchi |
| 4,444,498 | A | 4/1984 | Heinemann |
| 4,455,143 | A | 6/1984 | Theeuwes et al. |
| 4,455,145 | A | 6/1984 | Theeuwes |
| 4,522,811 | A | 6/1985 | Eppstein et al. |
| 4,530,840 | A | 7/1985 | Tice et al. |
| 4,552,561 | A | 11/1985 | Eckenhoff et al. |
| 4,588,614 | A | 5/1986 | Lauchenauer |
| 4,594,108 | A | 6/1986 | Greminger, Jr. et al. |
| 4,609,374 | A | 9/1986 | Ayer |
| 4,639,244 | A | 1/1987 | Rizk et al. |
| 4,655,462 | A | 4/1987 | Balsells |
| 4,673,405 | A | 6/1987 | Guittard et al. |
| 4,675,184 | A | 6/1987 | Hasegawa et al. |
| 4,695,623 | A | 9/1987 | Stabinsky |
| 4,727,138 | A | 2/1988 | Goeddel et al. |
| 4,734,284 | A | 3/1988 | Terada et al. |
| 4,737,437 | A | 4/1988 | Gutsell, Jr. et al. |
| 4,743,449 | A | 5/1988 | Yoshida et al. |
| 4,753,651 | A | 6/1988 | Eckenhoff |
| 4,762,791 | A | 8/1988 | Goeddel et al. |
| 4,765,989 | A | 8/1988 | Wong et al. |
| 4,783,337 | A | 11/1988 | Wong et al. |
| 4,818,517 | A | 4/1989 | Kwee et al. |
| 4,820,638 | A | 4/1989 | Swetly et al. |
| 4,826,144 | A | 5/1989 | Balsells |
| 4,830,344 | A | 5/1989 | Balsells |
| 4,840,896 | A | 6/1989 | Reddy et al. |
| 4,845,196 | A | 7/1989 | Cowling |
| 4,847,079 | A | 7/1989 | Kwan |
| 4,851,228 | A | 7/1989 | Zentner et al. |
| 4,865,845 | A | 9/1989 | Eckenhoff et al. |
| 4,873,080 | A | 10/1989 | Brickl et al. |
| 4,874,388 | A | 10/1989 | Wong et al. |
| 4,876,781 | A | 10/1989 | Balsells |
| 4,885,166 | A | 12/1989 | Meyer et al. |
| 4,886,668 | A | 12/1989 | Haslam et al. |
| 4,892,778 | A | 1/1990 | Theeuwes et al. |
| 4,893,795 | A | 1/1990 | Balsells |
| 4,897,471 | A | 1/1990 | Stabinsky |
| 4,907,788 | A | 3/1990 | Balsells |
| 4,915,366 | A | 4/1990 | Balsells |
| 4,915,949 | A | 4/1990 | Wong et al. |
| 4,915,954 | A | 4/1990 | Ayer et al. |
| 4,917,887 | A | 4/1990 | Hauptmann et al. |
| 4,917,895 | A | 4/1990 | Lee et al. |
| 4,923,805 | A | 5/1990 | Reddy et al. |
| 4,927,687 | A | 5/1990 | Nuwayser |
| 4,929,554 | A | 5/1990 | Goeddel et al. |
| 4,931,285 | A | 6/1990 | Edgren et al. |
| 4,934,666 | A | 6/1990 | Balsells |
| 4,940,465 | A | 7/1990 | Theeuwes et al. |
| 4,940,588 | A | 7/1990 | Sparks et al. |
| 4,952,402 | A | 8/1990 | Sparks et al. |
| 4,957,119 | A | 9/1990 | de Nijs |
| 4,961,253 | A | 10/1990 | Balsells |
| 4,964,204 | A | 10/1990 | Balsells |
| 4,969,884 | A | 11/1990 | Yum |
| 4,974,821 | A | 12/1990 | Balsells |
| 4,976,966 | A | 12/1990 | Theeuwes et al. |
| 5,004,689 | A | 4/1991 | Edgren et al. |
| 5,006,346 | A | 4/1991 | Theeuwes et al. |
| 5,019,382 | A | 5/1991 | Cummins, Jr. |
| 5,019,400 | A | 5/1991 | Gombotz et al. |
| 5,023,088 | A | 6/1991 | Wong et al. |
| 5,024,842 | A | 6/1991 | Edgren et al. |
| 5,030,216 | A | 7/1991 | Theeuwes et al. |
| 5,034,229 | A | 7/1991 | Magruder et al. |
| 5,057,318 | A | 10/1991 | Magruder et al. |
| 5,059,423 | A | 10/1991 | Magruder et al. |
| 5,066,436 | A | 11/1991 | Komen et al. |
| 5,071,642 | A | 12/1991 | Lahr et al. |
| 5,072,070 | A | 12/1991 | Balsells |
| 5,079,388 | A | 1/1992 | Balsells |
| 5,091,188 | A | 2/1992 | Haynes |
| 5,108,078 | A | 4/1992 | Balsells |
| 5,110,596 | A | 5/1992 | Magruder et al. |
| 5,112,614 | A | 5/1992 | Magruder et al. |
| 5,113,938 | A | 5/1992 | Clayton |
| 5,117,066 | A | 5/1992 | Balsells |
| D326,718 | S | 6/1992 | Maxwell et al. |
| 5,118,666 | A | 6/1992 | Habener |
| 5,120,306 | A | 6/1992 | Gosselin |
| 5,120,712 | A | 6/1992 | Habener |
| 5,120,832 | A | 6/1992 | Goeddel et al. |
| 5,122,128 | A | 6/1992 | Cardinal et al. |
| 5,122,377 | A | 6/1992 | Miller et al. |
| 5,126,141 | A | 6/1992 | Henry |
| 5,126,142 | A | 6/1992 | Ayer et al. |
| 5,126,147 | A | 6/1992 | Silvestri et al. |
| 5,134,244 | A | 7/1992 | Balsells |
| 5,137,727 | A | 8/1992 | Eckenhoff |
| D329,278 | S | 9/1992 | Gallup |
| 5,151,093 | A | 9/1992 | Theeuwes et al. |
| 5,160,122 | A | 11/1992 | Balsells |
| 5,160,743 | A | 11/1992 | Edgren et al. |
| 5,161,806 | A | 11/1992 | Balsells |
| 5,180,591 | A | 1/1993 | Margruder et al. |
| 5,190,765 | A | 3/1993 | Jao et al. |
| 5,203,849 | A | 4/1993 | Balsells |
| 5,204,108 | A | 4/1993 | Illum |
| 5,207,752 | A | 5/1993 | Sorensen et al. |
| 5,209,746 | A | 5/1993 | Balaban et al. |
| 5,213,809 | A | 5/1993 | Wright et al. |
| 5,213,810 | A | 5/1993 | Steber |
| 5,219,572 | A | 6/1993 | Sivaramakrishnan et al. |
| 5,221,278 | A | 6/1993 | Linkwitz et al. |
| 5,223,265 | A | 6/1993 | Wong |
| 5,225,205 | A | 7/1993 | Orsolini |
| 5,231,176 | A | 7/1993 | Goeddel et al. |
| 5,234,424 | A | 8/1993 | Yum et al. |
| 5,234,692 | A | 8/1993 | Magruder et al. |
| 5,234,693 | A | 8/1993 | Magruder et al. |
| 5,234,695 | A | 8/1993 | Hobbs et al. |
| 5,252,338 | A | 10/1993 | Jao et al. |
| 5,260,069 | A | 11/1993 | Chen |
| D342,855 | S | 1/1994 | Butler, II |
| 5,278,151 | A | 1/1994 | Korb et al. |
| 5,279,608 | A | 1/1994 | Cherif Cheikh |
| 5,284,655 | A | 2/1994 | Bogdansky et al. |
| 5,288,501 | A | 2/1994 | Nurnberg et al. |
| 5,288,502 | A | 2/1994 | Mcginity et al. |
| 5,290,271 | A | 3/1994 | Jernberg |
| 5,300,079 | A | 4/1994 | Niezink et al. |
| 5,300,302 | A | 4/1994 | Tachon et al. |
| 5,308,348 | A | 5/1994 | Balaban et al. |
| 5,312,335 | A | 5/1994 | McKinnon et al. |
| 5,312,389 | A | 5/1994 | Theeuwes et al. |
| 5,312,390 | A | 5/1994 | Wong |
| 5,318,558 | A | 6/1994 | Linkwitz et al. |
| 5,318,780 | A | 6/1994 | Viegas et al. |
| 5,320,616 | A | 6/1994 | Magruder et al. |
| 5,324,280 | A | 6/1994 | Wong et al. |
| 5,336,057 | A | 8/1994 | Fukuda et al. |
| 5,336,505 | A | 8/1994 | Ng et al. |

(56) References Cited

U.S. PATENT DOCUMENTS

| | | |
|---|---|---|
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,385,887 A | 1/1995 | Yim et al. |
| 5,407,609 A | 4/1995 | Tice et al. |
| D358,644 S | 5/1995 | Park |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,428,024 A | 6/1995 | Chu et al. |
| 5,429,602 A | 7/1995 | Hauser |
| 5,439,688 A | 8/1995 | Orsolini et al. |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,478,564 A | 12/1995 | Wantier et al. |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,541,172 A | 7/1996 | Labrie et al. |
| 5,542,682 A | 8/1996 | Goldstein et al. |
| 5,543,156 A | 8/1996 | Roorda et al. |
| 5,545,618 A | 8/1996 | Buckley et al. |
| 5,552,520 A | 9/1996 | Kim et al. |
| 5,556,642 A | 9/1996 | Kobayashi et al. |
| 5,557,318 A | 9/1996 | Gabriel |
| 5,571,525 A | 11/1996 | Roorda et al. |
| 5,574,008 A | 11/1996 | Johnson et al. |
| 5,574,010 A | 11/1996 | McFadden |
| 5,574,137 A | 11/1996 | Gray et al. |
| 5,580,578 A | 12/1996 | Oshlack et al. |
| 5,589,161 A | 12/1996 | Fuller |
| 5,589,167 A | 12/1996 | Cleland et al. |
| 5,595,751 A | 1/1997 | Bezwada et al. |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,630,796 A | 5/1997 | Bellhouse et al. |
| 5,633,011 A | 5/1997 | Dong et al. |
| 5,635,213 A | 6/1997 | Nystrom et al. |
| 5,639,477 A | 6/1997 | Maruyama et al. |
| 5,639,640 A | 6/1997 | Reddy et al. |
| 5,645,850 A | 7/1997 | Bezwada et al. |
| 5,648,088 A | 7/1997 | Bezwada et al. |
| 5,650,173 A | 7/1997 | Ramstack et al. |
| 5,654,008 A | 8/1997 | Herbert et al. |
| 5,654,010 A | 8/1997 | Johnson et al. |
| 5,656,297 A | 8/1997 | Bernstein et al. |
| 5,656,299 A | 8/1997 | Kino et al. |
| 5,658,593 A | 8/1997 | Orly et al. |
| 5,660,847 A | 8/1997 | Magruder et al. |
| 5,660,858 A | 8/1997 | Parikh et al. |
| 5,660,861 A | 8/1997 | Jao et al. |
| 5,667,808 A | 9/1997 | Johnson et al. |
| 5,668,170 A | 9/1997 | Gyory |
| 5,672,549 A | 9/1997 | Minami et al. |
| 5,676,942 A | 10/1997 | Testa et al. |
| 5,686,097 A | 11/1997 | Taskovich et al. |
| 5,688,801 A | 11/1997 | Mesens et al. |
| 5,690,925 A | 11/1997 | Gray et al. |
| 5,690,952 A | 11/1997 | Magruder et al. |
| 5,697,113 A | 12/1997 | Shatz et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,707,644 A | 1/1998 | Illum |
| 5,711,967 A | 1/1998 | Juch |
| 5,713,847 A | 2/1998 | Howard, III et al. |
| 5,718,922 A | 2/1998 | Herrero-Vanrell |
| 5,728,088 A | 3/1998 | Margruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Hahn et al. |
| 5,767,251 A | 6/1998 | Reddy et al. |
| 5,770,231 A | 6/1998 | Mesens et al. |
| 5,782,396 A | 7/1998 | Mastri et al. |
| 5,792,477 A | 8/1998 | Rickey et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| D399,821 S | 10/1998 | Tyneski et al. |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,851,451 A | 12/1998 | Takechi et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Magruder et al. |
| 5,871,778 A | 2/1999 | Kino et al. |
| 5,874,388 A | 2/1999 | Hsu |
| 5,876,746 A | 3/1999 | Jona et al. |
| 5,882,676 A | 3/1999 | Lee et al. |
| D408,917 S | 4/1999 | Hacker |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,916,598 A | 6/1999 | Rickey et al. |
| 5,922,253 A | 7/1999 | Herbert et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,942,253 A | 8/1999 | Gombotz et al. |
| 5,945,126 A | 8/1999 | Thanoo et al. |
| 5,948,430 A | 9/1999 | Zerbe et al. |
| 5,958,909 A | 9/1999 | Habener |
| D415,073 S | 10/1999 | Meehan et al. |
| 5,962,023 A | 10/1999 | Jamiolkowski et al. |
| 5,965,168 A | 10/1999 | Mesens et al. |
| 5,972,370 A | 10/1999 | Eckenhoff et al. |
| 5,972,373 A | 10/1999 | Yajima et al. |
| 5,976,109 A | 11/1999 | Heruth |
| 5,980,945 A | 11/1999 | Ruiz |
| 5,981,719 A | 11/1999 | Woiszwillo et al. |
| 5,984,890 A | 11/1999 | Gast et al. |
| 5,985,305 A | 11/1999 | Peery et al. |
| 5,989,463 A | 11/1999 | Tracy et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |

(56) References Cited

U.S. PATENT DOCUMENTS

| | | |
|---|---|---|
| 6,023,802 A | 2/2000 | King |
| 6,029,361 A | 2/2000 | Newman |
| 6,056,718 A | 5/2000 | Funderburk et al. |
| 6,060,450 A | 5/2000 | Soos et al. |
| 6,069,133 A | 5/2000 | Chiou et al. |
| 6,074,660 A | 6/2000 | Jamiolkowski et al. |
| 6,074,673 A | 6/2000 | Guillen |
| 6,100,346 A | 8/2000 | Jamiolkowski et al. |
| 6,110,503 A | 8/2000 | Rickey et al. |
| 6,113,938 A | 9/2000 | Chen et al. |
| 6,113,947 A | 9/2000 | Cleland et al. |
| 6,120,781 A | 9/2000 | Le Bras et al. |
| 6,120,787 A | 9/2000 | Gustafsson et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,190,700 B1 | 2/2001 | Okada et al. |
| 6,190,702 B1 | 2/2001 | Takada et al. |
| 6,191,102 B1 | 2/2001 | DiMarchi et al. |
| 6,204,022 B1 | 3/2001 | Johnson et al. |
| 6,217,893 B1 | 4/2001 | Pellet et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,349 B1 | 6/2001 | Yiv et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| D445,975 S | 7/2001 | Stratford |
| 6,258,377 B1 | 7/2001 | New et al. |
| 6,261,584 B1 | 7/2001 | Peery et al. |
| 6,268,343 B1 | 7/2001 | Knudsen et al. |
| 6,270,700 B1 | 8/2001 | Ignatious |
| 6,270,787 B1 | 8/2001 | Ayer |
| 6,277,413 B1 | 8/2001 | Sankaram |
| 6,283,949 B1 | 9/2001 | Roorda |
| 6,284,264 B1 | 9/2001 | Zerbe et al. |
| 6,284,725 B1 | 9/2001 | Coolidge et al. |
| 6,284,727 B1 | 9/2001 | Kim et al. |
| 6,287,295 B1 | 9/2001 | Chen et al. |
| 6,329,336 B1 | 12/2001 | Bridon et al. |
| 6,331,311 B1 | 12/2001 | Brodbeck et al. |
| 6,372,218 B1 | 4/2002 | Cummins |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,387 B1 | 10/2002 | Scott et al. |
| 6,458,924 B2 | 10/2002 | Knudsen et al. |
| 6,461,605 B1 | 10/2002 | Cutler et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,495,164 B1 | 12/2002 | Ramstack et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamilolkowski et al. |
| 6,524,305 B1 | 2/2003 | Peterson et al. |
| 6,528,093 B1 | 3/2003 | Kamei et al. |
| 6,528,486 B1 | 3/2003 | Larsen et al. |
| D472,896 S | 4/2003 | Peiker |
| 6,541,021 B1 | 4/2003 | Johnson et al. |
| 6,544,252 B1 | 4/2003 | Theeuwes et al. |
| 6,547,250 B1 | 4/2003 | Noble et al. |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,667,061 B2 | 12/2003 | Ramstack et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiewicz et al. |
| 6,767,887 B1 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B2 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |
| 6,899,887 B2 | 5/2005 | Ayer |
| 6,899,898 B2 | 5/2005 | Albayrak |
| 6,902,744 B1 | 6/2005 | Kolterman et al. |
| 6,903,186 B1 | 6/2005 | Dong |
| 6,913,767 B1 | 7/2005 | Cleland et al. |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,163,697 B2 | 1/2007 | Hanes et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,235,627 B2 | 6/2007 | Knudson et al. |
| 7,241,457 B2 | 7/2007 | Chen et al. |
| 7,258,869 B1 | 8/2007 | Berry et al. |

(56) References Cited

U.S. PATENT DOCUMENTS

| | | |
|---|---|---|
| D555,589 S | 11/2007 | Hussaini et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,589,169 B2 | 9/2009 | Bolotin |
| 7,612,176 B2 | 11/2009 | Wright et al. |
| 2,133,073 A1 | 12/2009 | Wright et al. |
| 7,635,463 B2 | 12/2009 | Bolotin et al. |
| D608,447 S | 1/2010 | Meyer et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 | 3/2010 | Alessi et al. |
| 7,727,519 B2 | 6/2010 | Moran |
| 7,731,947 B2 | 6/2010 | Eliaz et al. |
| 7,736,665 B2 | 6/2010 | Patel et al. |
| 7,741,269 B2 | 6/2010 | Young et al. |
| 7,790,140 B2 | 9/2010 | Bolotin |
| 7,825,091 B2 | 11/2010 | Bloom et al. |
| 7,829,109 B2 | 11/2010 | Chen et al. |
| 7,833,543 B2 | 11/2010 | Gibson et al. |
| 7,879,028 B2 | 2/2011 | Alessi et al. |
| 7,879,794 B2 | 2/2011 | Weyer et al. |
| 7,919,109 B2 | 4/2011 | Berry et al. |
| 7,928,065 B2 | 4/2011 | Young et al. |
| D638,478 S | 5/2011 | Block |
| 7,959,938 B2 | 6/2011 | Rohloff et al. |
| 7,964,183 B2 | 6/2011 | Eliaz et al. |
| 8,039,432 B2 | 10/2011 | Bridon et al. |
| 8,048,438 B2 | 11/2011 | Berry et al. |
| 8,052,996 B2 | 11/2011 | Lautenbach et al. |
| 8,058,233 B2 | 11/2011 | Cowley et al. |
| 8,101,576 B2 | 1/2012 | Bloom |
| 8,114,430 B2 | 2/2012 | Rohloff et al. |
| 8,114,437 B2 | 2/2012 | Rohloff et al. |
| 8,158,150 B2 | 4/2012 | Lautenbach et al. |
| 8,173,150 B2 | 5/2012 | Berry et al. |
| 8,202,836 B2 | 6/2012 | Moore et al. |
| 8,206,745 B2 | 6/2012 | Rohloff et al. |
| 8,211,467 B2 | 7/2012 | Rohloff et al. |
| 8,217,001 B2 | 7/2012 | Cowley et al. |
| 8,231,859 B2 | 7/2012 | Bolotin et al. |
| 8,257,682 B2 | 9/2012 | Bolotin et al. |
| 8,257,691 B2 | 9/2012 | Eliaz et al. |
| 8,262,667 B1 | 9/2012 | Silver et al. |
| 8,263,545 B2 | 9/2012 | Levy et al. |
| 8,263,736 B2 | 9/2012 | Bloom |
| 8,268,341 B2 | 9/2012 | Berry et al. |
| 8,273,365 B2 | 9/2012 | Lautenbach et al. |
| 8,273,713 B2 | 9/2012 | Pittner et al. |
| D669,589 S | 10/2012 | Delaey |
| 8,277,776 B2 | 10/2012 | Bolotin et al. |
| 8,278,267 B2 | 10/2012 | Weyer et al. |
| 8,288,338 B2 | 10/2012 | Young et al. |
| 8,298,561 B2 | 10/2012 | Alessi et al. |
| 8,299,025 B2 | 10/2012 | Alessi et al. |
| 8,343,140 B2 | 1/2013 | Alessi et al. |
| 8,367,095 B2 | 2/2013 | Lautenbach et al. |
| 8,372,424 B2 | 2/2013 | Berry et al. |
| D678,889 S | 3/2013 | Chiu |
| 8,398,967 B2 | 3/2013 | Eliaz et al. |
| 8,440,226 B2 | 5/2013 | Rohloff et al. |
| 8,460,694 B2 | 6/2013 | Rohloff et al. |
| 8,470,353 B2 | 6/2013 | Lautenbach et al. |
| 8,801,700 B2 | 8/2014 | Alessi et al. |
| 8,815,802 B2 | 8/2014 | Kalthoff et al. |
| 8,858,621 B2 | 10/2014 | Oba et al. |
| 8,865,202 B2 | 10/2014 | Zerbe et al. |
| 8,888,745 B2 | 11/2014 | Van Der Graaf et al. |
| 8,926,595 B2 | 1/2015 | Alessi et al. |
| 8,940,316 B2 | 1/2015 | Alessi et al. |
| 8,992,961 B2 | 3/2015 | Berry et al. |
| 8,992,962 B2 | 3/2015 | Lautenbach et al. |
| 9,044,209 B2 | 6/2015 | Dayton et al. |
| 9,078,900 B2 | 7/2015 | Kuzma et al. |
| 9,095,553 B2 | 8/2015 | Rohloff et al. |
| 9,241,722 B2 | 1/2016 | Yu |
| D750,764 S | 3/2016 | DeSocio |
| 9,332,995 B2 | 5/2016 | Russo et al. |
| D769,540 S | 10/2016 | Meier |
| 9,509,001 B2 | 11/2016 | Usami |
| 9,526,763 B2 | 12/2016 | Rohloff et al. |
| 9,539,200 B2 | 1/2017 | Lautenbach et al. |
| 9,572,889 B2 | 2/2017 | Alessi et al. |
| D789,539 S | 6/2017 | Kleiner et al. |
| 9,682,127 B2 | 6/2017 | Alessi et al. |
| RE46,577 E | 10/2017 | Collins et al. |
| 9,800,157 B2 | 10/2017 | Kawano et al. |
| 9,889,085 B1 | 2/2018 | Alessi et al. |
| 10,501,517 B2 * | 12/2019 | Blackwell ............ A61K 9/0004 |
| 11,214,607 B2 * | 1/2022 | Blackwell ............... A61P 25/04 |
| 2001/0012511 A1 | 8/2001 | Bezwada et al. |
| 2001/0021377 A1 | 9/2001 | Jamiolkowski et al. |
| 2001/0021822 A1 | 9/2001 | Ayer |
| 2001/0022974 A1 | 9/2001 | Ayer |
| 2001/0026793 A1 | 10/2001 | Jamiolkowski et al. |
| 2001/0027311 A1 | 10/2001 | Chen et al. |
| 2001/0031790 A1 | 10/2001 | Beisswenger et al. |
| 2001/0036472 A1 | 11/2001 | Wong et al. |
| 2001/0040326 A1 | 11/2001 | Balczun et al. |
| 2002/0001631 A1 | 1/2002 | Okumu |
| 2002/0004481 A1 | 1/2002 | Cleland et al. |
| 2002/0012818 A1 | 1/2002 | Ruppi et al. |
| 2002/0034532 A1 | 3/2002 | Brodbeck et al. |
| 2002/0037309 A1 | 3/2002 | Jaworowicz et al. |
| 2002/0048600 A1 | 4/2002 | Bhatt et al. |
| 2002/0098180 A1 | 7/2002 | Lei et al. |
| 2002/0136848 A1 | 9/2002 | Yoshii et al. |
| 2002/0137666 A1 | 9/2002 | Beeley et al. |
| 2002/0141985 A1 | 10/2002 | Pittner et al. |
| 2002/0197185 A1 | 12/2002 | Jamiolkowski et al. |
| 2002/0197235 A1 | 12/2002 | Moran |
| 2003/0032947 A1 | 2/2003 | Harper et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0060425 A1 | 3/2003 | Ahlem et al. |
| 2003/0097121 A1 | 5/2003 | Jolly et al. |
| 2003/0104063 A1 | 6/2003 | Babcock et al. |
| 2003/0108608 A1 | 6/2003 | Laridon et al. |
| 2003/0108609 A1 | 6/2003 | Berry et al. |
| 2003/0113380 A1 | 6/2003 | Ramstack et al. |
| 2003/0114837 A1 | 6/2003 | Peterson et al. |
| 2003/0118660 A1 | 6/2003 | Rickey et al. |
| 2003/0138403 A1 | 7/2003 | Drustrup |
| 2003/0138491 A1 | 7/2003 | Tracy et al. |
| 2003/0157178 A1 | 8/2003 | Chen et al. |
| 2003/0170289 A1 | 9/2003 | Chen et al. |
| 2003/0180364 A1 | 9/2003 | Chen et al. |
| 2003/0186858 A1 | 10/2003 | Arentsen |
| 2003/0191099 A1 | 10/2003 | Bohlmann et al. |
| 2003/0211974 A1 | 11/2003 | Brodbeck et al. |
| 2003/0215515 A1 | 11/2003 | Truong-Le et al. |
| 2004/0001689 A1 | 1/2004 | Goldsmith |
| 2004/0001889 A1 | 1/2004 | Chen et al. |
| 2004/0002442 A1 | 1/2004 | Pan et al. |
| 2004/0022859 A1 | 2/2004 | Chen et al. |
| 2004/0024068 A1 | 2/2004 | Levy et al. |
| 2004/0024069 A1 | 2/2004 | Chen et al. |
| 2004/0029784 A1 | 2/2004 | Hathaway |
| 2004/0039376 A1 | 2/2004 | Peery et al. |
| 2004/0097906 A1 | 5/2004 | Fereira et al. |
| 2004/0101557 A1 | 5/2004 | Gibson et al. |
| 2004/0102762 A1 | 5/2004 | Gilbert |
| 2004/0115236 A1 | 6/2004 | Chan et al. |
| 2004/0142867 A1 | 7/2004 | Oi et al. |
| 2004/0142902 A1 | 7/2004 | Struijker-Boudier |
| 2004/0151753 A1 | 8/2004 | Chen et al. |

(56) References Cited

U.S. PATENT DOCUMENTS

| | | |
|---|---|---|
| 2004/0157951 A1 | 8/2004 | Wolf |
| 2004/0198654 A1 | 10/2004 | Glaesner et al. |
| 2004/0209801 A1 | 10/2004 | Brand et al. |
| 2004/0224903 A1 | 11/2004 | Berry et al. |
| 2004/0225113 A1 | 11/2004 | LaFleur et al. |
| 2004/0243106 A1 | 12/2004 | Ayer |
| 2004/0265273 A1 | 12/2004 | Li et al. |
| 2004/0266683 A1 | 12/2004 | Hathaway et al. |
| 2004/0266692 A1 | 12/2004 | Young et al. |
| 2005/0004557 A1 | 1/2005 | Russell |
| 2005/0008661 A1 | 1/2005 | Fereira et al. |
| 2005/0009742 A1 | 1/2005 | Bertilsson et al. |
| 2005/0010196 A1 | 1/2005 | Fereira et al. |
| 2005/0010942 A1 | 1/2005 | Kim et al. |
| 2005/0070469 A1 | 3/2005 | Bloom et al. |
| 2005/0070883 A1 | 3/2005 | Brown et al. |
| 2005/0070927 A1 | 3/2005 | Feinberg |
| 2005/0079200 A1 | 4/2005 | Rathenow et al. |
| 2005/0079202 A1 | 4/2005 | Chen et al. |
| 2005/0095284 A1 | 5/2005 | Trautman |
| 2005/0101943 A1 | 5/2005 | Ayer et al. |
| 2005/0106214 A1 | 5/2005 | Chen |
| 2005/0112188 A1 | 5/2005 | Eliaz et al. |
| 2005/0118206 A1 | 6/2005 | Luk et al. |
| 2005/0118221 A1 | 6/2005 | Blakely et al. |
| 2005/0131386 A1 | 6/2005 | Freeman et al. |
| 2005/0131389 A1 | 6/2005 | Peterson et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0216087 A1 | 9/2005 | Zucherman et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0073182 A1 | 4/2006 | Wong et al. |
| 2006/0084604 A1 | 4/2006 | Kitaura et al. |
| 2006/0084922 A1 | 4/2006 | Botha |
| 2006/0094652 A1 | 5/2006 | Levy et al. |
| 2006/0094693 A1 | 5/2006 | Aziz et al. |
| 2006/0106399 A1 | 5/2006 | Taras et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0193918 A1 | 8/2006 | Rohloff et al. |
| 2006/0216242 A1 | 9/2006 | Rohloff et al. |
| 2006/0224145 A1 | 10/2006 | Gills |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1 | 11/2006 | Moberg et al. |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0149011 A1 | 6/2007 | Kent et al. |
| 2007/0166352 A1 | 7/2007 | Wright et al. |
| 2007/0207958 A1 | 9/2007 | Bridon et al. |
| 2007/0248572 A1 | 10/2007 | Moran et al. |
| 2007/0281024 A1 | 12/2007 | Lautenbach et al. |
| 2008/0020016 A1 | 1/2008 | Li et al. |
| 2008/0038316 A1 | 2/2008 | Wong et al. |
| 2008/0064636 A1 | 3/2008 | Bloom et al. |
| 2008/0065090 A1 | 3/2008 | Scribner et al. |
| 2008/0091176 A1 | 4/2008 | Alessi et al. |
| 2008/0110515 A1 | 5/2008 | Angelosanto et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0208194 A1 | 8/2008 | Bickenbach |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0269725 A1 | 10/2008 | Deem et al. |
| 2008/0312157 A1 | 12/2008 | Levy et al. |
| 2009/0022727 A1 | 1/2009 | Houston et al. |
| 2009/0036364 A1 | 2/2009 | Levy et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0234392 A1 | 9/2009 | Dziedzic et al. |
| 2009/0247463 A1 | 10/2009 | Wright et al. |
| 2009/0254143 A1 | 10/2009 | Tweden et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2010/0298840 A1 | 11/2010 | Schwartz |
| 2011/0076317 A1 | 3/2011 | Alessi et al. |
| 2011/0091527 A1 | 4/2011 | Moonen et al. |
| 2011/0104111 A1 | 5/2011 | Rohloff et al. |
| 2011/0152181 A1 | 6/2011 | Alsina-Fernandez et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0208755 A1 | 8/2012 | Leung |
| 2013/0030417 A1 | 1/2013 | Alessi et al. |
| 2013/0034210 A1 | 2/2013 | Rohloff et al. |
| 2013/0052237 A1 | 2/2013 | Eliaz et al. |
| 2014/0058425 A1 | 2/2014 | Porat |
| 2014/0121741 A1 | 5/2014 | Bennett et al. |
| 2014/0257272 A1 | 9/2014 | Clark, III et al. |
| 2014/0378900 A1 | 12/2014 | Alessi et al. |
| 2015/0001118 A1 | 1/2015 | Selepack et al. |
| 2015/0057227 A1 | 2/2015 | Leung |
| 2015/0133791 A1 | 5/2015 | Sato et al. |
| 2015/0231062 A1 | 8/2015 | Lautenbach et al. |
| 2015/0231256 A1 | 8/2015 | Berry et al. |
| 2015/0297509 A1 | 10/2015 | Schwartz |
| 2016/0022582 A1 | 1/2016 | Alessi et al. |
| 2016/0030337 A1 | 2/2016 | Kuzma et al. |
| 2016/0354115 A1 | 12/2016 | Smith et al. |
| 2016/0354305 A1 | 12/2016 | Alessi et al. |
| 2017/0056476 A1 | 3/2017 | Rohloff et al. |
| 2017/0079906 A1 | 3/2017 | Alessi et al. |
| 2017/0119854 A1 | 5/2017 | Alessi et al. |
| 2017/0119855 A1 | 5/2017 | Berry et al. |
| 2017/0181964 A1 | 6/2017 | Lautenbach et al. |
| 2017/0252409 A1 | 9/2017 | Leung |
| 2017/0273706 A1 | 9/2017 | Mirza et al. |
| 2017/0319470 A1 | 11/2017 | Eliaz et al. |
| 2017/0319662 A1 | 11/2017 | Berry et al. |
| 2017/0348392 A1 | 12/2017 | Rohloff et al. |
| 2017/0368145 A1 | 12/2017 | Alessi et al. |
| 2018/0009871 A1 | 1/2018 | Blackwell et al. |
| 2018/0185451 A1 | 7/2018 | Young et al. |
| 2020/0299350 A1 | 9/2020 | Blackwell et al. |

FOREIGN PATENT DOCUMENTS

| | | |
|---|---|---|
| EP | 0052510 A2 | 5/1982 |
| EP | 0079405 A1 | 5/1983 |
| EP | 0254394 A1 | 1/1988 |
| EP | 0295411 A1 | 12/1988 |
| EP | 0302582 A1 | 2/1989 |

(56) References Cited

FOREIGN PATENT DOCUMENTS

| | | | |
|---|---|---|---|
| EP | 0368339 A2 | 5/1990 |
| EP | 0373867 A1 | 6/1990 |
| EP | 0431942 A2 | 6/1991 |
| EP | 0486959 A1 | 5/1992 |
| EP | 0521586 A1 | 1/1993 |
| EP | 0596161 A1 | 5/1994 |
| EP | 0379147 B1 | 9/1994 |
| EP | 0627231 A2 | 12/1994 |
| EP | 0729747 B1 | 5/1997 |
| EP | 0771817 A2 | 5/1997 |
| EP | 0841359 A1 | 5/1998 |
| EP | 0767689 B1 | 6/1999 |
| EP | 1046399 A1 | 10/2000 |
| EP | 1084703 A1 | 3/2001 |
| EP | 1300129 A2 | 4/2003 |
| EP | 1300173 A2 | 4/2003 |
| EP | 1536767 A1 | 6/2005 |
| EP | 1600187 B1 | 1/2009 |
| EP | 2133073 A1 | 12/2009 |
| EP | 2020990 B1 | 9/2010 |
| EP | 3458084 A1 | 3/2019 |
| EP | 3733694 A1 | 11/2020 |
| FR | 640907 A | 7/1928 |
| GB | 1049104 A | 11/1966 |
| GB | 1518683 A | 7/1978 |
| GB | 2501400 A | 10/2013 |
| JP | H02124814 A | 5/1990 |
| JP | H07196479 A | 8/1995 |
| JP | H09241153 A | 9/1997 |
| JP | H11100353 A | 4/1999 |
| JP | 2006213727 A | 8/2006 |
| JP | 2014520789 A | 8/2014 |
| NL | 9100160 A | 8/1992 |
| NZ | 592113 A | 4/2012 |
| TW | 200634060 A | 10/2006 |
| WO | WO 1989003678 A1 | 5/1989 |
| WO | WO 1990013285 A1 | 11/1990 |
| WO | WO 1990013361 A1 | 11/1990 |
| WO | WO 1990013780 A1 | 11/1990 |
| WO | WO 1991007160 A1 | 5/1991 |
| WO | WO 1992019241 A1 | 11/1992 |
| WO | WO 1993006819 A1 | 4/1993 |
| WO | WO 1993006821 A1 | 4/1993 |
| WO | WO 1993008832 A1 | 5/1993 |
| WO | WO 1993009763 A1 | 5/1993 |
| WO | WO 1993023083 A1 | 11/1993 |
| WO | WO 1994009743 A1 | 5/1994 |
| WO | WO 1994010982 A1 | 5/1994 |
| WO | WO 1994021262 A1 | 9/1994 |
| WO | WO 1995001161 A1 | 1/1995 |
| WO | WO 1995009006 A1 | 4/1995 |
| WO | WO 1995009007 A1 | 4/1995 |
| WO | WO 1995013799 A1 | 5/1995 |
| WO | WO 1995034285 A1 | 12/1995 |
| WO | WO 1996001134 A1 | 1/1996 |
| WO | WO 1996003116 A1 | 2/1996 |
| WO | WO 1996036317 A1 | 11/1996 |
| WO | WO 1996039142 A1 | 12/1996 |
| WO | WO 1996040049 A1 | 12/1996 |
| WO | WO 1996040139 A1 | 12/1996 |
| WO | WO 1996040355 A1 | 12/1996 |
| WO | WO 1997015289 A1 | 5/1997 |
| WO | WO 1997015296 A1 | 5/1997 |
| WO | WO 1997028181 A1 | 8/1997 |
| WO | WO 1997031943 A1 | 9/1997 |
| WO | WO 1997044039 A1 | 11/1997 |
| WO | WO 1997046204 A1 | 12/1997 |
| WO | WO 1997047339 A1 | 12/1997 |
| WO | WO 1998000152 A1 | 1/1998 |
| WO | WO 1998000157 A1 | 1/1998 |
| WO | WO 1998000158 A1 | 1/1998 |
| WO | WO 1998002169 A2 | 1/1998 |
| WO | WO 1997041837 A3 | 2/1998 |
| WO | WO 1998007412 A1 | 2/1998 |
| WO | WO 1998016250 A1 | 4/1998 |
| WO | WO 1998017315 A1 | 4/1998 |
| WO | WO 1998020930 A1 | 5/1998 |
| WO | WO 1998027960 A2 | 7/1998 |
| WO | WO 1998027962 A1 | 7/1998 |
| WO | WO 1998027963 A1 | 7/1998 |
| WO | WO 1998030231 A1 | 7/1998 |
| WO | WO 1998032463 A2 | 7/1998 |
| WO | WO 1998042317 A2 | 10/1998 |
| WO | WO 1998047487 A1 | 10/1998 |
| WO | WO 1998051282 A1 | 11/1998 |
| WO | WO 1999003453 A1 | 1/1999 |
| WO | WO 1999004767 A2 | 2/1999 |
| WO | WO 1999004768 A2 | 2/1999 |
| WO | WO 1999012549 A2 | 3/1999 |
| WO | WO 1999016419 A1 | 4/1999 |
| WO | WO 1999025728 A1 | 5/1999 |
| WO | WO 1999029306 A1 | 6/1999 |
| WO | WO 1999033446 A1 | 7/1999 |
| WO | WO 1999033449 A1 | 7/1999 |
| WO | WO 1999039700 A1 | 8/1999 |
| WO | WO 1999040788 A1 | 8/1999 |
| WO | WO 1999044659 A1 | 9/1999 |
| WO | WO 1999062501 A1 | 12/1999 |
| WO | WO 1999064061 A1 | 12/1999 |
| WO | WO 2000013663 A1 | 3/2000 |
| WO | WO 2000029206 A1 | 5/2000 |
| WO | WO 2000038652 A1 | 7/2000 |
| WO | WO 2000039280 A2 | 7/2000 |
| WO | WO 2000040273 A2 | 7/2000 |
| WO | WO 2000041548 A1 | 7/2000 |
| WO | WO 2000045790 A2 | 8/2000 |
| WO | WO 2000054745 A2 | 9/2000 |
| WO | WO 2000059476 A1 | 10/2000 |
| WO | WO 2000066087 A1 | 11/2000 |
| WO | WO 2000066138 A2 | 11/2000 |
| WO | WO 2000067728 A2 | 11/2000 |
| WO | WO 2001019345 A1 | 3/2001 |
| WO | WO 2001028525 A2 | 4/2001 |
| WO | WO 2001029206 A1 | 4/2001 |
| WO | WO 2001043528 A2 | 6/2001 |
| WO | WO 2001051041 A1 | 7/2001 |
| WO | WO 2001078683 A2 | 10/2001 |
| WO | WO 2002028366 A2 | 4/2002 |
| WO | WO 2002036072 A2 | 5/2002 |
| WO | WO 2002043800 A2 | 6/2002 |
| WO | WO 2002045752 A2 | 6/2002 |
| WO | WO 2002047716 A2 | 6/2002 |
| WO | WO 2002067895 A2 | 9/2002 |
| WO | WO 2002069983 A1 | 9/2002 |
| WO | WO 2002076344 A1 | 10/2002 |
| WO | WO 2002085428 A2 | 10/2002 |
| WO | WO 2003000230 A1 | 1/2003 |
| WO | WO 2003007981 A1 | 1/2003 |
| WO | WO 2003011892 A2 | 2/2003 |
| WO | WO 2003020245 A1 | 3/2003 |
| WO | WO 2003024357 A2 | 3/2003 |
| WO | WO 2003024503 A2 | 3/2003 |
| WO | WO 2003030923 A1 | 4/2003 |
| WO | WO 2003041684 A2 | 5/2003 |
| WO | WO 2003041757 A2 | 5/2003 |
| WO | WO 2003053400 A1 | 7/2003 |
| WO | WO 2003066585 A2 | 8/2003 |
| WO | WO 2003072113 A1 | 9/2003 |
| WO | WO 2003072133 A2 | 9/2003 |
| WO | WO 2004002565 A1 | 1/2004 |
| WO | WO 2004034975 A2 | 1/2004 |
| WO | WO 2004035754 A2 | 4/2004 |
| WO | WO 2004035762 A2 | 4/2004 |
| WO | WO 2004036186 A2 | 4/2004 |
| WO | WO 2004052336 A2 | 6/2004 |
| WO | WO 2004056338 A2 | 7/2004 |
| WO | WO 2004089335 A2 | 10/2004 |
| WO | WO 2004103342 A2 | 12/2004 |
| WO | WO 2005048930 A2 | 6/2005 |
| WO | WO 2005048952 A2 | 6/2005 |
| WO | WO 2005102293 A1 | 11/2005 |
| WO | WO 2005110425 A1 | 11/2005 |
| WO | WO 2006017772 A1 | 2/2006 |
| WO | WO 2006023526 A2 | 3/2006 |

(56) References Cited

FOREIGN PATENT DOCUMENTS

| | | | |
|---|---|---|---|
| WO | WO 2006081279 A2 | 8/2006 |
| WO | WO 2006083761 A2 | 8/2006 |
| WO | WO 2006084139 A2 | 8/2006 |
| WO | WO 2006086727 A2 | 8/2006 |
| WO | WO 2006101815 A2 | 9/2006 |
| WO | WO 2006111169 A1 | 10/2006 |
| WO | WO 2006131730 A1 | 12/2006 |
| WO | WO 2007024700 A2 | 3/2007 |
| WO | WO 2007056681 A2 | 5/2007 |
| WO | WO 2007075534 A2 | 7/2007 |
| WO | WO 2007084460 A2 | 7/2007 |
| WO | WO 2007133778 A2 | 11/2007 |
| WO | WO 2007140416 A2 | 12/2007 |
| WO | WO 2008021133 A2 | 2/2008 |
| WO | WO 2008041245 A2 | 4/2008 |
| WO | WO 2008061355 A1 | 5/2008 |
| WO | WO 2008133908 A2 | 11/2008 |
| WO | WO 2008134425 A1 | 11/2008 |
| WO | WO 2009109921 A1 | 9/2009 |
| WO | WO 2009143285 A2 | 11/2009 |
| WO | WO 2013004983 A1 | 1/2013 |
| WO | WO 2013074910 A1 | 5/2013 |
| WO | WO 2014152460 A2 | 9/2014 |

OTHER PUBLICATIONS

U.S. Appl. No. 15/595,809 / 2018/0009871 A1 / U.S. Pat. No. 10,501,517, filed May 15, 2017 / Jan. 11, 2018 / Dec. 10, 2019, William Blackwell.
U.S. Appl. No. 16/667,502 / 2020/0299350 A1 / U.S. Pat. No. 11,214,607. filed Oct. 29, 2019/ Sep. 24, 2020 / Jan. 4, 2022, William Blackwell.
"Abstracts 2007," Diabetologia Clinical & Experimental Diabetes & Metabolism, Springer, Berlin, Germany, vol. 50 S243 (Aug. 21, 2007) (paragraph [0586]) (XP002538652).
Amylin Pharmaceuticals, Inc., Prescribing Information for BYETTA® (Exenatide) Injection, rev. Oct. 2009, 34 pages.
Astrazeneca Pharmaceuticals LP, Prescribing Information for Bydureon® (Exenatide Extended-Release for Injectable Suspension), rev. Mar. 2015, 60 pages.
CAS No. 56-81-5 (Nov. 16, 1984).
Eli Lilly & Company, Prescribing Information for Trulicity® (Dulaglutide) Injection, for Subcutaneous Use, rev. Mar. 2015, 19 pages.
Extended European Search Report Received for EP Patent Application No. 20166273.1, dated Oct. 7, 2020, 6 pages.
Glaxosmithkline LLC, Prescribing Information for Tanzeum® (Albiglutide) for Injection, for Subcutaneous Use, rev. Jun. 2014, 55 pages.
Glumetza Brochure 2009, 13 Pages.
"Implantable infusion pumps: technology poised for takeoff," BBI Newsletter 17(12):209211 (Dec. 1994).
International Search Report and Written Opinion received for PCT Patent Application No. PCT/US2009/000916, dated Aug. 12, 2009, 12 pages.
International Search Report and Written Opinion Received for PCT Application No. PCT/US2017/032714, dated Jul. 28, 2017, 9 pages.
"Introduction to Antibodies", http://www.chemicon.com/resource/ANT10$^1/_a$ 1 .asp, 8 pages (retrieved May 2, 2007).
"Intarcia Presents Positive ITCA 650 Phase 2 Study Results for Type 2 Diabetes at EASD," Intarcia Therapeutics, Inc. (Sep. 22, 2010) (Press Release).
Novo Nordisk A/S, Prescribing Information for Victoza® (Liraglutide [rDNA Origin] Injection), Solution for Subcutaneous Use, v. 1, Jan. 2010, 23 pages.
Sanofi-Aventis U.S. LLC, Prescribing Information for ADLYXINO (Lixisenatide) Injection, for Subcutaneous Use, rev. Jul. 2016, 31 pages.

"Sequence Listings for International Patent Application Publication No. WO2009109927, WIPO Patentscope", http://patentscope.wipo.int/search/docservicepdf_pct/id00000008776887, 1 page (last visited Nov. 14, 2012).
Written Opinion for International Patent Application No. PCT/US2009/005629 (corresponding to U.S. Appl. No. 12/587,946), 5 pages (dated Apr. 15, 2011).
Adamson et al., "Phase I trial and pharmacokinetic study of all-trans-retinoic acid administered on an intermittent schedule in combination with interferon-alpha2a in pediatric patients with refractory cancer", *Journal of Clinical Oncology* 15(11):3330-3337 (Nov. 1997).
Adolf et al., "Antigenic Structure of Human Interferon ω1 (Interferon αII1): Comparison with Other Human Interferons", *The Journal of General Virology* 68(6):1669-1676 (Jun. 1987).
Adolf, "Human Interferon Omega—A review", *Multiple Sclerosis* 1:S44-47 (1995).
Adolf et al., "Human Interferon ω1: Isolation of the Gene, Expression in Chinese Hamster Ovary Cells and Characterization of the Recombinant Protein", *Biochimca et Biophysica Acta* 108(9):167-174 (Jun. 1991).
Adolf et al., "Monoclonal Antibodies and Enzyme Immunoassays Specific for Human Interferon (IFN) Gw1: Evidence That IFN-ω1 Is a Component of Human Leukocyte IFN", *Virology* 175(2):410-471 (Apr. 1990).
Adolf et al., "Purification and Characterization of Natural Human Interferon ω1", *Journal of Biological Chemistry* 265(16):9290-9295 (Jun. 1990).
Ahn et al., "A New Approach to Search for the Bioactive Confirmation of Glucagon: Positional Cyclization Scanning", *Journal of Medicinal Chemistry* 44(19) 3109-3116 (2001).
Akers et al., "Formulation Design and Development of Parenteral Suspensions", *Journal of Parenteral Science and Technology* 41(3): 88-96 (1987).
Alonso et al., "Determinants of Release Rate of Tetanus Vaccine from Polyester Microspheres", *Pharmaceutical Research* 10(7):945-953 (1993).
Andrx Pharmaceuticals, LLC, ANDA for Concerta® Extended-Release Tablets, 6 pages (correspondence dated Sep. 6, 2005).
Ansel et al., "Dosage Form Design: Pharmaceutical and Formulation Considerations", *Pharmaceutical Dosage Forms and Drug Delivery Systems*, Ch. 3 at 87-92 (7th ed. Lippincott Williams & Wilkins 1999).
Ansel et al., "Modified-Release Dosage Forms and Drug Delivery Systems", *Pharmaceutical Dosage Forms and Drug Delivery Systems*, Ch. 8 at 229-243 (7th ed. Lippincott Williams & Wilkins 1999).
ASTM International, Annual Book of ASTM Standards, 8.02:208-211, 584-587 (1984).
Aulitzky et al., "Successful Treatment of Metastatic Renal Cell Carcinoma With a Biologically Active Dose of Recombinant Interferon-Gama", *Journal of Clinical Oncology* 7(12): 1875-1884 (1989).
Baggio et al., "Biology of Incretins: GLP-1 and GIP", *Gastroenterology* 132(6):2131-2157 (2007).
Bailon et al., "Rational Design of a Potent, Long-lasting Form of Interferon: A 40 kDa Branched Polyethylene Glycol-conjugated Interferon Alpha-2a for the Treatment of Hepatitis C", *Bioconjugate Chemistry* 12(2):195-202 (2001).
Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography", *Journal of Pharmaceutical Sciences* 85(9):908-914 (1996).
Bakhtiar et al., "Taking Delivery", *Soap Perfumery & Cosmetics* 76(3):59-65 (2003) (liposomes in cosmetic delivery systems).
Balkwill, "Interferons", *Lancet* 1(8646):1060-1063 (May 1989).
Bataille et al., "Bioactive Enteroglucagon (Oxyntomodulin): Present Knowledge on Its Chemical Structure and Its Biological Activities", *Peptides* 2(2):41-44 (1981).
Bauer et al., "Non-Aqueous Emulsions as Vehicles for Capsule Fillings", *Drug Development and Industrial Pharmacy* 10(5):699-712 (1984).

(56) References Cited

OTHER PUBLICATIONS

Beck et al., "Poly(dl-Lactide-Co-Glycolide)/norethisterone Microcapsules: An Injectable Biodegradable Contraceptive", *Biology of Reproduction* 28(1):186-195 (1983).

Bekkering, "Estimation of Early Hepatitis C Viral Clearance in Patients Receiving Daily Interferon and Ribavirin Therapy Using a Mathematical Model", *Hepatology* 33(2):419 (Feb. 2001).

Bell et al., "Hamster Preproglucagon Contains the Sequence of Glucagon and Two Related Peptides", *Nature* 302(5910):716-718 (1983).

Bell et al., "Impact of Moisture on Thermally Induced Denaturation and Decomposition of Lyophilized Bovine Somatotropin", *Drug Delivery Research and Development Biopolymers* 35(2):201-209 (1995).

Bertoncello et al., "Haematopoietic Radioprotection by Cremophor EL: A Polyethoxylated Castor Oil", *International Journal of Radiation Biology* 67(1):57-64 (1995).

Bodmeier et al., "Solvent Selection in the Preparation of Poly(dl-Lactide) Microspheres Prepared by the Solvent Evaporation Method", *International Journal of Pharmaceutics* 43(1-2):179-186 (Apr. 1988).

Bohlinder et al., "Use and Characteristics of a Novel Lipid Particle-Forming Matrix as a Drug-Carrier System", *European Journal of Pharmaceutical Sciences* 2(4):271-279 (1994).

Bolinger et al., "Recombinant Interferon γ for Treatment of Chronic Granulomatous Disease and Other Disorders", *Clinical Pharmacology* 11(10):834-850 (Oct. 1992).

Bonkovsky et al., "Outcomes Research in Chronic Viral Hepatitis C: Effects of Interferon Therapy", *Canadian Journal of Gastroenterology and Hepatology* 14(Supp. B):21B-29B (Jul.-Aug. 2000).

Borden et al., "Second-Generation Interferons for Cancer: Clinical Targets", *Seminars in Cancer Biology* 10(2):125-144 (Apr. 2000).

Boue et al., "Antiviral and Antiluteolytic Activity of Recombinant Bovine IFN-ω1 Obtained from Pichia Pastoris", *Journal of Interferon & Cytokine Research* 20:677-683 (2000).

Bray et al., "Gut Signals and Energy Balance: Ghrelin, Peptide YY, Leptin, and Amylin", (Slides and transcript for presentation at Medscape CME) (Dec. 19, 2007).

Buckwold et al. "Antiviral Activity of CHO-SS Cell-Derived Human Omega Interferon and Other Human Interferons Against HCV RNA Replicons and Related Viruses" *Antiviral Research* 73(2):118-25 (Feb. 2007) (Epub Sep. 11, 2006).

Cantor et al., "Theory of Lipid Monolayers Comprised of Mixtures of Flexible and Stiff Amphiphiles in Athermal Solvents: Fluid Phase Coexistence", *The Journal of Chemical Physics* 104(20):8082-8095 (1996).

Cha et al., "A One-Week Subdermal Delivery System for I-Methadone Based on Biodegradable Microcapsules", *Journal of Controlled Release* 7:69-78 (1988).

Cha et al., "The Acceleration of Degradation-Controlled Drug Delivery from Polyester Microspheres", *Journal of Controlled Release* 8(3):259-265 (1989).

Chang et al., "Biodegradable Polyester Implants and Suspension Injection for Sustained Release of a Cognitive Enhancer", *Pharmaceutical Technology* 20(1):80-84 (1996).

Chapman et al., "Physical Studies of Phospholipids. VI. Thermotropic and Lyotropic Mesomorphism of Some 1,2-Diacylphosphatidylcholines (Lecithins)", *Chemistry and Physics of Lipids* 1(5):445-475 (1967).

Chaumeil, "Micronization: A Method of Improving the Bioavailability of Poorly Soluble Drugs", *Methods & Findings in Experimental & Clinical Pharmacology* 20(3):211-215 (1998).

Clark et al., "The Diabetic Zucker Fatty Rat", *Proceedings of the Society for Experimental Biology and Medicine* 173(1):68-75 (1983).

Cohen et al. "Controlled Delivery Systems for Proteins Based on Poly(lactic/glycolic Acid) Microspheres", *Pharmaceutical Research* 8(6):713-720 (1991).

Condino-Neto et al., "Interferon-Gamma Improves Splicing Efficiency of CYBB Gene Transcripts in an Interferon-Responsive Variant of Chronic Granulomatous Disease Due to a Splice Site Consensus Region Mutation", *Blood* 95(11):3548-3554 (Jun. 2000).

Conti et al., "Use of Polylactic Acid for the Preparation of Microparticulate Drug Delivery Systems", *Journal of Microencapsulation* 9(2): 153-166 (1992).

Costantino et al., "Protein Spray Freeze Drying. 2. Effect of Formulation Variables on particle Size and Stability", *Journal of Pharmaceutical Sciences* 91:388-395 (2002).

Cox et al., "The Effects of Neuropeptide Y and Its Fragments Upon Basal and Electrically Stimulated Ion Secretion in Rat Jejunum Mucosa", *British Journal of Pharmacology* 101(2):246-252 (Oct. 1990).

Darney et al., "Subdermal Progestin Implant Contraception", *Current Opinion in Obstetrics & Gynecology* 3(4):470-476 (1991).

Das et al., "Reviewing Antisense Oligonucleotide Therapy: Part 2, Delivery Issues", *BioPharm* 2(11):44-51 (1999).

Dash et al., "Therapeutic Applications of Implantable Drug Delivery Systems", *Journal of Pharmacological and Toxicological Methods* 40(1):1-12 (1998).

Davis et al., "Durability of Viral Response to Interferon Alone or in Combination with Oral Ribavirin in Patients with Chronic Hepatitis C", Progress Abstract 50th Annual. Meeting Postgraduate Courses American Association Study Liver Disease, Dallas, TX (Nov. 5-9, 1999) (Abstract 570).

Deacon, "GLP-1-(9-36) Amide Reduces Blood Glucose in Anesthetized Pigs by a Mechanism That Does not Involve Insulin Secretion", *American Journal of Physiology—Endocrinology and Metabolism* 282(4):E873-E879 (2002).

Desai et al., "Protein Structure in the Lyophilized State: A Hydrogen Isotope Exchange/NMR Study with Bovine Pancreatic Trypsin Inhibitor", *Journal of the American Chemical Society* 116(21):9420-9422 (1994).

Di Marco et al., "Combined Treatment of Relapse of Chronic Hepatitis C with High-Dose α2b Interferon plus Ribavirin for 6 or 12 Months", Progress Abstract 50th Annual Meeting Postgraduate Courses American Association Study Liver Disease, Dallas, TX (Nov. 5-9, 1999) (Abstract 569).

Dorr et al., "Phase I-II Trial of Interferon-α 2b by Continuous Subcutaneous Infusion over 28 Days", *Journal of Interferon & Cytokine Research* 8(6):717-725 (1988).

Eberlein et al., "A New Molecular form of PYY: Structural Characterization of Human PYY(3-36) and PYY(1-36)", *Peptides* 10(4):797-803 (1989).

Efendic et al., "Overview of Incretin Hormones," *Hormone and Metabolic Research* 36(11-12):742-746 (2004).

Eissele et al., "Rat Gastric somatostatin and Gastrin Release: Interactions of Exendin-4 and Truncated Glucagon-Like Peptide-1 (GLP-1) Amide", *Life Sciences* 55(8):629-634 (1994).

Elias et al., "Infusional Interleukin-2 and 5-Fluorouracil with Subcutaneous Interferon-α for the Treatment of Patients with Advanced Renal Cell Carcinoma: A Southwest Oncology Group Phase II Study", *Cancer* 89(3):597-603 (Aug. 2000).

Eng et al., "Isolation And Characterization of Exendin-4, An Exendin-3 Analogue, From Heloderma Suspectum Venom. Further Evidence For An Exendin Receptor on Dispersed Acini From Guinea Pig Pancreas", *Journal of Biological Chemistry* 267(11):7402-7405 (1992).

Eng et al., Purification and Structure of Exendin-3, a New Pancreatic Secretagogue Isolated from Heloderma Horridum Venom, *Journal of Biological Chemistry* 265(33):20259-20262 (1990).

Eppstein et al., Biological Activity of Liposome-Encapsulated Murine Interferon Gamma is Mediated by a Cell Membrane Receptor, *PNAS USA* 82(11):3688-3692 (1985).

Eros et al., "Multiple Phase Emulsions as Controlled Drug Delivery Therapeutic Systems", *Proceeding of Conference Colloid Chemistry* 193-196 (1993).

Erowid, "Introduction to the Federal Controlled Substance Analog Act", 4 pages (2001).

Ertl et al., "Poly (DL-lactide-co-glycolide) Microspheres as Carriers for Peptide Vaccines", *Vaccine* 14(9):879-885.(1996).

Fang et al., "The Impact of Baseline Liver Histology on Virologic Response to Interferon α-2b±ρ Ribavirin Therapy in Patients with Chronic Hepatitis C", Progress Abstract 50th Annual Meeting Postgraduate Courses American Association Study Liver Disease, Dallas, TX (Nov. 5-9, 1999) (Abstract 572).

(56) References Cited

OTHER PUBLICATIONS

Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface", *The Journal of Nutritional Biochemistry* 4(11):630-634 (1993).

Ferenci et al., "Combination of Interferon (IFN) Induction Therapy and Ribavirin in Chronic Hepatitis C", Progress Abstract Digestive Disease Week 2000, San Diego, CA (May 21-24, 2000) (Abstract 977).

Fioravante et al., "Weight Loss and Resting Energy Expenditure in Patients With Chronic Hepatitis C Before and During Standard Treatment Kosmiski", *Nutrition* 28(6):630-634 (Jun. 2012).

Fontaine et al., "Recovery from Chronic Hepatitis C in Long-Term Responders to Ribavirin plus Interferon α", *Lancet* 356(9223):41 (Jul. 2000).

Franchetti et al., "Furanfurin and Thiophenfurin: Two Novel Tiazofurin Analogues. Synthesis, Structure, Antitumor Activity, and Interactions with Inosine Monophosphate Dehydrogenase", *Journal of Medicinal Chemistry* 38(19):3829-3837 (1995).

Fujii et al., "Effect of Phosphatidylcholine on Skin Permeation of Indomethacin from Gel Prepared with Liquid Paraffin and Hydrogenated Phospholipid", *International Journal of Pharmaceutics* 222(1):57-64 (2001).

Fujii et al., "Enhancement of Skin Permeation of Miconazole by Phospholipid and Dodecyl 2-(N, N-dimethylamino) propionate (DDAIP)", *International Journal of Pharmaceutics* 234(1-2):121-128 (2002).

Gan To Kagaku Ryoho, "Phase II Study of Recombinant Leukocyte a Interferon (Ro 22-8181) in Malignant Brain Tumors", *Cancer & Chemotherapy* 12(4):913-920 (Apr. 1985).

Gao et al., "Target-Mediated Pharmacokinetic and Pharmacodynamic Model of Exendin-4 in Rats, Monkeys, and Humans", *Drug Metabolism and Disposition* 40(5):990-997 (May 2012).

Gappa et al., "Juvenile Laryngeal Papillomatosis—A Case Report", *Pneumologie* 45(11):936-938 (Nov. 1991) (XP009079028).

Gause et al., "Phase I Study of Subcutaneously Administered Interleukin-2 in Combination with Interferon Alfa-2a in Patients with Advanced Cancer", *Journal of Clinical Oncology* 14(8):2234-2241 (Aug. 1996).

Ghiglione et al., "How Glucagon-Like is Glucagon-Like Peptide-1?", *Diabetologia* 27(6):599-600 (1984).

Glue et al., "A Dose-Ranging Study of Peg-Intron and Ribavirin in Chronic Hepatitis C-Safety, Efficacy, and Virological Rationale", Progress Abstract 50th Annual Meeting Postgraduate Courses American Association Study Liver Disease, Dallas, TX (Nov. 5-9, 1999) (Abstract 571).

Goke et al., "Exendin-4 is a High Potency Agonist and Truncated Exendin-(9-39)-Amide an Antagonist at the Glucagon-Like Peptide 1-(7-36)-Amide Receptor of Insulin-Secreting Beta-Cells", *Journal of Biological Chemistry* 268(26):19650-19655 (1993).

Gonzales et al., "Randomized Controlled Trial Including an Initial 4-Week 'Induction' Period During One Year of High-Dose Interferon α-2B Treatment for Chronic Hepatitis C", Progress Abstract Digestive Disease Week 2000, San Diego, CA (May 21-24, 2000) (Abstract 975).

Gonzalez, et al., "Hemoglobin A1c: A Reliable and Accurate Test for Diabetes Care? Prospective Study in Mexico", *Salud Pública de México* 55:462-468 (2013).

Gosland et al., "A Phase I Trial of 5-Day Continuous Infusion Cisplatin and Interferon α", *Cancer Chemotherapy and Pharmacology* 37(1-2):39-46 (1995).

Grant et al., "Combination Therapy with Interferon-α plus N-Acetyl Cysteine for Chronic Hepatitis C: A Placebo Controlled Double-Blind Multicentre Study", *Journal of Medical Virology* 61(4):439-442 (Aug. 2000).

Gutniak et al., "Antidiabetogenic Effect of Glucagon-Like Peptide-1 (7-36) Amide in Normal Subjects and Patients with Diabetes Mellitus", The New England Journal of Medicine 326(20):1316-1322 (1992).

Hageman, "The Role of Moisture in Protein Stability," Drug Development and Industrial Pharmacy 14(14):2047-2070 (1988).

Hauck, "Engineer's Guide to Plastics", *Materials Engineering* 5(72):38-45 (Jul. 17, 1972).

Heathcote et al., "Peginterferon alfa-2a in Patients With Chronic Hepatitis C and Cirrhosis", *The New England Journal of Medicine* 343(23):1673-1680 (2000).

Heim et al., "Intracellular Signaling and Antiviral Effects of Interferons," *Digestive and Liver Disease* 32(3):257-263 (Apr. 2000).

Heinrich et al., "Pre-Proglucagon Messenger Ribonucleic Acid: Nucleotide and Encoded Amino Acid Sequences of the Rat Pancreatic Complementary Deoxyribonucleic Acid", *Endocrinology* 115(6):2176-2181 (1984).

Hellstrand et al., "Histamine and Cytokine Therapy", *Acta Oncologica* 37(4):347-353 (1998).

Hellstrand et al., "Histamine and the Response to IFN-α in Chronic Hepatitis C", *Journal of Interferon & Cytokine Research* 18(1):21-22 (Jan. 1998).

Hellstrand et al., "Histamine in Immunotherapy of Advanced Melanoma: A Pilot Study", *Cancer Immunology, Immunotherapy* 39(6):416-419 (Dec. 1994).

Henry et al., "Comparing ITCA 650, continuous subcutaneous delivery of exenatide via DUROS® device, vs. twice daily exenatide injections in metformin-treated type 2 diabetes," Oral Presentation at the 46th Annual Meeting of the European Association for the Study of Diabetes in Stockholm, Sweden, 21 pages (Sep. 20-24, 2010).

Hisatomi et al., "Toxicity of Polyoxyethylene Hydrogenated Castor oil 60 (HCO-60) in Experimental Animals", *The Journal of Toxicological Sciences* 18(3):1-9 (1993).

Hodgman et al., Handbook of Chemistry and Physics, 35th Edition, 1024-1025 (1953).

Hodoshima et al., "Lipid Nanoparticles for Delivering Antitumor Drugs", *International Journal of Pharmaceutics* 146(1):81-92 (1997).

Hoffmann-La Roche Inc., Pegasys® (peginterferon alfa-2a), 15 pages (2002).

Holst, "Incretin Hormones and the Satiation Signal", *International Journal of Obesity* 37(9):1161-1168 (Jan. 2013).

Holst et al., "The Incretin System and its Role in Type 2 Diabetes Mellitus", *Molecular and Cellular Endocrinology* 297(1-2):127-136 (2008).

Horton et al., "Antitumor Effects of Interferon-ω: In Vivo Therapy of Human Tumor Xenografts in Nude Mice", *Cancer Research* 59(16):4064-4068 (Aug. 1999).

Hubel et al., "A Phase I/II Study of Idarubicin, Dexamethasone and Interferon-α (I-Dexa) in Patients with Relapsed or Refractory Multiple Myeloma" *Leukemia* 11 Suppl 5:S47-S51 (Dec. 1997).

Huggins et al., "Synergistic Antiviral Effects of Ribavirin and the C-Nucleoside Analogs Tiazofurin and Selenazofurin Against Togaviruses, Bunyaviruses, and Arenaviruses", *Antimicrobial Agents & Chemotherapy* 26(4):476-480 (1984).

Iacobelli et al., "A Phase 1 Study of Recombinant Interferon-α Administered as a Seven-Day Continuous Venous Infusion at Circadian-Rhythm Modulated Rate in Patients with Cancer", *American Journal of Clinical Oncology* 18(1):27-31 (1995).

IFNB Multiple Sclerosis Study Group, "Interferon β-1b Is Effective in Relapsing-Remitting Multiple Sclerosis", *Neurology* 43(4):655-667 (Apr. 1993).

Intarcia Therapeutics "Intarcia Therapeutics Announces Final Results from a Phase 2 Study of Injectable Omega Interferon plus Ribavirin for the Treatment of Hepatitis C Genotype-1", NLV Partners Press Coverage Portfolio News XP002504917 (Apr. 12, 2007) (Press Release).

Intermuner Inc., Infergen® (Interferon alfacon-1), 5 pages (2002).

Isaacs et al., "Virus interference. I. The interferon", *Proceedings of the Royal Society B: Biological Sciences* 147(927):258-267 (1957).

Ishiwata et al., "Clinical Effects of the Recombinant Feline Interferon-Omega on Experimental Parvovirus Infection in Beagle Dogs", *The Journal of Veterinary Medical Science* 60(8):911-917 (1998).

Jain et al., "Controlled Delivery of Drugs from a Novel Injectable in Situ Formed Biodegradable PLGA Microsphere System", *Journal of Microencapsulation* 17(3):343-362 (2000).

(56) References Cited

OTHER PUBLICATIONS

Jalil et al., "Biodegradable Poly(lactic Acid) and Poly(lactide-Co-Glycolide) Microcapsules: Problems Associated with Preparative Techniques and Release Properties", *Journal of Microencapsulation* 7(3):297-325 (Jul.-Sep. 1990).
Jetschmann et al., "Open-Label Rising-Dose Study of ω Interferon in IFN-Naive Patients with Chronic Hepatitis C", *Gastroenterology* 122:A278-A347 (Apr. 1, 2002) (Abstract M1454).
Johnson et al., "How Interferons Fight Disease", *Scientific American* 270(5):68-75 (May 1994).
Jordan et al., "Guidelines for Antiemetic Treatment of Chemotherapy-Induced Nausea and Vomiting: Past, Present and Future Recommendations", *The Oncologist* 12(9):1143-1150 (2007).
Kabalnov et al., "Macroemulsion Type and Stability of Alkane-Water-Phospholipid Systems", Abstracts of Papers, Part 1, 210th ACS National Meeting, 0-8412-3222-9, American Chemical Society, Chicago, IL (Aug. 20-24, 1995).
Kabalnov et al., "Phospholipids as Emulsion Stabilizers.2. Phase Behavior Versus Emulsion Stability", *Journal of Colloid and Interface Science* 184(1):227-235 (1996).
Khalili et al., "Interferon and Ribavirin Versus Interferon and Amantadine in Interferon Nonresponders with Chronic Hepatitis C", *The American Journal of Gastroenterology* 95(5):1284-1289 (May 2000).
Kildsig et al., "Theoretical Justification of Reciprocal Rate Plots in Studies of Water Vapor Transmission through Films", *Journal of Pharmaceutical Sciences* 29(11):1634-1637 (Nov. 17, 1970).
Kirkwood et al., "Interferon Alfa-2b Adjuvant Therapy of High-Risk Resected Cutaneous Melanoma: The Eastern Cooperative Oncology Group Trial EST 1684", *Journal of Clinical Oncology* 14(1):7-17 (1996).
Kita et al., "Characterization of a Polyethylene Glycol Conjugate of Recombinant Human Interferon-Yrmulations of Plasma Derived Factor IX and Recombinant Human Alpha Interferon at Elevated Temperatures", *Drug Design Development and Delivery Journal* 6(3):157-167 (Sep. 1990).
Kjems et al., "The Influence of GLP-1 on Glucose-Stimulated Insulin Secretion: Effects on Beta-cell Sensitivity in Type 2 and Nondiabetic Subjects", *Diabetes* 52(2):380-386 (Feb. 2003).
Knepp et al., "Identification of Antioxidants for Prevention of Peroxide-Mediated Oxidation of Recombinant Human Ciliary Neurotrophic Factor and Recombinant Human Nerve Growth Factor", *Journal of Pharmaceutical Science and Technology* 50(3):163-171 (1996).
Knepp et al., "Stability of Nonaqueous Suspension Formulations of Plasma Derived Factor IX and Recombinant Human Alpha Interferon at Elevated Temperatures", *Pharmaceutical Research* 15(7):1090-1095 (1998).
Knobler et al., "Systemic α-interferon Therapy of Multiple Sclerosis", *Neurology* 34(10):1273-1279 (Oct. 1984).
Kolterman et al., "Synthetic Exendin-4 (Exenatide) Significantly Reduces Postprandial and Fasting Plasma Glucose in Subjects with Type 2 Diabetes", *The Journal of Clinical Endocrinology & Metabolism* 88(7):3082-3089 (2003).
Kosmiski, "Energy Expenditure in HIV Infection", *The American Journal of Clinical Nutrition* 94(6):1677S-1682S (Dec. 2011).
Kovacevic et al., "Treatment of Chronic Viral Hepatitis B in Secondary Membranoproliferative Glomerulonephritis Using Recombinant Alfa-2 Interferon", Maksic Dj Vojnosanit. Pregl. 57(2):235-240 (Mar.-Apr. 2000).
Kracke et al., "Mx Proteins in Blood Leukocytes for Monitoring Interferon 13-1 B Therapy in Patients with MS", *Neurology* 54(1):193-199 (Jan. 2000).
Kronenberger et al., "Influence of Interferon-a on CD82-Expression in HCV-positive Patients", Prog. Abstr. Dig. Dis. Week 2000, San Diego, CA (May 21-24, 2000) (Abstract 976).
Krown et al., "Interferons and Interferon Inducers in Cancer Treatment", *Seminars in Oncology* 13(2):207-217 (1986).

Kubes et al., "Cross-Species Antiviral and Antiproliferative Activity of Human Interferon-Omega", *Journal of Interferon & Cytokine Research* 14:57-59 (1994).
Kunzi et al., "Role of Interferon-Stimulated Gene ISG-15 in the Interferon-W-Mediated Inhibition of Human Immunodeficiency Virus Replication", *Journal of Interferon & Cytokine Research* 16(11):919-927 (Nov. 1996).
Laburthe, "Peptide YY and Neuropeptide Y in the Gut: Availability, Biological Actions, and Receptors", *Trends in Endocrinology & Metabolism* 1(3):168-174 (1990).
Larsson, et al., "Stability of Emulsions Formed by Polar Lipids", *Progress in the Chemistry of Fats and Other Lipids* 16:163-169 (1978).
Lee et al., "The Stabilization of Proteins by Sucrose", *Journal of Biological Chemistry* 256(14):7193-7201 (Jul. 1981).
Lee et al., "Dynamics of Hepatitis C Virus Quasispecies Turnover During Interferon-A Treatment", Prog. Abstr. Dig. Dis. Week 2000, San Diego, CA (May 21-24, 2000) (Abstract 974).
Lee et al., "Therapy of Hepatitis C: Interferon alfa-2A Trials", *Hepatology* 26:89S-95S (XP000981288) (Sep. 1997).
Li et al., "Prediction of Solvent Removal Profile and Effect on Properties for Peptideloaded PLGA Microspheres Prepared by Solvent Extraction/evaporation Method", *Journal of Controlled Release*, 37:199-214 (1995).
Li et al., "Glucagon-Like Peptide-I Receptor Agonists Versus Insulin Glargine for Type 2 Diabetes Mellitus: A Systematic Review and Meta-Analysis of Randomized Controlled Trials", *Current Therapeutic Research* 71(4):211-238 (Aug. 2010).
Lopez et al., "Mammalian Pancreatic Preproglucagon contains Three Glucagon-related Peptides", *PNAS USA*, 80(18):5485-5489 (1983).
Lublin et al., "Defining the Clinical Course of Multiple Sclerosis: Results of an International Survey", *Neurology* 46:907-911 (1996).
Luft et al., "Electro-Osmotic Valve for the Controlled Administration of Drugs", *Medical & Biological Engineering & Computing* 16(1):45-50 (Jan. 1978).
Lukaszewski et al., "Pegylated α Interferon is an Effective Treatment for Virulent Venezuelan Equine encephalitis Virus and has Profound Effects on Host Immune Response to Infection", *Journal of Virology* 74(11):5006-5015 (Jun. 2000).
Lund et al., "Pancreatic Preproglucagon cDNA Contains Two Glucagon-Related Coding Sequences Arranged in Tandem", *PNAS USA* 79(2):345-349 (1982).
Lundberg, "A Submicron Lipid Emulsion Coated with Amphipathic Polyethylene Glycol for Parenteral Administration of Paclitaxel (Taxol)", *Journal of Pharmacy and Pharmacology* 49(1):16-21 (1997).
Maa et al., "Liquid-Liquid Emulsification by Static Mixers for Use in Microencapsulation", *Journal of Microencapsulation* 13(4):419-433 (Jul.-Aug. 1996).
MacFayden et al., "NPY Stimulates Nett Absorption Across Rat Intestinal Mucosa in Vivo", *Neuropeptides* 7:219-227 (1986).
Madsbad et al., "Exenatide and Liraglutide: Different Approaches to Develop GLP-1 Receptor Agonists (Incretin Mimetics)—Preclinical and Clinical Results", *Best Practice & Research Clinical Endocrinology & Metabolism* 23:463-77 (2009).
Magnuson et al. "Enhanced Recovery of a Secreted Mammalian Protein from Suspension Culture of Genetically Modified Tobacco Cells", *Protein Expression and Purification* 7(2):220-228 (1996).
Malley et al., "Chronic Toxicity and Oncogenicity of N-Methylpyrrolidone (Nmp) in Rats and Mice by Dietary Administration", *Drug and Chemical Toxicology* 24(4):315-38 (Nov. 2001).
Manning et al., "Stability of Protein Pharmaceuticals", *Pharmaceutical Research* 6(11):903-918 (1989).
Marincola et al., "Combination Therapy with Interferon alfa-2a and Interleukin-2 for the Treatment of Metastatic Cancer", *Journal of Clinical Oncology* 13(5):1110-1122 (XP009078965) (1995).
Massey et al., "Interaction of Vitamin E with Saturated Phospholipid Bilayers", *Biochemical and Biophysical Research Communications* 106(3):842-847 (1982).
Maulding et al., "Biodegradable Microcapsules: Acceleration of Polymeric Excipient Hydrolytic Rate by Incorporation of a Basic Medicament", *Journal of Controlled Release* 3(1-4):103-117 (1986).

(56) References Cited

OTHER PUBLICATIONS

McHutchison et al., "Interferon α-2b Alone or in Combination with Ribavirin as Initial Treatment for Chronic Hepatitis C", *The New England Journal of Medicine* 339(21):1485-1492 (Nov. 1998).

McHutchison et al., "Open-Label Phase 1B Study of Hepatitis C Viral Dynamics with Omega Interferon Treatment", *Hepatology* 34(4):A333 (Oct. 1, 2001) (XP004716177) (Abstract Only).

Mehta et al., "Peptide Containing Microspheres from Low Molecular Weight and Hydrophilic Poly(d, 1-Lactide-Co-Glycolide)", *Journal of Controlled Release* 41:249-257 (1996).

Meier et al., "Glucagon-like Peptide 1(GLP-1) in Biology and Pathology", *Diabetes/Metabolism Research and Reviews* 21(2):91-117 (Mar. 9, 2005).

Meier et al., "The Glucagon-Like Peptide-1 Metabolite GLP-1-(9-36) Amide Reduces Postprandial Glycemia Independently of Gastric Emptying and Insulin Secretion in Humans", *American Journal of Physiology-Endocrinology and Metabolism* 290(6):E1118-E1123 (2006).

Merad et al., "Generation of Monocyte-Derived Dendritic Cells from Patients with Renal Cell Cancer: Modulation of Their Functional Properties After Therapy with Biological Response Modifiers (IFN-α plus IL-2 and IL-12)", *Journal of Immunotherapy* 23(3):369-378 (May-Jun. 2000).

Milella et al., "Neutralizing Antibodies to Recombinant a-Interferon and Response to Therapy in Chronic Hepatitis C Virus Infection", *Liver* 13(3):146-150 (Jun. 1993).

Mohler et al., "Primer on Electrodeposited Coatings", *Materials Engineering* 5:38-45 (1972).

Mojsov, "Structural Requirements for Biological Activity of Glucagon-Like Peptide-I", International Journal of Peptide and Protein Research 40(3-4):333-343 (1992).

Morgan et al., "Structure and Moisture Permeability of Film-Forming Poloyers", *Industrial & Engineering Chemistry Research* 45(10):2296-2306 (1953).

Motzer et al., "Phase I Trial of 40-Kd Branched Pegylated Interferon α-2a for Patients with Advanced Renal Cell Carcinoma", *Journal of Clinical Oncology* 19(5):1312-1319 (2001).

Nauck et al., "Normalization of Fasting Glycaemia by Intravenous GLP-1 ([7-36 Amide] or [7-37]) in Type 2 Diabetic Patients", *Diabetic Medicine* 15(11):937-945 (1998).

NCBI "*Homo sapiens* Glucagon Receptor (GCGR), mRNA", NCBI Reference Sequence: NM_000160.1, Retrieved from: <<https://www.ncbi.nlm.nih.gov/nuccore/NM_000160.1>>, 4 pages (2006).

NCBI "*Homo sapiens* Glucagon-like Peptide 1 Receptor (GLP1R), mRN", NCBI Reference Sequence: NM_002062.1, Retrieved from: <<https://www.ncbi.nlm.nih.gov/nuccore/NM_002062.1>>, 3 pages (2000).

Neumann et al., "Hepatitis C Viral Dynamics In Vivo and the Antiviral Efficacy of Interferon-α Therapy", *Science* 282:103-107 (Dec. 1998).

Nieforth et al., "Use of an Indirect Pharmacodynamic Stimulation Model of MX Protein Induction to Compare in Vivo Activity of Interferon α-2a and a Polyethylene Glycol-Modified Derivative in Healthy Subjects", *Clinical Pharmacology & Therapeutics* 59(6):636-646 (Jun. 1996).

Nielsen et al. "Incretin Mimetics and DPP-IV Inhibitors for the Treatment of Type 2 Diabetes", *Drug Discovery Today* 20(10):703-710 (May 15, 2005).

Norden et al., "Physicochemical Characterisation of a Drug-Containing Phospholipid-Stabilised O/w Emulsion for Intravenous Administration", *European Journal of Pharmaceutical Sciences* 13(4):393-401 (2001).

Olaso et al., "Early Prediction of Lack of Response to Treatment with Interferon and Interferon plus Ribavirin Using Biochemical and Virological Criteria in Patients with Chronic Hepatitis C", *Esp Quimioter* 12(3):220-228 (Sep. 1999).

Ortiz et al., "A Differential Scanning Calorimetry Study of the Interaction of Alpha-Tocopherol with Mixtures of Phospholipids", *Biochimica et Biophysica Acta* 898(2):214-222 (1987).

Palmeri et al., "5-Fluorouracil and Recombinant Alpha Interferon-2a in the Treatment of Advanced Colorectal Carcinoma: A Dose Optimization Study", *Journal of Chemotherapy* 2(5):327-330 (Oct. 1990).

Panitch, "Interferons in Multiple Sclerosis", *Drugs* 44(6):946-962 (Dec. 1992).

Patti et al., "Natural Interferon-B Treatment of Relapsing-Remitting and Secondary-progressive Multiple Sclerosis Patients: Two-Year Study", *Acta Neurologica Scandinavica* 100:283-289 (1999).

Paty et al., "Interferon beta-1 b is effective in Relapsing-Remitting Multiple Sclerosis", *Neurology* 43:662-667 (1993).

Patzelt et al., "Identification and Processing of Proglucagon in Pancreatic Islets", *Nature* 282(5736):260-266 (1979).

Peterson et al., "Neuropathic complications in the Zucker Diabetic Fatty Rat", Frontiers in Diabetic Research: Lessons from Animal Diabetes III, Edited by E. Shafrir, London: Smith-Gordon 456-458 (1990).

Peterson et al., "Zucker Diabetic Fatty Rat as a Model for Non-Insulin-Dependent Diabetes Mellitus", Institute for Laboratory Animal Research (ILAR) Journal 32(3):16-19 (1990).

Pimstone et al., "High Dose (780 MIU/52 weeks) Interferon Monotherapy is Highly Effective Treatment for Hepatitis C", Prog. Abstr. Dig. Dis. Week 2000, San Diego, CA, (May 21-24-2000) (Abstract 973).

Plauth et al., "Open-Label Study of Omega Interferon in Previously Untreated HCV-Infected Patients", *Hepatology* 34(4):A331 (XP004716169) (Oct. 1, 2001) (Abstract Only).

Plauth et al., "Open-Label Study of Omega Interferon in Previously Untreated HCV-Infected Patients", *Journal of Hepatology* 36(Supp. 1):125, XP002511882 (Apr. 2002) (Abstract Only).

Playford et al., "Preliminary Report: Role of Peptide YY in Defence Against Diarrhoea", *The Lancet* 335(8705):1555-1557 (Jun. 30, 1990).

Pohl et al., "Molecular cloning of the helodermin and exendin-4 cDNAs in the Lizard", *Journal of Biological Chemistry* 273(16):9778-9784 (1998).

Poynard et al., "Is an "A La Carte" Combination Interferon α-2b plus Ribavirin Regimen Possible for the First Line Treatment in Patients with Chronic Hepatitis C? the ALGOVIRC Project Group", *Hepatology* 31(1):211-218 (Jan. 2000).

Poynard et al., "Randomised Trial of Interferon α2b plus Ribavirin for 48 Weeks or for 24 Weeks Versus Interferon α2b plus Placebo for 48 Weeks for Treatment of Chronic Infection with Hepatitis C Virus. International Hepatitis Interventional Therapy Group (IHIT)", *Lancet* 352(9138):1426-1432 (Oct. 1998).

Pratley et al., "Targeting Incretins in Type 2 Diabetes: Role of GLP-1 Receptor Agonists and DPP-4 Inhibitors", Review of Diabetic Studies 5(2):73-94 (2008).

Quesada et al., "Interferons in Hematological Malignancies", eds. Baron et al., U. Tex. 487-495 (1987).

Quianzon et al., "Lixisenatide-Once daily Glucagon-Like Peptide-1 Receptor Agonist in the Management of Type 2 Diabetes", *US Endocrinology* 7(2):104-109 (Dec. 2011).

Quintanar-Guerrero et al., "Applications of the Ion-Pair Concept to Hydrophilic Substances with Special Emphasis on Peptides", *Pharmaceutical Research* 14(2):119-127 (1997).

Rajkumar et al., "Phase I Evaluation of Radiation Combined with Recombinant Interferon α-2a and BCNU for Patients with High-Grade Glioma", *International Journal of Radiation Oncology* 40(2):297-302 (Jan. 15, 1998).

Ratner et al., "Dose-Dependent Effects of the Once-Daily GLP-1 Receptor Agonist Lixisenatide In Patients with Type 2 Diabetes Inadequately Controlled with Metformin: A Randomized Double-Blind, Placebo-Controlled Trial", *Diabetic Medicine* 27(9):1024-1032 (Aug. 2010).

Roberts et al., "The Evolution of the Type I Interferons", *Journal of Interferon & Cytokine Research* 18(10):805-816 (Oct. 1998).

Roche Pharmaceuticals, Roferon®-a (Interferon α-2a, Recombinant), 22 pages (2003).

Roff et al., "Handbook of Common Polymers", Cleveland Rubber Co. 72 pages (1971).

Rogers et al., "Permeability Valves", *Industrial & Engineering Chemistry Research* 49(11):1933-1936 (Nov. 17, 1957).

(56) References Cited

OTHER PUBLICATIONS

Rohloff et al., "DUROS Technology Delivers Peptides and Proteins at Consistent Rate Continuously for 3 to 12 Months", *Journal of Diabetes Science and Technology* 2(3):461-467 (May 2008).

Roman et al., "Cholestasis in the Rat by Means of Intravenous Administration of Cyclosporine Vehicle, Cremophor EL", *Transplantation* 48(4):554-558 (1989).

Roth et al., "Combination Therapy with Amylin and Peptide YY[3-36] in Obese Rodents: Anorexigenic Synergy and Weight Loss Additivity", *Endocrinology* 148(12):6054-6061 (Dec. 2007).

Roth et al., "High Dose Etretinate and Interferon-alpha-A Phase I Study in Squamous Cell Carcinomas and Transitional Cell Carcinomas", *Acta Oncologica* 38(5):613-617 (1999).

Sah et al., "A Novel Method of Preparing PLGA Microcapsules Utilizing Methylethyl Ketone" *Pharmaceutical Research* 13(3):360-367 (1996).

Sato et al., "Porous Biodegradable Microspheres for Controlled Drug Delivery. I. Assessment of Processing Conditions and Solvent Removal Techniques", *Pharmaceutical Research* 5(1):21-30 (1988).

Schepp et al., "Exendin-4 and Exendin-(9-39) NH2: Agonist and Antagonist, Respectively, at the Rat Parietal Cell Receptor for Glucagon-like Peptide-1-(7-36) NH2", *Journal of Pharmacology: Molecular Pharmacology* 269(2):183-191 (1994).

Schering Corporation, Intron® A for Injection, 6 pages (2001).

Schering Corporation, PEG-Intron™ (Peginterferon α-2b) Powder for Injection, 29 pages (2003).

Schmalfub et al., "Modification of Drug Penetration into Human Skin Using Microemulsions", *Journal of Controlled Release* 46(3):279-285 (1997).

Sen et al., "The Interferon System: A Bird's Eye View of Its Biochemistry", *Journal of Biological Chemistry* 267(8):5017-5020 (Mar. 1992).

Seufert et al., "The Extra-pancreatic Effects of GLP-1 Receptor Agonists: a Focus on the Cardiovascular, Gastrointestinal and Central Nervous Systems", *Diabetes, Obesity and Metabolism* 16(8):673-688 (Aug. 2014).

Shiffman et al., "A Decline in HCV-RNA Level During Interferon or Ihterferon/ribavirin Therapy in Patients with Virologic Nonresponse Is Associated with an Improvement in Hepatic Histology", Progress Abstract 50th Annual Meeting Postgraduate Courses American Association Study Liver Disease, Dallas, TX (Nov. 5-9, 1999) (Abstract 567).

Shima et al., "Serum Total Bile Acid Level as a Sensitive Indicator of Hepatic Histological Improvement in Chronic Hepatitis C Patients Responding to Interferon Treatment", *Journal of Gastroenterology & Hepatology* 15(3):294-299 (Mar. 2000).

Shiratori et al., "Histologic Improvement of Fibrosis in Patients with Hepatitis C Who Have Sustained Response to Interferon Therapy", *Annals of Internal Medicine* 132(7):517-524 (Apr. 2000).

Shire et al., "Challenges in the Development of High Protein Concentration Formulations," *Journal of Pharmaceutical Sciences* 93:1390-1402 (2004).

Simon et al., "A Longitudinal Study of T1 Hypointense Lesions in Relapsing MS: MSCRG Trial of Interferon β-1a", *Neurology* 55(2):185-192 (Jul. 2000).

Smith, "Peripheral Neuro-Horrnones as a Strategy to Treat Obesity", Oral Presentation at the 2007 Cardiometabolic Health Congress in Boston, MA, pp. 1-35 (Sep. 26-29, 2007).

Sparks et al., "Lipoprotein alterations in 10- and 20-week-old Zucker diabetic fatty rats: hyperinsulinemic versus insulinopenic hyperglycemia", *Metabolism* 47(11):1315-1324 (1998).

Sulkowski et al., "Peginterferon-a-2a (40kD) and ribavirin in patients with chronic hepatitis C: a phase II open label study," *Gastroenterology* 118(4, Supp. 2) (2000) (Abstract 236).

Sulkowski et al., "Peginterferon-α-2a (40kD) and Ribavirin in Patients with Chronic Hepatitis C: A Phase II Open-Label Study", *Biodrugs* 16(2):105-109 (2002).

Szayna et al., "Exendin-4 Decelerates Food Intake, Weight Gain, and Fat Deposition in Zucker Rats", *Endocrinology* 141(6):1936-1941 (2000).

Talpaz et al., "Phase I Study of Polyethylene Glycol Formulation of Interferon α-2B (Schering 54031) in Philadelphia Chromosome-Positive Chronic Myelogenous Leukemia", *Blood* 98(6):1708-1713 (2001).

Talsania et al., "Peripheral Exendin-4 and Peptide YY(3-36) Synergistically Reduce Food Intake Through Different Mechanisms in Mice", *Endocrinology* 146(9):3748-56 (Sep. 2005).

Tanaka et al., "Effect of Interferon Therapy on the Incidence of Hepatocellular Carcinoma and Mortality of Patients with Chronic Hepatitis C: A Retrospective Cohort Study of 738 Patients", *International Journal of Cancer* 87(5):741-749 (Sep. 2000).

Taylor et al., "Day-long Subcutaneous Infusion of Exenatide Lowers Glycemia in Patients with Type 2 Diabetes", *Hormone and Metabolic Research* 37(10):627-632 (Aug. 2010).

Thomasin et al., "VA Contribution to Overcoming the Problem of Residual Solvents in Biodegradable Microspheres Prepared by Coacervation", *European Journal of Pharmaceutics and Biopharmaceutics* 42(1):16-24 (1996).

Thompson et al., "Biodegradable Microspheres as a Delivery System for Rismorelin Porcine, a Porcine-Growth-Hormone-Releasing-Hormone", *Journal of Controlled Release* 43(1):9-22 (1997).

Tong et al., "Prediction of Response During Interferon a 2b Therapy in Chronic Hepatitis C Patients Using Viral and Biochemical Characteristics: A Comparison", *Hepatology* 26(6):1640-1645 (Dec. 1997).

Touza Rey et al., "The Clinical Response to Interferon-Gamma in a Patient with Chronic Granulomatous Disease and Brain Abscesses Due to Aspergillus Fumigatus", *Anales de Medicina Interna* 17(2):86-87 (Feb. 2000).

Tracy et al., "Factors Affecting the Degradation Rate of Poly(lactide-Co-Glycolide) Microspheresin Vivo and in Vitro", *Biomaterials* 20(11:):1057-1062 (1999).

Trudeau et al., "A Phase I Study of Recombinant Human Interferon α-2b Combined with 5-Fluorouracil and Cisplatin in Patients with Advanced Cancer", *Cancer Chemotherapy and Pharmacology* 35(6):496-500 (1995).

Tseng et al., "Glucose-Dependent Insulinotropic Peptide: Structure of the Precursor and Tissue-Specific Expression in Rat", *PNAS USA*, 90(5):1992-1996 (Mar. 1993).

Tsung et al., "Preparation and Stabilization of Heparin/Gelatin Complex Coacervate Microcapsules," *Journal of Pharmaceutical Sciences* 86(5):603-607 (May 1997).

Uhlig et al., "The Electro-Osmotic Actuation of Implantable Insulin Micropumps", *Journal of Biomedical Materials Research* 17(6):931-943 (1983).

Unniappan et al., "Effects of Dipeptidyl Peptidase IV on the Satiety Actions of Peptide YY", *Diabetologia; Clinical and Experimental Diabetes and Metabolism* 49(8):1915-1923 (Jun. 27, 2006).

Van Santbrink et al., "Urinary Follicle-Stimulating Hormone for Normogonadotropic Clomiphene-Resistant Anovulatory Infertility: Prospective, Randomized Comparison Between Low Dose Step-up and Step-down Dose Regimens", *The Journal of Clinical Endocrinology and Metabolism* 82(11):3597-3602 (1997).

Vlasakakis et al., "Pharmacokinetics and Tolerability of Exenatide Delivered by 7-Day Continuous Subcutaneous Infusion in Healthy Volunteers", *Advances in Therapy* 32:650-661 (Jul. 10, 2015).

Vokes et al., "A Phase I Trial of Concomitant Chemoradiotherapy with Cisplatin Dose Intensification and Granulocyte-Colony Stimulating Factor Support for Advanced Malignancies of the Chest", *Cancer Chemotherapy and Pharmacology* 35(4):304-312 (1995).

Vrabec, "Tympanic Membrane Perforations in the Diabetic Rat: A Model of Impaired Wound Healing", *Otolaryngology—Head and Neck Surgery* 118(3):304-308 (Mar. 1998).

Wang et al., "Parenteral Formulations of Proteins and Peptides: Stability and Stabilizersple Sclerosis?", *Journal of Parenteral Science and Technology* 42(2S):S4-S26 (1988).

Wang et al., "Preferential Interaction of α-Tocopherol with Phosphatidylcholines in Mixed Aqueous Dispersions of Phosphatidylcholine and Phosphatidylethanolamine", European Journal of Biochemistry 267(21):6362-6368 (2000).

Wang et al., "Ripple Phases Induced by Alpha-Tocopherol in Saturated Diacylphosphatidylcholines", *Archives of Biochemistry and Biophysics* 377(2):304-314 (2000).

(56) References Cited

OTHER PUBLICATIONS

Wang et al., "The Distribution of α-Tocopherol in Mixed Aqueous Dispersions of Phosphatidylcholine and Phosphattidylethanolamine", *Biochimica et Biophysica Acta-Biomembranes* 1509(1-2):361-372 (2000).
Weinstock-Guttman et al., "What is New in the Treatment of Multiple Sclerosis?", *Drugs* 59(3):401-410 (Mar. 2000).
Weissmann et al., "The Interferon Genes", *Progress in Nucleic Acid Research and Molecular Biology* 33:251-300 (1986).
Wright et al., "Preliminary Experience with α-2b-Interferon Therapy of Viral Hepatitis in Liver Allograft Recipients", *Transplantation* 53(1):121-124 (Jan. 1992).
Wynne et al., "Oxyntomodulin Increases Energy Expenditure in Addition to Decreasing Energy Intake in Overweight and Obese Humans: a Randomised Controlled Trial", *International Journal of Obesity* 30:1729-1736 (2006).
Young et al., "Glucose-Lowering and Insulin-Sensitizing Actions of Exendin-4", *Diabetes* 48(5):1026-1034 (May 1999).
Younossi et al., "The Roles of Amantadine, Rimantadine, Ursodeoxycholic Acid, and NSAIDs, Alone or in Combination with Alpha Interferons, in the Treatment of Chronic Hepatitis C", *Seminars in Liver Disease* 19(Supp. 1):95-102 (1999).
Yu et al., "Glucagon-Like Peptide-1 Prevented Abdominal Aortic Aneurysm Development in Rats", *Surgery Today* 46(9):1099-1107 (Sep. 2016).
Yu et al., "Preparation, Characterization, and in Vivo Evaluation of an Oil Suspension of a Bovine Growth Hormone Releasing Factor Analog", *Journal of Pharmaceutical Sciences* 85(4):396-401 (1996).
Zeidner et al., "Treatment of FeLV-Induced Immunodeficiency Syndrome (feLVFAIDS) with Controlled Release Capsular Implantation of 2',3'-Dideoxycytidine", *Antiviral Research* 11(3):147-160 (Apr. 1989).
Zein et al., "Interferons in the Management of Viral Hepatitis," *Cytokines, Cellular & Molecular Therapy* 4(4):229-241 (Dec. 1998).
Zeuzem et al., "Hepatitis C Virus Dynamics in Vivo: Effect of Ribavirin and Interferon a on Viral Turnover", *Hepatology* 28(1):245-252 (Jul. 1998).
Zeuzem et al., "Peginterferon α-2a in Patients with Chronic Hepatitis C", *The New England Journal of Medicine* 343(23):1666-1672 (2000).
Zhang et al., "A New Strategy for Enhancing the Stability of Lyophilized Protein: The Effect of the Reconstitution Medium on Keratinocyte Growth Factor", *Pharmaceutical Research* 12(10):1447-1452 (1995).
Zhang et al., "Report on Large Dosage Interferon to Treat 30 Cases of Viral Encephalitis," *Journal of Clinical Pediatrics* 14(2):83-84 (1996).
Zhang et al., "Efficacy Observations of Different Dosages of Interferon to Treat 150 Hepatitis B Carrier", *Current Physician* 2(12):45-46 (1997).
Zheng et al. "Therapeutic Effect of Interferon Varied Dose in Treating Virus Encephalitis," *Beijing Medical Journal* 13(2):80-81 (1998).
Ziesche et al., "Preliminary Study of Long-Term Treatment with Interferon Y-1 Band Low-Dose Prednisolone in Patients with Idiopathic Pulmonary Fibrosis", *The New England Journal of Medicine* 341(17):1264-1269 (Oct. 1999).

* cited by examiner

GLUCAGON-RECEPTOR SELECTIVE POLYPEPTIDES AND METHODS OF USE THEREOF

RELATED APPLICATIONS

This application claims the benefit of U.S. Provisional Application No. 62/337,005, filed May 16, 2016; U.S. Provisional Application No. 62/414,146, filed Oct. 28, 2016; and U.S. Provisional Application No. 62/420,937, filed Nov. 11, 2016, the contents of each of which are incorporated herein by reference in their entirety.

FIELD

This invention relates to isolated polypeptides that are glucagon-receptor selective analogs and peptide derivatives thereof. These analogs and peptide derivatives have improved solubility, thermal stability, and physicochemical properties as compared to native endogenous glucagon. This invention also relates to methods of using such polypeptides in a variety of therapeutic and diagnostic indications, as well as methods of producing such polypeptides. These analogs are useful in methods of treating obesity, diabetes, metabolic disorders, and other diseases or disorders.

BACKGROUND

Glucagon, a peptide hormone produced by the alpha cells of the pancreas, and glucagon-like peptide-1 (GLP-1), a neuropeptide, are derived from pre-proglucagon, a 158 amino acid precursor polypeptide that is processed in different tissues to form a number of different proglucagon-derived peptides. These proglucagon-derived peptides which include, for example, glucagon, GLP-1, glucagon-like peptide-2 (GLP-2), and oxyntomodulin (OXM), are involved in a wide variety of physiological functions, including glucose homeostasis, insulin secretion, gastric emptying, and intestinal growth, as well as the regulation of food intake.

Accordingly, there exists a need for therapeutics and therapies that mimic GLP-1 and/or glucagon activity.

SUMMARY

This invention relates to isolated polypeptides that are glucagon-receptor selective analogs and peptide derivatives thereof. Glucagon is a 29 amino acid peptide hormone that is produced by alpha cells in the pancreas and that interacts with the glucagon receptor ("GCGR").

In some embodiments, an isolated polypeptide of the disclosure is a glucagon analog that binds to a glucagon receptor (GCGR) and is a selective glucagon receptor agonist. These isolated polypeptides of the disclosure are potent, stable, and soluble. The isolated polypeptides selectively bind the glucagon receptor as compared to native glucagon, for example, human glucagon, and as compared to the ability to bind to the GLP-1 receptor. The isolated polypeptides exhibit improved metabolic stability and clearance of the drug from the kidney at a rate close to glomerular filtration rate verses native glucagon, e.g., human glucagon. The isolated polypeptides exhibit an improved solubility as compared to native glucagon, for example, human glucagon. In preferred embodiments, the isolated polypeptides exhibit an improved solubility of at least 200 mg/ml. The isolated polypeptides exhibit an improved chemical stability at room temperature and at higher temperatures such as 37° C. or greater.

The isolated polypeptides of the disclosure are derived from a genus that imparts selectivity, solubility, and improved clearance of the molecule from the kidney. This genus is based on (a) a determination of the critical structure required for selectivity on the glucagon receptor, (b) the identification of critical amino acids and secondary structure motifs that provide for improved solubility while enhancing or at least maintaining the potency of human glucagon, and (c) the identification of amino acid substitutions for imparting chemical stability to the selective glucagon receptor agonists.

In some embodiments, an isolated polypeptide of the disclosure comprises a modified amino acid sequence based on the amino acid sequence of human glucagon: HSQGTFTSDYSKYLDSRRAQDFVQWLMNT-OH (SEQ ID NO: 140), where the modified amino acid sequence includes at least one amino acid substitution, at least two amino acid substitutions, at least three amino acid substitutions, at least four amino acid substitutions, at least five amino acid substitutions, at least six amino acid substitutions, at least seven amino acid substitutions, at least eight amino acid substitutions, at least nine amino acid substitutions, at least 10 amino acid substitutions, at least 11 amino acid substitutions, at least 12 amino acid substitutions, at least 13 amino acid substitutions, at least 14 amino acid substitutions, at least 15 amino acid substitutions, at least 16 amino acid substitutions, at least 17 amino acid substitutions, at least 18 amino acid substitutions, at least 19 amino acid substitutions, at least 20 amino acid substitutions, at least 21 amino acid substitutions, at least 22 amino acid substitutions, at least 23 amino acid substitutions, at least 24 amino acid substitutions, at least 25 amino acid substitutions, at least 26 amino acid substitutions, at least 27 amino acid substitutions, at least 28 amino acid substitutions, and/or at least 29 amino acid substitutions, provided that the isolated polypeptide having a modified amino acid sequence retains the ability to function as a selective glucagon analog.

In some embodiments, an isolated polypeptide of the disclosure comprises a modified amino acid sequence based on the amino acid sequence of human glucagon: HSQGTFTSDYSKYLDSRRAQDFVQWLMNT-OH (SEQ ID NO: 140), where the modified amino acid sequence includes at least one amino acid substitution, at least two amino acid substitutions, at least three amino acid substitutions, at least four amino acid substitutions, at least five amino acid substitutions, at least six amino acid substitutions, at least seven amino acid substitutions, at least eight amino acid substitutions, at least nine amino acid substitutions, at least 10 amino acid substitutions, at least 11 amino acid substitutions, at least 12 amino acid substitutions, at least 13 amino acid substitutions, at least 14 amino acid substitutions, at least 15 amino acid substitutions, or at least 16 amino acid substitutions, wherein the amino acid substitution(s) is selected from the group consisting of:
  (i) an amino acid substitution at position 1 selected from the group consisting of Y and W;
  (ii) an amino acid substitution at position 2 selected from the group consisting of G and T;
  (iii) an amino acid substitution at position 3 with H;
  (iv) an amino acid substitution at position 10 with H;
  (v) an amino acid substitution at position 11 with T;
  (vi) an amino acid substitution at position 12 with R;
  (vii) an amino acid substitution at position 13 selected from the group consisting of L and W;

(viii) an amino acid substitution at position 15 with E;
(ix) an amino acid substitution at position 16 selected from the group consisting of 2-Aminoisobutyric acid (Aib), A, E, I, K, L, and Q;
(x) an amino acid substitution at position 17 selected from the group consisting of A, E, K, S, and T;
(xi) an amino acid substitution at position 18 selected from the group consisting of A, E, L, and T;
(xii) an amino acid substitution at position 21 with E;
(xiii) an amino acid substitution at position 23 with T;
(xiv) an amino acid substitution at position 24 selected from the group consisting of 2-Aminoisobutyric acid (Aib), K, and L;
(xv) an amino acid substitution at position 25 with H; and
(xvi) an amino acid substitution at position 30 with a Z-tail selected from the group consisting of EEPSSGAPPPS-OH (SEQ ID NO: 4); EPSSGAPPPS-OH (SEQ ID NO: 5);
GAPPPS-OH (SEQ ID NO: 6); GGPSSGAPPPS-OH (SEQ ID NO: 7); GPSSGAPPPS-OH (SEQ ID NO: 8); KRNKNPPPS-OH (SEQ ID NO: 9); KRNKNPPS-OH (SEQ ID NO: 10);
KRNKPPIA-OH (SEQ ID NO: 11); KRNKPPPA-OH (SEQ ID NO: 150); KRNKPPPS-OH (SEQ ID NO: 12); KSSGKPPPS-OH (SEQ ID NO: 13); PESGAPPPS-OH (SEQ ID NO: 14);
PKSGAPPPS-OH (SEQ ID NO: 15); PKSKAPPPS-NH$_2$ (SEQ ID NO: 16); PKSKAPPPS-OH (SEQ ID NO: 17); PKSKEPPPS-NH$_2$ (SEQ ID NO: 18); PKSKEPPPS-OH (SEQ ID NO: 19);
PKSKQPPPS-OH (SEQ ID NO: 20); PKSKSPPPS-NH$_2$ (SEQ ID NO: 21); PKSKSPPPS-OH (SEQ ID NO: 22); PRNKNNPPS-OH (SEQ ID NO: 23); PSKGAPPPS-OH (SEQ ID NO: 24);
PSSGAPPPSE-OH (SEQ ID NO: 25); PSSGAPPPS-NH$_2$ (SEQ ID NO: 26); PSSGAPPPS-OH (SEQ ID NO: 27); PSSGAPPPSS-OH (SEQ ID NO: 28); PSSGEPPPS-OH (SEQ ID NO: 29);
PSSGKKPPS-OH (SEQ ID NO: 30); PSSGKPPPS-NH$_2$ (SEQ ID NO: 31); PSSGKPPPS-OH (SEQ ID NO: 32); PSSGSPPPS-OH (SEQ ID NO: 33); PSSKAPPPS-OH (SEQ ID NO: 34);
PSSKEPPPS-OH (SEQ ID NO: 35); PSSKGAPPPS-OH (SEQ ID NO: 36); PSSKQPPPS-OH (SEQ ID NO: 37); PSSKSPPPS-OH (SEQ ID NO: 38); SGAPPPS-OH (SEQ ID NO: 39); and
SSGAPPPS-OH(SEQ ID NO: 40); and
(xvii) combinations thereof,
provided that the isolated polypeptide having a modified amino acid sequence retains the ability to function as a selective glucagon receptor agonist.

In some embodiments, an isolated polypeptide of the disclosure comprises an amino acid sequence selected from the group consisting of amino acid sequences represented by the consensus sequence of SEQ ID NO: 1:

(SEQ ID NO: 1)
$X_1X_2X_3$GTFTSD$X_{10}X_{11}X_{12}X_{13}$L$X_{15}X_{16}X_{17}X_{18}$AQEF$X_{23}X_{24}X_{25}$

LEDE-Z-tail-(OH/NH$_2$), wherein:
$X_1$ is Y or W;
$X_2$ is S, G or T;
$X_3$ is Q or H;
$X_{10}$ is Y or H;
$X_{11}$ is S or T;
$X_{12}$ is K or R;
$X_{13}$ is Y, L or W;
$X_{15}$ is D or E;
$X_{16}$ is S, 2-Aminoisobutyric acid (Aib), A, E, L, Q, K, or I;
$X_{17}$ is K, E, S, T, or A;
$X_{18}$ is A, R, S, E, L, T or Y;
$X_{23}$ is T or V;
$X_{24}$ is K, I, L, or Aib;
$X_{25}$ is H or W; and
Z-tail is absent or is selected from the group consisting of EEPSSGAPPPS-OH (SEQ ID NO: 4); EPSSGAPPPS-OH (SEQ ID NO: 5); GAPPPS-OH (SEQ ID NO: 6); GGPSSGAPPPS-OH (SEQ ID NO: 7); GPSSGAPPPS-OH (SEQ ID NO: 8); KRNKNPPPS-OH (SEQ ID NO: 9); KRNKNPPS-OH (SEQ ID NO: 10);
KRNKPPIA-OH (SEQ ID NO: 11); KRNKPPPA-OH (SEQ ID NO: 150);
KRNKPPPS-OH (SEQ ID NO: 12); KSSGKPPPS-OH (SEQ ID NO: 13);
PESGAPPPS-OH (SEQ ID NO: 14); PKSGAPPPS-OH (SEQ ID NO: 15);
PKSKAPPPS-NH$_2$ (SEQ ID NO: 16); PKSKAPPPS-OH (SEQ ID NO: 17);
PKSKEPPPS-NH$_2$ (SEQ ID NO: 18); PKSKEPPPS-OH (SEQ ID NO: 19);
PKSKQPPPS-OH (SEQ ID NO: 20); PKSKSPPPS-NH$_2$ (SEQ ID NO: 21);
PKSKSPPPS-OH (SEQ ID NO: 22); PRNKNNPPS-OH (SEQ ID NO: 23);
PSKGAPPPS-OH (SEQ ID NO: 24); PSSGAPPPSE-OH (SEQ ID NO: 25);
PSSGAPPPS-NH$_2$ (SEQ ID NO: 26); PSSGAPPPS-OH (SEQ ID NO: 27);
PSSGAPPPSS-OH (SEQ ID NO: 28); PSSGEPPPS-OH (SEQ ID NO: 29);
PSSGKKPPS-OH (SEQ ID NO: 30); PSSGKPPPS-NH$_2$ (SEQ ID NO: 31);
PSSGKPPPS-OH (SEQ ID NO: 32); PSSGSPPPS-OH (SEQ ID NO: 33);
PSSKAPPPS-OH (SEQ ID NO: 34); PSSKEPPPS-OH (SEQ ID NO: 35);
PSSKGAPPPS-OH (SEQ ID NO: 36); PSSKQPPPS-OH (SEQ ID NO: 37);
PSSKSPPPS-OH (SEQ ID NO: 38); SGAPPPS-OH (SEQ ID NO: 39); and
SSGAPPPS-OH(SEQ ID NO: 40).

In some embodiments, an isolated polypeptide of the disclosure comprises an amino acid sequence selected from the group consisting of amino acid sequences represented by the consensus sequence of SEQ ID NO: 2:

(SEQ ID NO: 2)
$X_1X_2X_3$GTFTSD$X_{10}X_{11}X_{12}X_{13}$L$X_{15}X_{16}X_{17}X_{18}$AQEFV$X_{24}$WLEDE-

Z-tail-(OH/NH$_2$), wherein:
$X_1$ is Y or W;
$X_2$ is S or G;
$X_3$ is Q or H;
$X_{10}$ is Y or H;
$X_{11}$ is S or T;
$X_{12}$ is K or R;
$X_{13}$ is Y, L or W;
$X_{15}$ is D or E;

X$_{16}$ is 2-Aminoisobutyric acid (Aib), A, or S;
X$_{17}$ is A or K;
X$_{18}$ is R, S, L, or Y;
X$_{24}$ is K, I, or Aib;
X$_{25}$ is H or W; and
Z-tail is absent or is selected from the group consisting of PSSGAPPPS-NH$_2$ (SEQ ID NO: 26); PSSGAPPPS-OH (SEQ ID NO: 27); and PKSKSPPPS-NH$_2$ (SEQ ID NO: 21).

In some embodiments, an isolated polypeptide of the disclosure comprises an amino acid sequence selected from the group consisting of amino acid sequences represented by the consensus sequence of SEQ ID NO: 3:

(SEQ ID NO: 3)
YSX$_3$GTFTSDYSKYLDX$_{16}$X$_{17}$X$_{18}$AQEFVX$_{24}$WLEDE-Z-tail-(OH/NH$_2$), wherein:
X$_3$ is Q or H;
X$_{16}$ is 2-Aminoisobutyric acid (Aib) or A;
X$_{17}$ is A or K;
X$_{18}$ is R, S, or Y;
X$_{24}$ is K or Aib;
Z-tail is selected from the group consisting of PSSGAPPPS-OH (SEQ ID NO: 27) and PKSKSPPPS-NH$_2$ (SEQ ID NO: 21).

In some embodiments, an isolated polypeptide of the disclosure comprises an amino acid sequence selected from the group consisting of
YSHGTFTSDYSKYLD(Aib)KYAQEFV(Aib)WLEDEPSSGAPPPS-OH (SEQ ID NO: 41), which is also referred to herein as Compound A1;
YSHGTFTSDYSKYLD(Aib)KSAQEFV(Aib)WLEDEPSSGAPPPS-OH (SEQ ID NO: 42), which is also referred to herein as Compound A2;
YSQGTFTSDYSKYLDAARAQEFVKWLEDEPKSKSPPPS-NH$_2$ (SEQ ID NO: 43), which is also referred to herein as Compound A3;
YSHGTFTSDYSKYLD(Aib)KRAQEFVIWLEDEPSSGAPPPS-OH (SEQ ID NO: 44), which is also referred to herein as Compound A4;
YSHGTFTSDYSKYLDSARAQEFVKWLEDEPSSGAPPPS-NH$_2$ (SEQ ID NO: 45), which is also referred to herein as Compound A5; and
WSQGTFTSDYSKYLD(Aib)KRAQEFV(Aib)WLEDEPSSGAPPPS-OH (SEQ ID NO: 46), which is also referred to herein as Compound A6.

In some embodiments, an isolated polypeptide of the disclosure comprises the amino acid sequence YSHGTFTSDYSKYLD(Aib)KYAQEFV(Aib)WLEDEPSSGAPPPS-OH (SEQ ID NO: 41). In some embodiments, an isolated polypeptide of the disclosure comprises the amino acid sequence YSHGTFTSDYSKYLD(Aib)KSAQEFV(Aib)WLEDEPSSGAPPPS-OH (SEQ ID NO: 42). In some embodiments, an isolated polypeptide of the disclosure comprises the amino acid sequence YSQGTFTSDYSKYLDAARAQEFVKWLEDEPKSKSPPPS-NH$_2$ (SEQ ID NO: 43). In some embodiments, an isolated polypeptide of the disclosure comprises the amino acid sequence YSHGTFTSDYSKYLD(Aib)KRAQEFVIWLEDEPSSGAPPPS-OH (SEQ ID NO: 44). In some embodiments, an isolated polypeptide of the disclosure comprises the amino acid sequence YSHGTFTSDYSKYLDSARAQEFVKWLEDEPSSGAPPPS-NH$_2$ (SEQ ID NO: 45). In some embodiments, an isolated polypeptide of the disclosure comprises the amino acid sequence WSQGTFTSDYSKYLD(Aib)KRAQEFV(Aib)WLEDEPSSGAPPPS-OH (SEQ ID NO: 46).

In some embodiments, an isolated polypeptide of the disclosure consists of the amino acid sequence YSHGTFTSDYSKYLD(Aib)KYAQEFV(Aib)WLEDEPSSGAPPPS-OH (SEQ ID NO: 41). In some embodiments, an isolated polypeptide of the disclosure consists of the amino acid sequence YSHGTFTSDYSKYLD(Aib)KSAQEFV(Aib)WLEDEPSSGAPPPS-OH (SEQ ID NO: 42). In some embodiments, an isolated polypeptide of the disclosure consists of the amino acid sequence YSQGTFTSDYSKYLDAARAQEFVKWLEDEPKSKSPPPS-NH$_2$ (SEQ ID NO: 43). In some embodiments, an isolated polypeptide of the disclosure consists of the amino acid sequence YSHGTFTSDYSKYLD(Aib)KRAQEFVIWLEDEPSSGAPPPS-OH (SEQ ID NO: 44). In some embodiments, an isolated polypeptide of the disclosure consists of the amino acid sequence YSHGTFTSDYSKYLDSARAQEFVKWLEDEPSSGAPPPS-NH$_2$ (SEQ ID NO: 45). In some embodiments, an isolated polypeptide of the disclosure consists of the amino acid sequence WSQGTFTSDYSKYLD(Aib)KRAQEFV(Aib)WLEDEPSSGAPPPS-OH (SEQ ID NO: 46).

In some embodiments, an isolated polypeptide of the disclosure comprises an amino acid sequence selected from the group consisting of
YSHGTFTSDYSKYLDAARAQEFVKWLEDEPSSGAPPPS-OH (SEQ ID NO: 143), which is also referred to herein as Compound A97;
YSHGTFTSDYTRLLESKRAQEFVKWLEDEPSSGAPPPS-OH (SEQ ID NO: 144), which is also referred to herein as Compound A98;
YSHGTFTSDYSKYLD(Aib)KRAQEFV(Aib)WLEDEPSSGAPPPS-OH (SEQ ID NO: 145), which is also referred to herein as Compound A99;
YSHGTFTSDYSKYLD(Aib)KRAQEFV(Aib)WLEDE-OH (SEQ ID NO: 146), which is also referred to herein as Compound A100;
YGHGTFTSDHSKYLD(Aib)KRAQEFVKWLEDE-OH (SEQ ID NO: 147), which is also referred to herein as Compound A101;
YSHGTFTSDYSKWLD(Aib)KRAQEFVKWLEDE-OH (SEQ ID NO: 148), which is also referred to herein as Compound A102; and
YSHGTFTSDYSKYLD(Aib)ARAQEFV(Aib)WLEDEPSSGAPPPS-OH (SEQ ID NO: 149), which is also referred to herein as Compound A103.

In some embodiments, an isolated polypeptide of the disclosure comprises the amino acid sequence YSHGTFTSDYSKYLDAARAQEFVKWLEDEPSSGAPPPS-OH (SEQ ID NO: 143), which is also referred to herein as Compound A97.

In some embodiments, an isolated polypeptide of the disclosure comprises the amino acid sequence YSHGTFTSDYTRLLESKRAQEFVKWLEDEPSSGAPPPS-OH (SEQ ID NO: 144), which is also referred to herein as Compound A98.

In some embodiments, an isolated polypeptide of the disclosure comprises the amino acid sequence YSHGTFTSDYSKYLD(Aib)KRAQEFV(Aib)WLEDEPSSGAPPPS-OH (SEQ ID NO: 145), which is also referred to herein as Compound A99.

In some embodiments, an isolated polypeptide of the disclosure comprises the amino acid sequence YSHGTFTSDYSKYLD(Aib)KRAQEFV(Aib)WLEDE-OH (SEQ ID NO: 146), which is also referred to herein as Compound A100.

In some embodiments, an isolated polypeptide of the disclosure comprises the amino acid sequence YGHGTFTSDHSKYLD(Aib)KRAQEFVKWLEDE-OH (SEQ ID NO: 147), which is also referred to herein as Compound A101.

In some embodiments, an isolated polypeptide of the disclosure comprises the amino acid sequence YSHGTFTSDYSKWLD(Aib)KRAQEFVKWLEDE-OH (SEQ ID NO: 148), which is also referred to herein as Compound A102.

In some embodiments, an isolated polypeptide of the disclosure comprises the amino acid sequence YSHGTFTSDYSKYLD(Aib)ARAQEFV(Aib)WLEDEPSSGAPPPS-OH (SEQ ID NO: 149), which is also referred to herein as Compound A103.

In some embodiments, the polypeptide consists of an amino acid sequence selected from the group consisting of SEQ ID NOs: 143-149.

In some embodiments, an isolated polypeptide of the disclosure comprises an amino acid sequence selected from the group consisting of YSHGTFTSDYSKYLD(Aib)ARAQEFV(Aib)
  WLEDEPSSGAPPPS-OH (SEQ ID NO: 47); which is also referred to herein as Compound A7;
YSHGTFTSDYSKYLD(Aib)KRAQEFV(Aib)
  WLEDEPSSGAPPPS-NH₂ (SEQ ID NO: 48); which is also referred to herein as Compound A8;
YSHGTFTSDYSKYLD(Aib)KRAQEFV(Aib)
  WLEEEPSSGAPPPS-OH (SEQ ID NO: 49); which is also referred to herein as Compound A9;
YSHGTFTSDYSKYLD(Aib)KRAQEFV(Aib)
  WLEDEEPSSGAPPPS-OH (SEQ ID NO: 50); which is also referred to herein as Compound A10;
YSHGTFTSDYSKYLD(Aib)KRAQEFV(Aib)
  WLEDEEEPSSGAPPPS-OH (SEQ ID NO: 51); which is also referred to herein as Compound A11;
YSHGTFTSDYSKYLD(Aib)KRAQEFV(Aib)WLEDE-GAPPPS-OH (SEQ ID NO: 52); which is also referred to herein as Compound A12;
YSHGTFTSDYSKYLD(Aib)KRAQEFV(Aib)
  WLEDESGAPPPS-OH (SEQ ID NO: 53); which is also referred to herein as Compound A13;
YSHGTFTSDYSKYLD(Aib)KRAQEFV(Aib)
  WLEDESSGAPPPS-OH (SEQ ID NO: 54); which is also referred to herein as Compound A14;
YSHGTFTSDYSKYLD(Aib)SRAQEFV(Aib)
  WLEDEPSSGAPPPS-OH (SEQ ID NO: 55); which is also referred to herein as Compound A15;
YSHGTFTSDYSKYLD(Aib)TRAQEFV(Aib)
  WLEDEPSSGAPPPS-OH (SEQ ID NO: 56); which is also referred to herein as Compound A16;
YSHGTFTSDYSKYLD(Aib)ERAQEFV(Aib)
  WLEDEPSSGAPPPS-OH (SEQ ID NO: 57); which is also referred to herein as Compound A17;
YSHGTFTSDYSKWLD(Aib)ARAQEFV(Aib)
  WLEDEPSSGAPPPS-OH (SEQ ID NO: 58); which is also referred to herein as Compound A18;
YSHGTFTSDYSKWLD(Aib)SRAQEFV(Aib)
  WLEDEPSSGAPPPS-OH (SEQ ID NO: 59); which is also referred to herein as Compound A19;
YSHGTFTSDYSKYLD(Aib)KRAQEFV(Aib)
  WLEDEPSSGKPPPS-OH (SEQ ID NO: 60); which is also referred to herein as Compound A20;
YSHGTFTSDYSKYLD(Aib)KRAQEFV(Aib)
  WLEDEPSSGEPPPS-OH (SEQ ID NO: 61); which is also referred to herein as Compound A21;
YSHGTFTSDYSKYLD(Aib)KRAQEFV(Aib)
  WLEDEPSSGSPPPS-OH (SEQ ID NO: 62); which is also referred to herein as Compound A22;
YSHGTFTSDYSKYLD(Aib)KRAQEFV(Aib)
  WLEDEPSSKAPPPS-OH (SEQ ID NO: 63); which is also referred to herein as Compound A23;
YSHGTFTSDYSKYLD(Aib)KRAQEFV(Aib)
  WLEDEPSSKGAPPPS-OH (SEQ ID NO: 64); which is also referred to herein as Compound A24;
YSHGTFTSDYSKYLD(Aib)KRAQEFV(Aib)
  WLEDEPSSGAPPPSS-OH (SEQ ID NO: 65); which is also referred to herein as Compound A25;
YSHGTFTSDYSKYLD(Aib)KRAQEFV(Aib)
  WLEDEPSSGAPPPSE-OH (SEQ ID NO: 66); which is also referred to herein as Compound A26;
YSHGTFTSDYSKYLD(Aib)KRAQEFV(Aib)WLEDE-GGPSSGAPPPS-OH (SEQ ID NO: 67); which is also referred to herein as Compound A27;
YSHGTFTSDYSKYLD(Aib)KRAQEFV(Aib)WLEDE-GPSSGAPPPS-OH (SEQ ID NO: 68); which is also referred to herein as Compound A28;
YSHGTFTSDYSKYLD(Aib)KRAQEFV(Aib)
  WLEDEPKSGAPPPS-OH (SEQ ID NO: 69); which is also referred to herein as Compound A29;
YSHGTFTSDYSKYLD(Aib)KRAQEFV(Aib)
  WLEDEPSKGAPPPS-OH (SEQ ID NO: 70); which is also referred to herein as Compound A30;
YSHGTFTSDYSKYLD(Aib)KRAQEFV(Aib)
  WLEDEPESGAPPPS-OH (SEQ ID NO: 71); which is also referred to herein as Compound A31;
YTHGTFTSDYSKWLD(Aib)KRAQEFV(Aib)
  WLEDEPSSGAPPPS-OH (SEQ ID NO: 72); which is also referred to herein as Compound A32;
YSHGTFTSDHSKWLD(Aib)KRAQEFV(Aib)
  WLEDEPSSGAPPPS-OH (SEQ ID NO: 73); which is also referred to herein as Compound A33;
YTHGTFTSDHSKWLD(Aib)KRAQEFV(Aib)
  WLEDEPSSGAPPPS-OH (SEQ ID NO: 74); which is also referred to herein as Compound A34;
YTHGTFTSDYSKWLD(Aib)ARAQEFV(Aib)
  WLEDEPSSGAPPPS-OH (SEQ ID NO: 75); which is also referred to herein as Compound A35;
YSHGTFTSDHSKWLD(Aib)ARAQEFV(Aib)
  WLEDEPSSGAPPPS-OH (SEQ ID NO: 76); which is also referred to herein as Compound A36;
YSHGTFTSDYSKYLDSARA-QEFVKWLEDEPSSGAPPPS-OH (SEQ ID NO: 77); which is also referred to herein as Compound A37;
YSHGTFTSDYSKWLDSARA-QEFVKWLEDEPSSGAPPPS-OH (SEQ ID NO: 78); which is also referred to herein as Compound A38;
YTHGTFTSDYSKWLDSARA-QEFVKWLEDEPSSGAPPPS-OH (SEQ ID NO: 79); which is also referred to herein as Compound A39;
YSHGTFTSDHSKWLDSARA-QEFVKWLEDEPSSGAPPPS-OH (SEQ ID NO: 80); which is also referred to herein as Compound A40;
YTHGTFTSDHSKWLDEAR-AQEFVKWLEDEPSSGAPPPS-OH (SEQ ID NO: 81); which is also referred to herein as Compound A41;

YTHGTFTSDYSKWLDSK-
RAQEFVKWLEDEPSSGAPPPS-OH (SEQ ID NO: 82); which is also referred to herein as Compound A42;

YSHGTFTSDYSKYLDKARA-
QEFVKWLEDEPSSGAPPPS-OH (SEQ ID NO: 83); which is also referred to herein as Compound A43;

YSHGTFTSDYSKY-
LDQARAQEFVKWLEDEPSSGAPPPS-OH (SEQ ID NO: 84); which is also referred to herein as Compound A44;

YSHGTFTSDYSKYLD(Aib)KRAQEFV(Aib)
WLEDEKRNKPPPA-OH (SEQ ID NO: 85); which is also referred to herein as Compound A45;

YSHGTFTSDYSKYLD(Aib)KRAQEFV(Aib)
WLEDEKRNKPPIA-OH (SEQ ID NO: 86); which is also referred to herein as Compound A46;

YSHGTFTSDYSKYLD(Aib)KRAQEFV(Aib)
WLEDEKRNKNPPS-OH (SEQ ID NO: 87); which is also referred to herein as Compound A47;

YSHGTFTSDYSKYLD(Aib)KRAQEFV(Aib)
WLEDEKRNKNPPPS-OH (SEQ ID NO: 88); which is also referred to herein as Compound A48;

YSHGTFTSDYSKYLD(Aib)KRAQEFV(Aib)
WLEDEPRNKNNPPS-OH (SEQ ID NO: 89); which is also referred to herein as Compound A49;

YSHGTFTSDYSKYLD(Aib)KRAQEFV(Aib)
WLEDEKRNKPPPS-OH (SEQ ID NO: 90); which is also referred to herein as Compound A50;

YSHGTFTSDYSKYLDLKRAQEFV(Aib)
WLEDEPSSGAPPPS-OH (SEQ ID NO: 91); which is also referred to herein as Compound A51;

YSHGTFTSDYSKYLDIKRAQEFV(Aib)
WLEDEPSSGAPPPS-OH (SEQ ID NO: 92); which is also referred to herein as Compound A52;

YSHGTFTSDYSKYLD(Aib)
KRAQEFVLWLEDEPSSGAPPPS-OH (SEQ ID NO: 93); which is also referred to herein as Compound A53;

YSHGTFTSDYSKYLD(Aib)KRAQEFV(Aib)
WLEDEPSSKEPPPS-OH (SEQ ID NO: 94); which is also referred to herein as Compound A54;

YSHGTFTSDYSKYLD(Aib)KRAQEFV(Aib)
WLEDEPSSKSPPPS-OH (SEQ ID NO: 95); which is also referred to herein as Compound A55;

YSHGTFTSDYSKYLD(Aib)KRAQEFV(Aib)
WLEDEPKSKAPPPS-OH (SEQ ID NO: 96); which is also referred to herein as Compound A56;

YSHGTFTSDYSKYLD(Aib)KRAQEFV(Aib)
WLEDEPKSKQPPPS-OH (SEQ ID NO: 97); which is also referred to herein as Compound A57;

YSHGTFTSDYSKYLD(Aib)KRAQEFV(Aib)
WLEDEPKSKSPPPS-OH (SEQ ID NO: 98); which is also referred to herein as Compound A58;

YSHGTFTSDYSKYLD(Aib)KRAQEFV(Aib)
WLEDEPSSKQPPPS-OH (SEQ ID NO: 99); which is also referred to herein as Compound A59;

YTHGTFTSDYSKYLD(Aib)KRAQEFV(Aib)
WLEDEPSSGKPPPS-OH (SEQ ID NO: 100); which is also referred to herein as Compound A60;

YSHGTFTSDYSKYLDSARA-
QEFVKWLEDEPSSGKPPPS-OH (SEQ ID NO: 101); which is also referred to herein as Compound A61;

YTHGTFTSDYSKYLD(Aib)KRAQEFV(Aib)
WLEDEPSSGAPPPS-OH (SEQ ID NO: 102); which is also referred to herein as Compound A62;

YTHGTFTSDYSKYLDSARA-
QEFVKWLEDEPSSGAPPPS-OH (SEQ ID NO: 103); which is also referred to herein as Compound A63;

YTHGTFTSDYSKYLD(Aib)ARAQEFV(Aib)
WLEDEPSSGAPPPS-OH (SEQ ID NO: 104); which is also referred to herein as Compound A64;

YSHGTFTSDYSKYLD(Aib)KRAQEFV(Aib)
WLEDEPKSKEPPPS-NH$_2$ (SEQ ID NO: 105); which is also referred to herein as Compound A65;

YSHGTFTSDYSKYLD(Aib)KRAQEFV(Aib)
WLEDEPKSKSPPPS-NH$_2$ (SEQ ID NO: 106); which is also referred to herein as Compound A66;

YSHGTFTSDYSKYLD(Aib)ARAQEFV(Aib)
WLEDEPKSKSPPPS-NH$_2$ (SEQ ID NO: 107); which is also referred to herein as Compound A67;

YSHGTFTSDYSKYLD(Aib)ARAQEFV(Aib)
WLEDEPKSKEPPPS-NH$_2$ (SEQ ID NO: 108); which is also referred to herein as Compound A68;

YSHGTFTSDYSKYLDSARAQEFVKWLEDEPK-
SKEPPPS-OH (SEQ ID NO: 109); which is also referred to herein as Compound A69;

YSHGTFTSDYSKYLDSARAQEFVKWLEDEPKSK-
SPPPS-OH (SEQ ID NO: 110); which is also referred to herein as Compound A70;

YSHGTFTSDYSKYLDSARAQEFVKWLEDEPK-
SKAPPPS-OH (SEQ ID NO: 111); which is also referred to herein as Compound A71;

YSHGTFTSDYSKYLDSARAQEFVKWLEDEPK-
SKEPPPS-NH$_2$ (SEQ ID NO: 112); which is also referred to herein as Compound A72;

YSHGTFTSDYSKYLDSARAQEFVKWLEDEPKSK-
SPPPS-NH$_2$ (SEQ ID NO: 113); which is also referred to herein as Compound A73;

YSHGTFTSDYSKYLDSARAQEFVKWLEDEPK-
SKAPPPS-NH$_2$ (SEQ ID NO: 114); which is also referred to herein as Compound A74;

WSHGTFTSDYSKYLD(Aib)KRAQEFV(Aib)
WLEDEPSSGAPPPS-OH (SEQ ID NO: 115); which is also referred to herein as Compound A75;

YSHGTFTSDYSKYLD(Aib)KAAQEFV(Aib)
WLEDEPSSGAPPPS-OH (SEQ ID NO: 116); which is also referred to herein as Compound A76;

YSHGTFTSDYSKYLD(Aib)KTAQEFV(Aib)
WLEDEPSSGAPPPS-OH (SEQ ID NO: 117); which is also referred to herein as Compound A77;

YSHGTFTSDYSKYLD(Aib)KLAQEFV(Aib)
WLEDEPSSGAPPPS-OH (SEQ ID NO: 118); which is also referred to herein as Compound A78;

YSHGTFTSDYSKYLD(Aib)KEAQEFV(Aib)
WLEDEPSSGAPPPS-OH (SEQ ID NO: 119); which is also referred to herein as Compound A79;

YSHGTFTSDYSKYLDAARAQEFVKWLEDEPKSK-
SPPPS-NH$_2$ (SEQ ID NO: 120); which is also referred to herein as Compound A80;

YSQGTFTSDYSKYLDSARAQEFVKWLEDEPKSK-
SPPPS-OH (SEQ ID NO: 121); which is also referred to herein as Compound A81;

YSQGTFTSDYSKYLDSARAQEFVKWLEDEPK-
SKAPPPS-OH (SEQ ID NO: 122); which is also referred to herein as Compound A82;

YSHGTFTSDYSKYLDSARAQEFTKWLEDEPKSK-
SPPPS-OH (SEQ ID NO: 123); which is also referred to herein as Compound A83;

YSHGTFTSDYSKYLDSARAQEFVKHLEDEPKSK-
SPPPS-OH (SEQ ID NO: 124); which is also referred to herein as Compound A84;

YSHGTFTSDYSKYLD(Aib)KRAQEFV(Aib)
WLEDEPSSGKPPPS-NH$_2$ (SEQ ID NO: 125); which is also referred to herein as Compound A85;

YSQGTFTSDYSKYLD(Aib)KRAQEFV(Aib)
WLEDEPSSGKPPPS-OH (SEQ ID NO: 126); which is also referred to herein as Compound A86;
YSHGTFTSDYSKYLD(Aib)KRAQEFV(Aib)
WLEDEKSSGKPPPS-OH (SEQ ID NO: 127); which is also referred to herein as Compound A87;
YSHGTFTSDYSKYLD(Aib)KRAQEFV(Aib)
WLEDEPSSGKKPPS-OH (SEQ ID NO: 128); which is also referred to herein as Compound A88;
YSHGTFTSDYSKYLD(Aib)KRAQEFV(Aib)
HLEDEPSSGKPPPS-OH (SEQ ID NO: 129); which is also referred to herein as Compound A89;
YSHGTFTSDYSKYLD(Aib)KAAQEFV(Aib)
WLEDEPSSGKPPPS-OH (SEQ ID NO: 130); which is also referred to herein as Compound A90;
WSQGTFTSDYSKYLD(Aib)KRAQEFV(Aib)
WLEDEPSSGKPPPS-OH (SEQ ID NO: 131); which is also referred to herein as Compound A91;
WSQGTFTSDYSKYLD(Aib)KAAQEFV(Aib)
WLEDEPSSGAPPPS-OH (SEQ ID NO: 132); which is also referred to herein as Compound A92;
WSQGTFTSDYSKYLD(Aib)KAAQEFV(Aib)
WLEDEPSSGKPPPS-OH (SEQ ID NO: 133); which is also referred to herein as Compound A93;
YSQGTFTSDYSKYLD(Aib)KRAQEFV(Aib)
WLEDEPSSGAPPPS-OH (SEQ ID NO: 134); which is also referred to herein as Compound A94;
YSQGTFTSDYSKYLD(Aib)KAAQEFV(Aib)
WLEDEPSSGAPPPS-OH (SEQ ID NO: 135); which is also referred to herein as Compound A95; and
YSQGTFTSDYSKYLD(Aib)KAAQEFV(Aib)
WLEDEPSSGKPPPS-OH (SEQ ID NO: 136); which is referred to herein as Compound A96. In some embodiments, the polypeptide consists of an amino acid sequence selected from the group consisting of SEQ ID NOs: 47-136.

In some embodiments, an isolated polypeptide of the disclosure comprises an amino acid sequence selected from the group consisting of amino acid sequences represented by the consensus sequence of SEQ ID NO: 137:

(SEQ ID NO: 137)
YSQGTFTSDYSKYLDSX$_{17}$RAQX$_{21}$FVX$_{24}$WLX$_{27}$X$_{28}$T-OH, wherein:
X$_{17}$ is K*, where K* is in a lactam bridge with E* at X$_{21}$;
X$_{21}$ is E*, where E* is in a lactam bridge with K* at X$_{17}$;
X$_{24}$ is K or K, where K is in a lactam bridge with E** at X$_{28}$;
X$_{27}$ is Q or D; and
X$_{28}$ is E or E, where E is in a lactam bridge with K** at X$_{24}$ In some embodiments, an isolated polypeptide of the disclosure comprises an amino acid sequence selected from the group consisting of YSQGTFTSDYSKYLDSK*RAQE*FVKWLDET-OH (SEQ ID NO: 138), referred to herein as Compound A104 and YSQGTFTSDYSKYLDSK*RAQE*FVKWLQET-OH (SEQ ID NO: 139), referred to herein as Compound A105. In some embodiments, the polypeptide consists of an amino acid sequence selected from the group consisting of SEQ ID NOs: 138 and 139.

The isolated polypeptides of the disclosure contain amino acid motifs that allow for maintaining characteristics such as solubility, and/or stability, e.g., metabolic stability, of the glucagon-receptor selective analogs as compared to the native human glucagon molecule, as well as amino acid motifs that allow for maintaining additional characteristics such as glucagon selectivity over GLP-1.

In some embodiments, the C-terminus of the isolated polypeptide of the disclosure is extended with a sequence that binds to serum albumin, for example, to human serum albumin. In some embodiments, the C-terminus of the isolated polypeptide of the disclosure is extended with a sequence selected from the group consisting of EEPSSGAPPPS-OH (SEQ ID NO: 4); EPSSGAPPPS-OH (SEQ ID NO: 5); GAPPPS-OH (SEQ ID NO: 6); GGPSSGAPPPS-OH (SEQ ID NO: 7); GPSSGAPPPS-OH (SEQ ID NO: 8); KRNKNPPPS-OH (SEQ ID NO: 9); KRNKNPPS-OH (SEQ ID NO: 10); KRNKPPIA-OH (SEQ ID NO: 11); KRNKPPPA-OH (SEQ ID NO: 150); KRNKPPPS-OH (SEQ ID NO: 12); KSSGKPPPS-OH (SEQ ID NO: 13); PESGAPPPS-OH (SEQ ID NO: 14); PKSGAPPPS-OH (SEQ ID NO: 15); PKSKAPPPS-NH$_2$ (SEQ ID NO: 16); PKSKAPPPS-OH (SEQ ID NO: 17); PKSKEPPPS-NH$_2$ (SEQ ID NO: 18); PKSKEPPPS-OH (SEQ ID NO: 19); PKSKQPPPS-OH (SEQ ID NO: 20); PKSKSPPPS-NH$_2$ (SEQ ID NO: 21); PKSKSPPPS-OH (SEQ ID NO: 22); PRNKNNPPS-OH (SEQ ID NO: 23); PSKGAPPPS-OH (SEQ ID NO: 24); PSSGAPPPSE-OH (SEQ ID NO: 25); PSSGAPPPS-NH$_2$ (SEQ ID NO: 26); PSSGAPPPS-OH (SEQ ID NO: 27); PSSGAPPPSS-OH (SEQ ID NO: 28); PSSGEPPPS-OH (SEQ ID NO: 29); PSSGKKPPS-OH (SEQ ID NO: 30); PSSGKPPPS-NH$_2$ (SEQ ID NO: 31); PSSGKPPPS-OH (SEQ ID NO: 32); PSSGSPPPS-OH (SEQ ID NO: 33); PSSKAPPPS-OH (SEQ ID NO: 34); PSSKEPPPS-OH (SEQ ID NO: 35); PSSKGAPPPS-OH (SEQ ID NO: 36); PSSKQPPPS-OH (SEQ ID NO: 37); PSSKSPPPS-OH (SEQ ID NO: 38); SGAPPPS-OH (SEQ ID NO: 39); and SSGAPPPS-OH (SEQ ID NO: 40).

In some embodiments, the carboxyl group of the C-terminal amino acid residue of an isolated polypeptide of the disclosure is amidated. In some embodiments, the carboxyl group of the C-terminal amino acid residue of an isolated polypeptide of the disclosure unmodified.

In some embodiments, an isolated polypeptide provided herein is an agonist of glucagon activity. In some embodiments, an isolated polypeptide provided herein can bind to a glucagon receptor. In some embodiments, the glucagon receptor is a human glucagon receptor. In some embodiments, the isolated polypeptide of the disclosure binds to a human glucagon receptor with a pEC50 in the cAMP assay using an 11 point curve starting at 1 nM to 500 micromolar range (as described herein) in the range of greater than about 9.0. In some embodiments, the isolated polypeptide of the disclosure binds to a human glucagon receptor with a pEC50 in the cAMP assay using an 11 point curve starting at 1 nM to 500 micromolar range (as described herein) in the range of greater than about 11.0.

In some embodiments, an isolated polypeptide of the disclosure binds to a human glucagon receptor, but does not substantially bind to a human GLP-1 receptor. As used herein, the term "does not substantially bind" and variations thereof refer to polypeptides that exhibit low affinity to no affinity for a human GLP-1 receptor. In some embodiments, an isolated polypeptide of the disclosure binds to a human glucagon receptor at an affinity that is at least 100-fold greater than the affinity of the same isolated polypeptide for a human GLP-1 receptor. In preferred embodiments, an isolated polypeptide of the disclosure binds to a human glucagon receptor at an affinity that is at least 1,000-fold greater than the affinity of the same isolated polypeptide for a human GLP-1 receptor. In some embodiments, the isolated polypeptide of the disclosure binds to a human glucagon receptor with a pEC50 in the cAMP assay using an 11 point curve starting at 1 nM to 500 micromolar range in the range of greater than about 9.0, and the isolated polypeptide of the disclosure binds to human GLP-1 receptor with a pEC50 in the cAMP assay that is less than about 10.0. In some embodiments, the isolated polypeptide of the disclosure binds to a human glucagon receptor with a pEC50 in the cAMP assay using an 11 point curve starting at 1 nM to 500 micromolar range in the range of greater than about 11.0, and the isolated polypeptide of the disclosure binds to human GLP-1 receptor with a pEC50 in the cAMP assay that is less than about 9.0.

In some embodiments, an isolated polypeptide as provided herein can further comprise a heterologous moiety associated with the polypeptide. In some embodiments, the heterologous moiety is a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, or any combination of two or more of such moieties.

The isolated polypeptides provided herein exhibit glucagon receptor agonistic activity, for example by binding a glucagon receptor. The isolated polypeptides provided herein completely or partially agonize or otherwise stimulate glucagon activity upon binding to or otherwise interacting with a glucagon receptor. The stimulation or modulation of a biological function of glucagon is complete or partial upon interaction between the glucagon receptor agonist and the glucagon receptor.

These isolated polypeptides of the disclosure, which are selective glucagon receptor agonists, are useful alone or in combination with at least a second agent. In preferred embodiments, the second agent is a polypeptide. In preferred embodiments, the second polypeptide is an insulinotrophic peptide. For example, the insulinotrophic polypeptide is selected from the group consisting of exenatide, a derivative of exenatide, an analogue of exenatide, glucagon-like peptide-1 (GLP-1), a derivative of GLP-1, and an analogue of GLP-1.

In preferred embodiments, the insulinotrophic polypeptide is exenatide, a derivative of exenatide, or an analog of exenatide. In preferred embodiments, the exenatide is synthetic exenatide. In preferred embodiments, the synthetic exenatide comprises the amino acid sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$ (SEQ ID NO: 142).

In combination therapies, the use of a selective glucagon analog allows for the titration of proper therapeutic doses of glucagon and any GLP-1 receptor agonist. This allows for the desired effects of glucagon/GLP-1 agonism (i.e., weight-loss, increase in energy expenditure), without a deleterious spike in blood glucose.

In some embodiments, an isolated polypeptide as provided herein and the additional agent are formulated into a single therapeutic composition, and the isolated polypeptide and additional agent are administered simultaneously. In some embodiments, the isolated polypeptide and additional agent are separate from each other, e.g., each is formulated into a separate therapeutic composition, and the isolated polypeptide and the additional agent are administered simultaneously, or the isolated polypeptide and the additional agent are administered at different times during a treatment regimen. For example, the isolated polypeptide is administered prior to the administration of the additional agent, the isolated polypeptide is administered subsequent to the administration of the additional agent, or the isolated polypeptide and the additional agent are administered in an alternating fashion. As described herein, the isolated polypeptide and additional agent are administered in single doses or in multiple doses.

Also provided herein are methods for treating, delaying the onset of, delaying the progression of, or otherwise ameliorating a symptom of a disease or condition caused, characterized by, or otherwise associated with aberrant glucagon activity. In some embodiments, the disease or condition is type 2 diabetes mellitus.

Also provided herein are methods of treating a metabolic disorder by administering an isolated polypeptide of the disclosure or any pharmaceutical composition described herein to a subject in need thereof.

Also provided herein are methods of treating obesity by administering an isolated polypeptide of the disclosure or any pharmaceutical composition described herein to a subject in need thereof.

Also provided herein are methods of treating, preventing, delaying the onset of, delaying the progression of, and/or otherwise ameliorating a symptom of a metabolic disease or disorder associated with elevated blood glucose in a patient by administering an isolated polypeptide of the disclosure or any pharmaceutical composition described herein to the patient in need thereof.

Also provided herein are methods of treating, preventing, delaying the onset of, delaying the progression of, and/or otherwise ameliorating a symptom of a disease or disorder in which agonism at the glucagon receptor is desired, such as, by way of non-limiting example, chronic pain, hemophilia and other blood disorders, endocrine disorders, metabolic disorders, non-alcoholic fatty liver disease (NAFLD), non-alcoholic steatohepatitis (NASH), Alzheimer's disease, cardiovascular diseases, hypoglycemia unawareness, restrictive lung disease, chronic obstructive pulmonary disease, lipoatrophy, metabolic syndrome, leukemia, hepatitis, renal failure, autoimmune diseases (e.g., Grave's disease, systemic lupus erythematosus, multiple sclerosis, and rheumatoid arthritis), shock and/or wasting disorders, pancreatitis, and neurological disorders and diseases such as Parkinson's disease.

Also provided herein are methods of treating, preventing, delaying the onset of, delaying the progression of, and/or otherwise ameliorating a symptom of an infectious disease requiring chronic treatment(s).

In the methods disclosed herein, the isolated polypeptides of the disclosure and/or pharmaceutical compositions described herein are administered alone or in combination with pharmaceutically acceptable carriers and/or excipients and/or polymers and/or organic solvent, in either single or multiple doses.

Pharmaceutical compositions according to the invention can include a polypeptide of the disclosure, along with a suitable carrier. These pharmaceutical compositions can be included in kits, such as, for example, diagnostic kits.

BRIEF DESCRIPTION OF THE DRAWINGS

FIG. 1A demonstrates that the peptides referred to herein as Compound A2 and Compound A1 and glucagon are nearly equipotent on GCGR, while GLP-1 (7-37) activates GCGR at a much lower potency. FIG. 1B demonstrates that in contrast to the results in FIG. 1A, peptides Compound A2 and Compound A1 are inactive on GLP-1R demonstrating that peptides Compound A2 and Compound A1 profile as GCGR selective agonists.

FIG. 2A depicts the glucagon analogs referred to herein as Compound A99 (SEQ ID NO: 145), Compound A102 (SEQ ID NO: 148), Compound A98 (SEQ ID NO: 144), Compound A100 (SEQ ID NO: 146), and Compound A101 (SEQ ID NO: 147), where n=3 to 6, and the error bars in the graph represent standard error, and where the CL values in the table are shown as mean±standard error (n=3 to 6). FIG. 2B depicts the glucagon analogs referred to herein as Compound A2, Compound A1, Compound A5, Compound A6, Compound A4, and Compound A3, where n=3 to 5, and the error bars in the graph represent standard error, and where the CL values in the table are shown as mean±standard error (n=3 to 5).

FIG. 3A depicts the efficacy of the glucagon analog referred to herein as Compound A104, when administered along (i.e., singly) or in combination with exendin-4. FIG. 3B depicts the efficacy of the glucagon analog referred to herein as Compound A2, and FIG. 3C depicts the efficacy of the glucagon analog referred to herein as Compound A1. For all graphs, p<0.05 as compared to vehicle control.

FIG. 7 shows that clearance of certain glucagon analogs, including Compounds A1, A2 and A3 are less than that of exenatide and glucagon.

DETAILED DESCRIPTION

Figure 1A:
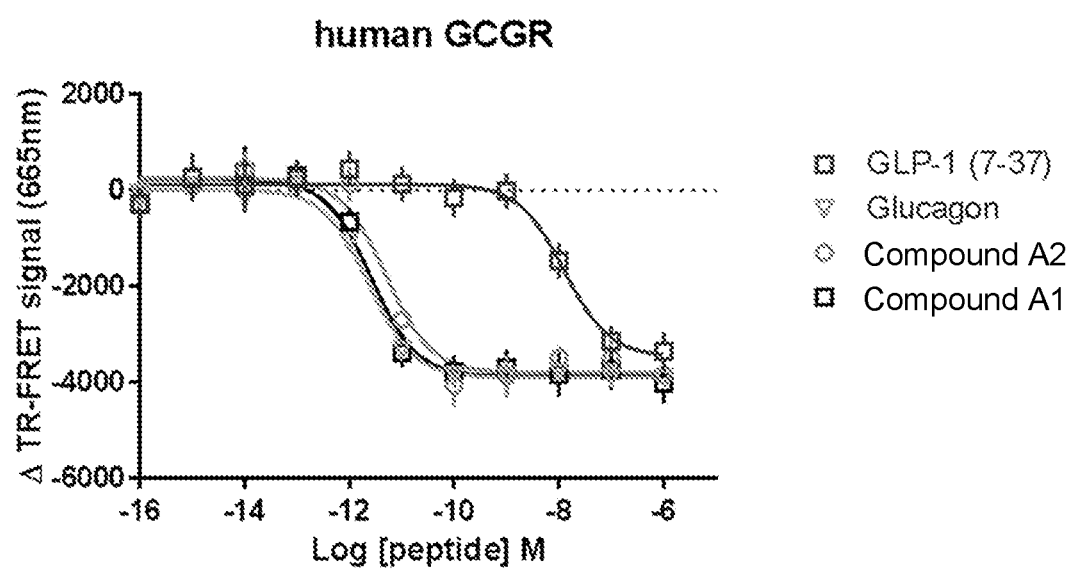
FIGS. 1A and 1B are a series of graphs depicting peptide-receptor activation profiles at the human glucagon receptor (GCGR) and the human GLP-1 receptor (GLP-1R) by human glucagon, GLP-1 (7-37), and two glucagon receptor selective peptide agonists.

This invention relates to isolated polypeptides that are glucagon-receptor selective analogs and peptide derivatives thereof. Glucagon is produced by the pancreas and interacts with the glucagon receptor ("GCGR"). In some embodiments, an isolated polypeptide of the disclosure is a selective glucagon receptor agonist. In some embodiments, an isolated polypeptide of the disclosure binds to a glucagon receptor.

Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "an osmotic delivery device" includes one or more osmotic delivery devices, and the like. Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the term "substantially" is understood as within a narrow range of variation or otherwise normal tolerance in the art. Substantially can be understood as within 5%, 4%, 3%, 2%, 1%, 0.5%, 0.1%, 0.05%, 0.01% or 0.001% of the stated value.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "drug," "therapeutic agent," and "beneficial agent" are used interchangeably to refer to any therapeutically active substance that is delivered to a subject to produce a desired beneficial effect. In one embodiment of the present invention, the drug is a polypeptide. In another embodiment of the present invention, the drug is a small molecule, for example, hormones such as androgens or estrogens. The devices and methods of the present invention are well suited for the delivery of proteins, small molecules and combinations thereof.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetic). Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). The term peptide also includes modifications, such as but not limited to those described above, of amino acids falling between the amino and carboxy termini. In one embodiment, a peptide may be modified by addition of a small-molecule drug.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "insulinotrophic" as used herein typically refers to the ability of a compound, e.g., a peptide, to stimulate or affect the production and/or activity of insulin (e.g., an insulinotrophic hormone). Such compounds typically stimulate or otherwise affect the secretion or biosynthesis of insulin in a subject. Thus, an "insulinotrophic peptide" is an amino acid-containing molecule capable of stimulating or otherwise affecting secretion or biosynthesis of insulin.

The term "insulinotrophic peptide" as used herein includes, but is not limited to, glucagon-like peptide 1 (GLP-1), as well as derivatives and analogues thereof, exenatide, exenatide having the amino acid sequence of SEQ ID NO; 1, as well as derivatives and analogues thereof.

The phrase "incretin mimetics" as used herein includes, but is not limited to GLP-1 peptide, peptide derivatives of GLP-1, peptide analogs of GLP-1; exenatide, exenatide having the amino acid sequence of SEQ ID NO: 1, exenatide peptide, peptide derivatives of exenatide, and peptide analogs of exenatide. Examples of preferred incretin mimetics include exenatide, exenatide having the amino acid sequence of exendin-4 (the naturally-occurring form of exenatide, and has the amino acid sequence of SEQ ID NO: 1), exenatide-LAR, lixisenatide, GLP-1 (7-36), liraglutide, semaglutide, dulaglutide, albiglutide, and taspoglutide. Incretin mimetics are also referred to herein as "insulinotrophic peptides." Incretin mimetics which target the GLP-1 receptor are also known in the literature as "GLP-1 receptor agonists."

The term "an exenatide" as used herein includes, but is not limited to exenatide, exenatide having the amino acid sequence of SEQ ID NO: 1, native exendin-4, exenatide peptides, exenatide peptide analogs, and exenatide peptide derivatives.

The term "GLP-1" refers to a polypeptide that is produced by the L-cell located mainly in the ileum and colon, and to a lesser extent by L-cells in the duodenum and jejunum. GLP-1 is a regulatory peptides to a G-coupled protein receptor on β cell and via adenyl cyclase activity and production of cAMP stimulates the insulin response to the nutrients that are absorbed from the gut [Baggio 2007, "Biology of incretins: GLP-1 and GIP," Gastroenterology, vol. 132(6):2131-57; Holst 2008, "The incretin system and its role in type 2 diabetes mellitus," Mol Cell Endocrinology, vol. 297(1-2):127-36]. The effects of GLP-1R agonism are multiple. GLP-1 maintains glucose homeostasis by enhancing endogenous glucose dependent insulin secretion, rendering the β cells glucose competent and sensitive to GLP-1, suppressing glucagon release, restoring first and second phase insulin secretion, slowing gastric emptying, decreasing food intake, and increasing satiety [Holst 2008 Mol. Cell Endocrinology; Kjems 2003 "The influence of GLP-1 on glucose-stimulated insulin secretion: effects on beta-cell sensitivity in type 2 and nondiabetic subjects," Diabetes, vol. 52(2): 380-86; Holst 2013 "Incretin hormones and the satiation signal," Int J Obes (Lond), vol. 37(9):1161-69; Seufert 2014, "The extra-pancreatic effects of GLP-1 receptor agonists: a focus on the cardiovascular, gastrointestinal and central nervous systems," Diabetes Obes Metab, vol. 16(8): 673-88]. The risk of hypoglycemia is minimal given the mode of action of GLP-1.

The term "glucagon" refers to a 29 amino acid peptide hormone that is produced by alpha cells in the pancreas and that interacts with GCGR. The amino acid sequence of glucagon is HSQGTFTSDYSKYLDSR-RAQDFVQWLMNT-OH (SEQ ID NO: 140).

As used herein, the term "glucagon analog" implies structural similarity to glucagon and the term "glucagon receptor agonist" describes a compound that is, functionally, an agonist of the glucagon receptor. The terms "glucagon analog" and "glucagon receptor agonist" are used alternatively to describe the peptides disclosed herein.

Glucagon originates from the 158 amino acid pre-pro-glucagon peptide which also acts as a precursor for the peptide hormones GLP-1, GLP-2, oxyntomodulin, glicentin, and glicentin-related pancreatic polypeptide via tissue-specific processing. Glucagon corresponds to the amino acid residues 33 to 61 of the precursor peptide and acts via interaction with a class B seven transmembrane G protein-coupled receptor located primarily in the liver. Immunostaining has also indicated the presence of glucagon receptors in the kidneys, gastrointestinal tract, heart, spleen, brain, adipocytes, and lymphoblasts. In response to low blood glucose levels, glucagon is released and stimulates hepatic glucose output via glycogenolysis and gluconeogenesis. Glucagon acts as a counter to the glucose-lowering effect of insulin and tight regulation via a feed-back system between the two hormones allows for effective glucose homeostasis.

In addition to its effect on blood glucose levels, glucagon is also known to increase energy expenditure and thermogenesis. Increased signaling has a direct effect on the regulation of triglycerides, free fatty acids, apolipoprotein, and bile acid metabolism. Current therapeutic uses for glucagon have primarily focused on its use as a rescue agent for hypoglycemic episodes. However, recent work has taken advantage of the hormone's ability to affect energy balance and lipid metabolism resulting in potential treatments for various metabolic disorders.

The poor solubility of glucagon (<1.0 mg/ml in aqueous or saline buffer) has prevented the opportunity for chronic study via continuous infusion. A summary of the solubility and the pEC50 value of glucagon with respect to glucagon receptor (GLUR) and GLP1, as determined in cAMP assays, is shown in Table 1 below:

The term "dispersed" as used herein refers to dissolving, dispersing, suspending, or otherwise distributing a compound, for example, a drug particle formulation, in a suspension vehicle.

The phrase "chemically stable" as used herein refers to formation in a formulation of an acceptable percentage of degradation products produced over a defined period of time by chemical pathways, such as deamidation (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \quad \text{(Equation 1)}$$

where F/A=shear stress (force per unit area),
$\mu$=a proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometry performed under selected conditions (for example, a temperature of about 37° C.). Other methods for the determination of viscosity include, measurement of a kinematic viscosity using viscometers, for example, a Cannon-Fenske viscometer, a Ubbelohde viscometer for the Cannon-Fenske opaque solution, or a Ostwald viscometer. Generally, suspension vehicles of the present invention have a viscosity sufficient to prevent a particle formulation suspended therein from settling during storage and use in a method of delivery, for example, in an implantable, drug delivery device.

TABLE 1

| | Sequence | GLUR pEC50 (cAMP) | GLP1 pEC50 (cAMP) | Solubility in Aqueous |
|---|---|---|---|---|
| Glucagon | HSQGTFTSDYSKYLDSRRAQDFVQWLMNT-OH (SEQ ID NO: 140) | 10 | 9.9 | 0.03-10 µg/ml |

The term "vehicle" as used herein refers to a medium used to carry a compound, e.g., a drug or a particle containing a drug. Vehicles of the present invention typically comprise components such as polymers and solvents. The suspension vehicles of the present invention typically comprise solvents and polymers that are used to prepare suspension formulations further comprising drug particle formulations.

The phrase "phase separation" as used herein refers to the formation of multiple phases (e.g., liquid and gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "non-aqueous" as used herein refers to an overall moisture content, for example, of a suspension formulation, typically of less than or equal to about 10 wt %, for example, less than or equal to about 7 wt %, less than or equal to about 5 wt %, and/or less than about 4 wt %. Also, a particle formulation of the present invention comprises less than about 10 wt %, for example, less than about 5 wt %, residual moisture.

The term "subject" as used herein refers to any member of the subphylum Chordata, including, without limitation, humans and other primates, including non-human primates such as rhesus macaques and other monkey species and chimpanzees and other ape species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age or gender. Thus, both adult and newborn individuals are intended to be covered.

The term "osmotic delivery device" as used herein typically refers to a device used for delivery of a drug (e.g., an isolated glucagon-specific agonist polypeptide) to a subject, wherein the device comprises, for example, a reservoir (made, e.g., from a titanium alloy) having a lumen that contains a suspension formulation comprising a drug (e.g., an isolated glucagon-specific agonist polypeptide) and an osmotic agent formulation. A piston assembly positioned in the lumen isolates the suspension formulation from the osmotic agent formulation. A semi-permeable membrane is positioned at a first distal end of the reservoir adjacent the osmotic agent formulation and a diffusion moderator (which defines a delivery orifice through which the suspension formulation exits the device) is positioned at a second distal end of the reservoir adjacent the suspension formulation. Typically, the osmotic delivery device is implanted within the subject, for example, subdermally or subcutaneously (e.g., in the inside, outside, or back of the upper arm and in the abdominal area). An exemplary osmotic delivery device is the DUROS® (ALZA Corporation, Mountain View, Calif.) delivery device. Examples of terms synonymous to "osmotic delivery device" include but are not limited to "osmotic drug delivery device", "osmotic drug delivery system", "osmotic device", "osmotic delivery device", "osmotic delivery system", "osmotic pump", "implantable drug delivery device", "drug delivery system", "drug delivery device", "implantable osmotic pump", "implantable drug delivery system", and "implantable delivery system". Other terms for "osmotic delivery device" are known in the art.

The term "continuous delivery" as used herein typically refers to a substantially continuous release of drug from an osmotic delivery device and into tissues near the implantation site, e.g., subdermal and subcutaneous tissues. For example, an osmotic delivery device releases drug essentially at a predetermined rate based on the principle of osmosis. Extracellular fluid enters the osmotic delivery device through the semi-permeable membrane directly into the osmotic engine that expands to drive the piston at a slow and consistent rate of travel. Movement of the piston forces the drug formulation to be released through the orifice of the diffusion moderator. Thus release of the drug from the osmotic delivery device is at a slow, controlled, consistent rate.

The term "substantial steady-state delivery" as used herein typically refers to delivery of a drug at or near a target concentration over a defined period of time, wherein the amount of the drug being delivered from an osmotic delivery device is substantially zero-order delivery. Substantial zero-order delivery of an active agent (e.g., an isolated glucagon-specific analog) means that the rate of drug delivered is constant and is independent of the drug available in the delivery system; for example, for zero-order delivery, if the rate of drug delivered is graphed against time and a line is fitted to the data the line has a slope of approximately zero, as determined by standard methods (e.g., linear regression).

The phrase "drug half-life" as used herein refers how long it takes a drug to be eliminated from blood plasma by one half of its concentration. A drug's half-life is usually measured by monitoring how a drug degrades when it is administered via injection or intravenously. A drug is usually detected using, for example, a radioimmunoassay (RIA), a chromatographic method, an electrochemiluminescent (ECL) assay, an enzyme linked immunosorbent assay (ELISA) or an immunoenzymatic sandwich assay (IEMA).

The terms "µg" and "mcg" and "ug" are understood to mean "micrograms". Similarly, the terms "µl" and "uL" are understood to mean "microliter", and the terms "µM" and "uM" are understood to mean "micromolar".

The term "serum" is meant to mean any blood product from which a substance can be detected. Thus, the term serum includes at least whole blood, serum, and plasma. For example, "an amount of [a substance] in a subject's serum" would cover "an amount of [the substance] in a subject's plasma".

Baseline is defined as the last assessment on or before the day of the initial placement of an osmotic delivery device (containing drug or placebo).

2.0.0 General Overview of the Invention

Before describing the present invention in detail, it is to be understood that this invention is not limited to particular types of drug delivery devices, particular sources of drugs, particular solvents, particular polymers, and the like, as use of such particulars may be selected in view of the teachings of the present specification. It is also to be understood that the terminology used herein is for the purpose of describing particular embodiments of the invention only, and is not intended to be limiting.

In a first aspect, the present invention relates to isolated polypeptides that are glucagon-receptor selective analogs and peptide derivatives thereof. In some embodiments, an isolated polypeptide of the disclosure is a selective glucagon receptor agonist. In some embodiments, an isolated polypeptide of the disclosure binds to a glucagon receptor (GCGR).

In some embodiments, an isolated polypeptide of the disclosure comprises a modified amino acid sequence based on the amino acid sequence of human glucagon: HSQGTFTSDYSKYLDSRRAQDFVQWLMNT-OH (SEQ ID NO: 140), where the modified amino acid sequence includes at least one amino acid substitution, at least two amino acid substitutions, at least three amino acid substitutions, at least four amino acid substitutions, at least five amino acid substitutions, at least six amino acid substitutions, at least seven amino acid substitutions, at least eight amino acid substitutions, at least nine amino acid substitutions, at least 10 amino acid substitutions, at least 11 amino acid substitutions, at least 12 amino acid substitutions, at least 13 amino acid substitutions, at least 14 amino acid substitutions, at least 15 amino acid substitutions, at least 16 amino acid substitutions, at least 17 amino acid substitutions, at least 18 amino acid substitutions, at least 19 amino acid substitutions, at least 20 amino acid substitutions, at least 21 amino acid substitutions, at least 22 amino acid substitutions, at least 23 amino acid substitutions, at least 24 amino acid substitutions, at least 25 amino acid substitutions, at least 26 amino acid substitutions, at least 27 amino acid substitutions, at least 28 amino acid substitutions, and/or at least 29 amino acid substitutions, provided that the isolated polypeptide having a modified amino acid sequence retains the ability to function as a selective glucagon analog.

In some embodiments, an isolated polypeptide of the disclosure comprises a modified amino acid sequence based on the amino acid sequence of human glucagon: HSQGTFTSDYSKYLDSRRAQDFVQWLMNT-OH (SEQ ID NO: 140), where the modified amino acid sequence includes at least one amino acid substitution, at least two amino acid substitutions, at least three amino acid substitutions, at least four amino acid substitutions, at least five amino acid substitutions, at least six amino acid substitutions, at least seven amino acid substitutions, at least eight amino acid substitutions, at least nine amino acid substitutions, at least 10 amino acid substitutions, at least 11 amino acid substitutions, at least 12 amino acid substitutions, at least 13 amino acid substitutions, at least 14 amino acid substitutions, at least 15 amino acid substitutions, or at least 16 amino acid substitutions, wherein the amino acid substitution(s) is selected from the group consisting of:
  (i) an amino acid substitution at position 1 selected from the group consisting of Y and W;
  (ii) an amino acid substitution at position 2 selected from the group consisting of G and T;
  (iii) an amino acid substitution at position 3 with H;
  (iv) an amino acid substitution at position 10 with H;
  (v) an amino acid substitution at position 11 with T;
  (vi) an amino acid substitution at position 12 with R;
  (vii) an amino acid substitution at position 13 selected from the group consisting of L and W;
  (viii) an amino acid substitution at position 15 with E;
  (ix) an amino acid substitution at position 16 selected from the group consisting of 2-Aminoisobutyric acid (Aib), A, E, I, K, L, and Q;
  (x) an amino acid substitution at position 17 selected from the group consisting of A, E, K, S, and T;
  (xi) an amino acid substitution at position 18 selected from the group consisting of A, E, L, and T;
  (xii) an amino acid substitution at position 21 with E;
  (xiii) an amino acid substitution at position 23 with T;
  (xiv) an amino acid substitution at position 24 selected from the group consisting of 2-Aminoisobutyric acid (Aib), K, and L;
  (xv) an amino acid substitution at position 25 with H;
  (xvi) an amino acid substitution at position 30 with a Z-tail selected from the group consisting of EEPSSGAPPPS-OH (SEQ ID NO: 4); EPSSGAPPPS-OH (SEQ ID NO: 5); GAPPPS-OH (SEQ ID NO: 6); GGPSSGAPPPS-OH (SEQ ID NO: 7); GPSSGAPPPS-OH (SEQ ID NO: 8); KRNKNPPPS-OH (SEQ ID NO: 9); KRNKNPPS-OH (SEQ ID NO: 10); KRNKPPIA-OH (SEQ ID NO: 11); KRNKPPPA-OH (SEQ ID NO: 150); KRNKPPPS-OH (SEQ ID NO: 12); KSSGKPPPS-OH (SEQ ID NO: 13); PESGAPPPS-OH (SEQ ID NO: 14); PKSGAPPPS-OH (SEQ ID NO: 15); PKSKAPPPS-NH$_2$ (SEQ ID NO: 16); PKSKAPPPS-OH (SEQ ID NO: 17); PKSKEPPPS-NH$_2$ (SEQ ID NO: 18); PKSKEPPPS-OH (SEQ ID NO: 19); PKSKQPPPS-OH (SEQ ID NO: 20); PKSKSPPPS-NH$_2$ (SEQ ID NO: 21); PKSK-SPPPS-OH (SEQ ID NO: 22); PRNKNNPPS-OH (SEQ ID NO: 23); PSKGAPPPS-OH (SEQ ID NO: 24); PSSGAPPPSE-OH (SEQ ID NO: 25); PSSGAPPPS-NH$_2$ (SEQ ID NO: 26); PSSGAPPPS-OH (SEQ ID NO: 27); PSSGAPPPSS-OH (SEQ ID NO: 28); PSSGEPPPS-OH (SEQ ID NO: 29); PSSGKKPPS-OH (SEQ ID NO: 30); PSSGKPPPS-NH$_2$ (SEQ ID NO: 31); PSSGKPPPS-OH (SEQ ID NO: 32); PSSGSPPPS-OH (SEQ ID NO: 33); PSSKAPPPS-OH (SEQ ID NO: 34); PSSKEPPPS-OH (SEQ ID NO: 35); PSSKGAPPPS-OH (SEQ ID NO: 36); PSSKQPPPS-OH (SEQ ID NO: 37); PSSK-SPPPS-OH (SEQ ID NO: 38); SGAPPPS-OH (SEQ ID NO: 39); and SSGAPPPS-OH(SEQ ID NO: 40); and
  (xvii) combinations thereof,
  provided that the isolated polypeptide having a modified amino acid sequence retains the ability to function as a selective glucagon receptor agonist.

In some embodiments, an isolated polypeptide of the disclosure comprises an amino acid sequence selected from the group consisting of amino acid sequences represented by the consensus sequence of SEQ ID NO: 1:

```
                                                (SEQ ID NO: 1)
X₁X₂X₃GTFTSDX₁₀X₁₁X₁₂X₁₃LX₁₅X₁₆X₁₇X₁₈AQEFX₂₃X₂₄X₂₅LEDE-Z-
tail-(OH/NH₂),
``` wherein:
  $X_1$ is Y or W;
  $X_2$ is S, G or T;
  $X_3$ is Q or H;
  $X_{10}$ is Y or H;
  $X_{11}$ is S or T;
  $X_{12}$ is K or R;
  $X_{13}$ is Y, L or W;
  $X_{15}$ is D or E;
  $X_{16}$ is S, 2-Aminoisobutyric acid (Aib), A, E, L, Q, K, or I;
  $X_{17}$ is K, E, S, T, or A;
  $X_{18}$ is A, R, S, E, L, T or Y;
  $X_{23}$ is T or V;
  $X_{24}$ is K, I, L, or Aib;
  $X_{25}$ is H or W; and
  Z-tail is absent; or is selected from the group consisting of EEPSSGAPPPS-OH (SEQ ID NO: 4); EPSSGAPPPS-OH (SEQ ID NO: 5); GAPPPS-OH (SEQ ID NO: 6); GGPSSGAPPPS-OH (SEQ ID NO: 7); GPSSGAPPPS-OH (SEQ ID NO: 8); KRNKNPPPS-OH (SEQ ID NO: 9); KRNKNPPS-OH (SEQ ID NO: 10); KRNKPPIA-OH (SEQ ID NO: 11); KRNKPPPA-OH (SEQ ID NO: 150); KRNKPPPS-OH (SEQ ID NO: 12); KSSGKPPPS-OH (SEQ ID NO: 13); PESGAPPPS-OH (SEQ ID NO: 14); PKSGAPPPS-OH (SEQ ID NO: 15); PKSKAPPPS-NH$_2$ (SEQ ID NO: 16); PKSKAPPPS-OH (SEQ ID NO: 17); PKSKEPPPS-NH$_2$ (SEQ ID NO: 18); PKSKEPPPS-OH (SEQ ID NO: 19); PKSKQPPPS-OH (SEQ ID NO: 20); PKSKSPPPS-NH$_2$ (SEQ ID NO: 21); PKSK-SPPPS-OH (SEQ ID NO: 22); PRNKNNPPS-OH (SEQ ID NO: 23); PSKGAPPPS-OH (SEQ ID NO: 24); PSSGAPPPSE-OH (SEQ ID NO: 25); PSSGAPPPS-NH$_2$ (SEQ ID NO: 26); PSSGAPPPS-OH (SEQ ID NO: 27); PSSGAPPPSS-OH (SEQ ID NO: 28); PSSGEPPPS-OH (SEQ ID NO: 29); PSSGKKPPS-OH (SEQ ID NO: 30); PSSGKPPPS-NH$_2$ (SEQ ID NO: 31); PSSGKPPPS-OH (SEQ ID NO: 32); PSSGSPPPS-OH (SEQ ID NO: 33); PSSKAPPPS-OH (SEQ ID NO: 34); PSSKEPPPS-OH (SEQ ID NO: 35); PSSKGAPPPS-OH (SEQ ID NO: 36); PSSKQPPPS-OH (SEQ ID NO: 37); PSSK-SPPPS-OH (SEQ ID NO: 38); SGAPPPS-OH (SEQ ID NO: 39); and SSGAPPPS-OH(SEQ ID NO: 40).

In some embodiments, an isolated polypeptide of the disclosure comprises an amino acid sequence selected from the group consisting of amino acid sequences represented by the consensus sequence of SEQ ID NO: 2:

(SEQ ID NO: 2)
X₁X₂X₃GTFTSDX₁₀X₁₁X₁₂X₁₃LX₁₅X₁₆X₁₇X₁₈AQEFVX₂₄WLEDE-Z-tail-(OH/NH₂), wherein:
X₁ is Y or W;
X₂ is S or G;
X₃ is Q or H;
X₁₀ is Y or H;
X₁₁ is S or T;
X₁₂ is K or R;
X₁₃ is Y, L or W;
X₁₅ is D or E;
X₁₆ is 2-Aminoisobutyric acid (Aib), A, or S;
X₁₇ is A or K;
X₁₈ is R, S, L, or Y;
X₂₄ is K, I, or Aib;
X₂₅ is H or W; and
Z-tail is absent or is selected from the group consisting of PSSGAPPPS-NH₂ (SEQ ID NO: 26); PSSGAPPPS-OH (SEQ ID NO: 27); and PKSKSPPPS-NH₂ (SEQ ID NO: 21).

In some embodiments, an isolated polypeptide of the disclosure comprises an amino acid sequence selected from the group consisting of amino acid sequences represented by the consensus sequence of SEQ ID NO: 3:

(SEQ ID NO: 3)
YSX₃GTFTSDYSKYLDX₁₆X₁₇X₁₈AQEFVX₂₄WLEDE-Z-tail-(OH/NH₂), wherein:
X₃ is Q or H;
X₁₆ is 2-Aminoisobutyric acid (Aib) or A;
X₁₇ is A or K;
X₁₈ is R, S, or Y;
X₂₄ is K or Aib;
Z-tail is selected from the group consisting of PSSGAPPPS-OH (SEQ ID NO: 27) and PKSKSPPPS-NH₂ (SEQ ID NO: 21).

In some embodiments, an isolated polypeptide of the disclosure comprises an amino acid sequence selected from the group consisting of
YSHGTFTSDYSKYLD(Aib)KYAQEFV(Aib)WLEDEPSSGAPPPS-OH (SEQ ID NO: 41), which is also referred to herein as Compound A1;
YSHGTFTSDYSKYLD(Aib)KSAQEFV(Aib)WLEDEPSSGAPPPS-OH (SEQ ID NO: 42), which is also referred to herein as Compound A2;
YSQGTFTSDYSKYLDAARAQEFVKWLEDEPKSKSPPPS-NH₂ (SEQ ID NO: 43), which is also referred to herein as Compound A3;
YSHGTFTSDYSKYLD(Aib)KRAQEFVIWLEDEPSSGAPPPS-OH (SEQ ID NO: 44), which is also referred to herein as Compound A4;
YSHGTFTSDYSKYLDSARAQEFVKWLEDEPSSGAPPPS-NH₂ (SEQ ID NO: 45), which is also referred to herein as Compound A5; and
WSQGTFTSDYSKYLD(Aib)KRAQEFV(Aib)WLEDEPSSGAPPPS-OH (SEQ ID NO: 46), which is also referred to herein as Compound A6.

In some embodiments, an isolated polypeptide of the disclosure comprises the amino acid sequence YSHGTFTSDYSKYLD(Aib)KYAQEFV(Aib)WLEDEPSSGAPPPS-OH (SEQ ID NO: 41). In some embodiments, an isolated polypeptide of the disclosure comprises the amino acid sequence YSHGTFTSDYSKYLD(Aib)KSAQEFV(Aib)WLEDEPSSGAPPPS-OH (SEQ ID NO: 42). In some embodiments, an isolated polypeptide of the disclosure comprises the amino acid sequence YSQGTFTSDYSKYLDAARAQEFVKWLEDEPKSKSPPPS-NH₂ (SEQ ID NO: 43). In some embodiments, an isolated polypeptide of the disclosure comprises the amino acid sequence YSHGTFTSDYSKYLD(Aib)KRAQEFVIWLEDEPSSGAPPPS-OH (SEQ ID NO: 44). In some embodiments, an isolated polypeptide of the disclosure comprises the amino acid sequence YSHGTFTSDYSKYLDSARAQEFVKWLEDEPSSGAPPPS-NH₂ (SEQ ID NO: 45). In some embodiments, an isolated polypeptide of the disclosure comprises the amino acid sequence WSQGTFTSDYSKYLD(Aib)KRAQEFV(Aib)WLEDEPSSGAPPPS-OH (SEQ ID NO: 46).

In some embodiments, an isolated polypeptide of the disclosure consists of the amino acid sequence YSHGTFTSDYSKYLD(Aib)KYAQEFV(Aib)WLEDEPSSGAPPPS-OH (SEQ ID NO: 41). In some embodiments, an isolated polypeptide of the disclosure consists of the amino acid sequence YSHGTFTSDYSKYLD(Aib)KSAQEFV(Aib)WLEDEPSSGAPPPS-OH (SEQ ID NO: 42). In some embodiments, an isolated polypeptide of the disclosure consists of the amino acid sequence YSQGTFTSDYSKYLDAARAQEFVKWLEDEPKSKSPPPS-NH₂ (SEQ ID NO: 43). In some embodiments, an isolated polypeptide of the disclosure consists of the amino acid sequence YSHGTFTSDYSKYLD(Aib)KRAQEFVIWLEDEPSSGAPPPS-OH (SEQ ID NO: 44). In some embodiments, an isolated polypeptide of the disclosure consists of the amino acid sequence YSHGTFTSDYSKYLDSARAQEFVKWLEDEPSSGAPPPS-NH₂ (SEQ ID NO: 45). In some embodiments, an isolated polypeptide of the disclosure consists of the amino acid sequence WSQGTFTSDYSKYLD(Aib)KRAQEFV(Aib)WLEDEPSSGAPPPS-OH (SEQ ID NO: 46).

In some embodiments, an isolated polypeptide of the disclosure comprises an amino acid sequence selected from the group consisting of
YSHGTFTSDYSKYLD(Aib)ARAQEFV(Aib)WLEDEPSSGAPPPS-OH (SEQ ID NO: 47); which is also referred to herein as Compound A7;
YSHGTFTSDYSKYLD(Aib)KRAQEFV(Aib)WLEDEPSSGAPPPS-NH₂ (SEQ ID NO: 48); which is also referred to herein as Compound A8;
YSHGTFTSDYSKYLD(Aib)KRAQEFV(Aib)WLEEEPSSGAPPPS-OH (SEQ ID NO: 49); which is also referred to herein as Compound A9;
YSHGTFTSDYSKYLD(Aib)KRAQEFV(Aib)WLEDEEPSSGAPPPS-OH (SEQ ID NO: 50); which is also referred to herein as Compound A10;
YSHGTFTSDYSKYLD(Aib)KRAQEFV(Aib)WLEDEEPSSGAPPPS-OH (SEQ ID NO: 51); which is also referred to herein as Compound A11;
YSHGTFTSDYSKYLD(Aib)KRAQEFV(Aib)WLEDEGAPPPS-OH (SEQ ID NO: 52); which is also referred to herein as Compound A12;
YSHGTFTSDYSKYLD(Aib)KRAQEFV(Aib)WLEDESGAPPPS-OH (SEQ ID NO: 53); which is also referred to herein as Compound A13;
YSHGTFTSDYSKYLD(Aib)KRAQEFV(Aib)WLEDESSGAPPPS-OH (SEQ ID NO: 54); which is also referred to herein as Compound A14;

YSHGTFTSDYSKYLD(Aib)SRAQEFV(Aib)
WLEDEPSSGAPPPS-OH (SEQ ID NO: 55); which is
also referred to herein as Compound A15;
YSHGTFTSDYSKYLD(Aib)TRAQEFV(Aib)
WLEDEPSSGAPPPS-OH (SEQ ID NO: 56); which is
also referred to herein as Compound A16;
YSHGTFTSDYSKYLD(Aib)ERAQEFV(Aib)
WLEDEPSSGAPPPS-OH (SEQ ID NO: 57); which is
also referred to herein as Compound A17;
YSHGTFTSDYSKWLD(Aib)ARAQEFV(Aib)
WLEDEPSSGAPPPS-OH (SEQ ID NO: 58); which is
also referred to herein as Compound A18;
YSHGTFTSDYSKWLD(Aib)SRAQEFV(Aib)
WLEDEPSSGAPPPS-OH (SEQ ID NO: 59); which is
also referred to herein as Compound A19;
YSHGTFTSDYSKYLD(Aib)KRAQEFV(Aib)
WLEDEPSSGKPPPS-OH (SEQ ID NO: 60); which is
also referred to herein as Compound A20;
YSHGTFTSDYSKYLD(Aib)KRAQEFV(Aib)
WLEDEPSSGEPPPS-OH (SEQ ID NO: 61); which is
also referred to herein as Compound A21;
YSHGTFTSDYSKYLD(Aib)KRAQEFV(Aib)
WLEDEPSSGSPPPS-OH (SEQ ID NO: 62); which is
also referred to herein as Compound A22;
YSHGTFTSDYSKYLD(Aib)KRAQEFV(Aib)
WLEDEPSSKAPPPS-OH (SEQ ID NO: 63); which is
also referred to herein as Compound A23;
YSHGTFTSDYSKYLD(Aib)KRAQEFV(Aib)
WLEDEPSSKGAPPPS-OH (SEQ ID NO: 64); which
is also referred to herein as Compound A24;
YSHGTFTSDYSKYLD(Aib)KRAQEFV(Aib)
WLEDEPSSGAPPPSS-OH (SEQ ID NO: 65); which
is also referred to herein as Compound A25;
YSHGTFTSDYSKYLD(Aib)KRAQEFV(Aib)
WLEDEPSSGAPPPSE-OH (SEQ ID NO: 66); which
is also referred to herein as Compound A26;
YSHGTFTSDYSKYLD(Aib)KRAQEFV(Aib)WLEDE-
GGPSSGAPPPS-OH (SEQ ID NO: 67); which is also
referred to herein as Compound A27;
YSHGTFTSDYSKYLD(Aib)KRAQEFV(Aib)WLEDE-
GPSSGAPPPS-OH (SEQ ID NO: 68); which is also
referred to herein as Compound A28;
YSHGTFTSDYSKYLD(Aib)KRAQEFV(Aib)
WLEDEPKSGAPPPS-OH (SEQ ID NO: 69); which is
also referred to herein as Compound A29;
YSHGTFTSDYSKYLD(Aib)KRAQEFV(Aib)
WLEDEPSKGAPPPS-OH (SEQ ID NO: 70); which is
also referred to herein as Compound A30;
YSHGTFTSDYSKYLD(Aib)KRAQEFV(Aib)
WLEDEPESGAPPPS-OH (SEQ ID NO: 71); which is
also referred to herein as Compound A31;
YTHGTFTSDYSKWLD(Aib)KRAQEFV(Aib)
WLEDEPSSGAPPPS-OH (SEQ ID NO: 72); which is
also referred to herein as Compound A32;
YSHGTFTSDHSKWLD(Aib)KRAQEFV(Aib)
WLEDEPSSGAPPPS-OH (SEQ ID NO: 73); which is
also referred to herein as Compound A33;
YTHGTFTSDHSKWLD(Aib)KRAQEFV(Aib)
WLEDEPSSGAPPPS-OH (SEQ ID NO: 74); which is
also referred to herein as Compound A34;
YTHGTFTSDYSKWLD(Aib)ARAQEFV(Aib)
WLEDEPSSGAPPPS-OH (SEQ ID NO: 75); which is
also referred to herein as Compound A35;
YSHGTFTSDHSKWLD(Aib)ARAQEFV(Aib)
WLEDEPSSGAPPPS-OH (SEQ ID NO: 76); which is
also referred to herein as Compound A36;
YSHGTFTSDYSKYLDSARA-
QEFVKWLEDEPSSGAPPPS-OH (SEQ ID NO: 77);
which is also referred to herein as Compound A37;
YSHGTFTSDYSKWLDSARA-
QEFVKWLEDEPSSGAPPPS-OH (SEQ ID NO: 78);
which is also referred to herein as Compound A38;
YTHGTFTSDYSKWLDSARA-
QEFVKWLEDEPSSGAPPPS-OH (SEQ ID NO: 79);
which is also referred to herein as Compound A39;
YSHGTFTSDHSKWLDSARA-
QEFVKWLEDEPSSGAPPPS-OH (SEQ ID NO: 80);
which is also referred to herein as Compound A40;
YTHGTFTSDHSKWLDEAR-
AQEFVKWLEDEPSSGAPPPS-OH (SEQ ID NO:
81); which is also referred to herein as Compound A41;
YTHGTFTSDYSKWLDSK-
RAQEFVKWLEDEPSSGAPPPS-OH (SEQ ID NO:
82); which is also referred to herein as Compound A42;
YSHGTFTSDYSKYLDKARA-
QEFVKWLEDEPSSGAPPPS-OH (SEQ ID NO: 83);
which is also referred to herein as Compound A43;
YSHGTFTSDYSKY-
LDQARAQEFVKWLEDEPSSGAPPPS-OH (SEQ ID
NO: 84); which is also referred to herein as Compound
A44;
YSHGTFTSDYSKYLD(Aib)KRAQEFV(Aib)
WLEDEKRNKPPPA-OH (SEQ ID NO: 85); which is
also referred to herein as Compound A45;
YSHGTFTSDYSKYLD(Aib)KRAQEFV(Aib)
WLEDEKRNKPPIA-OH (SEQ ID NO: 86); which is
also referred to herein as Compound A46;
YSHGTFTSDYSKYLD(Aib)KRAQEFV(Aib)
WLEDEKRNKNPPS-OH (SEQ ID NO: 87); which is
also referred to herein as Compound A47;
YSHGTFTSDYSKYLD(Aib)KRAQEFV(Aib)
WLEDEKRNKNPPPS-OH (SEQ ID NO: 88); which is
also referred to herein as Compound A48;
YSHGTFTSDYSKYLD(Aib)KRAQEFV(Aib)
WLEDEPRNKNNPPS-OH (SEQ ID NO: 89); which is
also referred to herein as Compound A49;
YSHGTFTSDYSKYLD(Aib)KRAQEFV(Aib)
WLEDEKRNKPPPS-OH (SEQ ID NO: 90); which is
also referred to herein as Compound A50;
YSHGTFTSDYSKYLDLKRAQEFV(Aib)
WLEDEPSSGAPPPS-OH (SEQ ID NO: 91); which is
also referred to herein as Compound A51;
YSHGTFTSDYSKYLDIKRAQEFV(Aib)
WLEDEPSSGAPPPS-OH (SEQ ID NO: 92); which is
also referred to herein as Compound A52;
YSHGTFTSDYSKYLD(Aib)
KRAQEFVLWLEDEPSSGAPPPS-OH (SEQ ID NO:
93); which is also referred to herein as Compound A53;
YSHGTFTSDYSKYLD(Aib)KRAQEFV(Aib)
WLEDEPSSKEPPPS-OH (SEQ ID NO: 94); which is
also referred to herein as Compound A54;
YSHGTFTSDYSKYLD(Aib)KRAQEFV(Aib)
WLEDEPSSKSPPPS-OH (SEQ ID NO: 95); which is
also referred to herein as Compound A55;
YSHGTFTSDYSKYLD(Aib)KRAQEFV(Aib)
WLEDEPKSKAPPPS-OH (SEQ ID NO: 96); which is
also referred to herein as Compound A56;
YSHGTFTSDYSKYLD(Aib)KRAQEFV(Aib)
WLEDEPKSKQPPPS-OH (SEQ ID NO: 97); which is
also referred to herein as Compound A57;
YSHGTFTSDYSKYLD(Aib)KRAQEFV(Aib)
WLEDEPKSKSPPPS-OH (SEQ ID NO: 98); which is
also referred to herein as Compound A58;

YSHGTFTSDYSKYLD(Aib)KRAQEFV(Aib)WLEDEPSSKQPPPS-OH (SEQ ID NO: 99); which is also referred to herein as Compound A59;
YTHGTFTSDYSKYLD(Aib)KRAQEFV(Aib)WLEDEPSSGKPPPS-OH (SEQ ID NO: 100); which is also referred to herein as Compound A60;
YSHGTFTSDYSKYLDSARAQEFVKWLEDEPSSGKPPPS-OH (SEQ ID NO: 101); which is also referred to herein as Compound A61;
YTHGTFTSDYSKYLD(Aib)KRAQEFV(Aib)WLEDEPSSGAPPPS-OH (SEQ ID NO: 102); which is also referred to herein as Compound A62;
YTHGTFTSDYSKYLDSARAQEFVKWLEDEPSSGAPPPS-OH (SEQ ID NO: 103); which is also referred to herein as Compound A63;
YTHGTFTSDYSKYLD(Aib)ARAQEFV(Aib)WLEDEPSSGAPPPS-OH (SEQ ID NO: 104); which is also referred to herein as Compound A64;
YSHGTFTSDYSKYLD(Aib)KRAQEFV(Aib)WLEDEPKSKEPPPS-NH$_2$ (SEQ ID NO: 105); which is also referred to herein as Compound A65;
YSHGTFTSDYSKYLD(Aib)KRAQEFV(Aib)WLEDEPKSKSPPPS-NH$_2$ (SEQ ID NO: 106); which is also referred to herein as Compound A66;
YSHGTFTSDYSKYLD(Aib)ARAQEFV(Aib)WLEDEPKSKSPPPS-NH$_2$ (SEQ ID NO: 107); which is also referred to herein as Compound A67;
YSHGTFTSDYSKYLD(Aib)ARAQEFV(Aib)WLEDEPKSKEPPPS-NH$_2$ (SEQ ID NO: 108); which is also referred to herein as Compound A68;
YSHGTFTSDYSKYLDSARAQEFVKWLEDEPKSKEPPPS-OH (SEQ ID NO: 109); which is also referred to herein as Compound A69;
YSHGTFTSDYSKYLDSARAQEFVKWLEDEPKSKSPPPS-OH (SEQ ID NO: 110); which is also referred to herein as Compound A70;
YSHGTFTSDYSKYLDSARAQEFVKWLEDEPKSKAPPPS-OH (SEQ ID NO: 111); which is also referred to herein as Compound A71;
YSHGTFTSDYSKYLDSARAQEFVKWLEDEPKSKEPPPS-NH$_2$ (SEQ ID NO: 112); which is also referred to herein as Compound A72;
YSHGTFTSDYSKYLDSARAQEFVKWLEDEPKSKSPPPS-NH$_2$ (SEQ ID NO: 113); which is also referred to herein as Compound A73;
YSHGTFTSDYSKYLDSARAQEFVKWLEDEPKSKAPPPS-NH$_2$ (SEQ ID NO: 114); which is also referred to herein as Compound A74;
WSHGTFTSDYSKYLD(Aib)KRAQEFV(Aib)WLEDEPSSGAPPPS-OH (SEQ ID NO: 115); which is also referred to herein as Compound A75;
YSHGTFTSDYSKYLD(Aib)KAAQEFV(Aib)WLEDEPSSGAPPPS-OH (SEQ ID NO: 116); which is also referred to herein as Compound A76;
YSHGTFTSDYSKYLD(Aib)KTAQEFV(Aib)WLEDEPSSGAPPPS-OH (SEQ ID NO: 117); which is also referred to herein as Compound A77;
YSHGTFTSDYSKYLD(Aib)KLAQEFV(Aib)WLEDEPSSGAPPPS-OH (SEQ ID NO: 118); which is also referred to herein as Compound A78;
YSHGTFTSDYSKYLD(Aib)KEAQEFV(Aib)WLEDEPSSGAPPPS-OH (SEQ ID NO: 119); which is also referred to herein as Compound A79;
YSHGTFTSDYSKYLDAARAQEFVKWLEDEPKSKSPPPS-NH$_2$ (SEQ ID NO: 120); which is also referred to herein as Compound A80;
YSQGTFTSDYSKYLDSARAQEFVKWLEDEPKSKSPPPS-OH (SEQ ID NO: 121); which is also referred to herein as Compound A81;
YSQGTFTSDYSKYLDSARAQEFVKWLEDEPKSKAPPPS-OH (SEQ ID NO: 122); which is also referred to herein as Compound A82;
YSHGTFTSDYSKYLDSARAQEFTKWLEDEPKSKSPPPS-OH (SEQ ID NO: 123); which is also referred to herein as Compound A83;
YSHGTFTSDYSKYLDSARAQEFVKHLEDEPKSKSPPPS-OH (SEQ ID NO: 124); which is also referred to herein as Compound A84;
YSHGTFTSDYSKYLD(Aib)KRAQEFV(Aib)WLEDEPSSGKPPPS-NH$_2$ (SEQ ID NO: 125); which is also referred to herein as Compound A85;
YSQGTFTSDYSKYLD(Aib)KRAQEFV(Aib)WLEDEPSSGKPPPS-OH (SEQ ID NO: 126); which is also referred to herein as Compound A86;
YSHGTFTSDYSKYLD(Aib)KRAQEFV(Aib)WLEDEKSSGKPPPS-OH (SEQ ID NO: 127); which is also referred to herein as Compound A87;
YSHGTFTSDYSKYLD(Aib)KRAQEFV(Aib)WLEDEPSSGKKPPS-OH (SEQ ID NO: 128); which is also referred to herein as Compound A88;
YSHGTFTSDYSKYLD(Aib)KRAQEFV(Aib)HLEDEPSSGKPPPS-OH (SEQ ID NO: 129); which is also referred to herein as Compound A89;
YSHGTFTSDYSKYLD(Aib)KAAQEFV(Aib)WLEDEPSSGKPPPS-OH (SEQ ID NO: 130); which is also referred to herein as Compound A90;
WSQGTFTSDYSKYLD(Aib)KRAQEFV(Aib)WLEDEPSSGKPPPS-OH (SEQ ID NO: 131); which is also referred to herein as Compound A91;
WSQGTFTSDYSKYLD(Aib)KAAQEFV(Aib)WLEDEPSSGAPPPS-OH (SEQ ID NO: 132); which is also referred to herein as Compound A92;
WSQGTFTSDYSKYLD(Aib)KAAQEFV(Aib)WLEDEPSSGKPPPS-OH (SEQ ID NO: 133); which is also referred to herein as Compound A93;
YSQGTFTSDYSKYLD(Aib)KRAQEFV(Aib)WLEDEPSSGAPPPS-OH (SEQ ID NO: 134); which is also referred to herein as Compound A94;
YSQGTFTSDYSKYLD(Aib)KAAQEFV(Aib)WLEDEPSSGAPPPS-OH (SEQ ID NO: 135); which is also referred to herein as Compound A95; and
YSQGTFTSDYSKYLD(Aib)KAAQEFV(Aib)WLEDEPSSGKPPPS-OH (SEQ ID NO: 136);
which is referred to herein as Compound A96. In some embodiments, the polypeptide consists of an amino acid sequence selected from the group consisting of SEQ ID NOs: 47-136.

In some embodiments, the isolated polypeptide is selected from the group consisting of Compound A1, Compound A2, Compound A3, Compound A4, Compound A5 and Compound A6. In some embodiments, the isolated polypeptide is Compound A1. In some embodiments, the isolated polypeptide is Compound A2. In some embodiments, the isolated polypeptide is Compound A3. In some embodiments, the isolated polypeptide is Compound A4. In some embodiments, the isolated polypeptide is Compound A5. In some embodiments, the isolated polypeptide is Compound A6.

In some embodiments, an isolated polypeptide of the disclosure comprises an amino acid sequence selected from the group consisting of amino acid sequences represented by the consensus sequence of SEQ ID NO: 137:

```
                                        (SEQ ID NO: 137)
YSQGTFTSDYSKYLDSX₁₇RAQX₂₁FVX₂₄WLX₂₇X₂₈T-OH,
``` wherein:
$X_{17}$ is K*, where K* is in a lactam bridge with E* at $X_{21}$;
$X_{21}$ is E*, where E* is in a lactam bridge with K* at $X_{17}$;
$X_{24}$ is K or K, where K is in a lactam bridge with E** at $X_{28}$;
$X_{27}$ is Q or D; and
$X_{28}$ is E or E, where E is in a lactam bridge with K** at $X_{24}$ In some embodiments, an isolated polypeptide of the disclosure comprises an amino acid sequence selected from the group consisting of YSQGTFTSDYSKYLDSK*RAQE*FVKWLDET-OH (SEQ ID NO: 138), referred to herein as Compound A104 and YSQGTFTSDYSKYLDSK*RAQE*FVKWLQET-OH (SEQ ID NO: 139), referred to herein as Compound A105. In some embodiments, the polypeptide consists of an amino acid sequence selected from the group consisting of SEQ ID NOs: 138 and 139.

Conjugation of a Lipophilic Substituent to any of the Peptides, Optionally Via a Spacer In some embodiments, the disclosed peptide is optionally substituted with one or more lipophilic substituents each optionally via a bivalent spacer.

Conjugation of one or more lipophilic substituents, each optionally via a bivalent spacer, to a disclosed peptide is intended to prolong the action of the peptide by facilitating binding to serum albumin and delayed renal clearance of the conjugated peptide. Applicant has discovered that certain disclosed peptides, having affinity to albumin and prolonged elimination half-lives in humans, are particularly amenable to the disclosed methods of administration via an implantable osmotic drug delivery device.

In some embodiments, the disclosed peptide has an elimination half-life ($t_{1/2}$) in humans of at least about 5 hours following subcutaneous administration. In some embodiments, the disclosed peptide has an elimination half-life ($t_{1/2}$) in humans of at least about 8 hours, 10 hours, 12 hours, 16 hours, 24 hours or longer following subcutaneous administration.

As used herein, a "lipophilic substituent" comprises a substituent comprising 4 to 40 carbon atoms, 8 to 25 carbon atoms, or 12 to 22 carbon atoms. The lipophilic substituent may be attached to an amino group of the peptide (e.g., an ε-amino group of a lysine residue) by means of a carboxyl group of the lipophilic substituent, or optionally an amino group of the spacer, which spacer in turn forms an amide bond with an amino group of the amino acid (e.g., lysine) residue to which it is attached. In some embodiments, the peptide comprises three, two, or preferably one lipophilic substituent each with or without an optional spacer.

In some embodiments, the lipophilic substituent comprises a straight-chain or branched alkyl group. In some embodiments, the lipophilic substituent is an acyl group of a straight-chain or branched fatty acid. In some embodiments, the lipophilic substituent is the acyl group of the formula $CH_3(CH_2)_nCO-$, wherein n is an integer from 4 to 38, an integer from 4 to 24, such as $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ or $CH_3(CH_2)_{22}CO-$. In some embodiments, n is 6, 8, 10, 12, 14, 16, 18, 20 or 22. In some embodiments, the lipophilic substituent is an acyl group of the formula $CH_3(CH_2)_{14}CO-$.

In some embodiments, the lipophilic substituent is an acyl group of a straight-chain or branched fatty acid, further substituted with one or more carboxylic acid and/or hydroxamic acid groups. In some embodiments, the lipophilic substituent is an acyl group of the formula $HOOC(CH_2)_mCO-$, wherein m is an integer from 4 to 38, an integer from 4 to 24, such as $HOOC(CH_2)_{14}CO-$, $HOOC(CH_2)_{16}CO-$, $HOOC(CH_2)_{18}CO-$, $HOOC(CH_2)_{20}CO-$ or $HOOC(CH_2)_{22}CO-$. In some embodiments, the lipophilic substituent is $HOOC(CH_2)_{16}CO-$. In some embodiments, m is 6, 8, 10, 12, 14, 16, 18, 20 or 22.

In some embodiments, the lipophilic substituent is attached to the parent peptide by means of a bivalent "spacer." In some embodiments, the spacer comprises a bivalent group of Formula I:

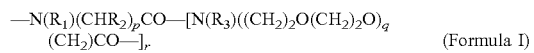

$$-N(R_1)(CHR_2)_pCO-[N(R_3)((CH_2)_2O(CH_2)_2O)_q(CH_2)CO-]_r \quad \text{(Formula I)}$$

wherein
each $R_1$ and $R_3$ is hydrogen or $C_1$-$C_4$ alkyl;
each $R_2$ is H or $CO_2H$;
p is 1, 2, 3, 4, 5 or 6;
q is 1, 2 or 3;
r is 0 or 1.
which spacer forms a bridge between an amino group of the disclosed peptide and a CO— group of the lipophilic substituent.

In some embodiments, each $R_1$ is hydrogen. In some embodiments, each $R_3$ is hydrogen. In some embodiments, each $R_1$ and each $R_3$ are hydrogen.

In some embodiments, at least one $R_2$ is $CO_2H$. In some embodiments, one $R_2$ is $CO_2H$.

In some embodiments, p is 1. In some embodiments, p is 2. In some embodiments, p is 3. In some embodiments, p is 4. In some embodiments, p is 5. In some embodiments, p is 6.

In some embodiments, q is 1. In some embodiments, q is 2. In some embodiments, q is 3.

In some embodiments, r is 0. In some embodiments, r is 1.

In some embodiments, the spacer is γ-glutamyl, i.e., $-NH(CHCO_2H)(CH_2)_2CO-$. In some embodiments, the spacer is γ-aminobutanoyl, i.e., $-NH(CH_2)_3CO-$. In some embodiments, the spacer is β-asparagyl, i.e., $-NH(CHCO_2H)(CH_2)CO-$. In some embodiments, the spacer is $-NH(CH_2)_2CO-$. In some embodiments, the spacer is glycyl. In some embodiments, the spacer is β-alanyl. In some embodiments, provided is the peptide of SEQ ID NO: 151, described below, wherein the lipophilic substituent is linked to the ε-amino group of a lysine via a spacer.

In some embodiments, the spacer is $-NHCH(CO_2H)(CH_2)_2CO-[N(R_3)((CH_2)_2O(CH_2)_2O)_q(CH_2)CO-]_r$. In some embodiments, the spacer is $-NH(CH_2)_3CO-[N(R_3)((CH_2)_2O(CH_2)_2O)_q(CH_2)CO-]_r$. In some embodiments, the spacer is $-NHCH(CO_2H)(CH_2)_2CO-NH((CH_2)_2O(CH_2)_2O)_2(CH_2)CO-$. In some embodiments, the spacer is $-NH(CH_2)_3CO-NH((CH_2)_2O(CH_2)_2O)_2(CH_2)CO-$. In some embodiments, the spacer is $-NHCH(CO_2H)CH_2CO-[N(R_3)((CH_2)_2O(CH_2)_2O)_q(CH_2)CO-]_r$. In some embodiments, the spacer is $-NH(CH_2)_2CO-[N(R_3)((CH_2)_2O(CH_2)_2O)_q(CH_2)CO-]_r$.

In some embodiments, the spacer is an amino acid, for example, Lys, Glu or Asp, or a dipeptide such as Gly-Lys. In some embodiments, when the spacer is Lys, Glu or Asp, one carboxyl group of the spacer may form an amide bond with an amino group of the disclosed peptide, and an amino group of the spacer may form an amide bond with a carboxyl group of the lipophilic substituent.

In some embodiments, the lipophilic substituent and spacer combine to form the structure of Formula II:

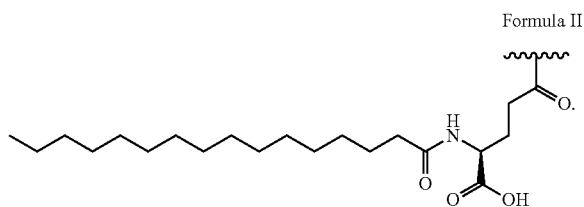 [SMILES: *C(=O)CC[C@H](NC(=O)CCCCCCCCCCCCCCC)C(=O)O]

Formula II

In some embodiments, the lipophilic substituent and spacer combine to form the structure of Formula III:

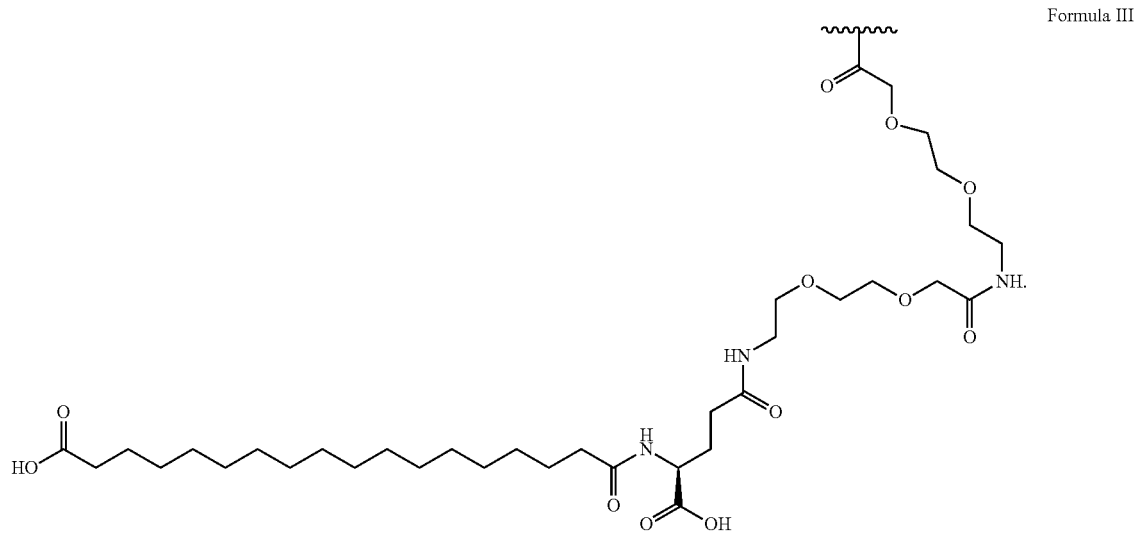 [SMILES: *C(=O)COCCOCCNC(=O)COCCOCCNC(=O)CC[C@H](NC(=O)CCCCCCCCCCCCCCCCC(=O)O)C(=O)O]

Formula III

In some embodiments, each lipophilic substituent is attached, optionally via a spacer, to the ε-amino group of a lysine residue contained in the parent peptide.

For example, in some embodiments, provided is isolated polypeptide, wherein the isolated polypeptide is selected from the group consisting of Compounds A1-A105, and the isolated polypeptide is covalently joined to a lipophilic substituent, optionally via a spacer.

In some embodiments, the isolated polypeptide is selected from the group consisting of Compounds A1-A6, and the isolated polypeptide is covalently joined to a lipophilic substituent, optionally via a spacer.

In some embodiments, the isolated polypeptide is selected from the group consisting of Compounds A97-A103, and the isolated polypeptide is covalently joined to a lipophilic substituent, optionally via a spacer.

In some embodiments, the lipophilic substituents is covalently bound to any of the peptides of Compounds A1-A105, such as any of Compounds A1, A2, A3, A4, A5 or A6, via a spacer, and the lipophilic substituent and spacer are of Formula II.

In some embodiments, the lipophilic substituents is covalently bound to any of the peptides of Compounds A1-A105, such as any of Compounds A1, A2, A3, A4, A5 or A6, via a spacer, and the lipophilic substituent and spacer are of Formula III.

In some embodiments, the lipophilic substituents is covalently bound to any of the peptides of Compounds A1-A105, such as any of Compounds A97, A98, A99, A100, A101, A102 or A103, via a spacer, and the lipophilic substituent and spacer are of Formula II.

In some embodiments, the lipophilic substituents is covalently bound to any of the peptides of Compounds A1-A105, such as any of Compounds A97, A98, A99, A100, A101, A102 or A103, via a spacer, and the lipophilic substituent and spacer are of Formula III.

In some embodiments, isolated polypeptide comprises a lysine, and the β-amino group of the lysine is covalently bound to the lipophilic substituent, optionally via a spacer.

In some embodiments, an isolated polypeptide of the disclosure comprises an amino acid sequence selected from the group consisting of amino acid sequences represented by the consensus sequence of SEQ ID NO: 151:

(SEQ ID NO: 151)
$X_1SX_3GTFTSDX_{10}SKYLDX_{16}X_{17}X_{18}AQX_{21}FVX_{24}WLEDEPX_{31}SX_{33}X_{34}PPPS-OH$, wherein:
X1=Y or W;
X3=H or Q;
X10=Y, K or K***;
X16=A, S, Aib, K or K***;
X17=A, K, Aib or K***;
X18=Y, S or R;
X21=E, K or K***;
X24=I, Aib, K or K***;
X31=S, K or K***;
X33=G, K or K***; and
X34=A or S;
where K*** is lysine, and the ε-amino group of the lysine sidechain is covalently joined to a lipophilic substituent, optionally via a spacer, both as defined herein.

In some embodiments, K* is lysine, and the ε-amino group of the lysine sidechain is covalently joined to a lipophilic substituent via a spacer. In some embodiments, K* is lysine, and the ε-amino group of the lysine sidechain is covalently joined to a lipophilic substituent in the absence of (i.e., without) a spacer.

In some embodiments, an isolated polypeptide of the disclosure comprises an amino acid sequence selected from the group consisting of amino acid sequences represented by the consensus sequence of SEQ ID NO: 151 wherein:
- X1=Y or W;
- X3=H or Q;
- X10=Y or K***;
- X16=A, S, Aib or K***;
- X17=A, K or Aib;
- X18=Y, S or R;
- X21=E or K***;
- X24=I, Aib or K***;
- X31=S or K***;
- X33=G, K or K***; and
- X34=A or S;
- where K*** is lysine, and the ε-amino group of the lysine sidechain is covalently joined to a lipophilic substituent, optionally via a spacer, both as defined herein.

In some embodiments, K* is lysine, and the ε-amino group of the lysine sidechain is covalently joined to a lipophilic substituent via a spacer. In some embodiments, K* is lysine, and the ε-amino group of the lysine sidechain is covalently joined to a lipophilic substituent in the absence of (i.e., without) a spacer.

In some embodiments, X1=Y. In some embodiments, X1=W.

In some embodiments, X3=H. In some embodiments, X3=Q.

In some embodiments, X10=Y. In some embodiments, X10=K. In some embodiments, X10=K***.

In some embodiments, X16=A. In some embodiments, X16=S. In some embodiments, X16=Aib. In some embodiments, X16=K. In some embodiments, X16=K***.

In some embodiments, X17=A. In some embodiments, X17=K. In some embodiments, X17=Aib. In some embodiments, X17=K***.

In some embodiments, X18=Y. In some embodiments, X18=S. In some embodiments, X18=R.

In some embodiments, X21=E. In some embodiments, X21=K. In some embodiments, X21=K***.

In some embodiments, X24=I. In some embodiments, X24=Aib. In some embodiments, X24=K. In some embodiments, X24=K***.

In some embodiments, X31=S. In some embodiments, X31=K. In some embodiments, X31=K***.

In some embodiments, X33=G. In some embodiments, X33=K. In some embodiments, X33=K***.

In some embodiments, X16 is K*; in some embodiments, X21 is K*; in some embodiments, X24 is K*; in some embodiments, X33 is K*, where K*** is lysine, and the ε-amino group of the lysine is covalently joined to a lipophilic substituent and a spacer of Formula II:

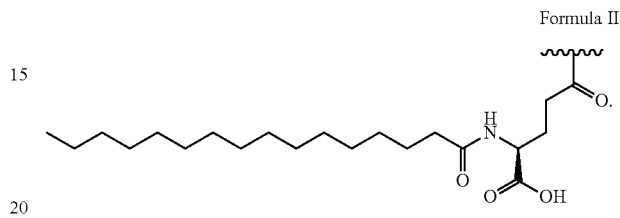

Formula II

In some embodiments, X16 is K*; in some embodiments, X21 is K*; in some embodiments, X24 is K*; in some embodiments, X33 is K*, where K*** is lysine, and the ε-amino group of the lysine is covalently joined to a lipophilic substituent and a spacer of Formula III:

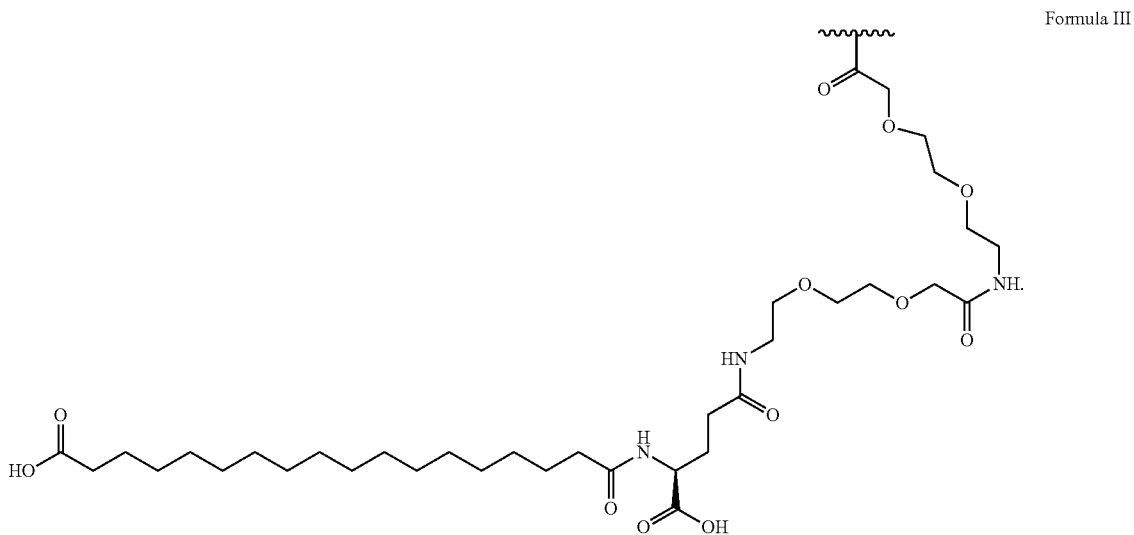 [SMILES: *C(=O)COCCOCCNC(=O)COCCOCCNC(=O)CC[C@H](NC(=O)CCCCCCCCCCCCCCCCC(=O)O)C(=O)O]

Formula III

In some embodiments, one or more of X10, X16, X17, X21, X24, X31 or X33 is K*, where K* is lysine, and the ε-amino group of the lysine is covalently joined to a lipophilic substituent and a spacer of Formula II.

In some embodiments, one or more of X10, X16, X17, X21, X24, X31 or X33 is K*, where K* is lysine, and the ε-amino group of the lysine is covalently joined to a lipophilic substituent and a spacer of Formula III.

In some embodiments, one of X10, X16, X17, X21, X24, X31 or X33 is K*, where K* is lysine, and the ε-amino group of the lysine is covalently joined to a lipophilic substituent and a spacer of Formula II.

In some embodiments, one of X10, X16, X17, X21, X24, X31 or X33 is K*, where K* is lysine, and the ε-amino group of the lysine is covalently joined to a lipophilic substituent and a spacer of Formula III.

In some embodiments, provided is a pharmaceutical composition comprising any of the disclosed peptides formulated as a trifluoroacetate salt, acetate salt or hydrochloride salt. In some embodiments, provided is a pharmaceutical composition comprising any of the disclosed peptides formulated as a trifluoroacetate salt. In some embodiments, provided is a pharmaceutical composition comprising any of the disclosed peptides formulated as an acetate salt. In some embodiments, provided is a pharmaceutical composition comprising any of the disclosed peptides formulated as a hydrochloride salt.

In some embodiments, provided is a pharmaceutical composition comprising any of the disclosed peptides formulated as a trifluoroacetate salt, acetate salt or hydrochloride salt, and the peptide comprises an amino acid sequence selected from the group consisting of amino acid sequences represented by the consensus sequence of SEQ ID NO: 151. In some embodiments, provided is a pharmaceutical composition comprising any of the disclosed peptides formulated as a trifluoroacetate salt and the peptide comprises an amino acid sequence selected from the group consisting of amino acid sequences represented by the consensus sequence of SEQ ID NO: 151. In some embodiments, provided is a pharmaceutical composition comprising any of the disclosed peptides formulated as an acetate salt and the peptide comprises an amino acid sequence selected from the group consisting of amino acid sequences represented by the consensus sequence of SEQ ID NO: 151. In some embodiments, provided is a pharmaceutical composition comprising any of the disclosed peptides formulated as a hydrochloride salt and the peptide comprises an amino acid sequence selected from the group consisting of amino acid sequences represented by the consensus sequence of SEQ ID NO: 151. In some embodiments, in the peptide of SEQ ID NO: 151, one of X10, X16, X17, X21, X24, X31 or X33 is K*, where K* is lysine, and the β-amino group of the lysine is covalently joined to a lipophilic substituent and a spacer of Formula II. In some embodiments, in the peptide of SEQ ID NO: 151, one of X10, X16, X17, X21, X24, X31 or X33 is K*, where K* is lysine, and the ε-amino group of the lysine is covalently joined to a lipophilic substituent and a spacer of Formula III.

In some embodiments, provided is any of the isolated polypeptides of the disclosure, wherein the polypeptide comprises one or more amino acid residues, each of which is covalently joined to a lipophilic substituent, optionally via a spacer, both as defined herein. In some embodiments, each of the one or more amino acid residues is covalently joined to a lipophilic substituent and a spacer of Formula II or III.

In some embodiments, any of the isolated polypeptides of the disclosure, wherein the polypeptide comprises at least one lysine residue, where the β-amino group of the lysine sidechain is covalently joined to a lipophilic substituent, optionally via a spacer, both as defined herein. In some embodiments, each of the at least one lysine residues has an β-amino group that is covalently joined to a lipophilic substituent and a spacer of Formula II or III.

In some embodiments, the isolated polypeptide is selected from the group consisting of Compounds B1-B48.

In some embodiments, an isolated polypeptide of the disclosure comprises the amino acid sequence YSHGTFTSDYSKYLD(Aib)KYAQEFV(Aib)WLEDEPSSK****APPPS-OH (SEQ ID NO: 152) which is also referred to herein as Compound B1.

In some embodiments, an isolated polypeptide of the disclosure comprises the amino acid sequence YSHGTFTSDYSKYLD(Aib)KYAQEFVK****WLEDEPSSGAPPPS-OH (SEQ ID NO: 153) which is also referred to herein as Compound B2.

In some embodiments, an isolated polypeptide of the disclosure comprises the amino acid sequence YSHGTFTSDYSKYLDK****KYAQEFV(Aib)WLEDEPSSGAPPPS-OH (SEQ ID NO: 154) which is also referred to herein as Compound B3.

In some embodiments, an isolated polypeptide of the disclosure comprises the amino acid sequence YSHGTFTSDK****SKYLD(Aib)KYAQEFV(Aib)WLEDEPSSGAPPPS-OH (SEQ ID NO: 155) which is also referred to herein as Compound B4.

In some embodiments, an isolated polypeptide of the disclosure comprises the amino acid sequence YSHGTFTSDYSKYLD(Aib)KYAQEFV(Aib)WLEDEPSSK***** APPPS-OH (SEQ ID NO: 156) which is also referred to herein as Compound B5.

In some embodiments, an isolated polypeptide of the disclosure comprises the amino acid sequence YSHGTFTSDYSKYLD(Aib)KYAQEFVK*****WLEDEPSSGAPPPS-OH (SEQ ID NO: 157) which is also referred to herein as Compound B6.

In some embodiments, an isolated polypeptide of the disclosure comprises the amino acid sequence YSHGTFTSDYSKYLDK*****KYAQEFV(Aib)WLEDEPSSGAPPPS-OH (SEQ ID NO: 158) which is also referred to herein as Compound B7.

In some embodiments, an isolated polypeptide of the disclosure comprises the amino acid sequence YSHGTFTSDK*****SKYLD(Aib)KYAQEFV(Aib)WLEDEPSSGAPPPS-OH (SEQ ID NO: 159) which is also referred to herein as Compound B8.

In some embodiments, an isolated polypeptide of the disclosure comprises the amino acid sequence YSHGTFTSDYSKYLD(Aib)KSAQEFV(Aib)WLEDEPSSK****APPPS-OH (SEQ ID NO: 160) which is also referred to herein as Compound B9.

In some embodiments, an isolated polypeptide of the disclosure comprises the amino acid sequence YSHGTFTSDYSKYLD(Aib)KSAQEFVK****WLEDEPSSGAPPPS-OH (SEQ ID NO: 161) which is also referred to herein as Compound B10.

In some embodiments, an isolated polypeptide of the disclosure comprises the amino acid sequence YSHGTFTSDYSKYLDK****KSAQEFV(Aib)WLEDEPSSGAPPPS-OH (SEQ ID NO: 162) which is also referred to herein as Compound B11.

In some embodiments, an isolated polypeptide of the disclosure comprises the amino acid sequence YSHGTFTSDK****SKYLD(Aib)KSAQEFV(Aib)WLEDEPSSGAPPPS-OH (SEQ ID NO: 163) which is also referred to herein as Compound B12.

In some embodiments, an isolated polypeptide of the disclosure comprises the amino acid sequence YSHGTFTSDYSKYLD(Aib)KSAQEFV(Aib)WLEDEPSSK***** APPPS-OH (SEQ ID NO: 164) which is also referred to herein as Compound B13.

In some embodiments, an isolated polypeptide of the disclosure comprises the amino acid sequence YSHGTFTSDYSKYLD(Aib)KSAQEFVK*****WLEDEPSSGAPPPS-OH (SEQ ID NO: 165) which is also referred to herein as Compound B14.

In some embodiments, an isolated polypeptide of the disclosure comprises the amino acid sequence YSHGTFTSDYSKYLDK*****KSAQEFV(Aib)WLEDEPSSGAPPPS-OH (SEQ ID NO: 166) which is also referred to herein as Compound B15.

In some embodiments, an isolated polypeptide of the disclosure comprises the amino acid sequence YSHGTFTSDK*****SKYLD(Aib)KSAQEFV(Aib)WLEDEPSSGAPPP S-OH (SEQ ID NO: 167) which is also referred to herein as Compound B16.

In some embodiments, an isolated polypeptide of the disclosure comprises the amino acid sequence WSQGTFTSDYSKYLD(Aib)KRAQEFV(Aib)WLEDEPSSK****APPPS-OH (SEQ ID NO: 168) which is also referred to herein as Compound B17.

In some embodiments, an isolated polypeptide of the disclosure comprises the amino acid sequence WSQGTFTSDYSKYLD(Aib)KRAQEFVK****WLEDEPSSGAPPPS-OH (SEQ ID NO: 169) which is also referred to herein as Compound B18.

In some embodiments, an isolated polypeptide of the disclosure comprises the amino acid sequence WSQGTFTSDYSKYLDK****KRAQEFV(Aib)WLEDEPSSGAPPPS-OH (SEQ ID NO: 170) which is also referred to herein as Compound B19.

In some embodiments, an isolated polypeptide of the disclosure comprises the amino acid sequence WSQGTFTSDK****SKYLD(Aib)KRAQEFV(Aib)WLEDEPSSGAPPPS-OH (SEQ ID NO: 171) which is also referred to herein as Compound B20.

In some embodiments, an isolated polypeptide of the disclosure comprises the amino acid sequence WSQGTFTSDYSKYLD(Aib)KRAQEFV(Aib)WLEDEPSSK***** APPPS-OH (SEQ ID NO: 172) which is also referred to herein as Compound B21.

In some embodiments, an isolated polypeptide of the disclosure comprises the amino acid sequence WSQGTFTSDYSKYLD(Aib)KRAQEFVK*****WLEDEPSSGAPPPS-OH (SEQ ID NO: 173) which is also referred to herein as Compound B22.

In some embodiments, an isolated polypeptide of the disclosure comprises the amino acid sequence WSQGTFTSDYSKYLDK*****KRAQEFV(Aib)WLEDEPSSGAPPPS-OH (SEQ ID NO: 174) which is also referred to herein as Compound B23.

In some embodiments, an isolated polypeptide of the disclosure comprises the amino acid sequence WSQGTFTSDK*****SKYLD(Aib)KRAQEFV(Aib)WLEDEPSS GAPPPS-OH (SEQ ID NO: 175) which is also referred to herein as Compound B24.

In some embodiments, an isolated polypeptide of the disclosure comprises the amino acid sequence YSHGTFTSDYSKYLD(Aib)KRAQEFVIWLEDEPSSK****APPPS-OH (SEQ ID NO: 176) which is also referred to herein as Compound B25.

In some embodiments, an isolated polypeptide of the disclosure comprises the amino acid sequence YSHGTFTSDYSKYLDK****KRAQEFVIWLEDEPSSGAPPPS-OH (SEQ ID NO: 177) which is also referred to herein as Compound B26.

In some embodiments, an isolated polypeptide of the disclosure comprises the amino acid sequence YSHGTFTSDK****SKYLD(Aib)KRAQEFVIWLEDEPSSGAPPPS-OH (SEQ ID NO: 178) which is also referred to herein as Compound B27.

In some embodiments, an isolated polypeptide of the disclosure comprises the amino acid sequence YSHGTFTSDYSKYLD(Aib)KRAQK****FVIWLEDEPSSGAPPPS-OH (SEQ ID NO: 179) which is also referred to herein as Compound B28.

In some embodiments, an isolated polypeptide of the disclosure comprises the amino acid sequence YSHGTFTSDYSKYLD(Aib)KRAQEFVIWLEDEPSSK*****APPPS-OH (SEQ ID NO: 180) which is also referred to herein as Compound B29.

In some embodiments, an isolated polypeptide of the disclosure comprises the amino acid sequence YSHGTFTSDYSKYLD(Aib)KRAQK*****FVIWLEDEPSSGAPPPS-OH (SEQ ID NO: 181) which is also referred to herein as Compound B30.

In some embodiments, an isolated polypeptide of the disclosure comprises the amino acid sequence YSHGTFTSDYSKYLDK*****KRAQEFVIWLEDEPSS GAPPPS-OH (SEQ ID NO: 182) which is also referred to herein as Compound B31.

In some embodiments, an isolated polypeptide of the disclosure comprises the amino acid sequence YSHGTFTSDK*****SKYLD(Aib)KRAQEFVIWLEDEPSSGAPPPS-OH (SEQ ID NO: 183) which is also referred to herein as Compound B32.

In some embodiments, an isolated polypeptide of the disclosure comprises the amino acid sequence YSQGTFTSDYSKY-LDAARAQEFVKWLEDEPKSK**** SPPPS-NH$_2$ (SEQ ID NO: 184) which is also referred to herein as Compound B33.

In some embodiments, an isolated polypeptide of the disclosure comprises the amino acid sequence YSQGTFTSDYSKYLDAARAQEFVK****WLEDEPKS KSPPPS-NH$_2$ (SEQ ID NO: 185) which is also referred to herein as Compound B34.

In some embodiments, an isolated polypeptide of the disclosure comprises the amino acid sequence YSQGTFTSDYSKYLDK****ARAQEFVKWLEDEPKS KSPPPS-NH$_2$ (SEQ ID NO: 186) which is also referred to herein as Compound B35.

In some embodiments, an isolated polypeptide of the disclosure comprises the amino acid sequence YSQGTFTSDK****SKYLDAARAQEFVKWLEDEPKS KSPPPS-NH$_2$ (SEQ ID NO: 187) which is also referred to herein as Compound B36.

In some embodiments, an isolated polypeptide of the disclosure comprises the amino acid sequence YSQGTFTSDYSKYLDAARAQEFVKWLEDEPKSK*****SPPPS-NH$_2$ (SEQ ID NO: 188) which is also referred to herein as Compound B37.

In some embodiments, an isolated polypeptide of the disclosure comprises the amino acid sequence YSQGTFTSDYSKYLDAARAQEFVK*****WLEDEPKS KSPPPS-NH$_2$ (SEQ ID NO: 189) which is also referred to herein as Compound B38.

In some embodiments, an isolated polypeptide of the disclosure comprises the amino acid sequence YSQGTFTSDYSKYLDK*****ARAQEFVKWLEDEPK SKSPPPS-NH$_2$ (SEQ ID NO: 190) which is also referred to herein as Compound B39.

In some embodiments, an isolated polypeptide of the disclosure comprises the amino acid sequence YSQGTFTSDK*****SKYLDAARAQEFVKWLEDEPK SKSPPPS-NH$_2$ (SEQ ID NO: 191) which is also referred to herein as Compound B40.

In some embodiments, an isolated polypeptide of the disclosure comprises the amino acid sequence YSHGTFTSDYSKYLDSARAQEFVKWLEDEPSSK****APPPS-NH$_2$ (SEQ ID NO: 192) which is also referred to herein as Compound B41.

In some embodiments, an isolated polypeptide of the disclosure comprises the amino acid sequence YSHGTFTSDYSKYLDSARAQEFVK****WLEDEPSSG APPPS-NH$_2$ (SEQ ID NO: 193) which is also referred to herein as Compound B42.

In some embodiments, an isolated polypeptide of the disclosure comprises the amino acid sequence YSHGTFTSDYSKYLDK****ARAQEFVKWLEDEPSSG APPPS-NH$_2$ (SEQ ID NO: 194) which is also referred to herein as Compound B43.

In some embodiments, an isolated polypeptide of the disclosure comprises the amino acid sequence YSHGTFTSDK****SKYLDSARAQEFVKWLEDEPSSG APPPS-NH$_2$ (SEQ ID NO: 195) which is also referred to herein as Compound B44.

In some embodiments, an isolated polypeptide of the disclosure comprises the amino acid sequence YSHGTFTSDYSKYLDSARAQEFVKWLEDEPSSK*****APPPS-NH$_2$ (SEQ ID NO: 196) which is also referred to herein as Compound B45.

In some embodiments, an isolated polypeptide of the disclosure comprises the amino acid sequence YSHGTFTSDYSKYLDSARAQEFVK*****WLEDEPSS GAPPPS-NH$_2$ (SEQ ID NO: 197) which is also referred to herein as Compound B46.

In some embodiments, an isolated polypeptide of the disclosure comprises the amino acid sequence YSHGTFTSDYSKYLDK*****ARAQEFVKWLEDEPSS GAPPPS-NH$_2$ (SEQ ID NO: 198) which is also referred to herein as Compound B47.

In some embodiments, an isolated polypeptide of the disclosure comprises the amino acid sequence YSHGTFTSDK*****SKYLDSARAQEFVKWLEDEPSS GAPPPS-NH$_2$ (SEQ ID NO: 199) which is also referred to herein as Compound B48.

In the above embodiments, each ε-amino group of the lysine residue located at the indicated peptide residue (K****) in the disclosed compounds is covalently bound to the indicated carbonyl of Formula II to form an amide:

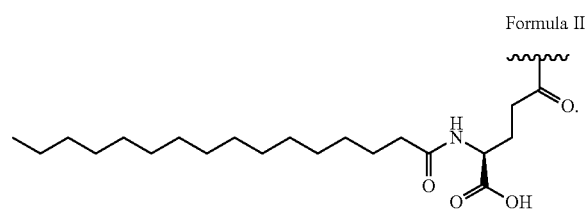 [SMILES: *C(=O)CC[C@H](NC(=O)CCCCCCCCCCCCCCC)C(=O)O]

Formula II

In the above embodiments, each ε-amino group of the lysine residue located at the indicated peptide residue (K*****) in the disclosed compounds is covalently bound to the indicated carbonyl of Formula III to form an amide:

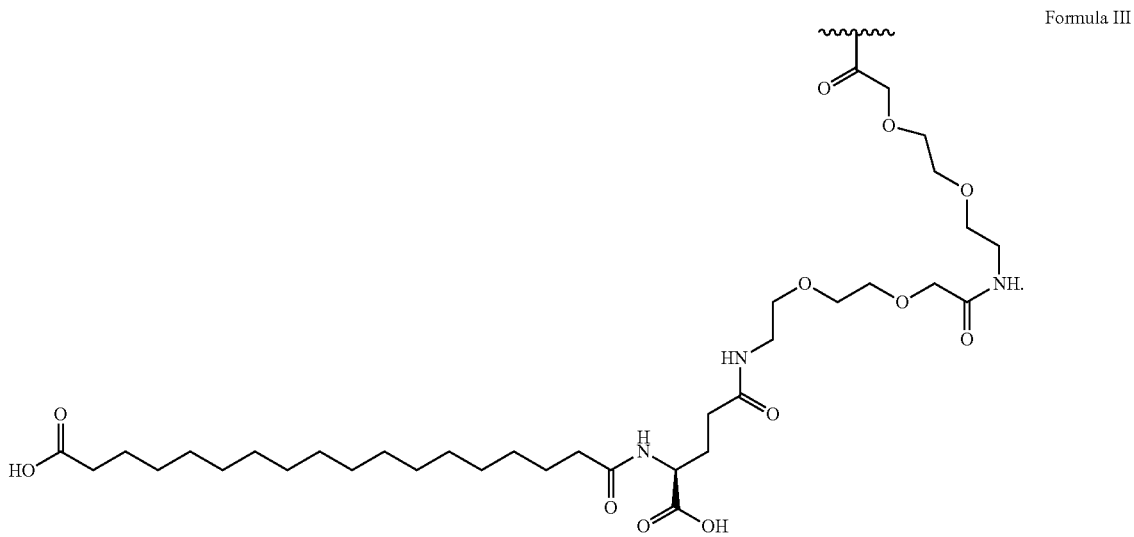 [SMILES: *C(=O)COCCOCCNC(=O)COCCOCCNC(=O)CC[C@H](NC(=O)CCCCCCCCCCCCCCCCC(=O)O)C(=O)O]

Formula III

In some embodiments, an isolated polypeptide of the disclosure comprises an amino acid sequence selected from the group consisting of amino acid sequences represented by SEQ ID NO: 152 through SEQ ID NO: 199.

In some embodiments, an isolated polypeptide of the disclosure is selected from the group consisting of Compound B1 through Compound B8.

In some embodiments, an isolated polypeptide of the disclosure is selected from the group consisting of Compound B9 through Compound B16.

In some embodiments, an isolated polypeptide of the disclosure is selected from the group consisting of Compound B17 through Compound B24.

In some embodiments, an isolated polypeptide of the disclosure is selected from the group consisting of Compound B25 through Compound B32.

In some embodiments, an isolated polypeptide of the disclosure is selected from the group consisting of Compound B33 through Compound B40.

In some embodiments, an isolated polypeptide of the disclosure is selected from the group consisting of Compound B41 through Compound B48.

In some embodiments, an isolated polypeptide of the disclosure comprises an amino acid sequence selected from the group consisting of amino acid sequences represented by SEQ ID NO: 154, SEQ ID NO: 157, SEQ ID NO: 158, SEQ ID NO: 160, SEQ ID NO: 161, SEQ ID NO: 162, SEQ ID NO: 165, SEQ ID NO: 166, SEQ ID NO: 168, SEQ ID NO: 172, SEQ ID NO: 173, SEQ ID NO: 185, SEQ ID NO: 188, SEQ ID NO: 189, SEQ ID NO: 190 and SEQ ID NO: 192.

In some embodiments, an isolated polypeptide of the disclosure comprises an amino acid sequence selected from the group consisting of amino acid sequences represented by SEQ ID NO: 160, SEQ ID NO: 165, and SEQ ID NO: 166.

In some embodiments, an isolated polypeptide of the disclosure is selected from the group consisting of Compound B1 through Compound B48.

In some embodiments, an isolated polypeptide of the disclosure is selected from the group consisting of Compound B3, Compound B6, Compound B7, Compound B9, Compound B10, Compound B11, Compound B14, Compound B15, Compound B17, Compound B21, Compound B22, Compound B34, Compound B37, Compound B38, Compound B39 and Compound B41.

In some embodiments, an isolated polypeptide of the disclosure is selected from the group consisting of Compound B9, Compound B14 and Compound B15.

In some embodiments, an isolated polypeptide of the disclosure is Compound B9. In some embodiments, an isolated polypeptide of the disclosure is Compound B14. In some embodiments, an isolated polypeptide of the disclosure is Compound B15.

In some embodiments, an isolated polypeptide of the disclosure comprises an amino acid sequence selected from the group consisting of amino acid sequences represented by Compound B1 through Compound B48.

2.0.2 Peptide Combinations

In some embodiments, an isolated glucagon analog polypeptide of the disclosure, which is a selective glucagon receptor agonist, is co-formulated in combination with a second agent selected from the group consisting of oxyntomodulin, exenatide, a derivative of exenatide, an analogue of exenatide, glucagon-like peptide-1 (GLP-1), a derivative of GLP-1, and an analogue of GLP-1. In some embodiments, any of the glucagon analogs of the disclosure is co-formulated in combination with exenatide.

In some embodiments, any of the glucagon analogs of the disclosure is formulated in combination with exenatide, wherein the glucagon analog is not covalently joined to a lipophilic substituent and a spacer, as described herein.

In some embodiments, a glucagon analog of the disclosure is formulated in combination with exenatide, wherein the glucagon analog is selected from the group consisting of Compounds A1-A105. In some embodiments, a glucagon analog of the disclosure is formulated in combination with exenatide, wherein the glucagon analog is selected from the group consisting of Compounds A1, A2, A3, A4, A5 and A6. In some embodiments, a glucagon analog of the disclosure is formulated in combination with exenatide, wherein the glucagon analog is Compound A1. In some embodiments, a glucagon analog of the disclosure is formulated in combination with exenatide, wherein the glucagon analog is Compound A2. In some embodiments, a glucagon analog of the disclosure is formulated in combination with exenatide, wherein the glucagon analog is Compound A3. In some embodiments, a glucagon analog of the disclosure is formulated in combination with exenatide, wherein the glucagon analog is Compound A4. In some embodiments, a glucagon analog of the disclosure is formulated in combination with exenatide, wherein the glucagon analog is Compound A5. In some embodiments, a glucagon analog of the disclosure is formulated in combination with exenatide, wherein the glucagon analog is Compound A6.

In some embodiments, any of the glucagon analogs of the disclosure is formulated in combination with exenatide, wherein the glucagon analog has at least one amino acid that is covalently joined to a lipophilic substituent and a spacer, as described herein. In some embodiments, any of the glucagon analogs of the disclosure is formulated in combination with exenatide, wherein the glucagon analog has at least one lysine residue that has an ε-amino group that is covalently joined to a lipophilic substituent and a spacer of Formula II or III.

In some embodiments, a glucagon analog of the disclosure is formulated in combination with exenatide, wherein the glucagon analog is selected from the group consisting of Compounds B1-B48. In some embodiments, any of the glucagon analogs of the disclosure is formulated in combination with exenatide, wherein the glucagon analog is selected from the group consisting of amino acid sequences represented by SEQ ID NO: 152-SEQ ID NO: 199.

In some embodiments, a glucagon analog of the disclosure is formulated in combination with exenatide, wherein the glucagon analog is selected from the group consisting of Compound B3, Compound B6, Compound B7, Compound B9, Compound B10, Compound B11, Compound B14, Compound B15, Compound B17, Compound B21, Compound B22, Compound B34, Compound B37, Compound B38, Compound B39 and Compound B41.

In some embodiments, a glucagon analog of the disclosure is formulated in combination with exenatide, wherein the glucagon analog is selected from the group consisting of Compound B9, Compound B14 and Compound B15.

In some embodiments, a glucagon analog of the disclosure is formulated in combination with exenatide, wherein the glucagon analog is Compound B9. In some embodiments, a glucagon analog of the disclosure is formulated in combination with exenatide, wherein the glucagon analog is Compound B14. In some embodiments, a glucagon analog of the disclosure is formulated in combination with exenatide, wherein the glucagon analog is Compound B15.

In some embodiments, any of the glucagon analogs of the disclosure is formulated in combination with exenatide in a fixed ratio of glucagon analog:exenatide of 1000:1 to 1:1000. In some embodiments, any of the glucagon analogs of the disclosure is formulated in combination with exenatide in a fixed ratio of glucagon analog:exenatide of 500:1 to 1:500. In some embodiments, any of the glucagon analogs of the disclosure is formulated in combination with exenatide in a fixed ratio of glucagon analog:exenatide of 100:1 to 1:100. In some embodiments, any of the glucagon analogs of the disclosure is formulated in combination with exenatide in a fixed ratio of glucagon analog:exenatide of 50:1 to 1:50. In some embodiments, any of the glucagon analogs of the disclosure is formulated in combination with exenatide in a fixed ratio of glucagon analog:exenatide of 25:1 to 1:25. In some embodiments, any of the glucagon analogs of the disclosure is formulated in combination with exenatide in a fixed ratio of glucagon analog:exenatide of 10:1 to 1:10. In some embodiments, any of the glucagon analogs of the disclosure is formulated in combination with exenatide in a fixed ratio of glucagon analog:exenatide of 1:1 to 1:10. In some embodiments, any of the glucagon analogs of the disclosure is formulated in combination with exenatide in a fixed ratio of glucagon analog:exenatide of 10:1 to 1:1. In some embodiments, any of the glucagon analogs of the disclosure is formulated in combination with exenatide in a fixed ratio of glucagon analog:exenatide of 5:1 to 1:5. In some embodiments, any of the glucagon analogs of the disclosure is formulated in combination with exenatide in a fixed ratio of glucagon analog:exenatide of 1:1 to 1:5. In some embodiments, any of the glucagon analogs of the disclosure is formulated in combination with exenatide in a fixed ratio of glucagon analog:exenatide of 5:1 to 1:1.

The invention also provides a method of treating type 2 diabetes mellitus in a subject in need of treatment. The method comprises providing one or more of the isolated glucagon-receptor selective agonist polypeptides of the disclosure. In some embodiments, the method comprises providing continuous delivery of an isolated glucagon-receptor selective agonist polypeptide from an osmotic delivery device, wherein substantial steady-state delivery of the isolated glucagon-specific agonist polypeptide at a therapeutic concentration is achieved within a time period of about 7 days or less after implantation of the osmotic delivery device in the subject. The substantial steady-state delivery of the isolated glucagon-specific agonist polypeptide from the osmotic delivery device is continuous over an administration period. Humans are preferred subjects for the practice of the present invention.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, at least about 10 months to about a year, at least about one year to about two years, at least about two years to about three years.

In some embodiments of the present invention, the substantial steady-state delivery of an isolated glucagon-specific agonist polypeptide at therapeutic concentrations is achieved within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the substantial steady-state delivery of the isolated glucagon-specific agonist polypeptide at therapeutic concentrations is achieved within about 2 days or less, more preferably within about 1 day or less after implantation of the osmotic delivery device in the subject.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days or less after implantation of the osmotic delivery device in the subject, within about 6 days or less after implantation of the osmotic delivery device in the subject, within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the significant decrease in the subject's fasting plasma glucose concentration after implantation of the osmotic delivery device, relative to the subject's fasting plasma glucose concentration before implantation, is achieved within about 2 days or less, preferably within about 1 day or less after implantation of the osmotic delivery device in the subject, or more preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In yet further embodiments of the first aspect of the present invention, the treatment methods further comprise the capability to terminate the continuous delivery of the glucagon-specific agonist polypeptide such that the concentration of the glucagon-specific agonist polypeptide is substantially undetectable in a blood sample from the subject within about 6 half-lives or less of the glucagon-specific agonist polypeptide after termination of continuous delivery, within about 5 half-lives or less of the glucagon-specific agonist polypeptide after termination of continuous delivery, within about 4 half-lives or less of the glucagon-specific agonist polypeptide after termination of continuous delivery, or within about 3 half-lives or less of the glucagon-specific agonist polypeptide after termination of continuous delivery. The glucagon-specific agonist polypeptide may be detected, for example, by an RIA, a chromatographic method, an ECL assay, an ELISA, or an IEMA. Termination of the continuous delivery can be accomplished, for example, by removal of the osmotic delivery device from the subject.

In related embodiments of the present invention, the treatment methods further comprise the capability to terminate the continuous delivery of the glucagon-receptor selective agonist polypeptide such that the concentration of the polypeptide is substantially undetectable in a blood sample from the subject in less than about 72 hours after termination of continuous delivery, in less than about 48 hours after termination of continuous delivery, in less than about 24 hours after termination of continuous delivery, in less than about 18 hours after termination of continuous delivery, in less than about 14 hours after termination of continuous delivery, in less than about 12 hours after termination of continuous delivery, in less than about 6 hours after termination of continuous delivery, or in less than about 4 hours after termination of continuous delivery. In preferred embodiments, the glucagon-specific agonist polypeptide is substantially undetectable in a blood sample from the subject in less than about 24 hours after termination of continuous delivery, in less than about 18 hours after termination of continuous delivery, or more preferably in less than about 14 hours after termination of continuous delivery.

In some embodiments, the glucagon-receptor selective agonist polypeptide is formulated in a suspension formulation. In some embodiments, the suspension formulation comprises a particle formulation comprising the glucagon-receptor selective agonist polypeptide, and a vehicle formulation. In some embodiments, the glucagon-receptor selective agonist polypeptide comprises an isolated polypeptide of the disclosure, a peptide analog thereof, or a peptide derivative thereof. In some embodiments, the glucagon-receptor selective agonist polypeptide comprises an amino acid sequence encompassed by the amino acid sequence of SEQ ID NO: 1, SEQ ID NO: 2, SEQ ID NO: 3, or SEQ ID NO: 137. In some embodiments, the glucagon-receptor selective agonist polypeptide comprises an amino acid sequence selected from the group consisting of SEQ ID NOs: 4-139.

In embodiments of all aspects of the present invention relating to methods of treating type 2 diabetes mellitus, suspension formulations for use in the methods can, for example, comprise a particle formulation comprising an isolated glucagon-receptor selective agonist polypeptide, and a vehicle formulation.

The reservoir of the osmotic delivery devices may, for example, comprise titanium or a titanium alloy.

In a fifth aspect, the present invention relates to a method of treating a disease or condition in a subject in need of treatment. The method comprises providing continuous delivery of a drug from an osmotic delivery device, wherein substantial steady-state delivery of the drug at therapeutic concentrations is achieved within a time period of about 7 days or less after implantation of the osmotic delivery device in the subject. The substantial steady-state delivery of the drug from the osmotic delivery device is continuous over an administration period of at least about 3 months. The drug has a known or determined half-life in a typical subject. Humans are preferred subjects for the practice of the present invention. The present invention includes a drug effective for treatment of the disease or condition, as well as an osmotic delivery device comprising the drug for use in the present methods of treating the disease or condition in a subject in need of treatment. Advantages of the present invention include mitigation of peak-associated drug toxicities and attenuation of sub-optimal drug therapy associated with troughs.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, or at least about 10 months to about a year.

In some embodiments of this aspect of the present invention, the substantial steady-state delivery of a drug at therapeutic concentrations is achieved within a period of about 7 days or less after implantation of the osmotic delivery device in the subject, about 5 days or less after implantation of the osmotic delivery device in the subject, about 4 days or less after implantation of the osmotic delivery device in the subject, about 3 days or less after implantation of the osmotic delivery device in the subject, about 2 days or less after implantation of the osmotic delivery device in the subject, or about 1 day or less after implantation of the osmotic delivery device in the subject.

In some embodiments of this aspect of the present invention, establishment of the substantial steady-state delivery of the drug at therapeutic concentrations, after implantation of the osmotic delivery device in the subject, may take a longer period of time, for example, a period of about 2 weeks or less, or within less than about 6 half-lives of the drug within the subject after implantation of the device.

The invention also provides a method for promoting weight loss in a subject in need thereof, a method for treating excess weight or obesity in a subject in need thereof, and/or a method for suppressing appetite in a subject in need thereof. The method comprises providing delivery of an isolated glucagon-receptor selective agonist polypeptide. In some embodiments, the isolated glucagon-receptor selective agonist polypeptide is continuously delivered from an osmotic delivery device, wherein substantial steady-state delivery of the glucagon-receptor selective agonist polypeptide at a therapeutic concentration is achieved within a time period of about 7 days or less after implantation of the osmotic delivery device in the subject. The substantial steady-state delivery of the glucagon-receptor selective agonist polypeptide from the osmotic delivery device is continuous over an administration period. Humans are preferred subjects for the practice of the present invention. The present invention includes an isolated glucagon-receptor selective agonist polypeptide, as well as an osmotic delivery device comprising an isolated glucagon-receptor selective agonist polypeptide for use in the present methods in a subject in need of treatment. They subject may have type 2 diabetes. The subject in need thereof may have a baseline HbA1c % of greater than 10.0%, i.e., a high baseline (HBL) subject. The subject may not have previously received a drug for treating type 2 diabetes mellitus.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, or at least about 10 months to about a year, at least about one year to about two years, or at least about two years to about three years.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days or less after implantation of the osmotic delivery device in the subject, within about 6 days or less after implantation of the osmotic delivery device in the subject, within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the significant decrease in the subject's fasting plasma glucose concentration after implantation of the osmotic delivery device, relative to the subject's fasting plasma glucose concentration before implantation, is achieved within about 2 days or less, preferably within about 1 day or less after implantation of the osmotic delivery device in the subject, or more preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In embodiments of all aspects of the present invention relating to methods of treating a disease or condition in a subject, an exemplary osmotic delivery device comprises the following: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a drug formulation or suspension formulation comprising the drug, wherein the second chamber comprises the drug formulation or suspension formulation and the drug formulation or suspension formulation is flowable; and a diffusion moderator inserted in the second open end of the reservoir, the diffusion moderator adjacent the suspension formulation. In preferred embodiments, the reservoir comprises titanium or a titanium alloy.

In embodiments of all aspects of the present invention relating to methods of treating a disease or condition in a subject, the drug formulation can comprise the drug and a vehicle formulation. Alternatively, suspension formulations are used in the methods and can, for example, comprise a particle formulation comprising the drug and a vehicle formulation. Vehicle formulations for use in forming the suspension formulations of the present invention can, for example, comprise a solvent and a polymer.

The reservoir of the osmotic delivery devices may, for example, comprise titanium or a titanium alloy.

In embodiments of all aspects of the present invention the implanted osmotic delivery device can be used to provide subcutaneous delivery.

In embodiments of all aspects of the present invention the continuous delivery can, for example, be zero-order, controlled continuous delivery.

Any of the above aspects and embodiments can be combined with any other aspect or embodiment as disclosed herein.

3.0.0 Formulations and Compositions

Drugs for use in the practice of the present invention are typically uniformly suspended, dissolved or dispersed in a suspension vehicle to form a suspension formulation.

The isolated polypeptides of the disclosure (also referred to herein as "active compounds"), and derivatives, fragments, analogs and homologs thereof, can be incorporated into pharmaceutical compositions suitable for administration. Such compositions typically comprise the fusion protein and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subdermal, subcutaneous, oral (e.g., inhalation), transdermal (i.e., topical), transmucosal, rectal, or combinations thereof. In some embodiments, a pharmaceutical composition or an isolated polypeptide of the disclosure is formulated for administration by topical administration. In some embodiments, a pharmaceutical composition or an isolated polypeptide of the disclosure is formulated for administration by inhalation administration. In some embodiments, the pharmaceutical composition is formulated for administration by a device or other suitable delivery mechanism that is suitable for subdermal or subcutaneous implantation and delivers the pharmaceutical composition subcutaneously. In some embodiments, the pharmaceutical composition is formulated for administration by an implant device that is suitable for subdermal or subcutaneous implantation and delivers the pharmaceutical composition subcutaneously. In some embodiments, the pharmaceutical composition is formulated for administration by an osmotic delivery device, e.g., an implantable osmotic delivery device, that is suitable for subdermal or subcutaneous placement or other implantation and delivers the pharmaceutical composition subcutaneously. Solutions or suspensions used for parenteral application, intradermal application, subdermal application, subcutaneous application, or combinations thereof can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

3.1.0 Drug Particle Formulations

In one aspect, the present invention provides drug particle formulations for pharmaceutical use. The particle formulation typically comprises a drug and includes one or more stabilizing component (also referred to herein as "excipients"). Examples of stabilizing components include, but are not limited to, carbohydrates, antioxidants, amino acids, buffers, inorganic compounds, and surfactants.

In any of the embodiments, the particle formulation may comprise about 50 wt % to about 90 wt % drug, about 50 wt % to about 85 wt % drug, about 55 wt % to about 90 wt % drug, about 60 wt % to about 90 wt % drug, about 65 wt % to about 85 wt % drug, about 65 wt % to about 90 wt % drug, about 70 wt % to about 90 wt % drug, about 70 wt % to about 85 wt % drug, about 70 wt % to about 80 wt % drug, or about 70 wt % to about 75 wt % drug.

In any of the embodiments, a particle formulation comprises a drug, as described above, and one or more stabilizer. The stabilizers may be, for example, carbohydrate, antioxidant, amino acid, buffer, inorganic compound, or surfactant. The amounts of stabilizers in the particle formulation can be determined experimentally based on the activities of the stabilizers and the desired characteristics of the formulation, in view of the teachings of the present specification.

Typically, the amount of carbohydrate in the formulation is determined by aggregation concerns. In general, the carbohydrate amount should not be too high so as to avoid promoting crystal growth in the presence of water due to excess carbohydrate unbound to drug.

Typically, the amount of antioxidant in the formulation is determined by oxidation concerns, while the amount of amino acid in the formulation is determined by oxidation concerns and/or formability of particles during spray drying.

Typically, the amount of buffer in the formulation is determined by pre-processing concerns, stability concerns, and formability of particles during spray drying. Buffer may be required to stabilize drug during processing, e.g., solution preparation and spray drying, when all stabilizers are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinisitol). Suitable carbohydrates include disaccharides and/or nonreducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteine, thioglycerol, thioglycolic acid, thiosorbitol, butylated hydroxyanisol, butylated hydroxytoluene, and propyl gallate. Further, amino acids that readily oxidize can be used as antioxidants, for example, cysteine, methionine, and tryptophan.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, proline, phenylalanine, tryptophan, serine, asparagines, cysteine, tyrosine, lysine, and norleucine. Suitable amino acids include those that readily oxidize, e.g., cysteine, methionine, and tryptophan.

Examples of buffers that may be included in the particle formulation include, but are not limited to, citrate, histidine, succinate, phosphate, maleate, tris, acetate, carbohydrate, and gly-gly. Suitable buffers include citrate, histidine, succinate, and tris.

Examples of inorganic compounds that may be included in the particle formulation include, but are not limited to, NaCl, $Na_2SO_4$, $NaHCO_3$, KCl, $KH_2PO_4$, $CaCl_2$), and $MgCl_2$.

In addition, the particle formulation may include other stabilizers/excipients, such as surfactants and salts. Examples of surfactants include, but are not limited to, Polysorbate 20, Polysorbate 80, PLURONIC© (BASF Corporation, Mount Olive, N.J.) F68, and sodium dodecyl sulfate (SDS). Examples of salts include, but are not limited to, sodium chloride, calcium chloride, and magnesium chloride.

3.1.1 Exemplary Drugs

The drug particle formulations comprise a drug. The drug may be any physiologically or pharmacologically active substance, particularly those known to be delivered to the body of a human or an animal.

Suitable drugs include, but are not limited to: peptides, proteins, polypeptides or synthetic analogs of these species, as well as mixtures thereof.

In one embodiment, preferred drugs include macromolecules. Such macromolecules include, but are not limited to, pharmacologically active peptides, proteins, or polypeptides. Numerous peptides, proteins, or polypeptides that are useful in the practice of the present invention are described herein. In addition to the peptides, proteins, or polypeptides described, modifications of these peptides, proteins, or polypeptides are also known to one of skill in the art and can be used in the practice of the present invention following the guidance presented herein. Such modifications include, but are not limited to, amino acid analogs, amino acid mimetics, analog polypeptides, or derivative polypeptides. Further, the drugs disclosed herein may be formulated or administered singly or in combination (e.g., using mixtures of drugs or multiple devices; U.S. Patent Publication No. 2009/0202608).

Some embodiments of the present invention comprise use of polypeptides of SEQ ID NOs: 4-136, 138, 139 and 143-149.

Some embodiments of the present invention comprise use of a glucagon-receptor selective agonist polypeptide in combination with a second polypeptide, such as, by way of, non-limiting example, insulinotrophic peptides, peptide hormones, for example, glucagon and incretin mimetics (e.g., GLP-1 and exenatide), as well as peptide analogs and peptide derivatives thereof; PYY (also known as peptide YY, peptide tyrosine tyrosine), as well as peptide analogs and peptide derivatives thereof, for example, PYY(3-36); oxyntomodulin, as well as peptide analogs and peptide derivatives thereof); and gastric inhibitory peptide (GIP), as well as peptide analogs and peptide derivatives thereof.

GLP-1, including three forms of the peptide, GLP-1(1-37), GLP-1(7-37) and GLP-1(7-36) amide, as well as peptide analogs of GLP-1 have been shown to stimulate insulin secretion (i.e., is insulinotropic), which induces glucose uptake by cells and results in decreases in serum glucose concentrations (see, e g., Mojsov, S., Int. J. Peptide Protein Research, 40:333-343 (1992)).

Numerous GLP-1 peptide derivatives and peptide analogs demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217), as well as in clinical trials (e.g., taspoglutide and albiglutide). One example of a GLP-1 peptide derivative useful in the practice of the present invention is Victoza® (Novo Nordisk A/S, Bagsvaerd D K) (liraglutide; U.S. Pat. Nos. 6,268,343, 6,458,924, and 7,235,627). Once-daily injectable Victoza® (liraglutide) is commercially available in the United States, Europe, and Japan. For ease of reference herein, the family of GLP-1 peptides, GLP-1 peptide derivatives and GLP-1 peptide analogs having insulinotropic activity is referred to collectively as "GLP-1."

The molecule exenatide has the amino acid sequence of exendin-4 (Kolterman O. G., et al., J. Clin. Endocrinol. Metab. 88(7):3082-9 (2003)) and is produced by chemical synthesis or recombinant expression. Twice-daily injectable exenatide is commercially available in the United States and Europe, and sold under the trade name of Byetta® (Amylin Pharmaceuticals, Inc., San Diego, Calif.). Exendin-3 and exendin-4 are known in the art and were originally isolated from Heloderma spp. (Eng, J., et al., J. Biol. Chem., 265: 20259-62 (1990); Eng., J., et al., J. Biol. Chem., 267:7402-

05 (1992)). Use of exendin-3 and exendin-4 for the treatment of type 2 diabetes mellitus and the prevention of hyperglycemia has been proposed (see, e.g., U.S. Pat. No. 5,424,286). Numerous exenatide peptide derivatives and peptide analogs (including, e.g., exendin-4 agonists) are known in the art (see, e.g., U.S. Pat. Nos. 5,424,286; 6,268,343; 6,329,336; 6,506,724; 6,514,500; 6,528,486; 6,593,295; 6,703,359; 6,706,689; 6,767,887; 6,821,949; 6,849,714; 6,858,576; 6,872,700; 6,887,470; 6,887,849; 6,924,264; 6,956,026; 6,989,366; 7,022,674; 7,041,646; 7,115,569; 7,138,375; 7,141,547; 7,153,825; and 7,157,555). One example of an exenatide derivative useful in the practice of the present invention is lixisenatide (also known as ZP10, AVE0010) (see, e.g., U.S. Pat. No. 6,528,486), which is in clinical trials. For ease of reference herein, the family of exenatide peptides (e.g., including exendin-3, exendin-4, and exendin-4-amide), exenatide peptide derivatives, and exenatide peptide analogs is referred to collectively as "exenatide."

Peptide YY (PYY) is a 36 amino acid residue peptide amide. PYY inhibits gut motility and blood flow (Laburthe, M., *Trends Endocrinol Metab.* 1(3):168-74 (1990), mediates intestinal secretion (Cox, H. M., et al., *Br J Pharmacol* 101(2):247-52 (1990); Playford, R. J., et al., *Lancet* 335 (8705):1555-7 (1990)), and stimulate net absorption (MacFayden, R. J., et al., *Neuropeptides* 7(3):219-27 (1986)). Two major in vivo variants, PYY(1-36) and PYY (3-36), have been identified (e.g., Eberlein, G. A., et al., *Peptides* 10(4), 797-803 (1989)). The sequence of PYY, as well as peptide analogs and peptide derivatives thereof, are known in the art (e.g., U.S. Pat. Nos. 5,574,010 and 5,552,520).

Oxyntomodulin is a naturally occurring 37 amino acid peptide hormone found in the colon that has been found to suppress appetite and facilitate weight loss (Wynne K, et al., *Int J Obes* (Lond) 30(12):1729-36(2006)). The sequence of oxyntomodulin, as well as peptide analogs and peptide derivatives thereof, are known in the art (e.g., Bataille D, et al., *Peptides* 2(Suppl 2):41-44 (1981); and U.S. Patent Publication Nos. 2005/0070469 and 2006/0094652).

Gastric Inhibitory Peptide (GIP) is an insulinotropic peptide hormone (Efendic, S., et al., *Horm Metab Res.* 36:742-6 (2004)) and is secreted by the mucosa of the duodenum and jejunum in response to absorbed fat and carbohydrate that stimulate the pancreas to secrete insulin. GIP circulates as a biologically active 42-amino acid peptide. GIP is also known as glucose-dependent insulinotropic protein. GIP is a 42-amino acid gastrointestinal regulatory peptide that stimulates insulin secretion from pancreatic beta cells in the presence of glucose (Tseng, C., et al., *PNAS* 90:1992-1996 (1993)). The sequence of GIP, as well as peptide analogs and peptide derivatives thereof, are known in the art (e.g., Meier J. J., *Diabetes Metab Res Rev.* 21(2):91-117 (2005) and Efendic S., *Horm Metab Res.* 36(11-12):742-6 (2004)).

Glucagon is a peptide hormone, produced by alpha cells of the pancreas, which raises the concentration of glucose in the bloodstream. Its effect is opposite that of insulin, which lowers the glucose concentration. The pancreas releases glucagon when the concentration of glucose in the bloodstream falls too low. Glucagon causes the liver to convert stored glycogen into glucose, which is released into the bloodstream. High blood glucose levels stimulate the release of insulin. Insulin allows glucose to be taken up and used by insulin-dependent tissues. Thus, glucagon and insulin are part of a feedback system that keeps blood glucose levels at a stable level.

Glucagon-like peptide-2 (GLP-2) is a 33 amino acid peptide with the sequence HADGSFSDEMNTILDN-LAARDFINWLIQTKITD (SEQ ID NO: 200) in humans. GLP-2 is created by specific post-translational proteolytic cleavage of proglucagon in a process that also liberates the related glucagon-like peptide-1 (GLP-1). GLP-2 is produced by the intestinal endocrine L cell and by various neurons in the central nervous system. Intestinal GLP-2 is co-secreted along with GLP-1 upon nutrient ingestion. When externally administered, GLP-2 produces a number of effects in humans and rodents, including intestinal growth, enhancement of intestinal function, reduction in bone breakdown and neuroprotection. GLP-2 may act in an endocrine fashion to link intestinal growth and metabolism with nutrient intake.

Examples of half-lives of some of the peptides are as follows: exenatide, approximately 2.5 hours; GLP-1, approximately 2 minutes; GIP, approximately 5 minutes; PYY, approximately 8 minutes; glucagon, approximately 6 minutes; oxyntomodulin, approximately 6 minutes; and GLP-2, approximately 6 minutes.

The drugs can also be in various forms including, but not limited to, the following: uncharged molecules; components of molecular complexes; and pharmacologically acceptable salts such as hydrochloride, hydrobromide, sulfate, laurates, palmitates, phosphate, nitrate, borate, acetate, maleate, tartrate, oleates, or salicylates. For acidic drugs, salts of metals, amines or organic cations, for example, quaternary ammonium, can be employed. Furthermore, simple derivatives of the drug such as esters, ethers, amides and the like that have solubility characteristics suitable for the purpose of the invention can also be used herein.

The above drugs and other drugs known to those of skill in the art are useful in methods of treatment for a variety of conditions including but not limited to the following: chronic pain, hemophilia and other blood disorders, endocrine disorders, metabolic disorders, non-alcoholic fatty liver disease (NAFLD), non-alcoholic steatohepatitis (NASH), Alzheimer's disease, cardiovascular diseases (e.g., heart failure, atherosclerosis, and acute coronary syndrome), rheumatologic disorders, diabetes (including type 1, type 2 diabetes mellitus, human immunodeficiency virus treatment-induced, latent autoimmune diabetes in adults, and steroid-induced), hypoglycemia unawareness, restrictive lung disease, chronic obstructive pulmonary disease, lipoatrophy, metabolic syndrome, leukemia, hepatitis, renal failure, infectious diseases (including bacterial infection, viral infection (e.g., infection by human immunodeficiency virus, hepatitis C virus, hepatitis B virus, yellow fever virus, West Nile virus, Dengue virus, Marburg virus, and Ebola virus), and parasitic infection), hereditary diseases (such as cerbrosidase deficiency and adenosine deaminase deficiency), hypertension, septic shock, autoimmune diseases (e.g., Grave's disease, systemic lupus erythematosus, multiple sclerosis, and rheumatoid arthritis), shock and wasting disorders, cystic fibrosis, lactose intolerance, Crohn's diseases, inflammatory bowel disease, gastrointestinal cancers (including colon cancer and rectal cancer), breast cancer, leukemia, lung cancer, bladder cancer, kidney cancer, non-Hodgkin lymphoma, pancreatic cancer, thyroid cancer, endometrial cancer, and other cancers. Further, some of the above agents are useful for the treatment of infectious diseases requiring chronic treatments including, but not limited to, tuberculosis, malaria, leishmaniasis, trypanosomiasis (sleeping sickness and Chagas disease), and parasitic worms.

The amount of drug in drug particle formulations is that amount necessary to deliver a therapeutically effective amount of the agent to achieve the desired therapeutic result in the subject to which the drug is being delivered. In practice, this will vary depending upon such variables, for example, as the particular agent, the severity of the condition, and the desired therapeutic effect. Beneficial agents and their dosage unit amounts are known to the prior art in Goodman & Gilman's The Pharmacological Basis of Therapeutics, 11th Ed., (2005), McGraw Hill; Remington's Pharmaceutical Sciences, 18th Ed., (1995), Mack Publishing Co.; and Martin's Physical Pharmacy and Pharmaceutical Sciences, 1.00 edition (2005), Lippincott Williams & Wilkins. Further, highly concentrated drug particles are described in U.S. Patent Publication No. 2010/0092566. Typically, for an osmotic delivery system, the volume of the chamber comprising the drug formulation is between about 100 µl to about 1000 µl, more preferably between about 140 µl and about 200 µl. In one embodiment, the volume of the chamber comprising the drug formulation is about 150 µl.

Drug particle formulations of the invention are preferably chemically and physically stable for at least 1 month, preferably at least 3 months, more preferably at least 6 months, more preferably at least 12 months at delivery temperature. The delivery temperature is typically normal human body temperature, for example, about 37° C., or slightly higher, for example, about 40° C. Further, drug particle formulations of the present invention are preferably chemically and physically stable for at least 3 months, preferably at least 6 months, more preferably at least 12 months, at storage temperature. Examples of storage temperatures include refrigeration temperature, for example, about 5° C.; or room temperature, for example, about 25° C.

A drug particle formulation may be considered chemically stable if less than about 25%; preferably less than about 20%, more preferably less than about 15%, more preferably less than about 10%, and more preferably less than about 5% breakdown products of the drug particles are formed after about 3 months, preferably after about 6 months, preferably after about 12 months at delivery temperature and after about 6 months, after about 12 months, and preferably after about 24 months at storage temperature.

A drug particle formulation may be considered physically stable if less than about 10%, preferably less than about 5%, more preferably less than about 3%, more preferably less than 1% aggregates of the drug are formed after about 3 months, preferably after about 6 months, at delivery temperature and about 6 months, preferably about 12 months, at storage temperature.

When the drug in the drug particle formulation is a protein, the protein solution is kept in a frozen condition and lyophilized or spray dried to a solid state. Tg (glass transition temperature) may be one factor to consider in achieving stable compositions of protein. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., peptide products will not have mobility when stored at room temp or even at 40° C. because the storage temperature is below the Tg. Calculations using molecular information have shown that if a glass transition temperature is above a storage temperature of 50° C. that there is zero mobility for molecules. Zero mobility of molecules correlates with better stability. Tg is also dependent on the moisture concentration in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. In one embodiment of the invention the particles are spray dried. The particles are preferably substantially uniform in shape and size.

The particles are typically sized such that they can be delivered via an implantable osmotic delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, more preferably is less than about 20%, more preferably is less than about than 10%, of the diameter of the delivery orifice. In an embodiment of the particle formulation for use with an osmotic delivery system, wherein the delivery orifice diameter of the implant is about 0.5 mm, particle sizes may be, for example, less than about 150 microns to about 50 microns. In an embodiment of the particle formulation for use with an osmotic delivery system, wherein the delivery orifice diameter of the implant is about 0.1 mm, particle sizes may be, for example, less than about 30 microns to about 10 microns. In one embodiment, the orifice is about 0.25 mm (250 microns) and the particle size is about 2 microns to about 5 microns.

Those of ordinary skill in the art will appreciate that a population of particles follow principles of particle size distribution. Widely used, art-recognized methods of describing particle size distributions include, for example, average diameters and D values, such as the $D_{50}$ value, which is commonly used to represent the mean diameter of the range of the particle sizes of a given sample.

Particles of a particle formulation have diameters of between about 2 microns to about 150 micron, e.g., less than 150 microns in diameter, less than 100 microns in diameter, less than 50 microns in diameter, less than 30 microns in diameter, less than 10 microns in diameter, less than 5 microns in diameter, and about 2 microns in diameter. Preferably, particles have diameters of between about 2 microns and about 50 microns.

Particles of a particle formulation comprising an isolated glucagon-specific agonist polypeptide have average diameters of between about 0.3 microns to about 150 microns. Particles of a particle formulation comprising an isolated glucagon-specific agonist polypeptide have average diameters of between about 2 microns to about 150 microns, e.g., less than 150 microns in average diameter, less than 100 microns in average diameter, less than 50 microns in average diameter, less than 30 microns in average diameter, less than 10 microns in average diameter, less than 5 microns in average diameter, and about 2 microns in average diameter. In some embodiments, particles have average diameters of between about 0.3 microns and 50 microns, for example, between about 2 microns and about 50 microns. In some embodiments, the particles have an average diameter between 0.3 microns and 50 microns, for example, between about 2 microns and about 50 microns, where each particle is less than about 50 microns in diameter.

Typically, the particles of the particle formulations, when incorporated in a suspension vehicle, do not settle in less than about 3 months, preferably do not settle in less than about 6 months, more preferably do not settle in less than about 12 months, more preferably do not settle in less than about 24 months at delivery temperature, and most preferably do not settle in less than about 36 months at delivery temperature. The suspension vehicles typically have a viscosity of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise. Generally speaking, smaller particles tend to have a lower settling rate in viscous suspension vehicles than larger particles. Accordingly, micron- to nano-sized particles are typically desirable. In viscous suspension formulation, particles of about 2 microns to about 7 microns of the present invention will not settle for at least 20 years at room temperature based on simulation modeling studies. In an embodiment of the particle formulation of the present invention, for use in an implantable osmotic delivery device, comprises particles of sizes less than about 50 microns, more preferably less than about 10 microns, more preferably in a range from about 2 microns to about 7 microns.

In one embodiment, a drug particle formulation comprises a drug, as described above, one or more stabilizers, and optionally a buffer. The stabilizers may be, for example, carbohydrate, antioxidant, amino acid, buffer, inorganic compound, or surfactant. The amounts of stabilizers and buffer in the particle formulation can be determined experimentally based on the activities of the stabilizers and buffers and the desired characteristics of the formulation, in view of the teachings of the present specification. Typically, the amount of carbohydrate in the formulation is determined by aggregation concerns. In general, the carbohydrate amount should not be too high so as to avoid promoting crystal growth in the presence of water due to excess carbohydrate unbound to drug. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize drug during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinisitol). Preferred carbohydrates include disaccharides and/or non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteine, thioglycerol, thioglycolic acid, thiosorbitol, butylated hydroxyanisol, butylated hydroxytoluene, and propyl gallate. Further, amino acids that readily oxidize can be used as antioxidants, for example, cysteine, methionine, and tryptophan.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, tryptophan, serine, asparagines, cysteine, tyrosine, lysine, and norleucine.

Examples of buffers that may be included in the particle formulation include, but are not limited to, citrate, histidine, succinate, phosphate, maleate, tris, acetate, carbohydrate, and gly-gly.

Examples of inorganic compounds that may be included in the particle formulation include, but are not limited to, NaCl, $Na_2SO_4$, $NaHCO_3$, KCl, $KH_2PO_4$, $CaCl_2$), and $MgCl_2$.

In addition, the particle formulation may include other excipients, such as surfactants, and salts. Examples of surfactants include, but are not limited to, Polysorbate 20, Polysorbate 80, PLURONIC® (BASF Corporation, Mount Olive, N.J.) F68, and sodium dodecyl sulfate (SDS). Examples of salts include, but are not limited to, sodium chloride, calcium chloride, and magnesium chloride.

All components included in the particle formulation are typically acceptable for pharmaceutical use in mammals, particularly, in humans.

In summary, a selected drug or combination of drugs is formulated into dried powders in solid state, which preserve maximum chemical and biological stability of the drug. The particle formulation offers long-term storage stability at high temperature, and therefore, allows delivery to a subject of stable and biologically effective drug for extended periods of time.

3.2.0 Vehicle Formulations and Suspension Formulations

In one aspect, the suspension vehicle provides a stable environment in which the drug particle formulation is dispersed. The drug particle formulations are chemically and physically stable (as described above) in the suspension vehicle. The suspension vehicle typically comprises one or more polymer and one or more solvent that form a solution of sufficient viscosity to uniformly suspend the particles comprising the drug. The suspension vehicle may comprise further components, including, but not limited to, surfactants, antioxidants, and/or other compounds soluble in the vehicle.

The viscosity of the suspension vehicle is typically sufficient to prevent the drug particle formulation from settling during storage and use in a method of delivery, for example, in an implantable, osmotic delivery device. The suspension vehicle is biodegradable in that the suspension vehicle disintegrates or breaks down over a period of time in response to a biological environment, while the drug particle is dissolved in the biological environment and the active pharmaceutical ingredient (i.e., the drug) in the particle is absorbed.

In embodiments, the suspension vehicle is a "single-phase" suspension vehicle, which is a solid, semisolid, or liquid homogeneous system that is physically and chemically uniform throughout.

The solvent in which the polymer is dissolved may affect characteristics of the suspension formulation, such as the behavior of drug particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and mixtures thereof.

Examples of polymers for formulation of the suspension vehicles of the present invention include, but are not limited to, a polyester (e.g., polylactic acid and polylacticpolyglycolic acid), a polymer comprising pyrrolidones (e.g., polyvinylpyrrolidone having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. Polyvinylpyrrolidone can be characterized by its K-value (e.g., K-17), which is a viscosity index. In one embodiment, the polymer is polyvinylpyrrolidone having a molecular weight of 2,000 to 1,000,000. In a preferred embodiment, the polymer is polyvinylpyrrolidone K-17 (typically having an approximate average molecular weight range of 7,900-10,800). The polymer used in the suspension vehicle may include one or more different polymers or may include different grades of a single polymer. The polymer used in the suspension vehicle may also be dry or have a low moisture content.

Generally speaking, a suspension vehicle for use in the present invention may vary in composition based on the desired performance characteristics. In one embodiment, the suspension vehicle may comprise about 40 wt % to about 80 wt % polymer(s) and about 20 wt % to about 60 wt % solvent(s). Preferred embodiments of a suspension vehicle include vehicles formed of polymer(s) and solvent(s) combined at the following ratios: about 25 wt % solvent and about 75 wt % polymer; about 50 wt % solvent and about 50 wt % polymer; about 75 wt % solvent and about 25 wt % polymer. Accordingly, in some embodiments, the suspension vehicle may comprise selected components and in other embodiments consist essentially of selected components.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the drug contained in the drug particle formulation. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. In preferred embodiments, the suspension vehicles typically have a viscosity, at 33° C., of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise, at 33° C. The viscosity may be measured at 33° C., at a shear rate of $10^{-4}$/sec, using a parallel plate rheometer.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The drug particle formulation is added to the suspension vehicle to form a suspension formulation. In some embodiments, the suspension formulation may comprise a drug particle formulation and a suspension vehicle and in other embodiments consist essentially of a drug particle formulation and a suspension vehicle.

The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

In preferred embodiments, the suspension formulations of the present invention are substantially homogeneous and flowable to provide delivery of the drug particle formulation from the osmotic delivery device to the subject.

In summary, the components of the suspension vehicle provide biocompatibility. Components of the suspension vehicle offer suitable chemico-physical properties to form stable suspensions of drug particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

4.0.0 Delivery of Suspension Formulations

The suspension formulations described herein may be used in an implantable, osmotic delivery device to provide zero-order, continuous, controlled, and sustained delivery of a compound over an extended period of time, such as over weeks, months, or up to about one year or more. Such an implantable osmotic delivery device is typically capable of delivering the suspension formulation, comprising the drug, at a desired flow rate over a desired period of time. The suspension formulation may be loaded into the implantable, osmotic delivery device by conventional techniques.

A dose and delivery rate can be selected to achieve a desired blood concentration of a drug generally within less than about 6 half-lives of the drug within the subject after implantation of the device. The blood concentration of the drug is selected to give the optimal therapeutic effects of the drug while avoiding undesirable side effects that may be induced by excess concentration of the drug, while at the same time avoiding peaks and troughs that may induce side effects associated with peak or trough plasma concentrations of the drug.

The implantable, osmotic delivery device typically includes a reservoir having at least one orifice through which the suspension formulation is delivered. The suspension formulation may be stored within the reservoir. In a preferred embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; and 7,112,335; 7,163,688; U.S. Patent Publication Nos. 2005/0175701, 2007/0281024, 2008/0091176, and 2009/0202608).

The osmotic delivery device typically consists of a cylindrical reservoir which contains the osmotic engine, piston, and drug formulation. The reservoir is capped at one end by a controlled-rate, semi-permeable membrane and capped at the other end by a diffusion moderator through which suspension formulation, comprising the drug, is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The osmotic device releases a drug at a predetermined rate based on the principle of osmosis. Extracellular fluid enters the osmotic delivery device through a semi-permeable membrane directly into a salt engine that expands to drive the piston at a slow and even delivery rate. Movement of the piston forces the drug formulation to be released through the orifice or exit port at a predetermined shear rate. In one embodiment of the present invention, the reservoir of the osmotic device is loaded with a suspension formulation wherein the device is capable of delivering the suspension formulation to a subject over an extended period of time (e.g., about 1, about 3, about 6, about 9, about 10, and about 12 months) at a pre-determined, therapeutically effective delivery rate.

The release rate of the drug from the osmotic delivery device typically provides a subject with a predetermined target dose of a drug, for example, a therapeutically effective daily dose delivered over the course of a day; that is, the release rate of the drug from the device, provides substantial steady-state delivery of the drug at a therapeutic concentration to the subject.

Typically, for an osmotic delivery device, the volume of a beneficial agent chamber comprising the beneficial agent formulation is between about 100 μl to about 1000 μl, more preferably between about 120 μl and about 500 μl, more preferably between about 150 μl and about 200 μl.

Typically, the osmotic delivery device is implanted within the subject, for example, subdermally or subcutaneously to provide subcutaneous drug delivery. The device(s) can be implanted subdermally or subcutaneously into either or both arms (e.g., in the inside, outside, or back of the upper arm) or the abdomen. Preferred locations in the abdominal area are under the abdominal skin in the area extending below the ribs and above the belt line. To provide a number of locations for implantation of one or more osmotic delivery device within the abdomen, the abdominal wall can be divided into 4 quadrants as follows: the upper right quadrant extending at least 2-3 centimeters below the right ribs, e.g., at least about 5-8 centimeters below the right ribs, and at least 2-3 centimeters to the right of the midline, e.g., at least about 5-8 centimeters to the right of the midline; the lower right quadrant extending at least 2-3 centimeters above the belt line, e.g., at least about 5-8 centimeters above the belt line, and at least 2-3 centimeters to the right of the midline, e.g., at least about 5-8 centimeters to the right of the midline; the upper left quadrant extending at least 2-3 centimeters below the left ribs, e.g., at least about 5-8 centimeters below the left ribs, and at least 2-3 centimeters to the left of the midline, e.g., at least about 5-8 centimeters to the left of the midline; and the lower left quadrant extending at least 2-3 centimeters above the belt line, e.g., at least about 5-8 centimeters above the belt line, and at least 2-3 centimeters to the left of the midline, e.g., at least about 5-8 centimeters to the left of the midline. This provides multiple available locations for implantation of one or more devices on one or more occasions. Implantation and removal of osmotic delivery devices are generally carried out by medical professionals using local anesthesia (e.g., lidocaine).

Termination of treatment by removal of an osmotic delivery device from a subject is straightforward, and provides the important advantage of immediate cessation of delivery of the drug to the subject.

Preferably, the osmotic delivery device has a fail-safe mechanism to prevent an inadvertent excess or bolus delivery of drug in a theoretical situation like the plugging or clogging of the outlet (diffusion moderator) through which the drug formulation is delivered. To prevent an inadvertent excess or bolus delivery of drug the osmotic delivery device is designed and constructed such that the pressure needed to partially or wholly dislodge or expel the diffusion moderator from the reservoir exceeds the pressure needed to partially or wholly dislodge or expel the semi-permeable membrane to the extent necessary to de-pressurize the reservoir. In such a scenario, pressure would build within the device until it would push the semi-permeable membrane at the other end outward, thereby releasing the osmotic pressure. The osmotic delivery device would then become static and no longer deliver the drug formulation provided that the piston is in a sealing relationship with the reservoir.

The suspension formulations may also be used in infusion pumps, for example, the ALZET® (DURECT Corporation, Cupertino, Calif.) osmotic pumps which are miniature, infusion pumps for the continuous dosing of laboratory animals (e.g., mice and rats).

EXAMPLES

The following examples are put forth so as to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, and percent changes) but some experimental errors and deviations should be accounted for. Unless indicated otherwise, temperature is in degrees Centigrade and pressure is at or near atmospheric.

The compositions used to practice the methods of the present invention meet the specifications for content and purity required of pharmaceutical products.

Example 1: Generation of Glucagon-Receptor Selective Agonist Polypeptides

Glucagon polypeptides of the invention, as provided in Table 3, were synthesized on a Prelude peptide synthesizer (Protein Technologies Inc., Tucson, AZ) by solid-phase methods using Fmoc strategy with 2-(1H-benzotriazole-1-yl)-1,1,3,3-tetramethyl uranium hexafluorophosphate (HBTU) or 2-(6-chloro-1-H-benzotriazole-1-yl)-1,1,3,3-tetramethylaminium hexafluorophosphate (HCTU) activation (5 fold molar excess) in N,N-dimethylformamide (DMF), and N'N-Diisopropylethylamine (DIEA) as base, 20% piperidine/DMF for Fmoc deprotection. The resin was Rink Amide MBHA LL (Novabiochem) or N-α-Fmoc protected, pre-loaded Wang L L (Novabiochem), with loadings of 0.29-0.35 mmol/g on a 20-400 µmol scale. Final deprotection and cleavage of the peptide from the solid support was performed by treatment of the resin with (92.5% TFA, 2.5% phenol, 2.5% water and 2.5% triisopropylsilane) for 2-3 hours. The cleaved peptide was precipitated using cold diethyl ether. The diethyl ether was decanted and the solids triturated again with cold diethyl ether, pelleted by centrifugation and lyophilized. The lyophilized solid was re-dissolved in a 1:1 solution of acetonitrile/water, with 0.1% TFA (10-15 mL), purified via reverse phase HPLC on a Waters XBridge™ BEH 130, CIS, 10 pm, 130 Å, 30×250 mm ID column, using a 30 gradient within the ranges of 5-75% acetonitrile/water with 0.1% TFA over 30-45 minutes at a flow rate of 30 mL/min, λ—215 nm. The purified product was lyophilized and analyzed by ESI-LC/MS and analytical HPLC; and were demonstrated to be pure (>98%). Mass results all agreed with calculated values.

Characterizations of peptide analogs were performed via C18 HPLC and LC/MS analysis (Acquity SQD Waters Corp, Milford, MA) and UV detection provided by dual absorbance signals at 215 nm and 280 nm, using one of the three methods A or Method B or Method C.

LC/MS Conditions: Method A: Performed using a Phenomenex UPLC Aeris™ Peptide XB C18 35 column, 1.7 pm, 2.1×100 mm or ACQUiTY BEH300 or BEH130 CT8 column, 1.77 pm. 2.1×100 mm using 5-65% acetonitrile/water with 0.05% TFA over 30 minutes with a flow rate 0.5 mL/min, λ~215 nm, 280 nm.

C18 HPLC Conditions: Method A: UPLC analysis was conducted on an Acquity BEH130, C18 column, 1.7 µm, 100×2.10 mm column at 25° C., 5-65% acetonitrile/water with 0.05% TFA over 30 minutes, flow rate 0.5 mL/min, λ 215 nm, λ 280 nm.

Method B: UPLC analysis was conducted on an Acquity BEH130, C18 column, 1.7 µm, 100×2.10 mm column at 25° C., 5-65% acetonitrile/water with 0.05% TFA over 20 minutes, flow rate 0.5 mL/min, k 215 nm, k 280 nm.

Method C: UPLC analysis was conducted on an Acquity BEH130, C18 column, 1.7 µm, 100×2.10 mm column at 25° C., 5-65% acetonitrile/water with 0.05% TFA over 10 minutes, flow rate 0.5 mL/min, λ215 nm, λ 280 nm. 5.0 uL of sample was injected using a PLNO (partial loop w/needle overfill) injection mode.

Table 3 provides the amino acid sequence and experimental data for the selective glucagon receptor analogs of the disclosure, including the selective glucagon receptor analogs referred to herein as Compound A4 (SEQ ID NO: 44), Compound A5 (SEQ ID NO: 45), Compound A6 (SEQ ID NO: 46), Compound A2 (SEQ ID NO: 42), Compound A1 (SEQ ID NO: 41), Compound A3 (SEQ ID NO: 43), Compound A97 (SEQ ID NO: 143), Compound A98 (SEQ ID NO: 144), Compound A99 (SEQ ID NO: 145), Compound A100 (SEQ ID NO: 146), Compound A101 (SEQ ID NO: 147), Compound A102 (SEQ ID NO: 148), and Compound A97 (SEQ ID NO: 149).

Example 2: Generation of Lactam-Bridged Glucagon-Receptor Selective Agonist Polypeptides The synthesis, purification and analytical methods were performed as described in Example 1 with following modifications. Glucagon polypeptides of the invention, as provided in Table 3, were synthesized on a Prelude peptide synthesizer (Protein Technologies Inc., Tucson, AZ)) by solid-phase methods using Fmoc strategy and using Rink Amide MBHA LL (Novabiochem) or N-α-Fmoc protected, pre-loaded Wang L L (Novabiochem), with loadings of 0.29-0.35 mmol/g on a 20-400 µmol scale. Fmoc amino acid (4.0 eq, 1.0 mmol) residues were activated using 4.0 eq HBTU, 4.0 eq of HOBT, 8.0 eq DIEA and coupled to the resin for 1 hour. The Fmoc group was removed by treatment with 20% (v/v) piperidine in dimethylformamide. The side chain protection groups used were Trt for Asn, Gln, Cys and His; t-Bu for Ser, Thr, and Tyr; Boc for Lys and Trp; Ot-Bu for Asp and Glu; and Pbf for Arg.

The Lactam Bridges between positions 17-21 and between positions 24-27 were introduced using an orthogonally protected Lysine (Alloc)17 and Glu (Allyl)21; and Glu(Allyl)24 and Lysine (Alloc)27 is represented by E in parenthesis in the sequence Lysine (Alloc) is represented by K in parenthesis in the sequences shown in SEQ ID NO: 19 and SEQ ID NO: 20.

Synthesis was carried out from C-terminal to N-terminal on the solid support. To incorporate the first lactam bridge (residue 17-residue 21) the synthesis was paused at Phe21. The resin was washed with DCM (6×10 ml) that had been flushed previously with nitrogen for 30 minutes. Next, Palladium Tetrakis, Pd(PPh3)3 (3 equiv) was added to a solution of CHCl3/AcOH/NMM (37:2:1). Nitrogen was bubbled through the solution until all of the solid had dissolved leaving a dark amber solution. This solution was transferred to an amino acid bottle wherein it was degassed for an additional 5 minutes with nitrogen. It was then placed on to the prelude synthesizer. 20 ml of the Palladium solution was added to each RV and the reaction mixture was allowed to agitate for 3 hours. Synthesis was continued using standard protocol. To incorporate the second lactam bridge (residue 24-residue 28) the synthesis was paused at Leu14 and the above procedure for lactam bride formation was repeated.

Before cleaving peptide from resin the allyl protecting groups were removed using Pd(PPh3)$_3$ in CHCl3/AcOH/NMM (37:2:1). Cyclization to the lactam was effected using Pybop (6 equivs), HOBT (6 equivs), and DIEA (12 equivs). The resin was then washed with DMF and dried under vacuum for 15 minutes under nitrogen.

Final deprotection and cleavage of the peptide from the solid support was performed by treatment of the resin with reagent B (92.5% TFA, 2.5% phenol, 2.5% water and 2.5% triisopropylsilane) for 2-3 hours. The cleaved peptide was precipitated using cold diethyl ether, the diethyl ether was decanted and the solids triturated again with cold diethyl ether, pelleted by centrifugation and lyophilized. The pellet was re-dissolved in water (10-15 mL), filtered purified by reverse phase HPLC on a Waters XBridge™ BEH 130, CIS, 10 μm, 130 Å, 30×250 mm ID column, using a gradient within the ranges of 5-75% acetonitrile/water with 0.1% TFA over 30-45 minutes at a flow rate of 30 mL/min, λ~215 nm. Alternatively, purification was afforded using a Gilson Preparative HPLC System via reverse phase chromatography using a Waters XBridge BEH 130, C18, 10 μm, 130 Å, 30×250 mm ID column, with a gradient range of 5-45% acetonitrile/water with 0.1% TFA over 30-45 minutes at a flow rate of 30 mL/min, λ 215 nm. The purified product was lyophilized and analyzed by ESI-LC/MS and analytical HPLC; and are demonstrated to be pure (>98%). Mass results all agreed with calculated values.

Characterizations of peptide analogs were performed via C18 HPLC and LC/MS analysis (Acquity SQD Waters Corp, Milford, MA) and UV detection provided by dual absorbance signals at 215 nm and 280 nm, using one of the three methods A or Method B or Method C.

Figure 4A:
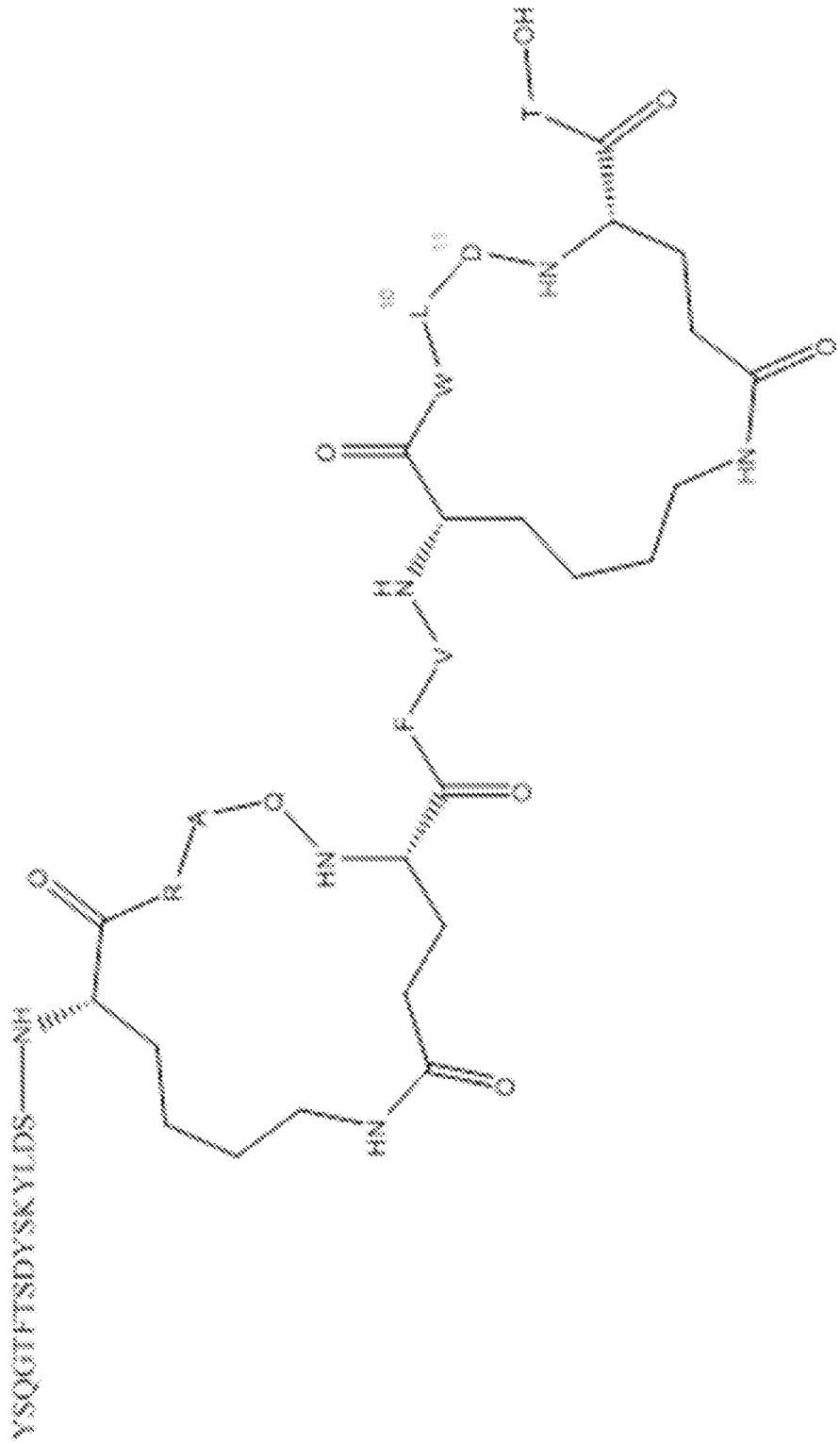
FIGS. 4A and 4B are schematic representations of the chemical structure of the cyclical peptide glucagon analogs referred to herein as Compound A104 (FIG. 4A) and Compound A105 (FIG. 4B).
Figure 4B:
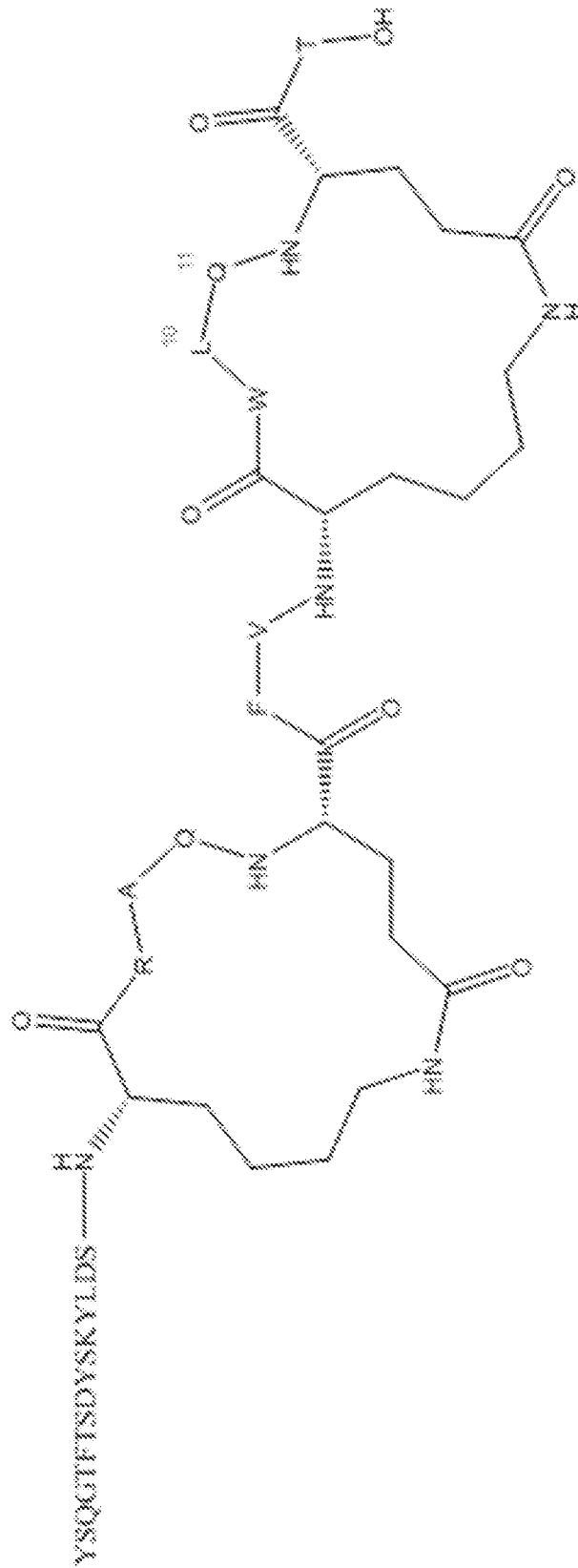

The chemical structure of Compound A104 is shown in FIG. 4A, and the chemical structure of Compound A105 is shown in FIG. 4B.

Example 3: Stability and Solubility of Glucagon-Receptor Selective Agonist Polypeptides Glucagon and the analogs described herein, e.g. Compound A98, Compound A99, Compound A100, Compound A101, Compound A102, Compound A2, Compound A1, Compound A5, Compound A6, Compound A3, Compound A44, and Compound A97, were tested for stability in saline 5% NaCl in water (i.e., bioassay buffer) or in aqueous (i.e., in water). Glucagon and these analogs were incubated at 37° C. and at room temperature. Samples were withdrawn at a regular interval for 30 days and analyzed by LC/MS and HPLC for determination of purity and mass of the degradation product. The results of this analysis are shown in Table 3.

Glucagon and the analogs described herein, e.g. Compound A98, Compound A99, Compound A100, Compound A101, Compound A102, Compound A2, Compound A1, Compound A5, Compound A6, Compound A3, Compound A44, and Compound A97 were tested for solubility in saline 5% NaCl in water (i.e., bioassay buffer) or in aqueous at room temperature. Samples were visually inspected for clarity of the sample, any appearance of turbidity or haziness. The results of this analysis are shown in Table 3.

Example 4: In Vitro Screening of Analogs, Peptide-Receptor Mediated cAMP Accumulation CMV promoter-driven plasmids encoding human GCGR (NM_000160) and human GLP-1R (NM_002062) were transfected into CHO-K1 cells for 36 hours using Lipofectamine 2000. Following transfection, cells were removed from the flask using cell disruption media and dispensed in white 384-well plates at 1000 cells per well in 5 uL of stimulation buffer. Peptide-receptor activity was determined using the LANCE Ultra cAMP detection kit according to the manufacturer's protocol (Perkin Elmer). Peptides were serially diluted in stimulation buffer and 5 uL of each peptide dilution was added to cells and incubated for thirty minutes at room temperature. For results shown in Table 2A, tested concentrations ranged from 1 nM to 15 fM in the GCGR and GLP-1R assays. For results shown in Table 2B, tested concentrations ranged from 1 uM to 0.1 fM for GCGR, and 500 uM to 10 fM for GLP-1R assays. Following peptide incubation, 5 uL Europium labelled cAMP and 5 uL Ulight™ anti-cAMP antibody were added to wells and incubated for an additional 60 minutes. Plates were read on an Envision® fluorescent plate reader and data was analyzed using GraphPad Prism®. Potency was determined from baseline-corrected fit curves using the formula:

$$Y=\text{Bottom}+(\text{Top}-\text{Bottom})/(1+10^{((\text{Log IC50}-X)*\text{HillSlope})})$$ with the Hill Slope constrained to −1.0.

TABLE 2A

| Compound | SEQ ID NO: | hGCGR pEC50 (cAMP) mean (n = 9): 11 point curve starting at 1 uM | hGLP1 pEC50 (cAMP) mean (n = 9): 11 point curve starting at 500 uM |
| --- | --- | --- | --- |
| Glucagon | 141 | 10 | 9.9 |
| A4 | 44 | 11.8 | <5 |
| A5 | 45 | 11.8 | 5.8 |
| A6 | 46 | 11.7 | 5.3 |
| A2 | 42 | 11.7 | 5.4 |
| A1 | 41 | 12.3 | 5.2 |
| A3 | 43 | 12.1 | 6.7 |

TABLE 2B

| Compound ID# | SEQ ID NO: | hGCGR pEC50 (cAMP) mean (n = 3): 11 point curve starting at 1 nM | hGLP1 pEC50 (cAMP) mean (n = 3): 11 point curve starting at 1 nM |
| --- | --- | --- | --- |
| A97 | 143 | 12.3 | <9 |
| A98 | 144 | 12.2 | <9 |
| A99 | 145 | 12.5 | <9 |
| A100 | 146 | 12.6 | <9 |
| A101 | 147 | 11.3 | <9 |
| A102 | 148 | 12.4 | <9 |
| A103 | 149 | 11.9 | <9 |

In some embodiments, provided is an isolated polypeptide of the disclosure corresponding to Compound A97, A98, A99, A100, A101, A102 or A103.

Figure 1B:
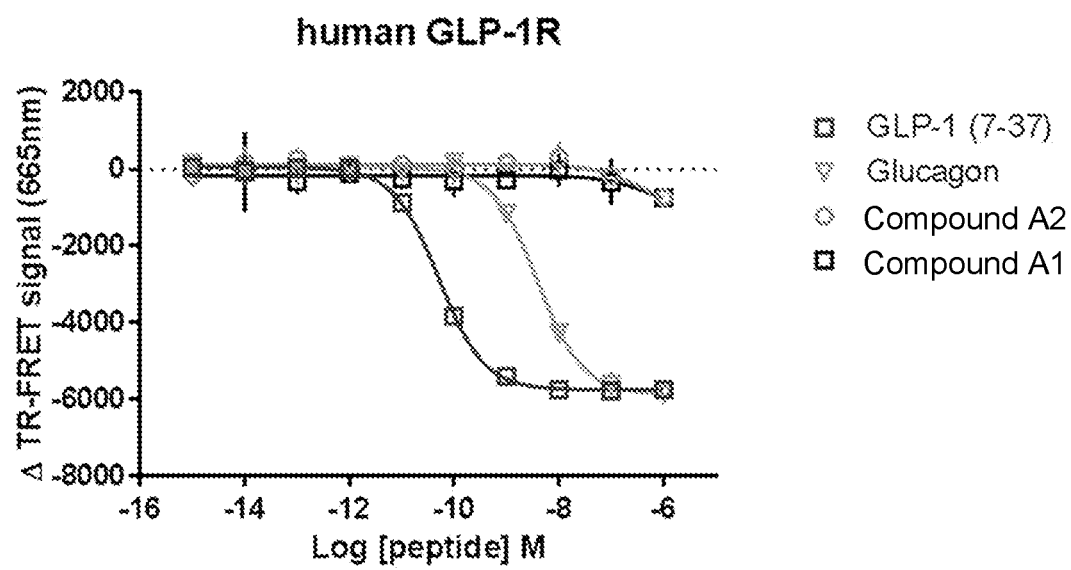

Peptide-receptor activation profiles at the human glucagon receptor (GCGR) and the human GLP-1 receptor (GLP-1R) by human glucagon, GLP-1 (7-37), and two glucagon receptor selective peptide agonists. FIG. 1A demonstrates that peptides Compound A2, Compound A1 and glucagon are nearly equipotent on GCGR, while GLP-1 (7-37) activates GCGR at a much lower potency. FIG. 1B demonstrates that, in contrast to the results shown FIG. 1A, peptides Compound A2 and Compound A1 are inactive on GLP-1R demonstrating that peptides Compound A2 and Compound A1 profile as GCGR selective agonists. Data of all the analogs are recorded in Table 3.

Sequences of synthesized glucagon receptor agonist peptides and their pEC50 values determined in cAMP assays are shown below in Table 3.

TABLE 3

| Compound | hGCGR pEC50 (cAMP mean (n = 3): 11 point curve starting at 1 nm | hGLP1 pEC50 (cAMP mean (n = 3): 11 point curve starting at 1 nm | CL (ml/min/kg) | Sequence | SEQ ID NO: | Calc. Mass (Parent MW) | Calc. Mass (Parent MW, M + 3/3)) | Observed Mass (M + 3/3) | Purity | solubility in water mg/ml | Stability 1 mg/ml in water at 37 degC |
|---|---|---|---|---|---|---|---|---|---|---|---|
| Glucagon | 10 | 9.9 | due to insolubility | HSQGTFTSDYSKYLDSRRAQDFVQWLMNT-OH | 140 | 3482.76 | 1161.92 | 1162.2 | >95% | 0.03-10 ug/ml | Aggregates |
| A1 | 12.3 | 5.2 | 11.5 | YSHGTFTSDYSKYLD(Aib)KYAQEFV(Aib)WLEDEPSSGAPPPS-OH | 41 | 4270.59 | 1424.5 | 1425.5 | >90% | >200 | >71% |
| A2 | 11.7 | 5.4 | 10.8 | YSHGTFTSDYSKYLD(Aib)KSAQEFV(Aib)WLEDEPSSGAPPPS-OH | 42 | 4194.49 | 1399.16 | 1400.1 | >90% | >200 | >84% |
| A3 | 12.1 | 6.7 | 10.7 | YSQGTFTSDYSKYLDAARAQEFVKWLEDEPKSKSPPPS-NH2 | 43 | 4353.78 | 1452.258 | 1453.4 | >95% | >200 | >64% |
| A4 | 11.8 | <5 | 12.6 | YSHGTFTSDYSKYLD(Aib)KRAQEFVIWLEDEPSSGAPPPS-OH | 44 | 4291.66 | 1431.55 | 1432.4 | >98% | >200 | >81% |
| A5 | 11.8 | 5.8 | 11.7 | YSHGTFTSDYSKYLDSARAQEFVKWLEDEPSSGAPPPS-NH2 | 45 | 4250.57 | 1417.83 | 1418.9 | >98% | >200 | >94% |
| A6 | 11.7 | 5.3 | 12.4 | WSQGTFTSDYSKYLD(Aib)KRAQEFV(Aib)WLEDEPSSGAPPPS-OH | 46 | 4277.63 | 1426.88 | 1427.5 | >98% | >200 | >80% |
| A7 | 11.9 | <9 | 28.5 | YSHGTFTSDYSKYLD(Aib)ARAQEFV(Aib)WLEDEPSSGAPPPS-OH | 47 | 4206.5 | 1403.17 | 1403.8 | >98% | — | — |
| A8 | 12.3 | <9 | 17 | YSHGTFTSDYSKYLD(Aib)KRAQEFV(Aib)WLEDEPSSGAPPPS-NH2 | 48 | 4262.6 | 1421.87 | 1423 | >98% | — | — |
| A9 | 13.0 | <9 | — | YSHGTFTSDYSKYLD(Aib)KRAQEFV(Aib)WLEEEPSSGAPPPS-OH | 49 | 4847.6 | 1426.87 | 1427 | >98% | — | — |
| A10 | 11.3 | <9 | — | YSHGTFTSDYSKYLD(Aib)KRAQEFV(Aib)WLEDEESSGAPPPS-OH | 50 | 4962.7 | 1465.23 | 1465.7 | >98% | — | — |
| A11 | 11.2 | <9 | — | YSHGTFTSDYSKYLD(Aib)KRAQEFV(Aib)WLEDEEEPSSGAPPPS-OH | 51 | 5091.8 | 1508.27 | 1509.6 | >98% | — | — |
| A12 | 13.2 | <9 | — | YSHGTFTSDYSKYLD(Aib)KRAQEFV(Aib)WLEDEGAPPPS-OH | 52 | 4562.3 | 1331.77 | 1332.5 | >98% | — | — |

TABLE 3-continued

| Compound | hGCGR pEC50 (cAMP) mean (n = 3): 11 point curve starting at 1 nm | hGLP1 pEC50 (cAMP) mean (n = 3): 11 point curve starting at 1 nm | CL (ml/min/kg) | Sequence | SEQ ID NO: | Calc. Mass (Parent MW) | Calc. Mass (Parent MW, M + 3/3) | Observed Mass (M + 3/3) | Purity | Solubility in water mg/ml | Stability 1 mg/ml in water at 37 degC |
|---|---|---|---|---|---|---|---|---|---|---|---|
| A13 | 12.3 | <9 | — | YSHGTFTSDYSKYLD(Aib)KRAQEF V(Aib)WLEDESGAPPPS-OH | 53 | 4649.4 | 1360.8 | 1361.6 | >98% | — | — |
| A14 | 12.0 | <9 | — | YSHGTFTSDYSKYLD(Aib)KRAQEF V(Aib)WLEDESSGAPPPS-OH | 54 | 4736.5 | 1389.83 | 1390.6 | >98% | — | — |
| A15 | 11.4 | <9 | — | YSHGTFTSDYSKYLD(Aib)SRAQEF V(Aib)WLEDEPSSGAPPPS-OH | 55 | 4222.5 | 1408.5 | 1409.4 | >98% | — | — |
| A16 | 11.9 | <9 | — | YSHGTFTSDYSKYLD(Aib)TRAQEF V(Aib)WLEDEPSSGAPPPS-OH | 56 | 4236.5 | 1413.17 | 1413.5 | >98% | — | — |
| A17 | 11.1 | <9 | — | YSHGTFTSDYSKYLD(Aib)ERAQEF V(Aib)WLEDEPSSGAPPPS-OH | 57 | 4264.5 | 1422.5 | 1422.9 | >98% | — | — |
| A18 | 12.4 | <9 | — | YSHGTFTSDYSKYLD(Aib)ARAQEF V(Aib)WLEDEPSSGAPPPS-OH | 58 | 4229.5 | 1410.83 | 1411.7 | >98% | — | — |
| A19 | 11.0 | <9 | — | YSHGTFTSDYSKWLD(Aib)SRAQEF V(Aib)WLEDEPSSGAPPPS-OH | 59 | 4245.5 | 1409.17 | 1417 | >90% | — | — |
| A20 | 13.3 | <9 | 15 | YSHGTFTSDYSKYLD(Aib)KRAQEF V(Aib)WLEDEPSSGKPPPS-OH | 60 | 4320.7 | 1441.23 | 1442.2 | >95% | — | — |
| A21 | 11.1 | <9 | — | YSHGTFTSDYSKYLD(Aib)KRAQEF V(Aib)WLEDEPSSGEPPPS-OH | 61 | 4321.6 | 1441.53 | 1442.9 | >98% | — | — |
| A22 | 11.0 | <9 | — | YSHGTFTSDYSKYLD(Aib)KRAQEF V(Aib)WLEDEPSSGSPPPS-OH | 62 | 4279.6 | 1427.53 | 1428.4 | >95% | — | — |
| A23 | 11.2 | <9 | — | YSHGTFTSDYSKYLD(Aib)KRAQEF V(Aib)WLEDEPSSKAPPPS-OH | 63 | 4334.7 | 1445.9 | 1447.1 | >98% | — | — |
| A24 | 12.2 | <9 | — | YSHGTFTSDYSKYLD(Aib)KRAQEF V(Aib)WLEDEPSSKGAPPPS-OH | 64 | 4391.7 | 1464.9 | 1465.2 | >98% | — | — |
| A25 | 11.3 | <9 | — | YSHGTFTSDYSKYLD(Aib)KRAQEF V(Aib)WLEDEPSSGAPPPSS-OH | 65 | 4350.7 | 1451.2 | 1451.8 | >98% | — | — |
| A26 | 11.1 | <9 | — | YSHGTFTSDYSKYLD(Aib)KRAQEF V(Aib)WLEDEPSSGAPPPSE-OH | 66 | 4392.72 | 1465.23 | 1465.9 | >98% | — | — |

TABLE 3-continued

| Compound | hGCGR pEC50 (cAMP mean (n = 3): 11 point curve starting at 1 nm | hGLP1 pEC50 (cAMP mean (n = 3): 11 point curve starting at 1 nm | CL (ml/min/kg) | Sequence | SEQ ID NO: | Calc. Mass (Parent MW) | Calc. Mass (Parent MW, M + 3/3) | Observed Mass (M + 3/3) | Purity | Solubility in water mg/ml | Stability 1 mg/ml in water at 37 degC |
|---|---|---|---|---|---|---|---|---|---|---|---|
| A27 | 12.1 | <9 | — | YSHGTFTSDYSKYLD(Aib)V(Aib)KRAQEF WLEDEGPSSGAPPPS-OH | 67 | 4377.71 | 1460.23 | 1461.4 | >98% | — | — |
| A28 | 12.2 | <9 | 34.7 | YSHGTFTSDYSKYLD(Aib)V(Aib)KRAQEF WLEDEGPSSGAPPPS-OH | 68 | 4320.66 | 1441.23 | 1441.6 | >98% | — | — |
| A29 | 11.1 | <9 | — | YSHGTFTSDYSKYLD(Aib)V(Aib)KRAQEF WLEDEPKSGAPPPS-OH | 69 | 4304.70 | 1435.9 | 1436.4 | >98% | — | — |
| A30 | 10.9 | <9 | — | YSHGTFTSDYSKYLD(Aib)V(Aib)KRAQEF WLEDEPSKGAPPPS-OH | 70 | 4304.70 | 1435.9 | 1436.6 | >98% | — | — |
| A31 | 11.7 | <9 | — | YSHGTFTSDYSKYLD(Aib)V(Aib)KRAQEF WLEDEPESGAPPPS-OH | 71 | 4305.64 | 1436.2 | 1436.4 | >98% | — | — |
| A32 | 12.5 | <9 | — | YSHGTFTSDYSKYLD(Aib)V(Aib)KRAQEF WLEDEPSSGAPPPS-OH | 72 | 4300.67 | 1434.56 | 1435.3 | >98% | — | — |
| A33 | 10.9 | <9 | — | YSHGTFTSDHSKWLD(Aib)V(Aib)KRAQEF WLEDEPSSGAPPPS-OH | 73 | 4260.61 | 1421.2 | 1422.8 | >98% | — | — |
| A34 | 10.3 | <9 | — | YTHGTFTSDHSKWLD(Aib)V(Aib)KRAQEF WLEDEPSSGAPPPS-OH | 74 | 4274.64 | 1425.88 | 1426.9 | >98% | — | — |
| A35 | 13.2 | <9 | 30.1 | YTHGTFTSDHSKWLD(Aib)V(Aib)ARAQEF WLEDEPSSGAPPPS-OH | 75 | 4243.57 | 1415.52 | 1416.3 | >98% | — | — |
| A36 | 10.2 | <9 | — | YSHGTFTSDHSKWLD(Aib)V(Aib)ARAQEF WLEDEPSSGAPPPS-OH | 76 | 4203.51 | 1402.17 | 1402.9 | >98% | — | — |
| A37 | 13.0 | <9 | — | YSHGTFTSDYSKYLDSARAQEFVKWL EDEPSSGAPPPS-OH | 77 | 4251.55 | 1418.17 | 1419.3 | >98% | — | — |
| A38 | 13.7 | <9 | — | YSHGTFTSDYSKWLDSARAQEFVKML EDEPSSGAPPPS-OH | 78 | 4274.59 | 1425.83 | 1426.9 | >98% | — | — |
| A39 | 9.4 | <9 | — | YTHGTFTSDYSKWLDSARAQEFVKWL EDEPSSGAPPPS-OH | 79 | 4288.62 | 1430.53 | 1431.9 | >98% | — | — |

TABLE 3-continued

| Compound | hGCGR pEC50 (cAMP mean (n = 3): 11 point curve starting at 1 nm | hGLP1 pEC50 (cAMP mean (n = 3): 11 point curve starting at 1 nm | CL (ml/min/kg) | Sequence | SEQ ID NO: | Calc. Mass (Parent MW) | Calc. Mass (Parent MW, M + 3/3) | Observed Mass (M + 3/3) | Purity | Solubility in water mg/ml | Stability 1 mg/ml in water at 37 degC |
|---|---|---|---|---|---|---|---|---|---|---|---|
| A40 | 10.1 | <9 | — | YSHGTFTSDHSKWLDSARAQEFVKWL EDEPSSGAPPPS-OH | 80 | 4248.55 | 1417.17 | 1418.1 | >98% | — | — |
| A41 | 9.2 | <9 | — | YTHGTFTSDHSKWLDEARAQEFVKWL EDEPSSGAPPPS-OH | 81 | 4304.62 | 1435.87 | 1436.6 | >98% | — | — |
| A42 | 9.4 | <9 | — | YTHGTFTSDYSKWLDSKRAQEFVKWL EDEPSSGAPPPS-OH | 82 | 4345.71 | 1449.57 | 1450.8 | >98% | — | — |
| A43 | 11.8 | <9 | 47 | YSHGTFTSDYSKYLDKARAQEFVKWL EDEPSSGAPPPS-OH | 83 | 4292.65 | 1431.88 | 1433 | >98% | — | — |
| A44 | 11.9 | <9 | 23.9 | YSHGTFTSDYSKYLDQARAQEFVKWL EDEPSSGAPPPS-OH | 84 | 4292.60 | 1431.87 | 1433 | >98% | — | — |
| A45 | 11.7 | <9 | — | YSHGTFTSDYSKYLD(Aib)KRAQEF V(Aib)WLEDEKRNKPPPA-OH | 85 | 4374.85 | 1459.27 | 1460.9 | >90% | — | — |
| A46 | 12.5 | <9 | — | YSHGTFTSDYSKYLD(Aib)KRAQEF V(Aib)WLEDEKRNKPPIA-OH | 86 | 4390.89 | 1464.63 | 1465.4 | >90% | — | — |
| A47 | 11.5 | <9 | — | YSHGTFTSDYSKYLD(Aib)KRAQEF V(Aib)WLEDEKRNKNPPS-OH | 87 | 4407.83 | 1470.28 | 1471.5 | >98% | — | — |
| A48 | 12.9 | <9 | 37 | YSHGTFTSDYSKYLD(Aib)KRAQEF V(Aib)WLEDEKRNKNPPPS-OH | 88 | 4504.95 | 1502.63 | 1503.1 | >98% | — | — |
| A49 | 12.4 | <9 | — | YSHGTFTSDYSKYLD(Aib)KRAQEF V(Aib)WLEDEPRNKNNPPS-OH | 89 | 4490.88 | 1497.96 | 1498.8 | >98% | — | — |
| A50 | 11.5 | <9 | — | YSHGTFTSDYSKYLD(Aib)KRAQEF V(Aib)WLEDEKRNKPPPS-OH | 90 | 4390.84 | 1464.6 | 1464.8 | >98% | — | — |
| A51 | 12.3 | <9 | — | YSHGTFTSDYSKYLDLKRAQEFV (Aib)WLEDEPSSGAPPPS-OH | 91 | 4291.66 | 1431.55 | 1432.55 | >98% | — | — |
| A52 | 12.4 | <9 | 29 | YSHGTFTSDYSKYLDIKRAQEFV (Aib)WLEDEPSSGAPPPS-OH | 92 | 4291.66 | 1431.55 | 1432.4 | >98% | — | — |

TABLE 3-continued

| Compound | hGCGR pEC50 (cAMP) mean (n = 3): 11 point curve starting at 1 nM | hGLP1 pEC50 (cAMP) mean (n = 3): 11 point curve starting at 1 nM | CL (ml/min/kg) | Sequence | SEQ ID NO: | Calc. Mass (Parent MW) | Calc. Mass (Parent MW, M + 3/3) | Observed Mass (M + 3/3) | Purity | Solubility in water mg/ml | Stability 1 mg/ml in water at 37 degC |
|---|---|---|---|---|---|---|---|---|---|---|---|
| A53 | 11.6 | <9 | — | YSHGTFTSDYSKYLD(Aib)KRAQEFVLWLEDEPSSGAPPPS-OH | 93 | 4291.66 | 1431.55 | 1432.4 | >98% | — | — |
| A54 | 12.4 | <9 | 24 | YSHGTFTSDYSKYLD(Aib)KRAQEFV(Aib)WLEDEPSSKEPPPS-OH | 94 | 4392.8 | 1465.27 | 1465.5 | >95% | — | — |
| A55 | 12.2 | <9 | — | YSHGTFTSDYSKYLD(Aib)KRAQEFV(Aib)WLEDEPSSKSPPPS-OH | 95 | 4350.7 | 1451.23 | 1465.7 | >95% | — | — |
| A56 | 12.3 | <9 | 39.9 | YSHGTFTSDYSKYLD(Aib)KRAQEFV(Aib)WLEDEPKSKAPPPS-OH | 96 | 4375.8 | 1459.6 | 1460.6 | >95% | — | — |
| A57 | 12.0 | <9 | — | YSHGTFTSDYSKYLD(Aib)KRAQEFV(Aib)WLEDEPKSKQPPPS-OH | 97 | 4432.9 | 1478.63 | 1479.7 | >95% | — | — |
| A58 | 12.2 | <9 | 37.7 | YSHGTFTSDYSKYLD(Aib)KRAQEFV(Aib)WLEDEPKSKSPPPS-OH | 98 | 4391.8 | 1464.94 | 1465.7 | >95% | — | — |
| A59 | 12.2 | <9 | — | YSHGTFTSDYSKYLD(Aib)KRAQEFV(Aib)WLEDEPSSKQPPPS-OH | 99 | 4391.8 | 1464.93 | 1465.5 | >95% | — | — |
| A60 | 11.3 | <9 | — | YSHGTFTSDYSKYLD(Aib)KRAQEFV(Aib)WLEDEPSSGKPPPS-OH | 100 | 4334.73 | 1445.9 | 1447.1 | >98% | — | — |
| A61 | 11.4 | <9 | 29.4 | YSHGTFTSDYSKYLDSARAQEFVKWLEDEPSSGKPPPS-OH | 101 | 4308.65 | 1437.23 | 1437.9 | >98% | — | — |
| A62 | 11.5 | <9 | — | YSHGTFTSDYSKYLD(Aib)KRAQEFV(Aib)WLEDEPSSGAPPPS-OH | 102 | 4277.63 | 1426.87 | 1427.4 | >98% | — | — |
| A63 | 10.4 | <9 | — | YTHGTFTSDYSKYLDSARAQEFVKWLEDEPSSGAPPPS-OH | 103 | 4265.58 | 1422.87 | 1424.1 | >98% | — | — |
| A64 | 10.7 | <9 | — | YTHGTFTSDYSKYLD(Aib)ARAQEFV(Aib)WLEDEPSSGAPPPS-OH | 104 | 4220.54 | 1407.83 | 1408.6 | >98% | — | — |
| A65 | 12.5 | <9 | — | YSHGTFTSDYSKYLD(Aib)KRAQEFV(Aib)WLEDEPKSKEPPPS-NH$_2$ | 105 | 4432.88 | 1478.6 | 1479.8 | >98% | — | — |

TABLE 3-continued

| Compound | hGCGR pEC50 (cAMP mean (n = 3): 11 point curve starting at 1 nm | hGLP1 pEC50 (cAMP mean (n = 3): 11 point curve starting at 1 nm | CL (ml/min/kg) | Sequence | SEQ ID NO: | Calc. Mass (Parent MW) | Calc. Mass (Parent MW, M + 3/3) | Observed Mass (M + 3/3) | Purity | Solubility in water mg/ml | Stability 1 mg/ml in water at 37 degC |
|---|---|---|---|---|---|---|---|---|---|---|---|
| A66 | 12.5 | <9 | — | YSHGTFTSDYSKYLD(Aib)V(Aib)KRAQEFWLEDEPKSKSPPPS-NH2 | 106 | 4390.84 | 1464.6 | 1465 | >90% | — | — |
| A67 | 10.9 | <9 | — | YSHGTFTSDYSKYLD(Aib)V(Aib)ARAQEFWLEDEPKSKSPPPS-NH2 | 107 | 4333.74 | 1445.57 | 1446.4 | >98% | — | — |
| A68 | 11.3 | <9 | — | YSHGTFTSDYSKYLD(Aib)V(Aib)ARAQEFWLEDEPKSKEPPPS-NH2 | 108 | 4375.78 | 1459.57 | 1460.6 | >98% | — | — |
| A69 | 11.8 | <9 | — | YSHGTFTSDYSKYLDSARAQEFVKWLEDEPKSKEPPPS-OH | 109 | 4421.81 | 1474.94 | 1476.2 | >98% | — | — |
| A70 | 12.0 | <9 | 20.9 | YSHGTFTSDYSKYLDSARAQEFVKWLEDEPKSKSPPPS-OH | 110 | 4379.77 | 1460.92 | 1461.4 | >98% | — | — |
| A71 | 11.7 | <9 | — | YSHGTFTSDYSKYLDSARAQEFVKWLEDEPKSKAPPPS-OH | 111 | 4363.77 | 1455.59 | 1456.6 | >98% | — | — |
| A72 | 12.1 | <9 | 31.3 | YSHGTFTSDYSKYLDSARAQEFVKWLEDEPKSKEPPPS-NH2 | 112 | 4420.82 | 1474.61 | 1475.1 | >98% | — | — |
| A73 | 11.7 | <9 | 23 | YSHGTFTSDYSKYLDSARAQEFVKWLEDEPKSKSPPPS-NH2 | 113 | 4378.79 | 1460.6 | 1461.2 | >98% | — | — |
| A74 | 11.6 | <9 | — | YSHGTFTSDYSKYLDSARAQEFVKWLEDEPKSKAPPPS-NH2 | 114 | 4362.79 | 1455.26 | 1456.3 | >98% | — | — |
| A75 | 11.3 | <9 | — | WSHGTFTSDYSKYLD(Aib)V(Aib)KRAQEFWLEDEPSSGAPPPS-OH | 115 | 4286.6 | 1429.88 | 1430.8 | >90% | — | — |
| A76 | 12.7 | <9 | 15.1 | YSHGTFTSDYSKYLD(Aib)V(Aib)KAAQEFWLEDEPSSGAPPPS-OH | 116 | 4178.50 | 1393.83 | 1394.8 | >98% | — | — |
| A77 | 11.5 | <9 | — | YSHGTFTSDYSKYLD(Aib)V(Aib)KTAQEFWLEDEPSSGAPPPS-OH | 117 | 4208.52 | 1403.83 | 1404.8 | >90% | — | — |
| A78 | 10.8 | <9 | — | YSHGTFTSDYSKYLD(Aib)V(Aib)KLAQEFWLEDEPSSGAPPPS-OH | 118 | 4220.58 | 1407.83 | 1408.6 | >90% | — | — |

TABLE 3-continued

| Compound | hGCGR pEC50 (cAMP mean (n = 3): 11 point curve starting at 1 nm | hGLP1 pEC50 (cAMP mean (n = 3): 11 point curve starting at 1 nm | CL (ml/min/kg) | Sequence | SEQ ID NO: | Calc. Mass (Parent MW) | Calc. Mass (Parent MW, M + 3/3) | Observed Mass (M + 3/3) | Purity | Solubility in water mg/ml | Stability 1 mg/ml in water at 37 degC |
|---|---|---|---|---|---|---|---|---|---|---|---|
| A79 | 10.2 | <9 | — | YSHGTFTSDYSKYLD(Aib)KRAQEFV(Aib)WLEDEPSSGAPPPS-OH | 119 | 4236.53 | 1413.17 | 1416.3 | >90% | — | — |
| A80 | 12.5 | <9 | — | YSHGTFTSDYSKYLDAARAQEFVKWLEDEPKSKSPPPS-NH2 | 120 | 4362.79 | 1455.262 | 1456.2 | >95% | — | — |
| A81 | 11.0 | <9 | — | YSHGTFTSDYSKYLDAARAQEFVKWLEDEPKSKSPPPS-OH | 121 | 4370.76 | 1457.9 | 1458.4 | >95% | — | — |
| A82 | 11.0 | <9 | — | YSQGTFTSDYSKYLDSARAQEFVKWLEDEPKSKAPPPS-OH | 122 | 4354.76 | 1452.57 | 1453.7 | >95% | — | — |
| A83 | 10.2 | <9 | — | YSHGTFTSDYSKYLDSARAQEFTKWLEDEPKSKSPPPS-OH | 123 | 4381.74 | 1461.57 | 1462.4 | >95% | — | — |
| A84 | 9.4 | <9 | — | YSHGTFTSDYSKYLDSARAQEFVKHLEDEPKSKSPPPS-OH | 124 | 4330.70 | 1444.57 | 1445.3 | >98% | — | — |
| A85 | 13.6 | <9 | — | YSHGTFTSDYSKYLD(Aib)KRAQEFV(Aib)WLEDEPSSGKPPPS-NH2 | 125 | 4319.72 | 1441.23 | 1441.3 | >98% | — | — |
| A86 | 13.3 | <9 | 14.7 | YSQGTFTSDYSKYLD(Aib)KRAQEFV(Aib)WLEDEPSSGKPPPS-OH | 126 | 4311.69 | 1438.2 | 1439.1 | >95% | — | — |
| A87 | 13.6 | <9 | — | YSHGTFTSDYSKYLD(Aib)KRAQEFV(Aib)WLEDEKSSGKPPPS-OH | 127 | 4351.76 | 1451.57 | 1452.2 | >95% | — | — |
| A88 | 13.8 | <9 | — | YSHGTFTSDYSKYLD(Aib)KRAQEFV(Aib)WLEDEPSSGKKPPS-OH | 128 | 4351.76 | 1451.57 | 1451.7 | >98% | — | — |
| A89 | 12.7 | <9 | — | YSHGTFTSDYSKYLD(Aib)KRAQEFV(Aib)HLEDEPSSGKPPPS-OH | 129 | 4271.63 | 1424.87 | 1426.1 | >98% | — | — |
| A90 | 13.1 | <9 | — | YSHGTFTSDYSKYLD(Aib)KAAQEFV(Aib)WLEDEPSSGKPPPS-OH | 130 | 4235.59 | 1412.83 | 1413.8 | >98% | — | — |
| A91 | 12.8 | <9 | 13.7 | WSQGTFTSDYSKYLD(Aib)KRAQEFV(Aib)WLEDEPSSGKPPPS-OH | 131 | 4334.73 | 1445.9 | 1446.7 | >98% | — | — |

TABLE 3-continued

| Compound | hGCGR pEC50 (cAMP mean (n = 3): 11 point curve starting at 1 nm | hGLP1 pEC50 (cAMP mean (n = 3): 11 point curve starting at 1 nm | CL (ml/min/kg) | Sequence | SEQ ID NO: | Calc. Mass (Parent MW) | Calc. Mass (Parent MW, M + 3/3) | Observed Mass (M + 3/3) | Purity | Solubility in water mg/ml | Stability 1 mg/ml in water at 37 degC |
|---|---|---|---|---|---|---|---|---|---|---|---|
| A92 | 10.7 | <9 | — | WSQGTFTSDYSKYLD(Aib)KAAQEFV(Aib)WLEDEPSSGAPPPS-OH | 132 | 4192.52 | 1398.5 | 1399.3 | >98% | — | — |
| A93 | 10.9 | <9 | — | WSQGTFTSDYSKYLD(Aib)KAAQEFV(Aib)WLEDEPSSGKPPPS-OH | 133 | 4249.62 | 1417.53 | 1418.7 | >98% | — | — |
| A94 | 14.1 | <9 | 16.5 | YSQGTFTSDYSKYLD(Aib)KAAQEFV(Aib)WLEDEPSSGAPPPS-OH | 134 | 4254.59 | 1419.17 | 1420.6 | >98% | — | — |
| A95 | 13.3 | <9 | 15.4 | YSQGTFTSDYSKYLD(Aib)KRAQEFV(Aib)WLEDEPSSGAPPPS-OH | 135 | 4169.48 | 1390.8 | 1391.5 | >98% | — | — |
| A96 | 13.0 | <9 | — | YSQGTFTSDYSKYLD(Aib)KAAQEFV(Aib)WLEDEPSSGKPPPS-OH | 136 | 4226.58 | 1409.83 | 1410.4 | >98% | — | — |
| A97 | 12.3 | <9 | 18.9 | YSHGTFTSDYSKYLDAARAQEFVKMLEDEPSSGAPPPS-OH | 143 | 4235.55 | 1412.87 | 1413.7 | >98% | >200 | >59 |
| A98 | 12.2 | <9 | — | YSHGTFTSDYTRLLESKRAQEFVKMLEDEPSSGAPPPS-OH | 144 | 4314.7 | 1439.23 | 1439.6 | 91% | >200 | >75 |
| A99 | 12.5 | <9 | 23 | YSHGTFTSDYSKYLD(Aib)KRAQEFV(Aib)WLEDEPSSGAPPPS-OH | 145 | 4263.6 | 1422.2 | 1423 | >98% | >200 | >64 |
| A100 | 12.6 | <9 | — | YSHGTFTSDYSKYLD(Aib)KRAQEFV(Aib)WLEDE-OH | 146 | 3485.8 | 1162.92 | 1163.9 | >98% | >200 | >69 |
| A101 | 11.3 | <9 | — | YGHGTFTSDHSKYLD(Aib)KRAQEFVKWLEDE-OH | 147 | 3472.8 | 1158.59 | 1159.5 | >98% | >200 | >50 |
| A102 | 12.4 | <9 | — | YSHGTFTSDYSKWLD(Aib)KRAQEFVKWLEDE-OH | 148 | 3551.9 | 1184.96 | 1185.4 | >98% | >200 | >51 |
| A103 | 11.9 | <9 | 28.5 | YSHGTFTSDYSKYLD(Aib)ARAQEFV(Aib)WLEDEPSSGAPPPS-OH | 149 | 4206.5 | 1403.17 | 1403.8 | >98% | >200 | — |

Example 5: Intravenous Infusion: Pharmacokinetic Studies to Assess Peptide Clearance from Kidney (CL)

Peptides were formulated in sterile saline and administered as a 3-hour intravenous infusion to non-fasted male Wistar Han or Sprague-Dawley rats (n=3 per group) via jugular vein cannula at a final dose of 0.3 or 0.1 mg/kg. Formulations were administered at a rate of 1.67 mL/kg/h. Blood samples (approximately 250 uL) were collected for pharmacokinetic analysis via a femoral vein cannula at 1, 2, 3, 3.17, 3.33, 3.5, 4, 4.5, 5 and 6 h post-start of infusion into microtainer tubes containing K2EDTA as anticoagulant and 25 uL of a protease inhibitor cocktail. Plasma was prepared by centrifugation and stored at −80° C. until analysis.

Example 6: Subcutaneous Infusion: Pharmacokinetic Studies to Assess Peptide Clearance from Kidney (CL)

Figure 2A:
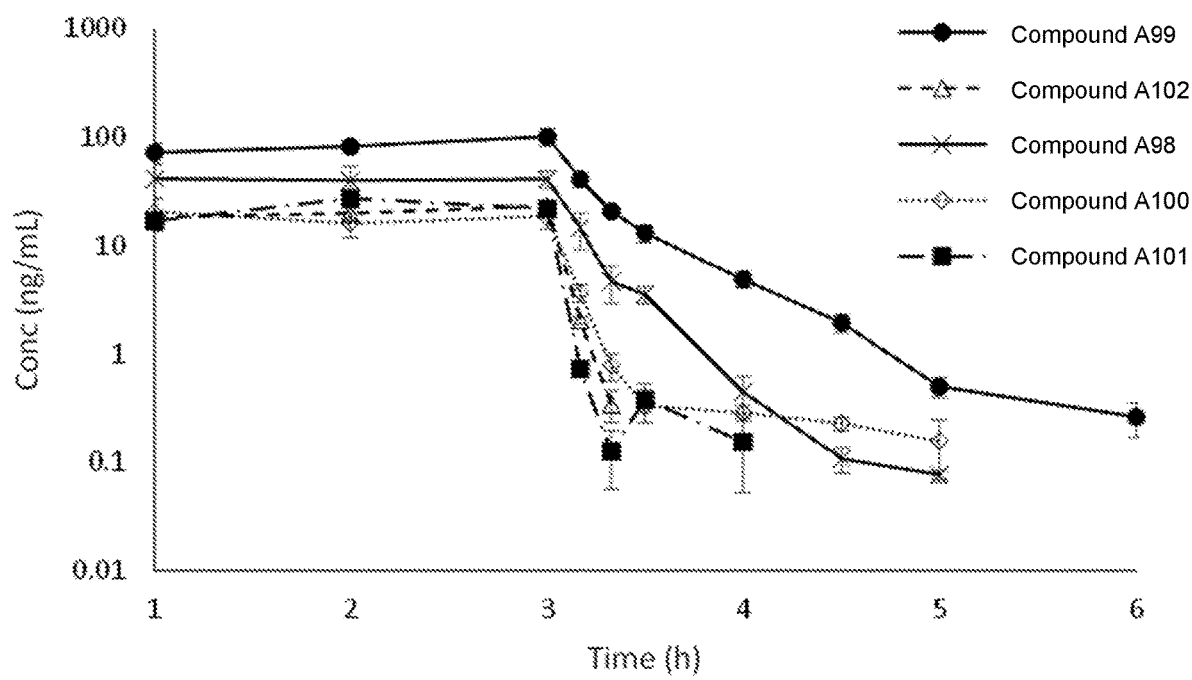
FIGS. 2A and 2B are a series of graphs and tables depicting mean plasma concentration vs. time plot of various glucagon analogs in male rats after a 3-hr intravenous infusion a 0.3 mg/kg dose.
Figure 2B:
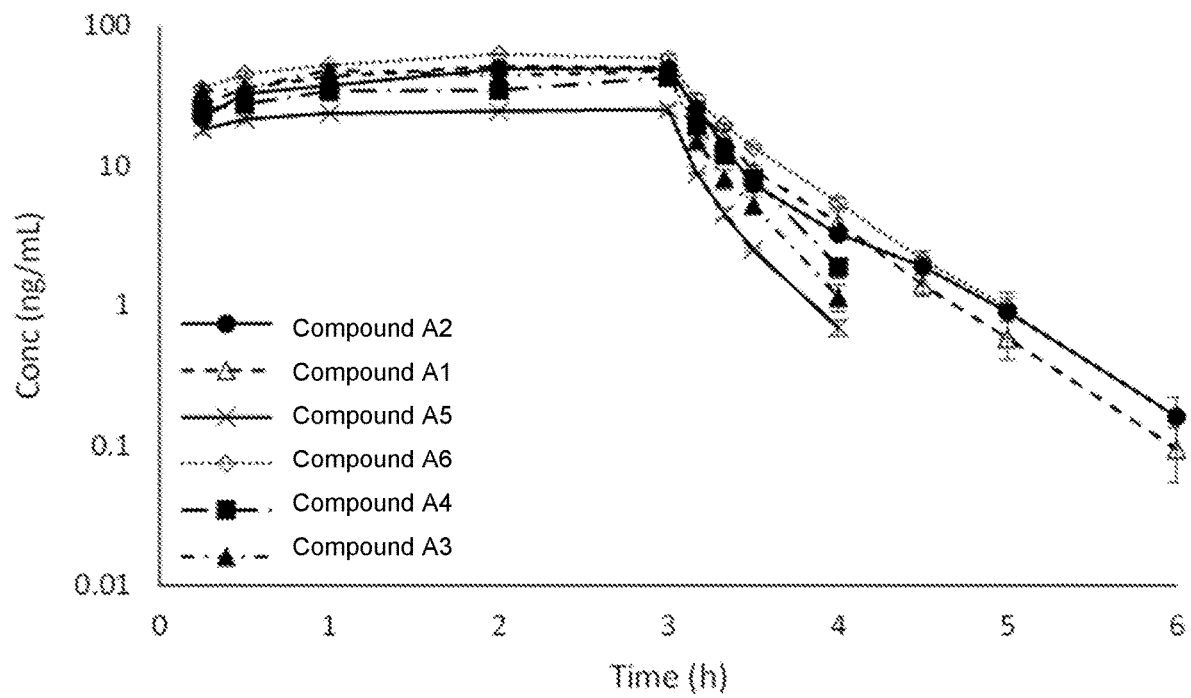

Peptides were formulated in sterile saline and administered as a 3-hour subcutaneous infusion to non-fasted male Wistar Han or Sprague-Dawley rats (n=3 per group) at a final dose of 0.3 or 0.1 mg/kg via a cannula placed into the subcutaneous space between the scapulae. Formulations were administered at a rate of 0.145 mL/kg/h. Blood samples (approximately 250 uL) were collected for pharmacokinetic analysis via a jugular vein cannula at 1, 2, 3, 3.17, 3.33, 3.5, 4, 4.5, 5 and 6 h post-start of infusion into microtainer tubes containing K2EDTA as anticoagulant and 25 uL of a protease inhibitor cocktail. Plasma was prepared by centrifugation and stored at −80° C. until analysis. The results of this analysis are shown below in Table 3 and in FIGS. 2A and 2B.

Example 7: Intravenous Bolus Injection: Pharmacokinetic Studies to Assess Peptide Clearance from Kidney (CL) Cyclic Peptide Glucagon Analogs Peptides were administered as a single intravenous bolus dose to non-fasted male Wistar Han rats (n=3 per group) via jugular vein cannula. Compounds were formulated as solutions in either sterile saline, acidified saline (pH 2.0 or 4.5), or 5% DMSO in water and administered at a volume of 1.5 mL/kg and a final dose of 0.1 mg/kg. Blood samples (approximately 250 uL) were collected for pharmacokinetic analysis via a femoral vein cannula at 0.083, 0.167, 0.25, 0.33, 0.5, 1, 2, 4, 8, 12 and 24 h post-dose into microtainer tubes containing K2EDTA as anticoagulant and 25 uL of a protease inhibitor cocktail. Plasma was prepared by centrifugation and stored at −80° C. until analysis. The results of this analysis are shown below in Table 4.

TABLE 4

| IV Bolus Clearance from Kidney (CL) | |
| --- | --- |
| Compound | IV Bolus Clearance Kidney (CL) |
| Glucagon | 94.1 ± 16.1 |
| Compound A104 | 80.7 ± 15.4 |
| Compound A105 | 67.0 ± 7.3 |

In some embodiments, provided is an isolated polypeptide of the disclosure corresponding to Compound A104 or A105.

Example 8: Generic Method of Plasma Sample Preparation for Pharmacokinetic Studies Protein Precipitation: All 96-well plates were coated with a blocking agent to mitigate non-specific binding of peptides. Plasma samples (75 uL) were added to a 96-well plate containing 200 uL of 2:1 ethanol:acetonitrile containing 0.1% TFA and mixed well via aspiration. Plates were capped, vortex-mixed and centrifuged. Supernatants (215 uL) were transferred to a clean 96-well plate, evaporated to dryness under nitrogen flow and then reconstituted in 75 μL of 20% acetonitrile in water containing 0.1% formic acid.

Solid-Phase Extraction: Samples were diluted 3-fold with 5% $NH_4OH$ (aq) and loaded onto an Oasis MAX microElution plate (Waters Corp, Milford, MA) that had been pre-conditioned with 200 uL each of methanol and 5% $NH_4OH$ (aq). The plate was washed with 200 uL 5% $NH_4OH$ (aq), followed by 200 uL 20% acetonitrile in water. Peptides were eluted using 200 uL 5% formic acid in methanol and evaporated under nitrogen flow. Samples were reconstituted in 80 uL 0.1% formic acid in water.

Example 9: LC/MS Quantification of Peptides in Plasma

All calibration standards were prepared in control rat plasma containing K2EDTA and protease inhibitor cocktail. Samples and standards were analyzed by TurboIonSpray™ UPLC-MS/MS using a system consisting of a CTC HTS PAL auto-injector (Leap, Carrboro, NC), an Agilent Infinity 1290 system with column oven (Palo Alto, CA), a Valco switching valve (Houston, TX), and either an AB Sciex API 5600 TripleTOF™ or Sciex API 4000QTrap mass spectrometer (Framingham, MA). Samples were injected onto a 2.1×50 mm reverse phase C18 analytical column, typically a Waters ACQUITY UPLC™ HSS T3, 1.8 μm (Waters Corporation, Milford, MA) or similar. Chromatographic separation was achieved with a gradient method using water containing 0.1% formic acid (A) and acetonitrile containing 0.1% formic acid (B) as mobile phase. Initial conditions consisted of 95% A and 5% B. The organic component was increased linearly to 95% B over a period of 3-4 minutes, depending on the peptide. Typical flow rates were 600 μL/min. The column temperature was held constant at 40 or 45° C. Peptides were quantified my monitoring one or more product ions produced from a multiply charged parent ion.

Example 10: In Vivo Efficacy of Glucagon Analogs with Reduction in Body Weight

Chronic (13 days) in vivo efficacy studies were conducted in a rodent model for obesity (diet-induced obese (DIO) Long Evans rat) to investigate the efficacy and durability of examples 11 and 12 singly and in combination with exendin-4 as anti-obesity agents.

Male Diet-Induced Obese (DIO) Long Evans (LE) rats were used (Harlan Laboratories, Inc., Indianapolis, IN) and beginning at weaning (about 3 weeks of age), the rats were fed a high fat chow (Teklad TD 95217, 40% kcal from fat, Harlan Laboratories, Madison, WI). Rats were 15-17 weeks old at the start of the study. The rats were housed 1 per cage and given ad libitum access to high fat diet (Harlan TD.95217, 4.3 kcal/g) and water, maintained on a 12 hr light/dark cycle from 5:00 AM to 5:00 PM at 21° C. and 50% relative humidity and allowed to acclimate for at least 10 days prior to the surgeries. Baseline fat mass and non-fat mass measurements were taken 3 days before the start of peptide infusion using a QMR instrument (Echo Medical Systems, Houston, TX). Body weight measurements were taken 2 times/week starting three days before the surgery. Rats were randomized according to their percent body fat mass and/or body weight into the various treatment groups (n=4-6 rats/group). Alzet mini-osmotic pumps (2 week; Model 2002, Durect Corporation, Cupertino, CA) were filled under sterile condition with either vehicle or peptide one day prior to the surgery. On the day of surgery, rats were anesthetized under isoflurane and the dorsal skin surface was shaved and cleansed. Rats were injected SC with Flunexin (2.5 mg/kg). A 1-2 cm surgical incision was made between the scapulae. Using blunt dissection, a 2-3 cm subcutaneous tunnel was created into which the sterile, filled, mini-osmotic pump was introduced. The skin opening was closed with a skin staple. Each rat was implanted with either one or two osmotic pumps containing vehicle or peptide according to their treatment group. All the data are presented as mean±SEM. The data were analyzed in Excel and/or Prism (GraphPad Software, Inc., La Jolla, CA) using one-way ANOVA to compare each group to the appropriate control group. $\beta$-values <0.05 were considered to indicate a significant difference between treatment groups.

Animals were housed and maintained in an AAALAC, international accredited care and use programs. All procedures were performed in compliance with the Animal Welfare Act, USDA regulations and approved by either the GlaxoSmithKline or the Mispro Institutional Animal Care and Use Committees.

Example 11: Efficacy: Body Weight Change in DIO Rats after 13 Days

Figure 3A:
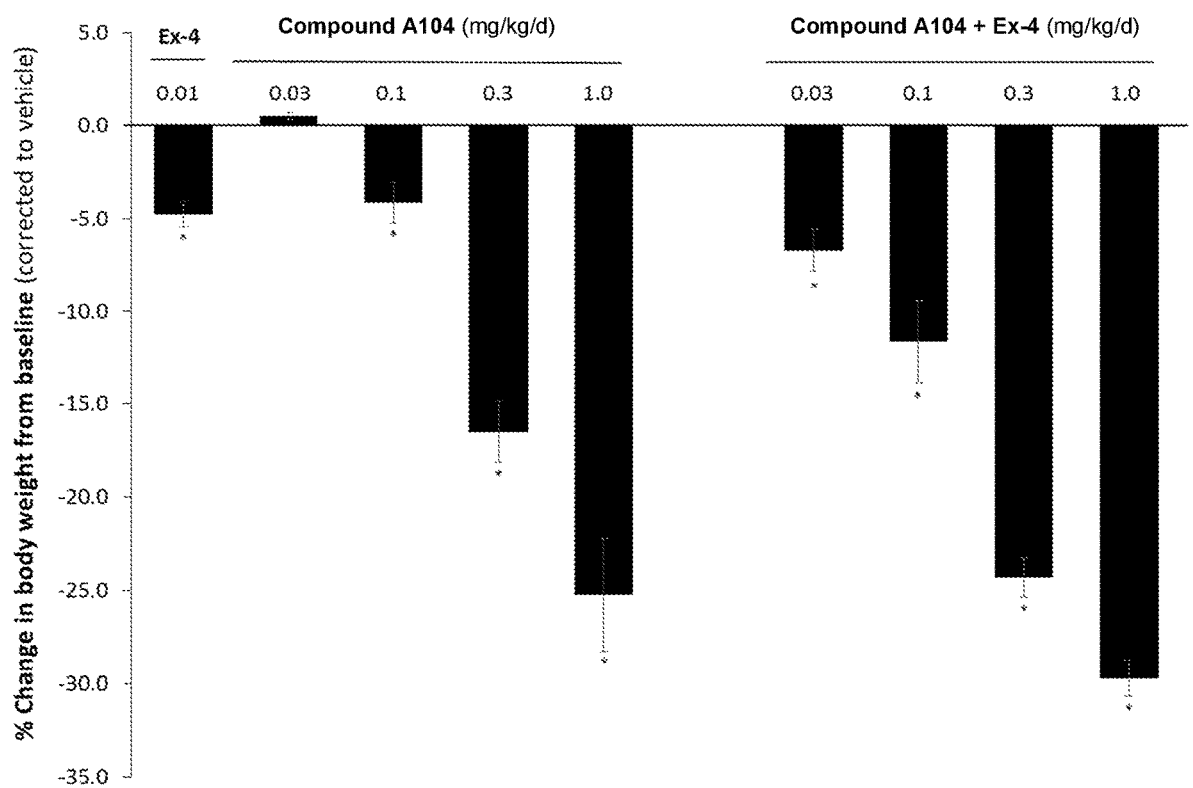
FIGS. 3A, 3B, and 3C are a series of graphs depicting the efficacy of various glucagon analogs as measured by body weight change in DIO rats after 13 days. In particular.
Figure 3B:
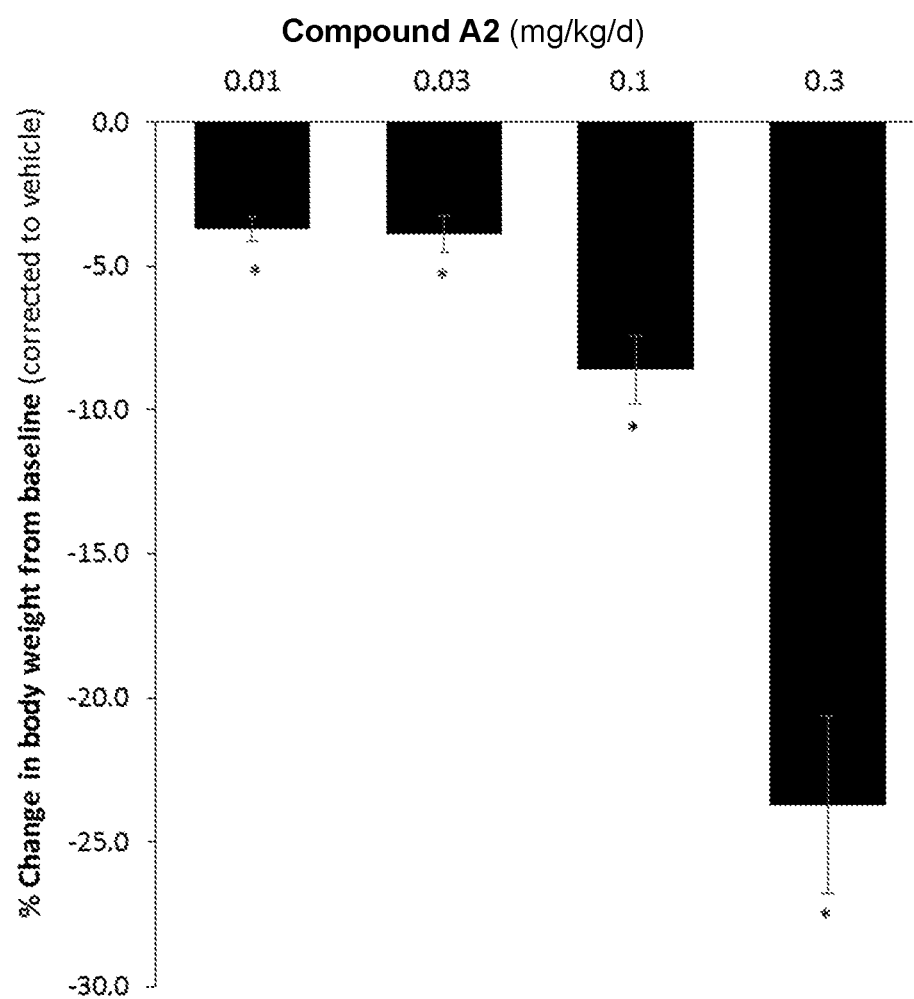
Figure 3C:
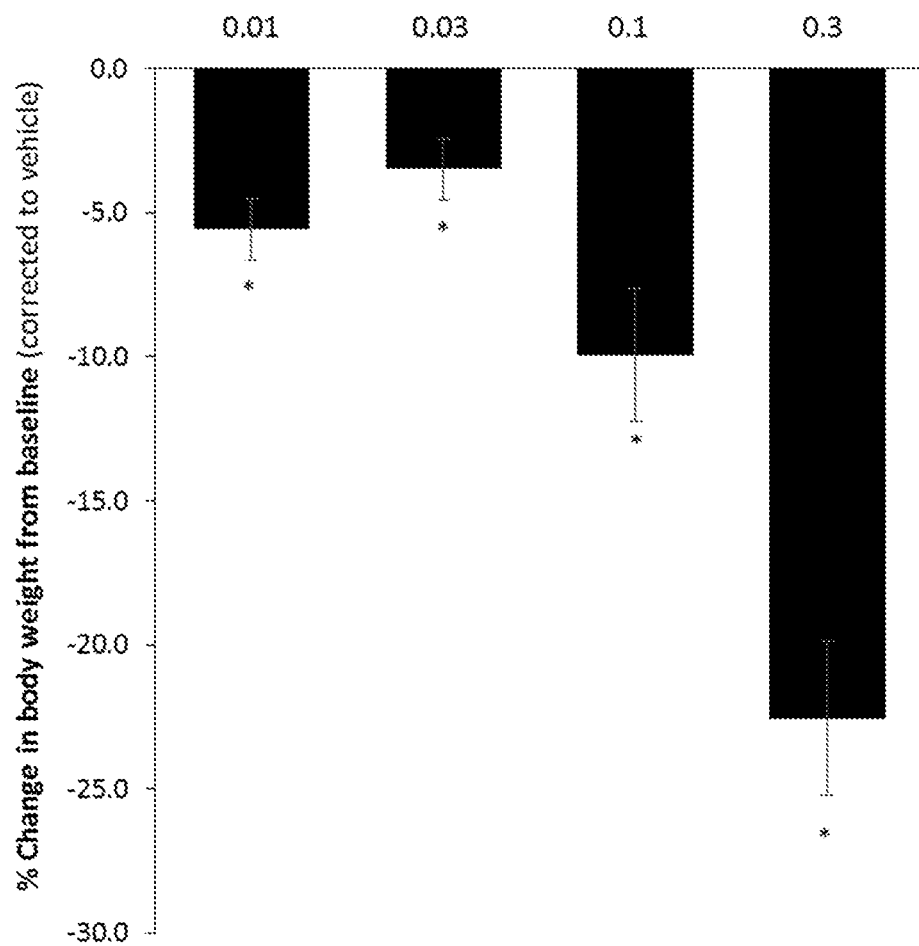

In DIO LE rats, continuous dosing of Compound A2 and Compound A1 led to dose-dependent decreases in body weight after 13 days. Significant efficacy of 3.7, 3.9, 8.6 and 23.7% weight loss was achieved at the 0.01, 0.03, 0.1 and 0.3 mg/kg/day doses of Compound A2 when compared to vehicle control (p<0.05), respectively (FIG. 3B). Whereas, Compound A1 achieved weight loss of 5.6, 3.5, 10 and 22.6% at the 0.01, 0.03, 0.1 and 0.3 mg/kg/day doses when compared to vehicle control (p<0.05), respectively (FIG. 3C).

Example 12. Efficacy of Compound A104 Singly or in Combination with Exendin-4 in DIO LE Rats Continuous dosing of Compound A104 led to dose-dependent decreases in body weight after 13 days of dosing in DIO LE rats. Significant efficacy of 4.2%, 16.5% and 25.2% weight loss was achieved at the 0.1, 0.3 and 1.0 mg/kg/day doses of Compound A104 when compared to vehicle control (p<0.05), respectively (FIG. 3A, left panel). The cyclic peptide glucagon analogs were then used in combination with Exendin-4, a polypeptide comprising the amino acid sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 142). In combination with Exendin-4 at 0.01 mg/kg/d (2.5% weight loss singly), doses of 0.03, 0.1, 0.3 and 1 mg/kg/d Compound A104 achieved 6.7, 11.7, 24.3 and 29.7% weight loss vs. vehicle control (p<0.05) after 13 days in DIO LE rats (FIG. 3A, right panel).

Example 13. Steady State Plasma Concentrations and Intravenous Infusion Rates for Exenatide and GLP-1

Figure 5:
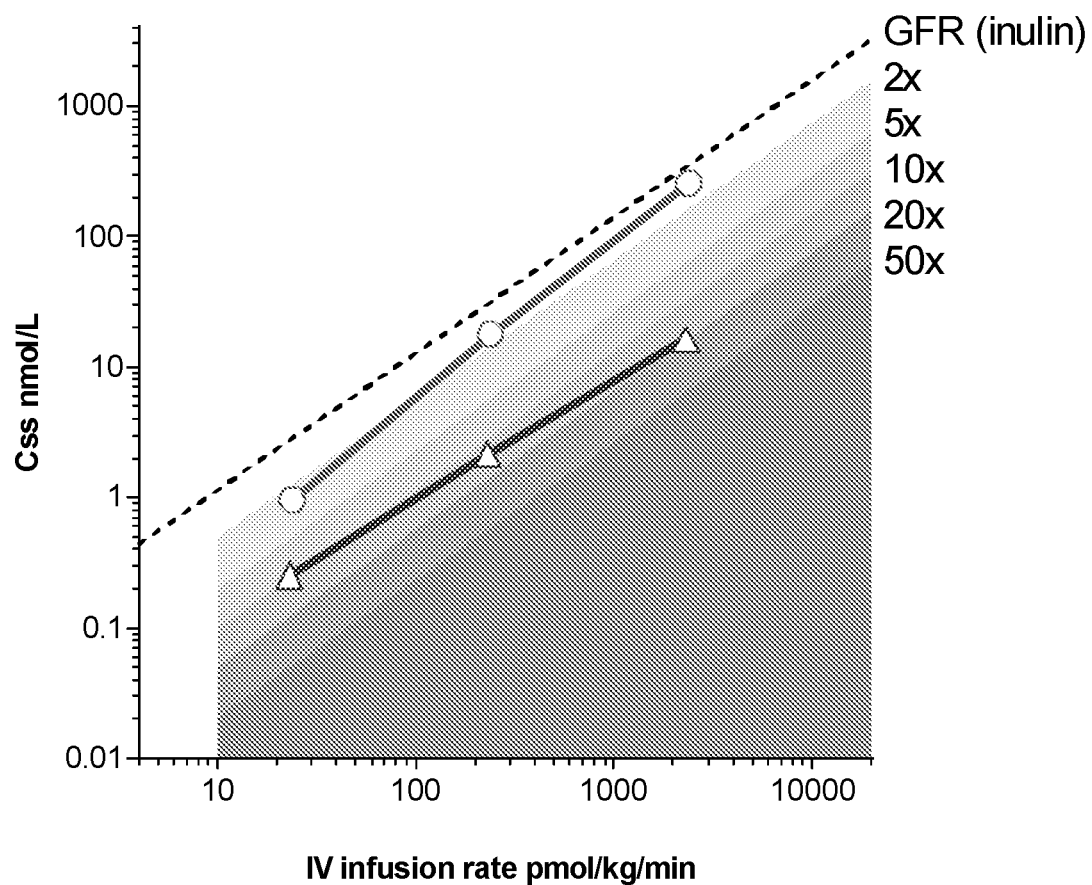
FIG. 5 is a graph that plots steady state plasma concentrations on the Y-axis against intravenous infusion rates on the X-axis of exenatide (circles) and GLP-1 (triangles) and compares these correlations against that for inulin (which is cleared by glomerular filtration). Data of FIG. 5 show that steady state plasma concentration of exenatide approaches that of inulin, consistent with exenatide being cleared mainly by glomerular filtration.

Methods: With reference to the graph of FIG. 5, male Sprague-Dawley rats (Harlan, Indianapolis, IN) weighing 350-370 g, had ad libitum access to water and ad libitum access to food (Diet LM-485, Teklad, Madison, WI) until 18 hours prior to experimentation. Animals were anesthetized with halothane during catheterization of right saphenous vein (for peptide infusions) and right femoral artery (for blood sampling and monitoring of arterial pressure). Colonic temperature was measured and controlled. Exenatide or GLP-1-(7-36)amide was continuously infused for 3 hours at one of 3 infusion rates, 0.5, 5, or 50 nmol/h (n=4-6 for each group). Arterial samples were collected every 30 min into heparinized Natelson capillaries, the plasma separated on a bench-top centrifuge and then frozen at −20° C. until assay. Protease inhibitors were added to blood samples collected for GLP-1 measurement, which was assayed using Linco, Kit No. EGLP-35K. Exenatide was assayed using a two-site sandwich assay.

Results: Plasma concentrations of exendin-4 and GLP-1 during infusions of 0.05, 0.5, 5, and 50 nmol/h approached steady state within ~30 min. Steady-state plasma concentrations of both peptides were each infusion rate-dependent. The relationship between infusion rate and steady state plasma concentration (mean of values in final 2 hours) is shown by the three data points that are farthest below GFR, and the relationship for exenatide is shown by the three data points nearest GFR (note that both X-axis and Y-axis are in logarithmic units). These relationships enabled calculation of clearance of each agent. Plasma clearance rates for exenatide ranged from 3.7±0.5 to 8.3±0.7 mL/min. Clearance of GLP-1 ranged from 34±4 to 38±3 mL/min, and was ~12-fold higher than that of exenatide. The clearance of exenatide approximated the reported clearance of inulin (a marker of glomerular filtration rate). The relationship between steady-state concentration and infusion rate expected for insulin (cleared only by glomerular filtration, GFR) is shown as a black dashed line.

Figure 6:
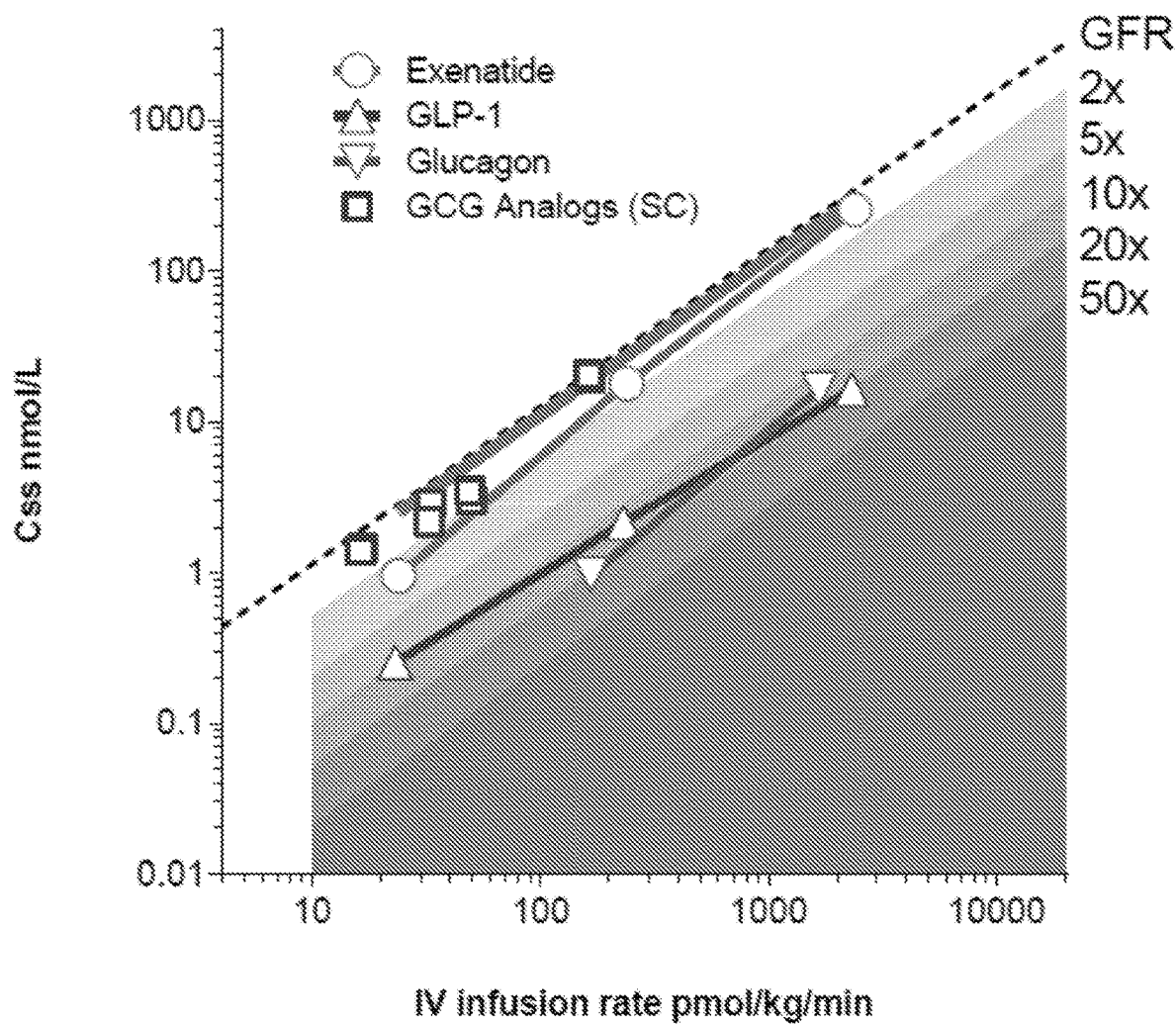
FIG. 6 is the graph of FIG. 5 that further plots steady state plasma concentrations on the Y-axis against intravenous infusion rates on the X-axis of glucagon (inverted triangles), and Compounds A1 and A2 (glucagon analogs, squares) in addition to exenatide (circles) and GLP-1 (triangles). These correlations are shown relative to that for inulin (as an estimate of glomerular filtration rate). Data of FIG. 6 show that steady state plasma concentrations of Compounds A1 and A2 approach that of inulin, consistent with these compounds being cleared mainly by glomerular filtration.

Example 14. Steady State Plasma Concentrations and Intravenous Infusion Rates for Selected Glucagon Analogs With reference to the graph of FIG. 6, these data include those shown in the graph of FIG. 5, and additionally contain steady state concentrations (inverted triangles) of native glucagon when it was infused intravenously at 2 different infusion rates into anesthetized rats (using procedures described in Example 13). The square data points, closest to GFR, denote measured plasma concentrations of 2 glucagon analogs (Compounds A1 and A2) when they were administered continuously into the subcutaneous space via osmotic minipump. The proximity of the square data points to the GFR dashed line indicates (a) that subcutaneous bioavailability was high, and that (b) clearance from the vascular compartment was consistent with being via glomerular filtration.

Example 15. Clearance Values for Selected Glucagon Analogs

Figure 7:
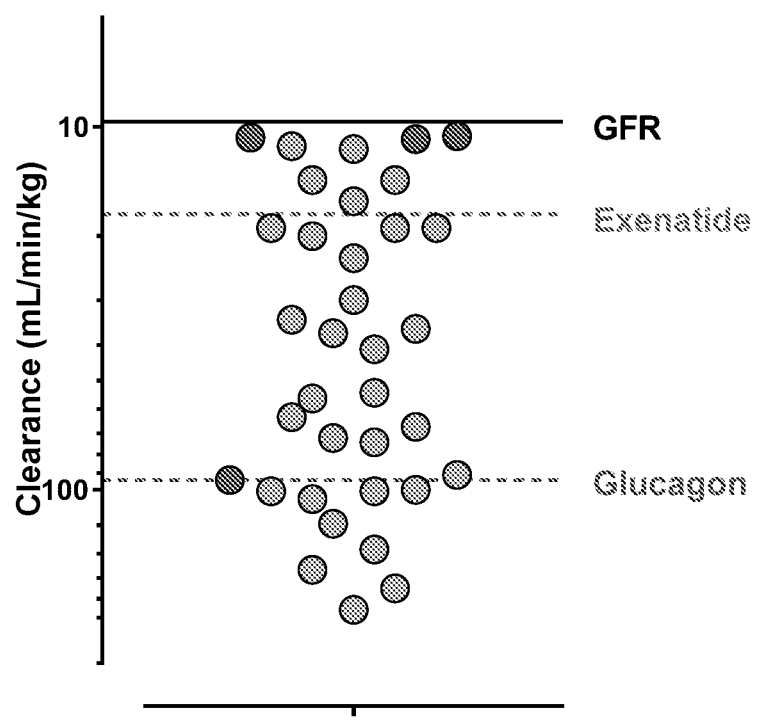
FIG. 7 is an illustration that plots clearance values for glucagon, Compounds A1, A2 and A3 (three points closest to GFR) and other glucagon analogs. Note that clearance values decrease along the y-axis. For the sake of comparison, the dashed upper line (closer to GFR) shows the clearance rate for exenatide and the dashed lower line (farther from GFR) shows the clearance rate for glucagon.

With reference to the illustration of FIG. 7, clearance was determined in numerous experiments performed as described above (for Example 14), except that intravenous infusion rate was uniformly 10 mcg/kg/hr. Selected values for clearance, expressed in mL/min per kg body weight, obtained such experiments, are provided in Table 5 below.

TABLE 5

| Row | Selected Compound # | CL mL/min/kg |
|---|---|---|
| 1 | A1 | 10.6 |
| 2 | A2 | 10.8 |
| 3 | A2 | 11.3 |
| 4 | A1 | 11.5 |
| 5 | A3 | 10.7 |
| 26 | Glucagon | 94 |

The three dark points at the top of the distribution, closest to GFR, are from rows 1, 2 and 5 in Table 5, corresponding to Compounds A1, A2 and A3. Duplicate experiments in rows 3 and 4 returned values very similar to those in rows 1 and 2. Note that the vertical axis is logarithmic and reversed, so that ligands with lowest clearance are at the top of the scatter plot. The solid line labelled GFR represents published values in rats. The values from rows 1, 2 and 5 are close to this bound, consistent with these analogs being cleared from plasma via glomerular filtration. The other dark point, on the dotted line labelled "glucagon," farthest from GFR, represents the value obtained for native (human/rat) glucagon in this study. The other dotted line, closest to GFR, labelled "exenatide" is from published values for exenatide obtained in this model system. It appears that clearance of exenatide is close to glomerular filtration, with a small fraction cleared by means other than glomerular filtration. Several analogs exceeded exenatide in approaching glomerular filtration as their limiting mode of clearance. Without being bound by theory, these analogs may be even more resistant to peptidase digestion than was exenatide. Several analogs had a higher clearance than did native glucagon, illustrating that all changes in sequence were not necessarily beneficial.

Figure 8:
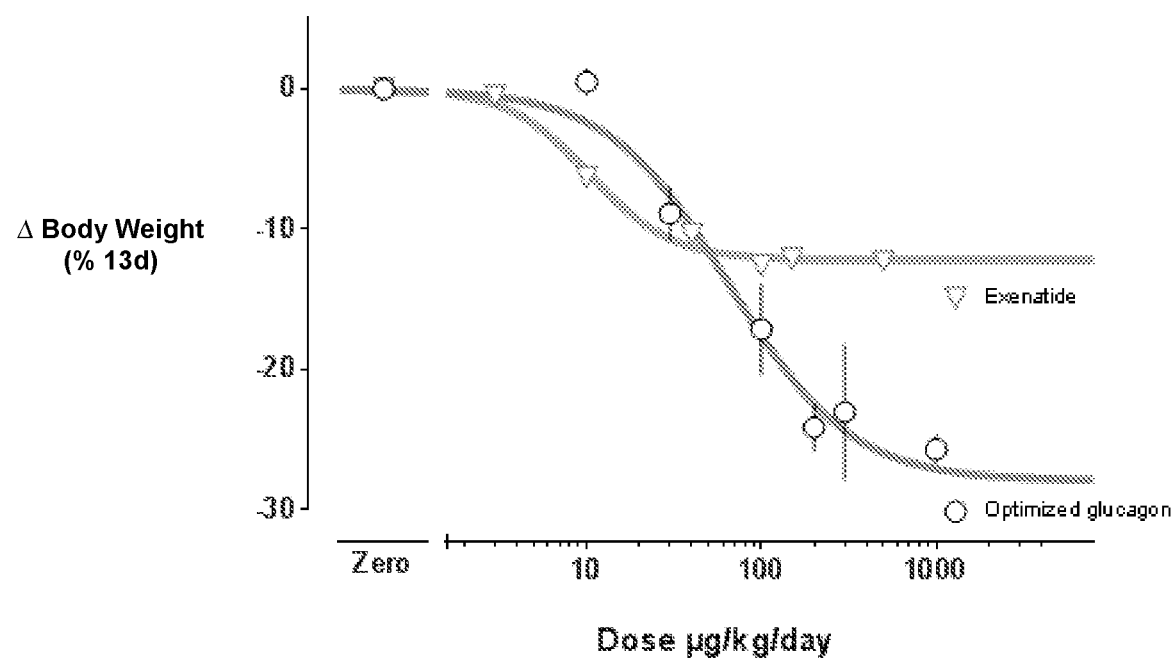
FIG. 8 is a graph that compares dose dependency of weight loss for male Sprague-Dawley rats upon subcutaneous administration of either exenatide or Compound A1.

Example 16. Comparison of Dose Dependency of Weight Loss in Rats Upon Continuous Administration of Exenatide or a Selected Glucagon Analog With reference to the graph of FIG. 8, the black circles plot mean change in body weight over 13 days, expressed as a percent of initial body weight, in diet-induced obese rats into which had been implanted mini pumps delivering Compound A1 (as described for example 10). Symbols are means±SEM (n=4/dose group). Delivery rates into the subcutaneous space were 10, 30, 100, 200, 300 and 1000 mcg/kg/day. Percent change in body weight is relative to the vehicle-infused group (at "zero" on the x-axis). The curve based on data point circles is the best-fitting 4-parameter sigmoid function, constraining vehicle response to 0, and maximal response to −28%. The derived ED50 was 65.7 mcg/kg/day. The Hill slope was −1.26.

Data for exenatide tested in the same model are shown as the inverted triangles. Exenatide infusion rates were 3, 10, 40, 100, 150 and 500 mcg/kg/day. The resulting curve, based on data point triangles is the best-fitting 4-parameter sigmoid function, constraining vehicle response to 0. The derived maximal response was −12.2% weight loss. ED50 was 10.4 mcg/kg/day and Hill slope was −1.85.

As illustrated by the data in Table 6 below, Compound A1 administered alone was almost as potent in vivo as exenatide, and invoked 2.3-fold greater maximal weight loss than did exenatide.

TABLE 6

| | Human in vitro Potency (pEC50) | | | Physiochemical Properties | | Rat PK | Rat in vivo Potency & Efficacy | | |
|---|---|---|---|---|---|---|---|---|---|
| | | | | | | | $ED_{50}$/ $EC_{50}$ | % Weight loss Single | % Weight loss Combo |
| | hGCGR | hGLP-1R | hGIPR | Solubility | Stability | Cl/% F | | | |
| Native Glucagon | 11.3 | 9.3 | <5 | <5 | No | 94; ~10-20% % F | nd | nd | — |
| Exenatide | 9.2 | 11.7 | <5 | >100 | >95% | 17; ~100 % F | 10.4 0.45 | 12% | — |
| Desired | >10.0 | <7 | <6 | >40 | >90% | 5-15; ≥40% F | <100 | >10% | >20% |
| Compound A1 | 12.3 | 5.2 | <5 | >200 | >95% | 11.5; 74% F | 65.7 4.4 | 26% | — |

Figure 9:
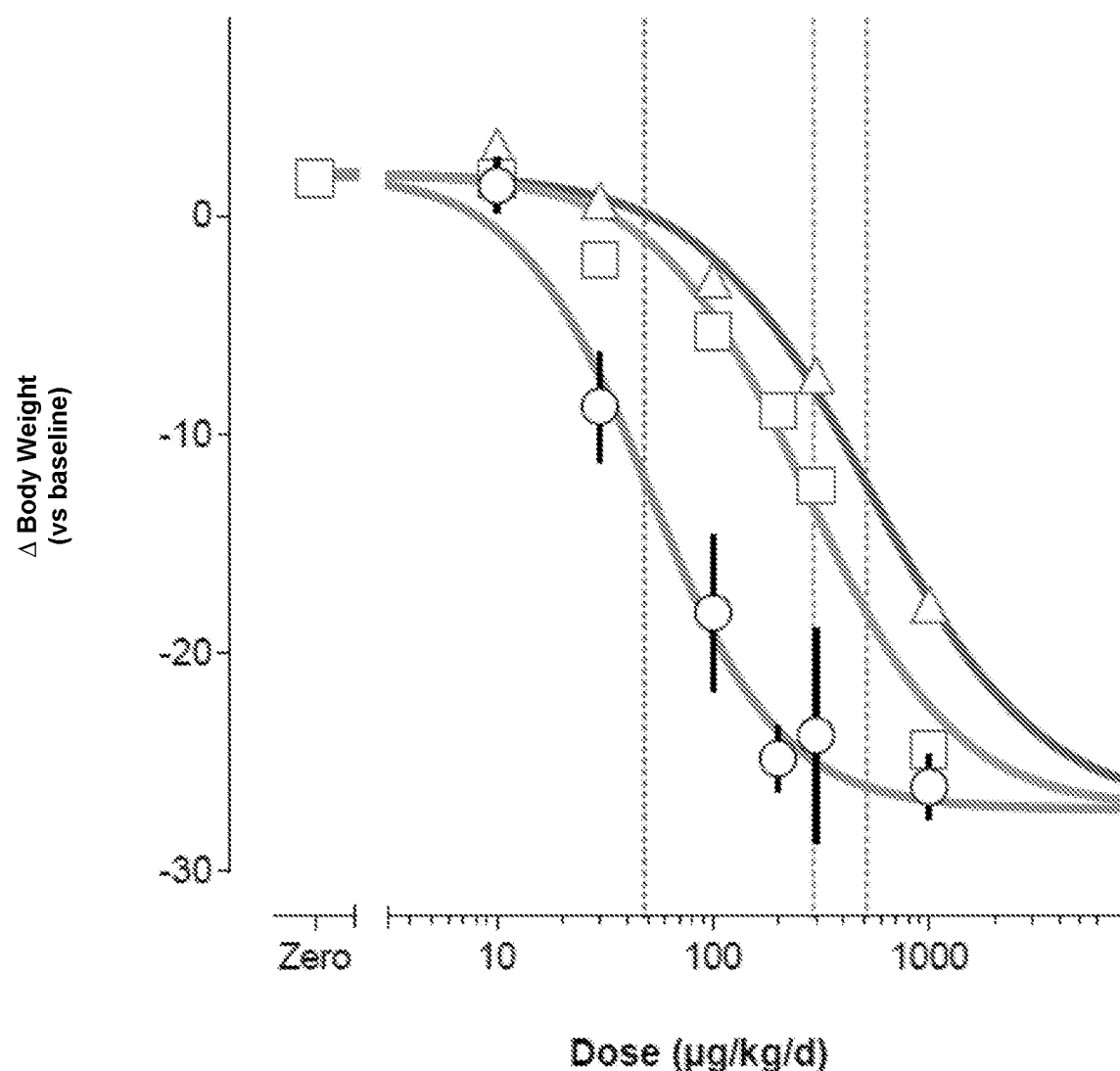
FIG. 9 is a graph that compares dose dependency of weight loss for male Sprague-Dawley rats upon subcutaneous administration of Compounds A1, A2 or A3.

Example 17. Comparison of Dose Dependency of Weight Loss in Rats Upon Continuous Administration of Selected Glucagon Analogs With reference to the graph of FIG. 9, symbols denote mean±SEM of percent change in body weight over 13 days' infusion of Compound A1 (circles), Compound A2 (squares) or Compound A3 (triangles) into diet-induced obese rats (as in FIG. 8). Infusion rates for Compound A1 were 0, 10, 30, 100, 200, 300 and 1000 mcg/kg/day. For Compound A2, they were 0, 3, 10, 30, 100, 200 and 300 mcg/kg/day, and for Compound A3, 0, 3, 10, 30, 100 and 300 mcg/kg/day.

The three curves denote the best-fitting 4-parameter sigmoid curves for each data set. The fits were constrained to share the same percent change in weight for vehicle groups. Because all were working via a common (glucagon signaling) pathway, they were constrained to share a common maximal weight loss response, derived as 27.2% over 13 days. For Compounds A1, A2 and A3, ED50's were 51, 271 and 535 mcg/kg/day, respectively. Hill slopes were −1.43, −1.25 and −1.12, respectively. The experiment demonstrates that even though each analog had been optimized for pharmacokinetic properties, in vivo potencies were different, and that it required experimentation to select the analog that had highest in vivo potency.

Figure 10:
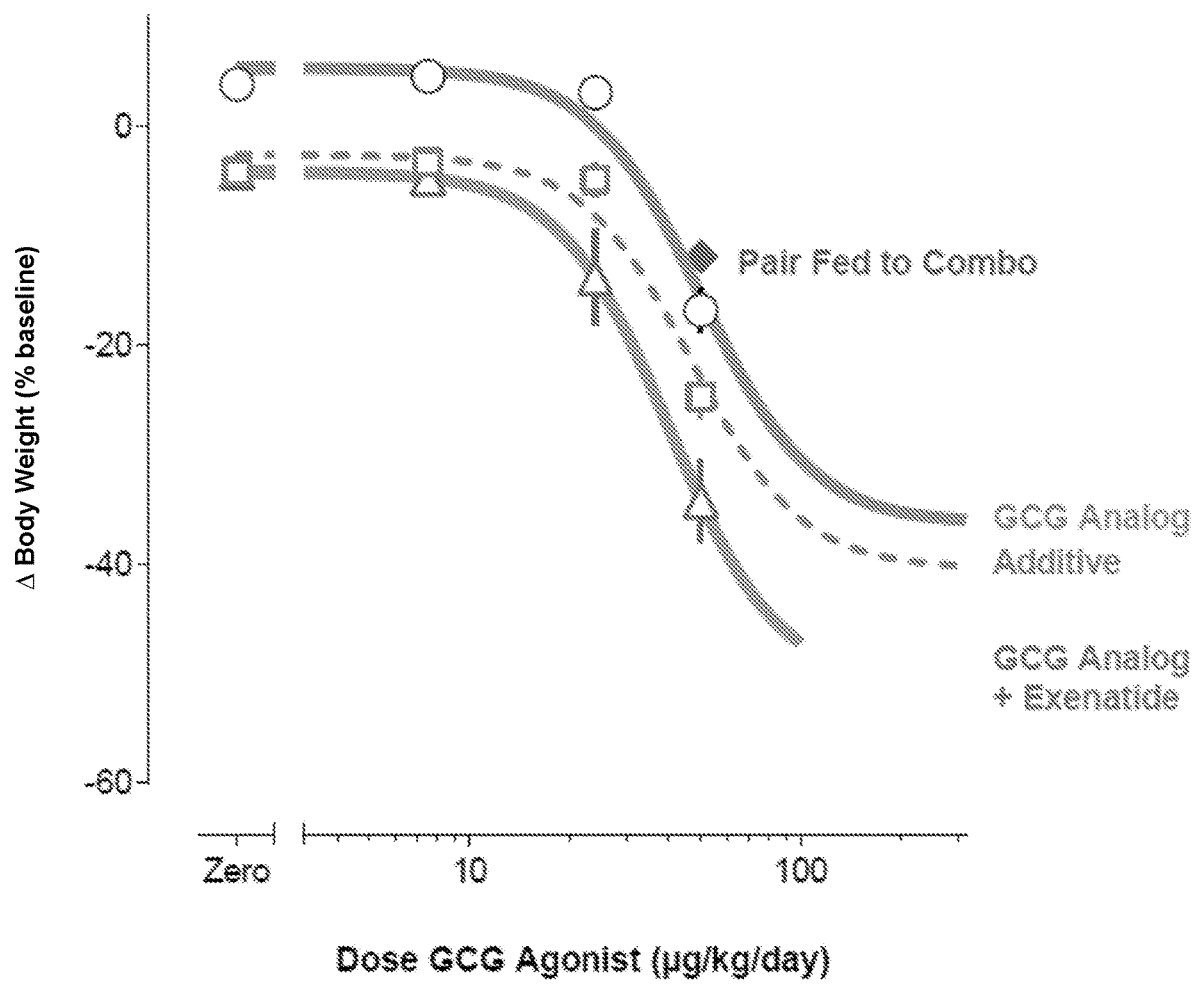
FIG. 10 is a graph that compares weight loss in DIO LE rats after administration of exenatide, a glucagon ("GCG") analog, Compound A1, or a combination of exenatide and the GCG analog, for 27 days at various doses.

Example 18. Comparison of Dose Dependency of Weight Loss in Rats Upon Continuous Administration of a Selected Glucagon Analog, Alone or in Combination with Exenatide Data on the graph of FIG. 10 illustrate mean (±SEM) percentage change in body weight of diet-induced obese rats over 27 days treatment. Mean initial body weight was 564±4 g. Animals (n=8/dose group) were implanted with osmotic mini pumps delivering Compound A1 with or without concomitant delivery of exenatide at 10 mcg/kg/day (as described for example 10). Compound A1 was delivered at rates of 0, 7.5, 24 or 50 mcg/kg/day. There were, therefore, 2 dose-response experiments for Compound A1, one without, and one with exenatide. There was an additional group, "pair-fed", that was offered each day, the same quantity of food that the group treated with Compound A1 50 mcg/kg/day+ exenatide 10 mcg/kg/day had consumed the previous day. The objective of the pair-fed group was to estimate the amount of weight loss in the latter group that was attributable to reduction in caloric intake versus via other mechanisms.

The black circles plot the 27-day change in body weight in animals treated with Compound A1 alone (or vehicle). Animals infused with vehicle or with Compound A1 at 7.5 and 24 mcg/kg/day showed a small increase in body weight of ~4%, while the highest infusion rate showed a 16.8% decrease.

The triangles denote the 27-day percent change in body weight in similarly-treated groups, but with exenatide at 10 mcg/kg/day added. This infusion on its own resulted in a 4.2% decrease in body weight, a relative difference from the vehicle-only group of 7.9%. The squares represent the 7.9% loss expected of exenatide-only, added to the observed weight changes in the Compound A1-only groups, representing the arithmetic sum of responses of each component.

The dotted line is the fitted sigmoid curve through the arithmetically summed responses obtained by this method. In contrast to the expected response (being the arithmetic sum of the responses of single agents), the observed responses of the combination of the 2 highest infusion rates of Compound A1 (24 and 50 mcg/kg/day) with exenatide gave weight loss that was greater than predicted. That is, there was a supra-additive (synergistic) effect. The maximal weight loss response, instead of being ~7%, was instead ~47%.

Figure 11:
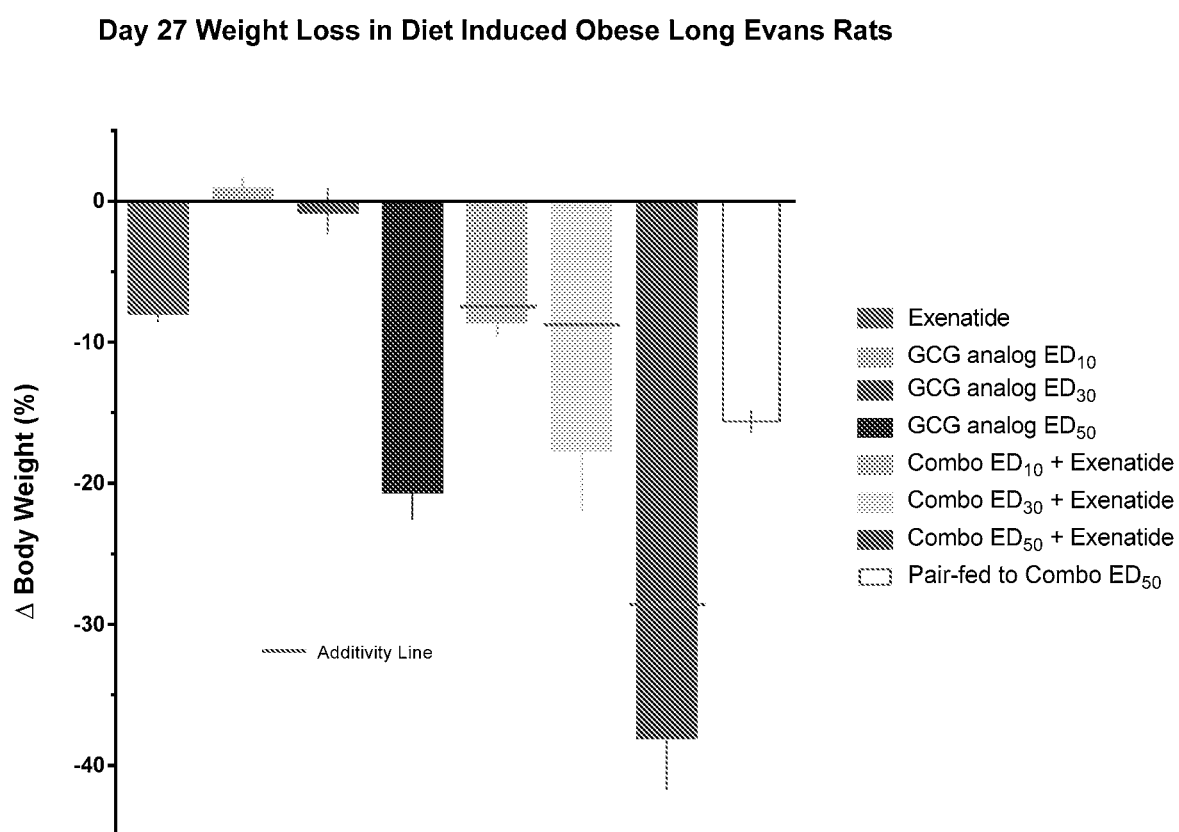
FIG. 11 is a bar graph that alternatively depicts that data shown in FIG. 10.

Example 19. Effects of a Glucagon Analog on Weight Loss in DIO LE Rats after 27 Days The above procedures were used to monitor weight loss in DIO LE rats upon administration of exenatide, a glucagon ("GCG") analog at derived ED10, ED30 and ED50 values, or a combination of exenatide and the GCG analog at derived ED10, ED30 and ED50 values. Weight loss percentages were calculated 27 days after treatment (FIG. 11). FIG. 11 is a bar graph that alternatively depicts that data shown in FIG. 10.

Example 20. Effects of a Glucagon Analog on Serum Triglycerides, Liver Fat Content and Liver Weight in Zucker Diabetic Fatty (ZDF) Rats after 14 Days Male Zucker Diabetic Fatty (ZDF) rats were obtained 6 weeks of age (Charles River, Raleigh, NC) and used on study at 8 weeks old. Upon receipt, the rats were housed 1 per cage on alpha dri bedding (Shepherd Specialty Papers, Inc., Kalamazoo, MI) with free access to Purina 5008 chow (Lab Diet, St. Louis, MO) and water, maintained on a 12 hr light/dark cycle from 5:00 AM to 5:00 PM at 21° C. and 50% relative humidity and allowed to acclimate for 9 days before the start of the study.

The rats were dosed with exenatide (0.01 mg/kg/day in 10% DMSO/water) and/or a glucagon analog, compound A104, (0.03, 0.1, 0.3, 1.0 or 3.0 mg/kg/day in 10% DMSO/water) via subcutaneously (s.c.) placed Alzet osmotic pumps, model 2002 (DURECT Corporation, Cupertino, CA). Alzet pumps were filled under sterile condition with either vehicle (10% DMSO/sterile water) or exenatide on the day of surgery. Rats were anesthetized under isoflurane and the dorsal skin surface was shaved and cleansed with chlorhexidine and sterile water. Rats were injected ID with Lidocaine (analgesic, 0.1 ml of 0.125% Lidocaine). A 1-2 cm surgical incision was made between the scapulae. Using blunt dissection, a 2-3 cm subcutaneous tunnel was created into which the sterile, filled, mini-osmotic pump was introduced. The skin opening was closed with a skin staple. Rats were monitored after surgery for their recovery from the isoflurane anesthesia.

Figure 13:
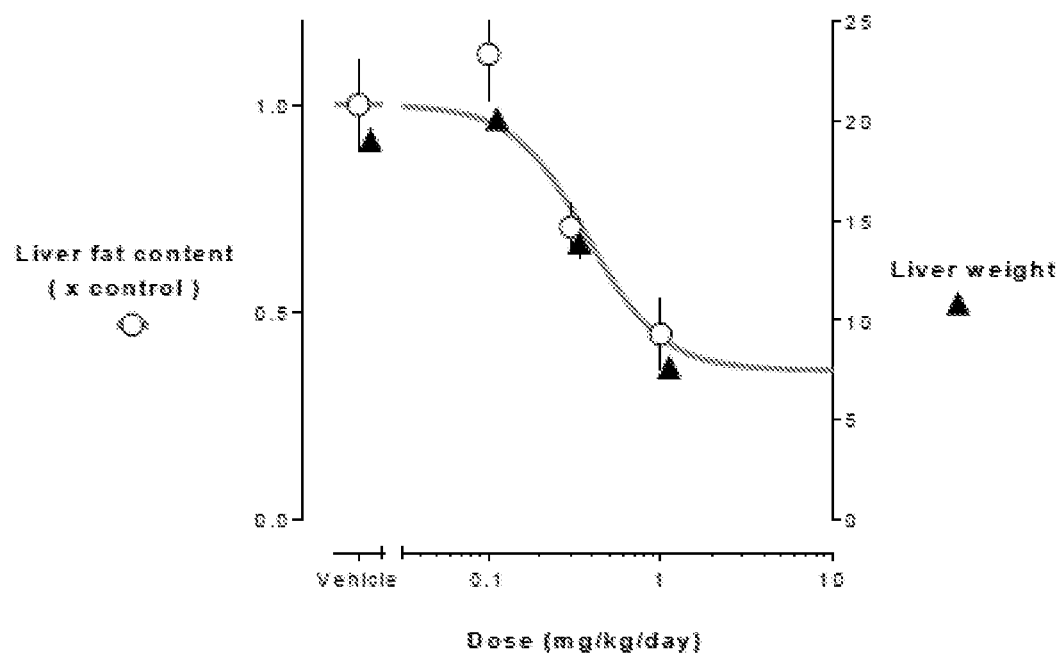
FIG. 13 is a graph that compares serum liver fat content and liver weight in Zucker Diabetic Fatty (ZDF) rats after 14 days after administration of different doses of compound A104. Note that liver weight is plotted on the left Y-axis as open circles. Liver fat is plotted on the right Y-axis as filled triangles.

Blood samples were taken for baseline bleeds (day −3) via tail vein to measure triglyceride levels. Final blood samples were collected by cardiac puncture under isoflurane anesthesia (day 14). Serums were prepared according to manufacturer's protocol using EDTA and T-MG tubes, respectively [Terumo Medical Corporation, Elkton, MD]. After the terminal bleeds, livers were collected, weighed and homogenized for biochemical analysis (FIG. 13). Clinical chemistry analysis of serum samples and liver homogenate was performed by using an Olympus AU640 Clinical Chemistry analyzer (Olympus America Inc., Melville, NY) with the protocol and method parameters as described by the manufacturer for the triglyceride assay.

Animals were housed and maintained in an AAALAC, internationally accredited care and use programs. All procedures were performed in compliance with the Animal Welfare Act, USDA regulations and approved by either the GlaxoSmithKline or the Mispro Institutional Animal Care and Use Committees.

Figure 12:
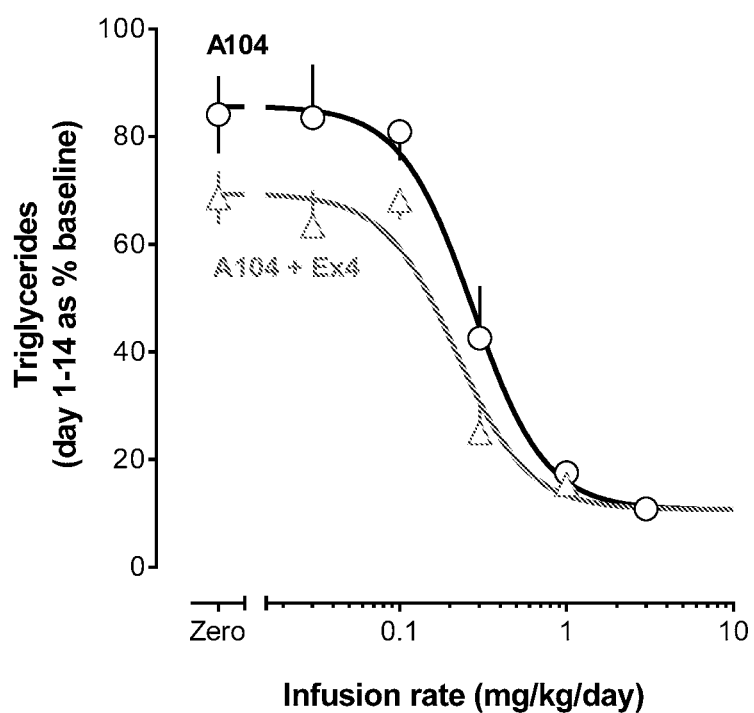
FIG. 12 is a graph that compares serum triglyceride levels in Zucker Diabetic Fatty (ZDF) rats after 14 days after administration of compound A104, alone or in combination with exenatide.

In ZDF rats, continuous dosing of compound A104, singly and in combination with exenatide (Ex4), led to dose-dependent decreases in serum triglycerides after 14 days (FIG. 12). Compound A104 also dose-dependently reduced liver fat content and liver weights after 14 days (FIG. 13).

Example 21. General Synthetic Method for Installation of Lipophilic Substituent and Spacer of Formula II The lipophilic substituent and spacer of Formula II was incorporated into numerous disclosed peptides:

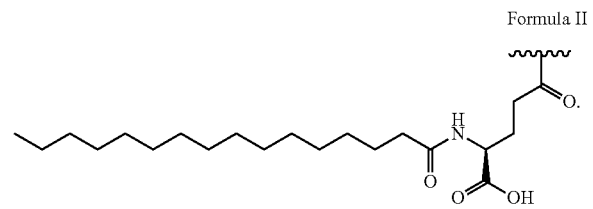 [SMILES: *C(=O)CC[C@H](NC(=O)CCCCCCCCCCCCCCC)C(=O)O]

Formula II where the indicated carbonyl on the structure of Formula II was covalently joined to an ε-amino group of a lysine residue of the disclosed peptide to form an amide linkage.

The linear peptide sequence was synthesized on a Prelude peptide synthesizer (Protein Technologies Inc., Tucson, AZ)) by solid-phase methods using Fmoc strategy with 2-(1H-benzotriazole-1-yl)-1,1,3,3-tetramethyl uranium hexafluorophosphate (HBTU) or 2-(6-chloro-1-H-benzotriazole-1-yl)-1,1,3,3-tetramethylaminium hexafluorophosphate (HCTU) activation (5 fold molar excess) in N,N-dimethylformamide (DMF), and N'N-Diisopropylethylamine (DIEA) as base, 20% piperidine/DMF for Fmoc deprotection. The resin was Rink Amide MBHA LL (Novabiochem) or N-α-Fmoc protected, pre-loaded Wang L L (Novabiochem), with loadings of 0.29-0.35 mmol/g on a 20-400 μmol scale. At the desired position for acyl-chain substitution, FMOC-Lys(Alloc)-OH was preferentially substituted into the peptide chain. Next, Boc-Tyr(tbu)-OH or Boc-Trp(Boc)-OH was used as the N-terminal amino acid residue. Upon completion of synthesis the resin was washed with Dichloromethane (DCM) and dried under vacuum for 30 minutes. Next, the Alloc protecting group was removed using a solution of Palladium Tetrakis in (CHCl3/Acetic Acid/N-methylmorpholine, 37:2:1 ratio). The resin was subsequently washed with a 0.5% solution of Sodium Diethyldithiocarbamate trihydrate in DMF, followed by a 0.5% solution of DIEA in DMF, and finally DMF. Next, FMOC-Glu(Otbu)-OH was coupled to the free Lysine side-chain using normal solid-phase conditions. The C-16 acyl side-chain was added using Palmitic Acid under normal solid-phase methods. Final deprotection and cleavage of the peptide from the solid support was performed by treatment of the resin with (92.5% TFA, 2.5% phenol, 2.5% water and 2.5% triisopropylsilane) for 2-3 hours. The cleaved peptide was precipitated using cold diethyl ether. The diethyl ether was decanted and the solids triturated again with cold diethyl ether, pelleted by centrifugation and lyophilized. The lyophilized solid was re-dissolved in a 1:1 solution of acetonitrile/water, with 0.1% TFA (10-15 mL), purified via reverse phase HPLC on a Waters XBridge™ BEH 130, CI8, 10 um, 130 Å, 30×250 mm ID column, using a gradient within the ranges of 5-75% acetonitrile/water with 0.1% TFA over 30 minutes at a flow rate of 30 mL/min, λ~215 nm. Column heater set at 60° C. The purified product was lyophilized and analyzed by ESI-LC/MS and analytical HPLC; and were demonstrated to be pure (>98%). Mass results all agreed with calculated values.

HPLC analysis conditions: 4.6×250 mm XBridge BEH130, 5 um, C18 column using an analytical Agilent 1100 with the following gradient: 20% to 100% over 15 minutes and holding at 100% to 20 minutes. The column temperature was set at 40° C. The flow rate was set at 1.0 mL/min. The solvents consisted of A=H2O+0.1% TFA and B=Acetonitrile+0.1% TFA. The crude and final LCMS were observed and product mass was identified using the following conditions: UV detection set at 215 and 280 nm.

LCMS analysis conditions: 4.6×250 mm XBridge BEH130, 5 um, C18 column using an analytical Agilent 1100 in combination with an API-4000 Sciex LC/MS/MS system with the following gradient: 20% B to 95% B over 10 minutes, holding at 95% to wash the column over 1.2 min. Equilibrate column at 5% B, 95% A to 12.5 min. The column temperature was set at 40° C. The flow rate was set at 1.5 mL/min. The solvents consisted of A=H2O+0.1% TFA and B=Acetonitrile+0.1% TFA. UV detection set at 215 and 280 nm. Method=Q1 MS. Syringe size 100 uL, UV range 190-400 nm, Slit width=4 mm, Sampling rate=>20 Hz., Ion source: Turbo spray, Polarity=Positive.

Example 22. General Synthetic Method for Installation of Lipophilic Substituent and Spacer of Formula III The lipophilic substituent and spacer of Formula III was incorporated into numerous disclosed peptides:

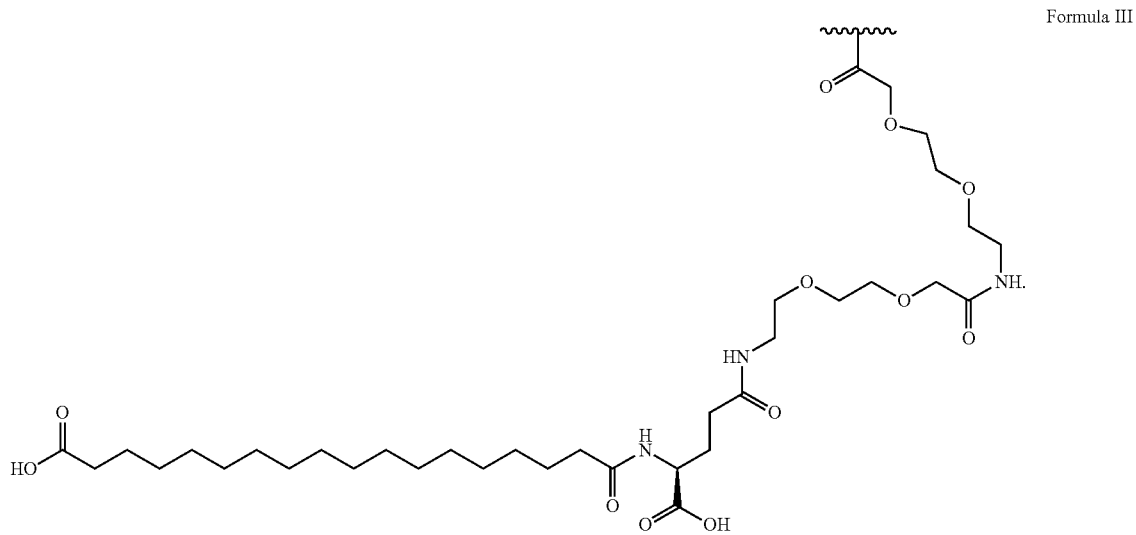 [SMILES: *C(=O)COCCOCCNC(=O)COCCOCCNC(=O)CC[C@H](NC(=O)CCCCCCCCCCCCCCCCC(=O)O)C(=O)O]

Formula III where the indicated carbonyl on the structure of Formula III was covalently joined to an ε-amino group of a lysine residue of the disclosed peptide to form an amide linkage.

The linear peptide sequence was synthesized on a Prelude peptide synthesizer (Protein Technologies Inc., Tucson, AZ)) by solid-phase methods using Fmoc strategy with 2-(1H-benzotriazole-1-yl)-1,1,3,3-tetramethyl uranium hexafluorophosphate (HBTU) or 2-(6-chloro-1-H-benzotri-azole-1-yl)-1,1,3,3-tetramethylaminium hexafluorophosphate (HCTU) activation (5 fold molar excess) in N,N-dimethylformamide (DMF), and N'N-Diisopropylethylamine (DIEA) as base, 20% piperidine/DMF for Fmoc deprotection. The resin was Rink Amide MBHA LL (Novabiochem) or N-α-Fmoc protected, pre-loaded Wang L L (Novabiochem), with loadings of 0.29-0.35 mmol/g on a 20-400 μmol scale. At the desired location for acyl-chain substitution, FMOC-Lys(Alloc)-OH was preferentially substituted into the peptide chain. Next, Boc-Tyr(tbu)-OH or Boc-Trp(Boc)-OH was used as the N-terminal amino acid residue. Upon completion of synthesis the resin was washed with Dichloromethane (DCM) and dried under vacuum for 30 minutes. Next, the Alloc protecting group was removed using a solution of Palladium Tetrakis in (CHCl3/Acetic Acid/N-methylmorpholine, 37:2:1 ratio). The resin was subsequently washed with a 0.5% solution of Sodium Diethyldithiocarbamate trihydrate in DMF, followed by a 0.5% solution of DIEA in DMF, and finally DMF. Next, elongation of the spacer region proceeded with coupling of {2-[2-(Fmoc-amino)ethoxy}acetic acid, followed by FMOC-Glu(Otbu)-OH using normal solid-phase conditions. The C-18, acid terminating side-chain, was added using Octadecanedioic Acid under normal solid-phase methods. Final deprotection and cleavage of the peptide from the solid support was performed by treatment of the resin with (92.5% TFA, 2.5% phenol, 2.5% water and 2.5% triisopropylsilane) for 2-3 hours. The cleaved peptide was precipitated using cold diethyl ether. The diethyl ether was decanted and the solids triturated again with cold diethyl ether, pelleted by centrifugation and lyophilized. The lyophilized solid was re-dissolved in a 1:1 solution of acetonitrile/water, with 0.1% TFA (10-15 mL), purified via reverse phase HPLC on a Waters XBridge™ BEH 130, CI8, 10 um, 130 Å, 30×250 mm ID column, using a gradient within the ranges of 5-75% acetonitrile/water with 0.1% TFA over 30 minutes at a flow rate of 30 mL/min, λ—215 nm. Column heater set at 60° C. The purified product was lyophilized and analyzed by ESI-LC/MS and analytical HPLC; and were demonstrated to be pure (>98%). Mass results all agreed with calculated values.

HPLC analysis conditions: 4.6×250 mm XBridge BEH130, 5 um, C18 column using an analytical Agilent 1100 with the following gradient: 5% to 70% over 15 minutes and holding at 70% to 20 minutes. The column temperature was set at 40° C. The flow rate was set at 1.5 mL/min. The solvents consisted of A=H2O+0.1% TFA and B=Acetonitrile+0.1% TFA. The crude and final LCMS were observed and product mass was identified using the following conditions: UV detection set at 215 and 280 nm.

LCMS analysis conditions: 4.6×250 mm XBridge BEH130, 5 um, C18 column using an analytical Agilent 1100 in combination with an API-4000 Sciex LC/MS/MS system with the following gradient: 5% to 65% over 10 minutes, ramping up to 95% to wash the column over 1 minute and equilibrating back to 5% organic to 12.5 minutes. The column temperature was set at 40° C. The flow rate was set at 1.5 mL/min. The solvents consisted of A=H2O±0.1% TFA and B=Acetonitrile+0.1% TFA. UV detection set at 215 and 280 nm. Method=Q1 MS. Syringe size 100 uL, UV range 190-400 nm, Slit width=4 mm, Sampling rate=>20 Hz., Ion source: Turbo spray, Polarity=Positive.

TABLE 7

| Compound ID | Modification: Lipophilic Substituent and Spacer | Site of Modification: Peptide Residue # | Sequence | GluR pEC50 | GLP-1R pEC50 |
|---|---|---|---|---|---|
| Compound A1 | none | n/a | YSHGTFTSDYSKYLD(Aib)KYAQEFV(Aib)WLEDEPSSGAPPPS-OH (SEQ ID NO: 41) | 10.6 | <6 |
| Compounds B1-B8: Substitutions & Modifications to Compound A1 ||||||
| Compound B1 | Formula II | 33 | YSHGTFTSDYSKYLD(Aib)KYAQEFV(Aib)WLEDEPSSK****APPPS-OH (SEQ ID NO: 152) | | |
| Compound B2 | Formula II | 24 | YSHGTFTSDYSKYLD(Aib)KYAQEFVK****WLEDEPSSGAPPPS-OH (SEQ ID NO: 153) | 11.1 | <6 |
| Compound B3 | Formula II | 16 | YSHGTFTSDYSKYLDK****KYAQEFV(Aib)WLEDEPSSGAPPPS-OH (SEQ ID NO: 154) | 11.4 | <6 |
| Compound B4 | Formula II | 10 | YSHGTFTSDK****SKYLD(Aib)KYAQEFV(Aib)WLEDEPSSGAPPPS-OH (SEQ ID NO: 155) | 9.1 | <6.0 |
| Compound B5 | Formula III | 33 | YSHGTFTSDYSKYLD(Aib)KYAQEFV(Aib)WLEDEPSSK*****APPPS-OH (SEQ ID NO: 156) | 9.6 | <6 |
| Compound B6 | Formula III | 24 | YSHGTFTSDYSKYLD(Aib)KYAQEFVK*****WLEDEPSSGAPPPS-OH (SEQ ID NO: 157) | 10.1 | <6 |
| Compound B7 | Formula III | 16 | YSHGTFTSDYSKYLDK*****KYAQEFV(Aib)WLEDEPSSGAPPPS-OH (SEQ ID NO: 158) | 8.6 | <6 |
| Compound B8 | Formula III | 10 | YSHGTFTSDK*****SKYLD(Aib)KYAQEFV(Aib)WLEDEPSSGAPPPS-OH (SEQ ID NO: 159) | 10.6 | <6 |
| Compound A2 | none | n/a | YSHGTFTSDYSKYLD(Aib)KSAQEFV(Aib)WLEDEPSSGAPPPS-OH (SEQ ID NO: 42) | | |
| Compounds B9-B16: Substitutions & Modifications to Compound A2 ||||||
| Compound B9 | Formula II | 33 | YSHGTFTSDYSKYLD(Aib)KSAQEFV(Aib)WLEDEPSSK****APPPS-OH (SEQ ID NO: 160) | 11.1 | <6 |
| Compound B10 | Formula II | 24 | YSHGTFTSDYSKYLD(Aib)KSAQEFVK****WLEDEPSSGAPPPS-OH (SEQ ID NO: 161) | 9.9 | <6 |
| Compound B11 | Formula II | 16 | YSHGTFTSDYSKYLDK****KSAQEFV(Aib)WLEDEPSSGAPPPS-OH (SEQ ID NO: 162) | 10.3 | 6.3 |
| Compound B12 | Formula II | 10 | YSHGTFTSDK****SKYLD(Aib)KSAQEFV(Aib)WLEDEPSSGAPPPS-OH (SEQ ID NO: 163) | 11.5 | 7.2 |
| Compound B13 | Formula III | 33 | YSHGTFTSDYSKYLD(Aib)KSAQEFV(Aib)WLEDEPSSK*****APPPS-OH (SEQ ID NO: 164) | 9.2 | <6 |
| Compound B14 | Formula III | 24 | YSHGTFTSDYSKYLD(Aib)KSAQEFVK*****WLEDEPSSGAPPPS-OH (SEQ ID NO: 165) | 9.3 | <6 |
| Compound B15 | Formula III | 16 | YSHGTFTSDYSKYLDK*****KSAQEFV(Aib)WLEDEPSSGAPPPS-OH (SEQ ID NO: 166) | 9.9 | <6.0 |
| Compound B16 | Formula III | 10 | YSHGTFTSDK*****SKYLD(Aib)KSAQEFV(Aib)WLEDEPSSGAPPPS-OH (SEQ ID NO: 167) | 8.5 | 8.3 |
| Compound A6 | none | n/a | WSQGTFTSDYSKYLD(Aib)KRAQEFV(Aib)WLEDEPSSGAPPPS-OH (SEQ ID NO: 42) | | |
| Compounds B17-B24: Substitutions & Modifications to Compound A6 ||||||
| Compound B17 | Formula II | 33 | WSQGTFTSDYSKYLD(Aib)KRAQEFV(Aib)WLEDEPSSK****APPPS-OH (SEQ ID NO: 168) | 10.5 | <6.0 |
| Compound B18 | Formula II | 24 | WSQGTFTSDYSKYLD(Aib)KRAQEFVK****WLEDEPSSGAPPPS-OH (SEQ ID NO: 169) | 10.2 | <6.0 |
| Compound B19 | Formula II | 16 | WSQGTFTSDYSKYLDK****KRAQEFV(Aib)WLEDEPSSGAPPPS-OH (SEQ ID NO: 170) | 10.6 | 6.3 |
| Compound B20 | Formula II | 10 | WSQGTFTSDK****SKYLD(Aib)KRAQEFV(Aib)WLEDEPSSGAPPPS-OH (SEQ ID NO: 171) | 11.1 | 6.5 |

TABLE 7-continued

| Compound ID | Modification: Lipophilic Substituent and Spacer | Site of Modification: Peptide Residue # | Sequence | GluR pEC50 | GLP-1R pEC50 |
|---|---|---|---|---|---|
| Compound B21 | Formula III | 33 | WSQGTFTSDYSKYLD(Aib)KRAQEFV(Aib)WLEDE PSSK*****APPPS-OH (SEQ ID NO: 172) | | |
| Compound B22 | Formula III | 24 | WSQGTFTSDYSKYLD(Aib)KRAQEFVK*****WLE DEPSSGAPPPS-OH (SEQ ID NO: 173) | | |
| Compound B23 | Formula III | 16 | WSQGTFTSDYSKYLDK*****KRAQEFV(Aib)WLE DEPSSGAPPPS-OH (SEQ ID NO: 174) | 9.5 | 6.5 |
| Compound B24 | Formula III | 10 | WSQGTFTSDK*****SKYLD(Aib)KRAQEFV(Aib)W LEDEPSSGAPPPS-OH (SEQ ID NO: 175) | 8.2 | 6.8 |
| Compound A4 | none | n/a | YSHGTFTSDYSKYLD(Aib)KRAQEFVIWLEDEPSS GAPPPS (SEQ ID NO: 44) | | |
| Compounds B25-B32: Substitutions & Modifications to Compound A4 | | | | | |
| Compound B25 | Formula II | 33 | YSHGTFTSDYSKYLD(Aib)KRAQEFVIWLEDEPSS K****APPPS-OH (SEQ ID NO: 176) | 10.5 | <6 |
| Compound B26 | Formula II | 16 | YSHGTFTSDYSKYLDK****KRAQEFVIWLEDEPSS GAPPPS-OH (SEQ ID NO: 177) | 11 | <6 |
| Compound B27 | Formula II | 10 | YSHGTFTSDK****SKYLD(Aib)KRAQEFVIWLEDE PSSGAPPPS-OH (SEQ ID NO: 178) | 11.5 | 6.6 |
| Compound B28 | Formula II | 21 | YSHGTFTSDYSKYLD(Aib)KRAQK****FVIWLEDE PSSGAPPPS-OH (SEQ ID NO: 179) | | |
| Compound B29 | Formula III | 33 | YSHGTFTSDYSKYLD(Aib)KRAQEFVIWLEDEPSS K*****APPPS-OH (SEQ ID NO: 180) | 9.8 | 7.0 |
| Compound B30 | Formula III | 21 | YSHGTFTSDYSKYLD(Aib)KRAQK*****FVIWLED EPSSGAPPPS-OH (SEQ ID NO: 181) | 9.7 | 7.0 |
| Compound B31 | Formula III | 16 | YSHGTFTSDYSKYLDK*****KRAQEFVIWLEDEPS SGAPPPS-OH (SEQ ID NO: 182) | 10.6 | 7.4 |
| Compound B32 | Formula III | 10 | YSHGTFTSDK*****SKYLD(Aib)KRAQEFVIWLED EPSSGAPPPS-OH (SEQ ID NO: 183) | 9.4 | 7.8 |
| Compound A3 | none | n/a | YSQGTFTSDYSKYLDAARAQEFVKWLEDEPKSKS PPPS-NH$_2$ (SEQ ID NO: 43) | | |
| Compounds B33-B40: Substitutions & Modifications to Compound A3 | | | | | |
| Compound B33 | Formula II | 33 | YSQGTFTSDYSKYLDAARAQEFVKWLEDEPKSK* ***SPPPS-NH$_2$ (SEQ ID NO: 184) | 10.6 | <6 |
| Compound B34 | Formula II | 24 | YSQGTFTSDYSKYLDAARAQEFVK****WLEDEPK SKSPPPS-NH$_2$ (SEQ ID NO: 185) | 9.8 | <6 |
| Compound B35 | Formula II | 16 | YSQGTFTSDYSKYLDK****ARAQEFVKWLEDEPK SKSPPPS-NH$_2$ (SEQ ID NO: 186) | 11.1 | 6.6 |
| Compound B36 | Formula II | 10 | YSQGTFTSDK****SKYLDAARAQEFVKWLEDEPK SKSPPPS-NH$_2$ (SEQ ID NO: 187) | 11.5 | 8.1 |

TABLE 7-continued

| Compound ID | Modification: Lipophilic Substituent and Spacer | Site of Modification: Peptide Residue # | Sequence | GluR pEC50 | GLP-1R pEC50 |
|---|---|---|---|---|---|
| Compound B37 | Formula III | 33 | YSQGTFTSDYSKYLDAARAQEFVKWLEDEPKSK*****SPPPS-NH$_2$ (SEQ ID NO: 188) | 10.1 | 6.2 |
| Compound B38 | Formula III | 24 | YSQGTFTSDYSKYLDAARAQEFVK*****WLEDEPKSKSPPPS-NH$_2$ (SEQ ID NO: 189) | 9.6 | 6 |
| Compound B39 | Formula III | 16 | YSQGTFTSDYSKYLDK*****ARAQEFVKWLEDEPKSKSPPPS-NH$_2$ (SEQ ID NO: 190) | 10.9 | 6 |
| Compound B40 | Formula III | 10 | YSQGTFTSDK*****SKYLDAARAQEFVKWLEDEPKSKSPPPS-NH$_2$ (SEQ ID NO: 191) | 11.9 | 7.2 |
| Compound A5 | none | n/a | YSHGTFTSDYSKYLDSARAQEFVKWLEDEPSSGAPPPS-NH$_2$ (SEQ ID NO: 45) | | |
| Compounds B41-B48: Substitutions & Modifications to Compound A5 | | | | | |
| Compound B41 | Formula II | 33 | YSHGTFTSDYSKYLDSARAQEFVKWLEDEPSSK*****APPPS-NH$_2$ (SEQ ID NO: 192) | 10.6 | <6 |
| Compound B42 | Formula II | 24 | YSHGTFTSDYSKYLDSARAQEFVK****WLEDEPSSGAPPPS-NH$_2$ (SEQ ID NO: 193) | 9.7 | <6 |
| Compound B43 | Formula II | 16 | YSHGTFTSDYSKYLDK****ARAQEFVKWLEDEPSSGAPPPS-NH$_2$ (SEQ ID NO: 194) | 11.1 | <6 |
| Compound B44 | Formula II | 10 | YSHGTFTSDK****SKYLDSARAQEFVKWLEDEPSSGAPPPS-NH$_2$ (SEQ ID NO: 195) | 11.9 | 7.2 |
| Compound B45 | Formula III | 33 | YSHGTFTSDYSKYLDSARAQEFVKWLEDEPSSK*****APPPS-NH$_2$ (SEQ ID NO: 196) | 9.8 | <6 |
| Compound B46 | Formula III | 24 | YSHGTFTSDYSKYLDSARAQEFVK*****WLEDEPSSGAPPPS-NH$_2$ (SEQ ID NO: 197) | 9.5 | <6 |
| Compound B47 | Formula III | 16 | YSHGTFTSDYSKYLDK*****ARAQEFVKWLEDEPSSGAPPPS-NH$_2$ (SEQ ID NO: 198) | 10.8 | <6 |
| Compound B48 | Formula III | 10 | YSHGTFTSDK*****SKYLDSARAQEFVKWLEDEPSSGAPPPS-NH$_2$ (SEQ ID NO: 199) | 9.2 | <6 |

Each ε-amino group of the lysine residue located at the indicated peptide residue (K****) in the disclosed compounds is covalently bound to the indicated carbonyl of the structure of Formula II to form an amide:

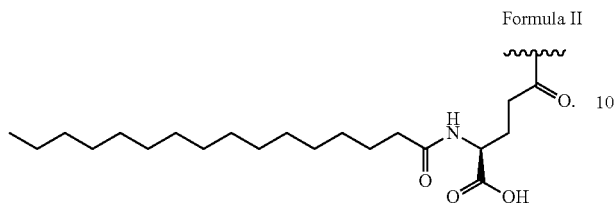

Formula II

Each ε-amino group of the lysine residue located at the indicated peptide residue (K*****) in the disclosed compounds is covalently bound to the indicated carbonyl of the structure of Formula III to form an amide:

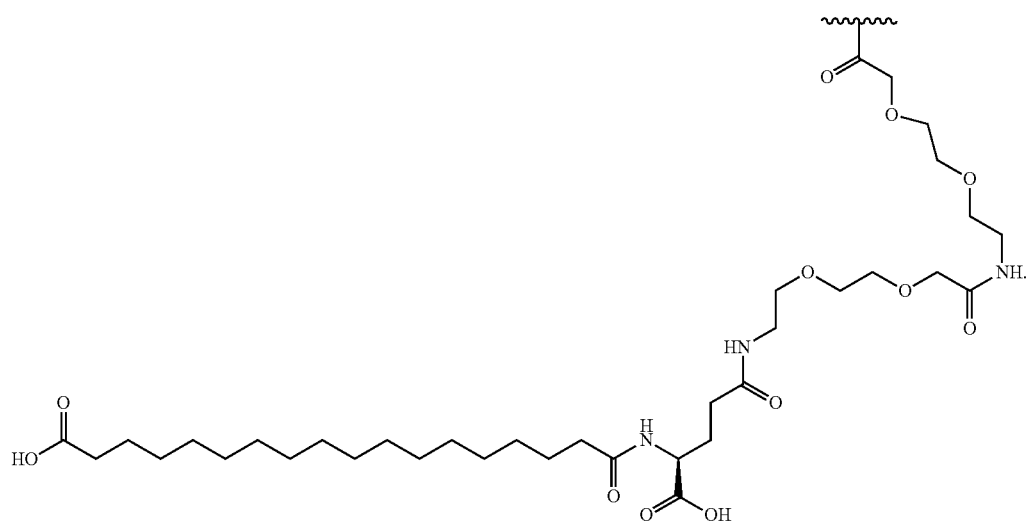

Formula III

Example 23. Clearance of Peptide from Kidney (CL) Following Intravenous Infusion Peptides were formulated in sterile saline and administered as a 3-hour intravenous infusion to non-fasted male Wistar Han or Sprague-Dawley rats (n=3 per group) via jugular vein cannula at a final dose of 0.3 or 0.1 mg/kg. Formulations were administered at a rate of 1.67 mL/kg/h. Blood samples (approximately 250 uL) were collected for pharmacokinetic analysis via a femoral vein cannula at 1, 2, 3, 3.17, 3.33, 3.5, 4, 4.5, 5 and 6 h post-start of infusion into microtainer tubes containing K2EDTA as anticoagulant and 25 uL of a protease inhibitor cocktail. Plasma was prepared by centrifugation and stored at −80° C. until analysis.

Acylated peptides were formulated in sterile saline and administered as a 1-hour intravenous infusion to non-fasted male Sprague-Dawley rats (n=3 per group) via jugular vein cannula at a final dose of 0.033 mg/kg. Formulations were administered at a rate of 1.67 mL/kg/h. Blood samples (approximately 250 uL) were collected for pharmacokinetic analysis via a femoral vein cannula at 0, 0.25, 0.5, 1, 1.17, 1.33, 1.5, 2, 4, 6, 8, 24, 30 and 48 h post-start of infusion into microtainer tubes containing K2EDTA as anticoagulant and 25 uL of a protease inhibitor cocktail. Plasma was prepared by centrifugation and stored at −80° C. until analysis. Representative results are provided in Table 8 below.

TABLE 8

| Compound ID | Modification: Lipophilic Substituent and Spacer | Site of Modification: Peptide Residue # | CL (IV/SubQ) | T ½ |
|---|---|---|---|---|
| Compound A1 | none | none | 11.5 | 0.83 |
| Compound B3 | Formula II | 16 | 18.8 | 1.79 |
| Compound B9 | Formula II | 33 | 0.594 | 4.98 |
| Compound B14 | Formula III | 24 | 2.65 | 13.9 |
| Compound B15 | Formula III | 16 | 0.457 | 9.34 |
| Compound B33 | Formula II | 33 | 6.96 | 0.429 |
| Compound B41 | Formula II | 33 | 4.856 | 1.09 |

Example 24. Weight Loss in Rats Upon Continuous Administration of Exenatide or a Glucagon Analog Diet-induced-obese LE rats with initial body weights of 586±86 (mean±SD) were each implanted with 2 osmotic minipumps (Alzet) delivering, respectively, exenatide or a glucagon analog i.e., selective glucagon receptor agonist (as described for example 10). The treatment groups comprised 30 different combinations of exenatide and glucagon analog, with 10-20 animals in each group.

Figure 14:
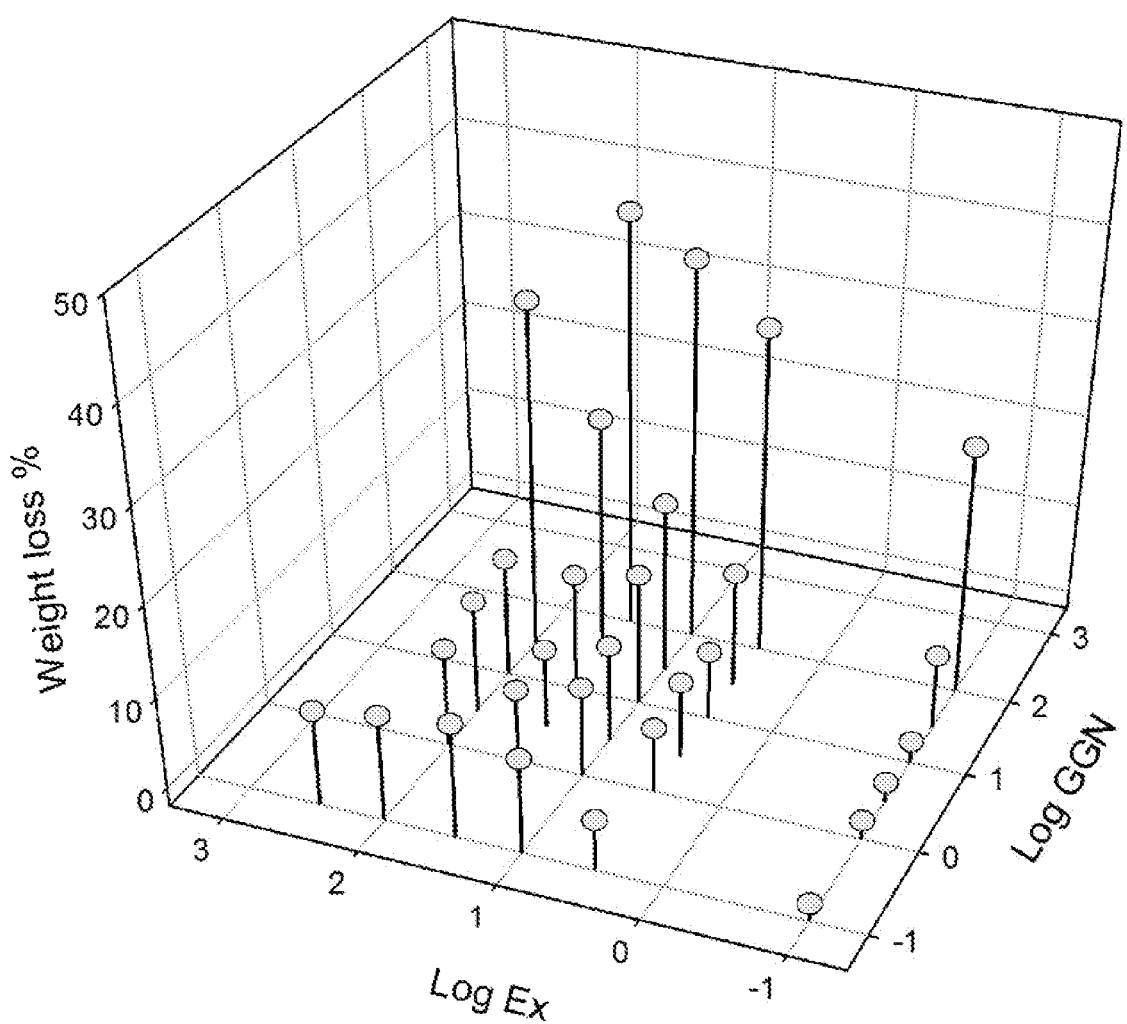
FIG. 14 illustrates a 3-D depiction of weight loss in DIO LE rats upon continuous administration of exenatide or a glucagon analog.

Body weight was measured every 7 days. Results are illustrated in FIG. 14 as a 3-D plot of weight loss on the vertical (Z) axis, represented as a percentage of initial body weight after 21 days of continuous dosing. A positive weight loss, shown as a circle atop a riser emerging from the base plane, thus represents a decrease in body weight relative to pre-treatment body weight. To maintain clarity, error bars are not shown.

The horizontal axes in FIG. 14 relate to the logarithm of the daily dose in units of micrograms per kg body weight per day for each of the exenatide and glucagon analog singletons. Log exenatide dose of −1 denotes treatments where exenatide dose was zero (glucagon analog-only treatments), and −1 on the glucagon log dose axis denotes treatments where glucagon was not dosed (exenatide-only treatments). The series of points in the left foreground and in the right foreground therefore depict dose-responses for exenatide alone, and for the glucagon analog alone, respectively.

The weight loss response to exenatide alone after 21 days treatment could be described by a 4-parameter sigmoid curve with a maximal response of 12.5% weight loss, an $ED_{50}$ of 9.6 μg/kg/day, with a Hill slope of 0.88. For the glucagon analog alone, the parameters for 21 day weight loss were a maximum of 28.5%, an $ED_{50}$ of 45 μg/kg/day, and a Hill slope of 2.7.

Example 25. Evaluation of Exenatide/Glucagon Analog Combinations

The raw data in FIG. 14 were fitted to a continuous function to enable characterization of certain key features of the response to exenatide/glucagon analog combinations. The general form of the continuous response surface was Response to combination=$(a*Resp_{EX})$+
$(b*Resp_{GGN})+(c*Resp_{EX}*Resp_{GGN})$ where $Resp_{EX}$ and $Resp_{GGN}$ represent the dose-dependent responses observed with each singleton.

The combination response was further constrained by a hyperbolic relationship such that it could not exceed 100% weight loss. The best-fitting continuous response surface (R=0.9) was obtained by least-squares iterative approximation of the above-mentioned user-defined equation using GraphPad Prism v7.0 (GraphPad software, San Diego, CA). Where C>0, a multiplicative (supra-additive) component was present.

Figure 15:
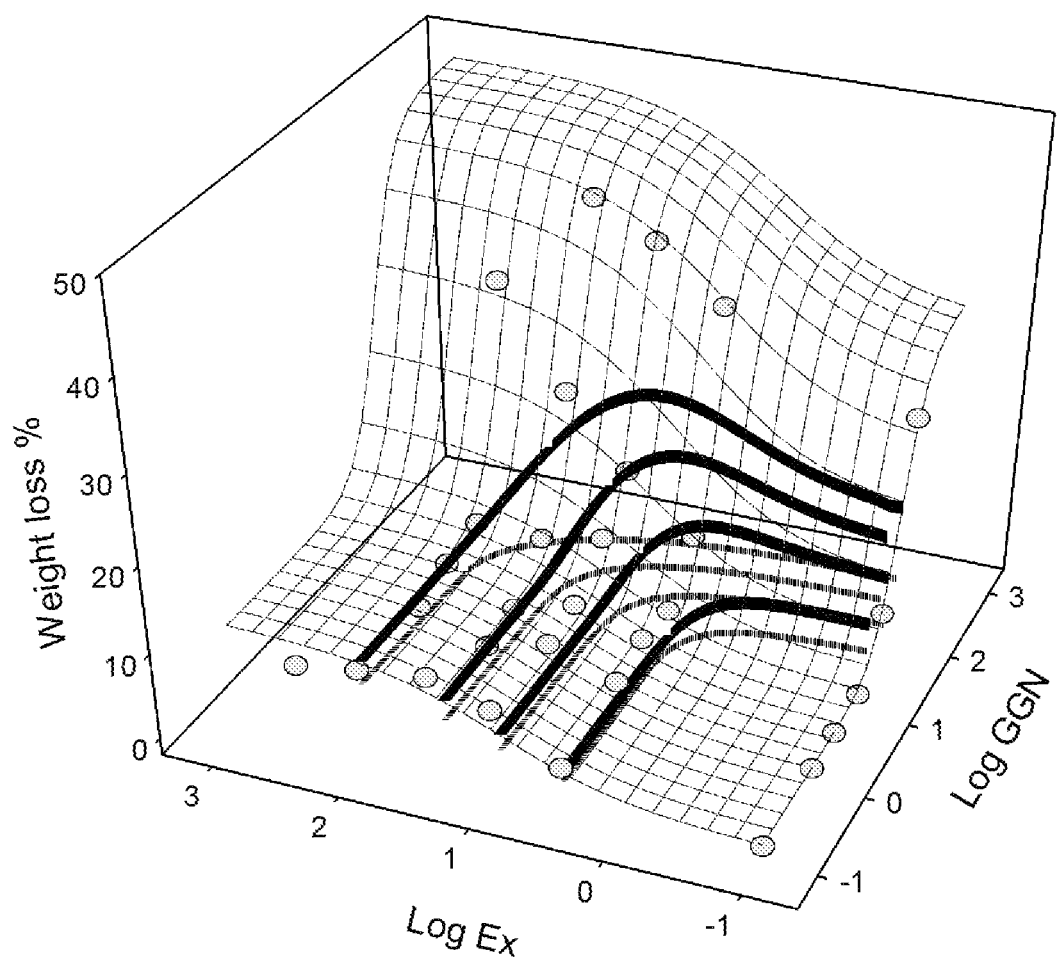
FIG. 15 illustrates a 3-D evaluation of weight loss in DIO LE rats upon continuous administration of exenatide/glucagon analog combinations.

The symbols representing each treatment group are shown as spheres embedded within the mesh of the best-fitting surface in FIG. 15. The 4 broken curves joining the exenatide-only and the glucagon analog-only planes represent lines of equal effect (isoboles) that would be obtained with an additive interaction as one agent was substituted for equi-effective doses of the other (expected 2%, 4%, 6% and 8% weight loss isoboles shown). The 4 heavy solid lines depict what was instead observed, being the response surface corresponding to such dose-substitution. The differences between the solid line (observed) and broken line (expected) define a synergistic interaction. For each level of predicted effect, there was a dose ratio where the effect peaked, and the synergy was maximal.

Example 26. Evaluation of Fixed-Ratio Combinations of Exenatide/Glucagon Analog Because a combination product may comprise agents administered in a fixed ratio, the response surface was analyzed from the viewpoint of increasing doses of fixed-ratio mixtures.

Figure 16:
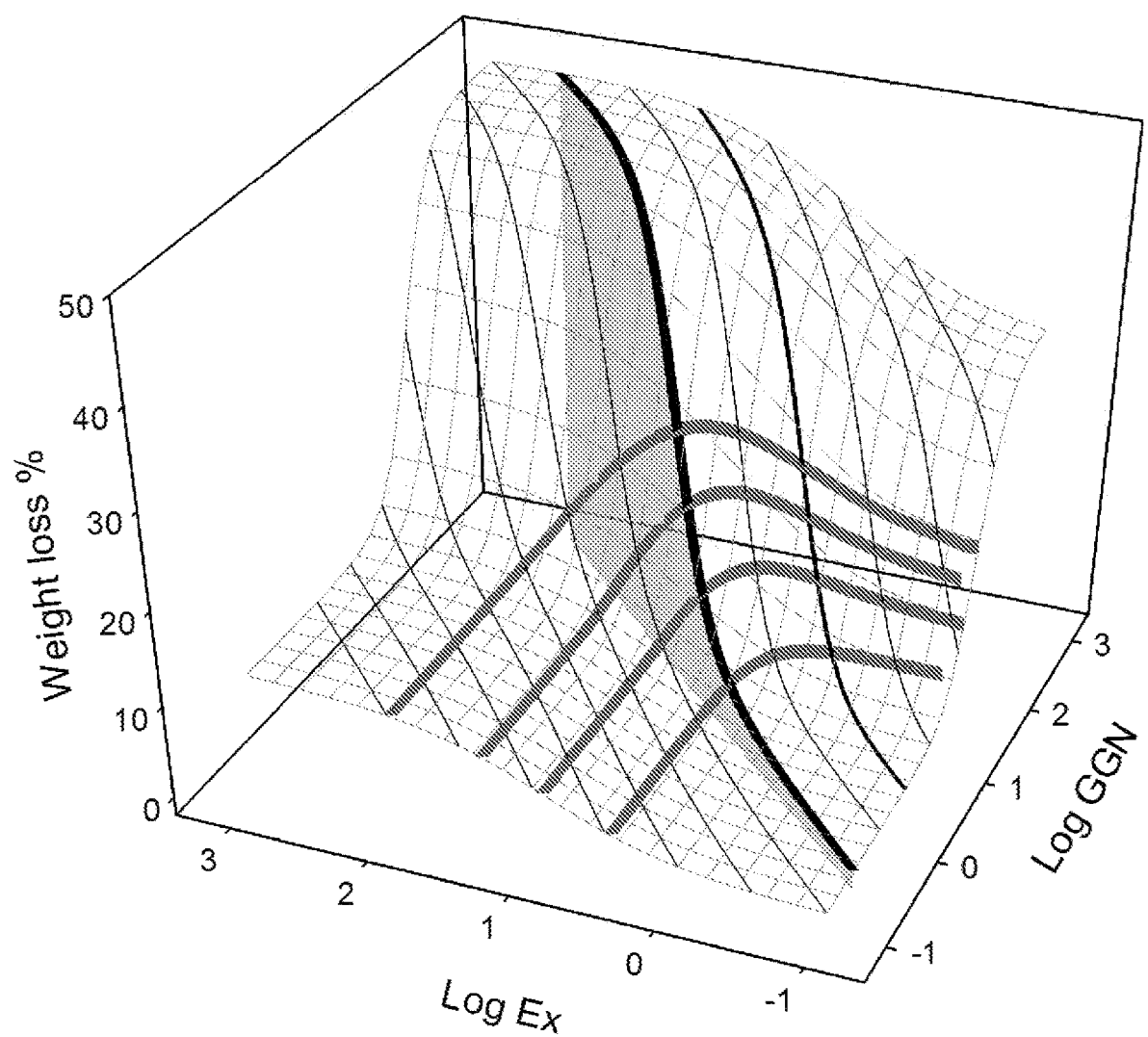
FIG. 16 illustrates a 3-D evaluation of weight loss in DIO LE rats upon continuous administration of fixed-ratio of exenatide/glucagon analog combinations.

Fixed dose ratios are depicted in FIG. 16 as parallel diagonal planes above the Log Exenatide ("EX") vs Log Glucagon Analog ("GGN") base plane. The dose-response of each mixture is shown as the series of black curves where the response surface intersects each plane. The 4 gray curves on the surface (shown as thick black lines in FIG. 15) are the observed responses when one agent is substituted for an equi-effective dose of the other, a so-called "dose-ratio scan".

The heavy black line, where the gray plane of a fixed dose ratio intersects with the response surface, appears to transect the 4 gray lines near their dose-ratio optima. The gray plane defines a 3:1 GGN:EX dose ratio. Mixtures of 10:1 and 1:1 GGN:EX also performed well.

Example 27. Evaluation of In Vivo Potencies

Evaluation of in vivo potencies, defined as effect per unit total mass of drug, was undertaken for different fixed-ratio combinations of exenatide/glucagon analog.

For some applications, such as in a mini osmotic pump where the volume of the drug reservoir is limited, the mixture with the highest apparent in vivo potency is most beneficial. The apparent in vivo potency of different mixtures may be defined as effect per unit total mass of drug (or more strictly, per volume of formulation).

Figure 17:
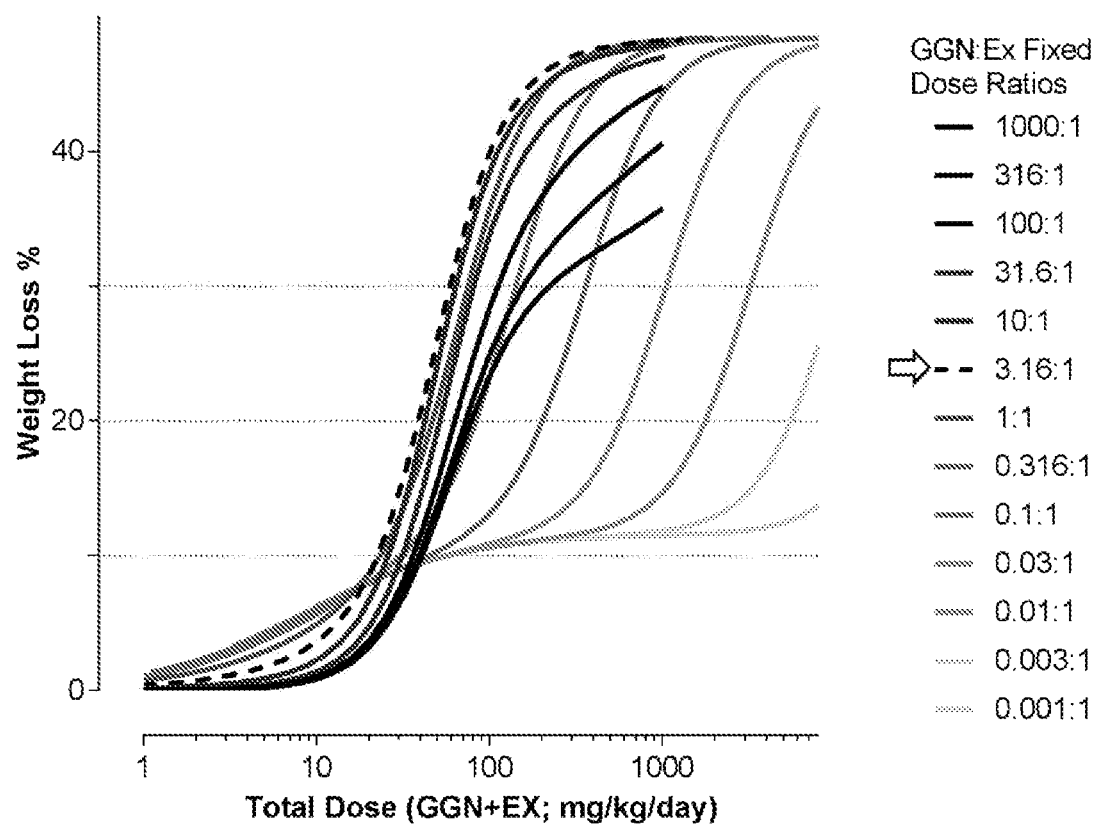
FIG. 17 is a graphical evaluation of in vivo potency, defined as effect per unit total mass of drug, of different fixed-ratio of exenatide/glucagon analog combinations.

The responses to mixtures shown as surfaces in FIG. 15 and FIG. 16 may thereby be reduced to the 2-D dose responses shown in FIG. 17. The X-axis in FIG. 17 is not the dose of a single agent, but is the mass of both agents in a fixed-ratio mixture.

The family of dose responses for different mixtures includes one where the least combined dose evokes a given effect (exemplified by 20% weight loss, as indicated by the horizontal arrow). A promising mixture thus identified was an approximately 3:1 mixture of GGN:EX. The response to this mixture, exhibiting highest apparent potency, is shown as a broken line.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

<160> NUMBER OF SEQ ID NOS: 200

<210> SEQ ID NO 1
<211> LENGTH: 29
<212> TYPE: PRT
<213> ORGANISM: Artificial Sequence

```
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: X is Y or W
<220> FEATURE:
<221> NAME/KEY: MISC_FEATURE
<222> LOCATION: (2)..(2)
<223> OTHER INFORMATION: X is S, G or T
<220> FEATURE:
<221> NAME/KEY: MISC_FEATURE
<222> LOCATION: (3)..(3)
<223> OTHER INFORMATION: X is Q or H
<220> FEATURE:
<221> NAME/KEY: MISC_FEATURE
<222> LOCATION: (10)..(10)
<223> OTHER INFORMATION: X is Y or H
<220> FEATURE:
<221> NAME/KEY: MISC_FEATURE
<222> LOCATION: (11)..(11)
<223> OTHER INFORMATION: X is S or T
<220> FEATURE:
<221> NAME/KEY: MISC_FEATURE
<222> LOCATION: (12)..(12)
<223> OTHER INFORMATION: X is K or R
<220> FEATURE:
<221> NAME/KEY: MISC_FEATURE
<222> LOCATION: (13)..(13)
<223> OTHER INFORMATION: X is Y, L or W
<220> FEATURE:
<221> NAME/KEY: MISC_FEATURE
<222> LOCATION: (15)..(15)
<223> OTHER INFORMATION: X is D or E
<220> FEATURE:
<221> NAME/KEY: MISC_FEATURE
<222> LOCATION: (16)..(16)
<223> OTHER INFORMATION: X is S, Aib, A, E, L, Q, K, or I
<220> FEATURE:
<221> NAME/KEY: MISC_FEATURE
<222> LOCATION: (17)..(17)
<223> OTHER INFORMATION: X is K, E, S, T, or A
<220> FEATURE:
<221> NAME/KEY: MISC_FEATURE
<222> LOCATION: (18)..(18)
<223> OTHER INFORMATION: X is A, R, S, E, L, T or Y
<220> FEATURE:
<221> NAME/KEY: MISC_FEATURE
<222> LOCATION: (23)..(23)
<223> OTHER INFORMATION: X is T or V
<220> FEATURE:
<221> NAME/KEY: MISC_FEATURE
<222> LOCATION: (24)..(24)
<223> OTHER INFORMATION: X is K, I, L, or Aib
<220> FEATURE:
<221> NAME/KEY: MISC_FEATURE
<222> LOCATION: (25)..(25)
<223> OTHER INFORMATION: X is H or W
<220> FEATURE:
<221> NAME/KEY: MISC_FEATURE
<222> LOCATION: (29)..(29)
<223> OTHER INFORMATION: E is optionally attached to a Z-tail as defined
      in the specification

<400> SEQUENCE: 1

Xaa Xaa Xaa Gly Thr Phe Thr Ser Asp Xaa Xaa Xaa Xaa Leu Xaa Xaa
1               5                   10                  15

Xaa Xaa Ala Gln Glu Phe Xaa Xaa Xaa Leu Glu Asp Glu
            20                  25

<210> SEQ ID NO 2
<211> LENGTH: 29
<212> TYPE: PRT
<213> ORGANISM: Artificial Sequence
<220> FEATURE:
<223> OTHER INFORMATION: chemically synthesized
```

```
<220> FEATURE:
<221> NAME/KEY: MISC_FEATURE
<222> LOCATION: (1)..(1)
<223> OTHER INFORMATION: X is Y or W
<220> FEATURE:
<221> NAME/KEY: MISC_FEATURE
<222> LOCATION: (2)..(2)
<223> OTHER INFORMATION: X is S or G
<220> FEATURE:
<221> NAME/KEY: MISC_FEATURE
<222> LOCATION: (3)..(3)
<223> OTHER INFORMATION: X is Q or H
<220> FEATURE:
<221> NAME/KEY: MISC_FEATURE
<222> LOCATION: (10)..(10)
<223> OTHER INFORMATION: X is Y or H
<220> FEATURE:
<221> NAME/KEY: MISC_FEATURE
<222> LOCATION: (11)..(11)
<223> OTHER INFORMATION: X is S or T
<220> FEATURE:
<221> NAME/KEY: MISC_FEATURE
<222> LOCATION: (12)..(12)
<223> OTHER INFORMATION: X is K or R
<220> FEATURE:
<221> NAME/KEY: MISC_FEATURE
<222> LOCATION: (13)..(13)
<223> OTHER INFORMATION: X is Y, L or W
<220> FEATURE:
<221> NAME/KEY: MISC_FEATURE
<222> LOCATION: (15)..(15)
<223> OTHER INFORMATION: X is D or E
<220> FEATURE:
<221> NAME/KEY: MISC_FEATURE
<222> LOCATION: (16)..(16)
<223> OTHER INFORMATION: X is Aib, A, or S
<220> FEATURE:
<221> NAME/KEY: MISC_FEATURE
<222> LOCATION: (17)..(17)
<223> OTHER INFORMATION: X is A or K
<220> FEATURE:
<221> NAME/KEY: MISC_FEATURE
<222> LOCATION: (18)..(18)
<223> OTHER INFORMATION: X is R, S, L or Y
<220> FEATURE:
<221> NAME/KEY: MISC_FEATURE
<222> LOCATION: (24)..(24)
<223> OTHER INFORMATION: X is K, I, or Aib
<220> FEATURE:
<221> NAME/KEY: MISC_FEATURE
<222> LOCATION: (25)..(25)
<223> OTHER INFORMATION: X is H or W
<220> FEATURE:
<221> NAME/KEY: MISC_FEATURE
<222> LOCATION: (29)..(29)
<223> OTHER INFORMATION: E is optionally attached to a Z-tail as defined
      in the specification

<400> SEQUENCE: 2

Xaa Xaa Xaa Gly Thr Phe Thr Ser Asp Xaa Xaa Xaa Xaa Leu Xaa Xaa
1               5                   10                  15

Xaa Xaa Ala Gln Glu Phe Val Xaa Trp Leu Glu Asp Glu
            20                  25

<210> SEQ ID NO 3
<211> LENGTH: 29
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(3)
<223> OTHER INFORMATION: X is Q or H
<220> FEATURE:
<221> NAME/KEY: MISC_FEATURE
```

```
<222> LOCATION: (16)..(16)
<223> OTHER INFORMATION: X is Aib or A
<220> FEATURE:
<221> NAME/KEY: MISC_FEATURE
<222> LOCATION: (17)..(17)
<223> OTHER INFORMATION: X is A or K
<220> FEATURE:
<221> NAME/KEY: MISC_FEATURE
<222> LOCATION: (18)..(18)
<223> OTHER INFORMATION: X is R, S or Y
<220> FEATURE:
<221> NAME/KEY: MISC_FEATURE
<222> LOCATION: (24)..(24)
<223> OTHER INFORMATION: X is K or Aib
<220> FEATURE:
<221> NAME/KEY: MISC_FEATURE
<222> LOCATION: (29)..(29)
<223> OTHER INFORMATION: E is attached to a Z-tail as defined in the
      specification

<400> SEQUENCE: 3

Tyr Ser Xaa Gly Thr Phe Thr Ser Asp Tyr Ser Lys Tyr Leu Asp Xaa
1               5                   10                  15

Xaa Xaa Ala Gln Glu Phe Val Xaa Trp Leu Glu Asp Glu
            20                  25

<210> SEQ ID NO 4
<211> LENGTH: 11
<212> TYPE: PRT
<213> ORGANISM: Artificial Sequence
<220> FEATURE:
<223> OTHER INFORMATION: chemically synthesized

<400> SEQUENCE: 4

Glu Glu Pro Ser Ser Gly Ala Pro Pro Pro Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: chemically synthesized

<400> SEQUENCE: 5

Glu Pro Ser Ser Gly Ala Pro Pro Pro Ser
1               5                   10

<210> SEQ ID NO 6
<211> LENGTH: 6
<212> TYPE: PRT
<213> ORGANISM: Artificial Sequence
<220> FEATURE:
<223> OTHER INFORMATION: chemically synthesized

<400> SEQUENCE: 6

Gly Ala Pro Pro Pro Ser
1               5

<210> SEQ ID NO 7
<211> LENGTH: 11
<212> TYPE: PRT
<213> ORGANISM: Artificial Sequence
<220> FEATURE:
<223> OTHER INFORMATION: chemically synthesized

<400> SEQUENCE: 7

Gly Gly Pro Ser Ser Gly Ala Pro Pro Pro Ser
1               5                   10
```

```
<210> SEQ ID NO 8
<211> LENGTH: 10
<212> TYPE: PRT
<213> ORGANISM: Artificial Sequence
<220> FEATURE:
<223> OTHER INFORMATION: chemically synthesized

<400> SEQUENCE: 8

Gly Pro Ser Ser Gly Ala Pro Pro Pro Ser
1               5                   10

<210> SEQ ID NO 9
<211> LENGTH: 9
<212> TYPE: PRT
<213> ORGANISM: Artificial Sequence
<220> FEATURE:
<223> OTHER INFORMATION: chemically synthesized

<400> SEQUENCE: 9

Lys Arg Asn Lys Asn Pro Pro Pro Ser
1               5

<210> SEQ ID NO 10
<211> LENGTH: 8
<212> TYPE: PRT
<213> ORGANISM: Artificial Sequence
<220> FEATURE:
<223> OTHER INFORMATION: chemically synthesized

<400> SEQUENCE: 10

Lys Arg Asn Lys Asn Pro Pro Ser
1               5

<210> SEQ ID NO 11
<211> LENGTH: 8
<212> TYPE: PRT
<213> ORGANISM: Artificial Sequence
<220> FEATURE:
<223> OTHER INFORMATION: chemically synthesized

<400> SEQUENCE: 11

Lys Arg Asn Lys Pro Pro Ile Ala
1               5

<210> SEQ ID NO 12
<211> LENGTH: 8
<212> TYPE: PRT
<213> ORGANISM: Artificial Sequence
<220> FEATURE:
<223> OTHER INFORMATION: chemically synthesized

<400> SEQUENCE: 12

Lys Arg Asn Lys Pro Pro Pro Ser
1               5

<210> SEQ ID NO 13
<211> LENGTH: 9
<212> TYPE: PRT
<213> ORGANISM: Artificial Sequence
<220> FEATURE:
<223> OTHER INFORMATION: chemically synthesized

<400> SEQUENCE: 13

Lys Ser Ser Gly Lys Pro Pro Pro Ser
1               5
```

<210> SEQ ID NO 14
<211> LENGTH: 9
<212> TYPE: PRT
<213> ORGANISM: Artificial Sequence
<220> FEATURE:
<223> OTHER INFORMATION: chemically synthesized

<400> SEQUENCE: 14

Pro Glu Ser Gly Ala Pro Pro Pro Ser
1               5

<210> SEQ ID NO 15
<211> LENGTH: 9
<212> TYPE: PRT
<213> ORGANISM: Artificial Sequence
<220> FEATURE:
<223> OTHER INFORMATION: chemically synthesized

<400> SEQUENCE: 15

Pro Lys Ser Gly Ala Pro Pro Pro Ser
1               5

<210> SEQ ID NO 16
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (9)..(9)
<223> OTHER INFORMATION: AMIDATION

<400> SEQUENCE: 16

Pro Lys Ser Lys Ala Pro Pro Pro Ser
1               5

<210> SEQ ID NO 17
<211> LENGTH: 9
<212> TYPE: PRT
<213> ORGANISM: Artificial Sequence
<220> FEATURE:
<223> OTHER INFORMATION: chemically synthesized

<400> SEQUENCE: 17

Pro Lys Ser Lys Ala Pro Pro Pro Ser
1               5

<210> SEQ ID NO 18
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (9)..(9)
<223> OTHER INFORMATION: AMIDATION

<400> SEQUENCE: 18

Pro Lys Ser Lys Glu Pro Pro Pro Ser
1               5

<210> SEQ ID NO 19
<211> LENGTH: 9
<212> TYPE: PRT
<213> ORGANISM: Artificial Sequence
<220> FEATURE:

```
<223> OTHER INFORMATION: chemically synthesized

<400> SEQUENCE: 19

Pro Lys Ser Lys Glu Pro Pro Pro Ser
1               5

<210> SEQ ID NO 20
<211> LENGTH: 9
<212> TYPE: PRT
<213> ORGANISM: Artificial Sequence
<220> FEATURE:
<223> OTHER INFORMATION: chemically synthesized

<400> SEQUENCE: 20

Pro Lys Ser Lys Gln Pro Pro Pro Ser
1               5

<210> SEQ ID NO 21
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (9)..(9)
<223> OTHER INFORMATION: AMIDATION

<400> SEQUENCE: 21

Pro Lys Ser Lys Ser Pro Pro Pro Ser
1               5

<210> SEQ ID NO 22
<211> LENGTH: 9
<212> TYPE: PRT
<213> ORGANISM: Artificial Sequence
<220> FEATURE:
<223> OTHER INFORMATION: chemically synthesized

<400> SEQUENCE: 22

Pro Lys Ser Lys Ser Pro Pro Pro Ser
1               5

<210> SEQ ID NO 23
<211> LENGTH: 9
<212> TYPE: PRT
<213> ORGANISM: Artificial Sequence
<220> FEATURE:
<223> OTHER INFORMATION: chemically synthesized

<400> SEQUENCE: 23

Pro Arg Asn Lys Asn Asn Pro Pro Ser
1               5

<210> SEQ ID NO 24
<211> LENGTH: 9
<212> TYPE: PRT
<213> ORGANISM: Artificial Sequence
<220> FEATURE:
<223> OTHER INFORMATION: chemically synthesized

<400> SEQUENCE: 24

Pro Ser Lys Gly Ala Pro Pro Pro Ser
1               5

<210> SEQ ID NO 25
<211> LENGTH: 10
```

```
<212> TYPE: PRT
<213> ORGANISM: Artificial Sequence
<220> FEATURE:
<223> OTHER INFORMATION: chemically synthesized

<400> SEQUENCE: 25

Pro Ser Ser Gly Ala Pro Pro Pro Ser Glu
1               5                   10

<210> SEQ ID NO 26
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (9)..(9)
<223> OTHER INFORMATION: AMIDATION

<400> SEQUENCE: 26

Pro Ser Ser Gly Ala Pro Pro Pro Ser
1               5

<210> SEQ ID NO 27
<211> LENGTH: 9
<212> TYPE: PRT
<213> ORGANISM: Artificial Sequence
<220> FEATURE:
<223> OTHER INFORMATION: chemically synthesized

<400> SEQUENCE: 27

Pro Ser Ser Gly Ala Pro Pro Pro Ser
1               5

<210> SEQ ID NO 28
<211> LENGTH: 10
<212> TYPE: PRT
<213> ORGANISM: Artificial Sequence
<220> FEATURE:
<223> OTHER INFORMATION: chemically synthesized

<400> SEQUENCE: 28

Pro Ser Ser Gly Ala Pro Pro Pro Ser Ser
1               5                   10

<210> SEQ ID NO 29
<211> LENGTH: 9
<212> TYPE: PRT
<213> ORGANISM: Artificial Sequence
<220> FEATURE:
<223> OTHER INFORMATION: chemically synthesized

<400> SEQUENCE: 29

Pro Ser Ser Gly Glu Pro Pro Pro Ser
1               5

<210> SEQ ID NO 30
<211> LENGTH: 9
<212> TYPE: PRT
<213> ORGANISM: Artificial Sequence
<220> FEATURE:
<223> OTHER INFORMATION: chemically synthesized

<400> SEQUENCE: 30

Pro Ser Ser Gly Lys Lys Pro Pro Ser
1               5
```

```
<210> SEQ ID NO 31
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (9)..(9)
<223> OTHER INFORMATION: AMIDATION

<400> SEQUENCE: 31

Pro Ser Ser Gly Lys Pro Pro Pro Ser
1               5

<210> SEQ ID NO 32
<211> LENGTH: 9
<212> TYPE: PRT
<213> ORGANISM: Artificial Sequence
<220> FEATURE:
<223> OTHER INFORMATION: chemically synthesized

<400> SEQUENCE: 32

Pro Ser Ser Gly Lys Pro Pro Pro Ser
1               5

<210> SEQ ID NO 33
<211> LENGTH: 9
<212> TYPE: PRT
<213> ORGANISM: Artificial Sequence
<220> FEATURE:
<223> OTHER INFORMATION: chemically synthesized

<400> SEQUENCE: 33

Pro Ser Ser Gly Ser Pro Pro Pro Ser
1               5

<210> SEQ ID NO 34
<211> LENGTH: 9
<212> TYPE: PRT
<213> ORGANISM: Artificial Sequence
<220> FEATURE:
<223> OTHER INFORMATION: chemically synthesized

<400> SEQUENCE: 34

Pro Ser Ser Lys Ala Pro Pro Pro Ser
1               5

<210> SEQ ID NO 35
<211> LENGTH: 9
<212> TYPE: PRT
<213> ORGANISM: Artificial Sequence
<220> FEATURE:
<223> OTHER INFORMATION: chemically synthesized

<400> SEQUENCE: 35

Pro Ser Ser Lys Glu Pro Pro Pro Ser
1               5

<210> SEQ ID NO 36
<211> LENGTH: 10
<212> TYPE: PRT
<213> ORGANISM: Artificial Sequence
<220> FEATURE:
<223> OTHER INFORMATION: chemically synthesized

<400> SEQUENCE: 36
```

```
Pro Ser Ser Lys Gly Ala Pro Pro Pro Ser
1               5                   10
```

<210> SEQ ID NO 37
<211> LENGTH: 9
<212> TYPE: PRT
<213> ORGANISM: Artificial Sequence
<220> FEATURE:
<223> OTHER INFORMATION: chemically synthesized

<400> SEQUENCE: 37

```
Pro Ser Ser Lys Gln Pro Pro Pro Ser
1               5
```

<210> SEQ ID NO 38
<211> LENGTH: 9
<212> TYPE: PRT
<213> ORGANISM: Artificial Sequence
<220> FEATURE:
<223> OTHER INFORMATION: chemically synthesized

<400> SEQUENCE: 38

```
Pro Ser Ser Lys Ser Pro Pro Pro Ser
1               5
```

<210> SEQ ID NO 39
<211> LENGTH: 7
<212> TYPE: PRT
<213> ORGANISM: Artificial Sequence
<220> FEATURE:
<223> OTHER INFORMATION: chemically synthesized

<400> SEQUENCE: 39

```
Ser Gly Ala Pro Pro Pro Ser
1               5
```

<210> SEQ ID NO 40
<211> LENGTH: 8
<212> TYPE: PRT
<213> ORGANISM: Artificial Sequence
<220> FEATURE:
<223> OTHER INFORMATION: chemically synthesized

<400> SEQUENCE: 40

```
Ser Ser Gly Ala Pro Pro Pro Ser
1               5
```

<210> SEQ ID NO 41
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 41

```
Tyr Ser His Gly Thr Phe Thr Ser Asp Tyr Ser Lys Tyr Leu Asp Xaa
1               5                   10                  15

Lys Tyr Ala Gln Glu Phe Val Xaa Trp Leu Glu Asp Glu Pro Ser Ser
            20                  25                  30
```

```
Gly Ala Pro Pro Pro Ser
        35

<210> SEQ ID NO 42
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 42

Tyr Ser His Gly Thr Phe Thr Ser Asp Tyr Ser Lys Tyr Leu Asp Xaa
1               5                   10                  15

Lys Ser Ala Gln Glu Phe Val Xaa Trp Leu Glu Asp Glu Pro Ser Ser
            20                  25                  30

Gly Ala Pro Pro Pro Ser
        35

<210> SEQ ID NO 43
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (38)..(38)
<223> OTHER INFORMATION: AMIDATION

<400> SEQUENCE: 43

Tyr Ser Gln Gly Thr Phe Thr Ser Asp Tyr Ser Lys Tyr Leu Asp Ala
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 44
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib

<400> SEQUENCE: 44

Tyr Ser His Gly Thr Phe Thr Ser Asp Tyr Ser Lys Tyr Leu Asp Xaa
1               5                   10                  15

Lys Arg Ala Gln Glu Phe Val Ile Trp Leu Glu Asp Glu Pro Ser Ser
            20                  25                  30

Gly Ala Pro Pro Pro Ser
        35

<210> SEQ ID NO 45
<211> LENGTH: 38
```

```
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (38)..(38)
<223> OTHER INFORMATION: AMIDATION

<400> SEQUENCE: 45

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 46
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 46

Trp Ser Gln Gly Thr Phe Thr Ser Asp Tyr Ser Lys Tyr Leu Asp Xaa
1               5                   10                  15

Lys Arg Ala Gln Glu Phe Val Xaa Trp Leu Asp Glu Pro Ser Ser
            20                  25                  30

Gly Ala Pro Pro Pro Ser
        35

<210> SEQ ID NO 47
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 47

Tyr Ser His Gly Thr Phe Thr Ser Asp Tyr Ser Lys Tyr Leu Asp Xaa
1               5                   10                  15

Ala Arg Ala Gln Glu Phe Val Xaa Trp Leu Glu Asp Glu Pro Ser Ser
            20                  25                  30

Gly Ala Pro Pro Pro Ser
        35

<210> SEQ ID NO 48
<211> LENGTH: 38
<212> TYPE: PRT
<213> ORGANISM: Artificial Sequence
```

```
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (38)..(38)
<223> OTHER INFORMATION: AMIDATION

<400> SEQUENCE: 48

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 49
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 49

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Glu Glu Pro Ser Ser
            20                  25                  30

Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 50

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Glu Pro Ser
            20                  25                  30

Ser Gly Ala Pro Pro Pro Ser
        35
```

-continued

```
<210> SEQ ID NO 51
<211> LENGTH: 40
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 51

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Glu Glu Pro
            20                  25                  30

Ser Ser Gly Ala Pro Pro Pro Ser
        35                  40

<210> SEQ ID NO 52
<211> LENGTH: 35
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 52

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Gly Ala Pro
            20                  25                  30

Pro Pro Ser
        35

<210> SEQ ID NO 53
<211> LENGTH: 36
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 53

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Ser Gly Ala
            20                  25                  30
```

```
Pro Pro Pro Ser
        35

<210> SEQ ID NO 54
<211> LENGTH: 37
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 54

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Ser Ser Gly
            20                  25                  30

Ala Pro Pro Pro Ser
        35

<210> SEQ ID NO 55
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 55

Tyr Ser His Gly Thr Phe Thr Ser Asp Tyr Ser Lys Tyr Leu Asp Xaa
1               5                   10                  15

Ser Arg Ala Gln Glu Phe Val Xaa Trp Leu Glu Asp Glu Pro Ser Ser
            20                  25                  30

Gly Ala Pro Pro Pro Ser
        35

<210> SEQ ID NO 56
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 56

Tyr Ser His Gly Thr Phe Thr Ser Asp Tyr Ser Lys Tyr Leu Asp Xaa
1               5                   10                  15

Thr Arg Ala Gln Glu Phe Val Xaa Trp Leu Glu Asp Glu Pro Ser Ser
```

```
            20                  25                  30

Gly Ala Pro Pro Ser
        35

<210> SEQ ID NO 57
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 57

Tyr Ser His Gly Thr Phe Thr Ser Asp Tyr Ser Lys Tyr Leu Asp Xaa
1               5                   10                  15

Glu Arg Ala Gln Glu Phe Val Xaa Trp Leu Glu Asp Glu Pro Ser Ser
            20                  25                  30

Gly Ala Pro Pro Ser
        35

<210> SEQ ID NO 58
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 58

Tyr Ser His Gly Thr Phe Thr Ser Asp Tyr Ser Lys Trp Leu Asp Xaa
1               5                   10                  15

Ala Arg Ala Gln Glu Phe Val Xaa Trp Leu Glu Asp Glu Pro Ser Ser
            20                  25                  30

Gly Ala Pro Pro Ser
        35

<210> SEQ ID NO 59
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 59

Tyr Ser His Gly Thr Phe Thr Ser Asp Tyr Ser Lys Trp Leu Asp Xaa
1               5                   10                  15
```

Ser Arg Ala Gln Glu Phe Val Xaa Trp Leu Glu Asp Glu Pro Ser Ser
            20                  25                  30

Gly Ala Pro Pro Pro Ser
            35

<210> SEQ ID NO 60
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 60

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Lys Pro Pro Pro Ser
            35

<210> SEQ ID NO 61
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 61

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Glu Pro Pro Pro Ser
            35

<210> SEQ ID NO 62
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 62

```
Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ser Pro Pro Pro Ser
        35

<210> SEQ ID NO 63
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 63

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Lys Ala Pro Pro Pro Ser
        35

<210> SEQ ID NO 64
<211> LENGTH: 39
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 64

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Lys Gly Ala Pro Pro Pro Ser
        35

<210> SEQ ID NO 65
<211> LENGTH: 39
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
```

```
<400> SEQUENCE: 65

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser Ser
            35

<210> SEQ ID NO 66
<211> LENGTH: 39
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 66

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser Glu
            35

<210> SEQ ID NO 67
<211> LENGTH: 40
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 67

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Gly Gly Pro
            20                  25                  30

Ser Ser Gly Ala Pro Pro Pro Ser
            35                  40

<210> SEQ ID NO 68
<211> LENGTH: 39
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
```

```
<223> OTHER INFORMATION: Aib

<400> SEQUENCE: 68

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Gly Pro Ser
            20                  25                  30

Ser Gly Ala Pro Pro Pro Ser
        35

<210> SEQ ID NO 69
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 69

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Lys Ser
            20                  25                  30

Gly Ala Pro Pro Pro Ser
        35

<210> SEQ ID NO 70
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 70

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Lys
            20                  25                  30

Gly Ala Pro Pro Pro Ser
        35

<210> SEQ ID NO 71
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
```

<221> NAME/KEY: MOD_RES
<222> LOCATION: (24)..(24)
<223> OTHER INFORMATION: Aib

<400> SEQUENCE: 71

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Glu Ser
            20                  25                  30

Gly Ala Pro Pro Pro Ser
        35

<210> SEQ ID NO 72
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 72

Tyr Thr His Gly Thr Phe Thr Ser Asp Tyr Ser Lys Trp Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 73
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 73

Tyr Ser His Gly Thr Phe Thr Ser Asp His Ser Lys Trp Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 74
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)

```
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 74

Tyr Thr His Gly Thr Phe Thr Ser Asp His Ser Lys Trp Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 75
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 75

Tyr Thr His Gly Thr Phe Thr Ser Asp Tyr Ser Lys Trp Leu Asp Xaa
1               5                   10                  15

Ala Arg Ala Gln Glu Phe Val Xaa Trp Leu Glu Asp Glu Pro Ser Ser
            20                  25                  30

Gly Ala Pro Pro Pro Ser
        35

<210> SEQ ID NO 76
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 76

Tyr Ser His Gly Thr Phe Thr Ser Asp His Ser Lys Trp Leu Asp Xaa
1               5                   10                  15

Ala Arg Ala Gln Glu Phe Val Xaa Trp Leu Glu Asp Glu Pro Ser Ser
            20                  25                  30

Gly Ala Pro Pro Pro Ser
        35

<210> SEQ ID NO 77
<211> LENGTH: 38
<212> TYPE: PRT
<213> ORGANISM: Artificial Sequence
<220> FEATURE:
<223> OTHER INFORMATION: chemically synthesized
```

```
<400> SEQUENCE: 77

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
            35

<210> SEQ ID NO 78
<211> LENGTH: 38
<212> TYPE: PRT
<213> ORGANISM: Artificial Sequence
<220> FEATURE:
<223> OTHER INFORMATION: chemically synthesized

<400> SEQUENCE: 78

Tyr Ser His Gly Thr Phe Thr Ser Asp Tyr Ser Lys Trp Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
            35

<210> SEQ ID NO 79
<211> LENGTH: 38
<212> TYPE: PRT
<213> ORGANISM: Artificial Sequence
<220> FEATURE:
<223> OTHER INFORMATION: chemically synthesized

<400> SEQUENCE: 79

Tyr Thr His Gly Thr Phe Thr Ser Asp Tyr Ser Lys Trp Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
            35

<210> SEQ ID NO 80
<211> LENGTH: 38
<212> TYPE: PRT
<213> ORGANISM: Artificial Sequence
<220> FEATURE:
<223> OTHER INFORMATION: chemically synthesized

<400> SEQUENCE: 80

Tyr Ser His Gly Thr Phe Thr Ser Asp His Ser Lys Trp Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
            35

<210> SEQ ID NO 81
<211> LENGTH: 38
<212> TYPE: PRT
<213> ORGANISM: Artificial Sequence
<220> FEATURE:
<223> OTHER INFORMATION: chemically synthesized

<400> SEQUENCE: 81

Tyr Thr His Gly Thr Phe Thr Ser Asp His Ser Lys Trp Leu Asp Glu
```

```
                1               5                   10                  15
Ala Arg Ala Gln Glu Phe Val Lys Trp Leu Glu Asp Glu Pro Ser Ser
                20                  25                  30

Gly Ala Pro Pro Pro Ser
        35

<210> SEQ ID NO 82
<211> LENGTH: 38
<212> TYPE: PRT
<213> ORGANISM: Artificial Sequence
<220> FEATURE:
<223> OTHER INFORMATION: chemically synthesized

<400> SEQUENCE: 82

Tyr Thr His Gly Thr Phe Thr Ser Asp Tyr Ser Lys Trp Leu Asp Ser
1               5                   10                  15

Lys Arg Ala Gln Glu Phe Val Lys Trp Leu Glu Asp Glu Pro Ser Ser
                20                  25                  30

Gly Ala Pro Pro Pro Ser
        35

<210> SEQ ID NO 83
<211> LENGTH: 38
<212> TYPE: PRT
<213> ORGANISM: Artificial Sequence
<220> FEATURE:
<223> OTHER INFORMATION: chemically synthesized

<400> SEQUENCE: 83

Tyr Ser His Gly Thr Phe Thr Ser Asp Tyr Ser Lys Tyr Leu Asp Lys
1               5                   10                  15

Ala Arg Ala Gln Glu Phe Val Lys Trp Leu Glu Asp Glu Pro Ser Ser
                20                  25                  30

Gly Ala Pro Pro Pro Ser
        35

<210> SEQ ID NO 84
<211> LENGTH: 38
<212> TYPE: PRT
<213> ORGANISM: Artificial Sequence
<220> FEATURE:
<223> OTHER INFORMATION: chemically synthesized

<400> SEQUENCE: 84

Tyr Ser His Gly Thr Phe Thr Ser Asp Tyr Ser Lys Tyr Leu Asp Gln
1               5                   10                  15

Ala Arg Ala Gln Glu Phe Val Lys Trp Leu Glu Asp Glu Pro Ser Ser
                20                  25                  30

Gly Ala Pro Pro Pro Ser
        35

<210> SEQ ID NO 85
<211> LENGTH: 37
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
```

<223> OTHER INFORMATION: Aib

<400> SEQUENCE: 85

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Lys Arg Asn
            20                  25                  30

Lys Pro Pro Ala
        35

<210> SEQ ID NO 86
<211> LENGTH: 37
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 86

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Lys Arg Asn
            20                  25                  30

Lys Pro Pro Ile Ala
        35

<210> SEQ ID NO 87
<211> LENGTH: 37
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 87

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Lys Arg Asn
            20                  25                  30

Lys Asn Pro Pro Ser
        35

<210> SEQ ID NO 88
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:

```
<221> NAME/KEY: MOD_RES
<222> LOCATION: (24)..(24)
<223> OTHER INFORMATION: Aib

<400> SEQUENCE: 88

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Lys Arg Asn
            20                  25                  30

Lys Asn Pro Pro Pro Ser
        35

<210> SEQ ID NO 89
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 89

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Arg Asn
            20                  25                  30

Lys Asn Asn Pro Pro Ser
        35

<210> SEQ ID NO 90
<211> LENGTH: 37
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 90

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Lys Arg Asn
            20                  25                  30

Lys Pro Pro Pro Ser
        35

<210> SEQ ID NO 91
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (24)..(24)
```

<223> OTHER INFORMATION: Aib

<400> SEQUENCE: 91

Tyr Ser His Gly Thr Phe Thr Ser Asp Tyr Ser Lys Tyr Leu Asp Leu
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 92
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (24)..(24)
<223> OTHER INFORMATION: Aib

<400> SEQUENCE: 92

Tyr Ser His Gly Thr Phe Thr Ser Asp Tyr Ser Lys Tyr Leu Asp Ile
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 93
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib

<400> SEQUENCE: 93

Tyr Ser His Gly Thr Phe Thr Ser Asp Tyr Ser Lys Tyr Leu Asp Xaa
1               5                   10                  15

Lys Arg Ala Gln Glu Phe Val Leu Trp Leu Glu Asp Glu Pro Ser Ser
            20                  25                  30

Gly Ala Pro Pro Pro Ser
        35

<210> SEQ ID NO 94
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 94

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Lys Glu Pro Pro Pro Ser
        35

<210> SEQ ID NO 95
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 95

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Lys Ser Pro Pro Pro Ser
        35

<210> SEQ ID NO 96
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 96

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Lys Ser
            20                  25                  30

Lys Ala Pro Pro Pro Ser
        35

<210> SEQ ID NO 97
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 97

```
Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Lys Ser
            20                  25                  30

Lys Gln Pro Pro Pro Ser
        35
```

<210> SEQ ID NO 98
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 98

```
Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Lys Ser
            20                  25                  30

Lys Ser Pro Pro Pro Ser
        35
```

<210> SEQ ID NO 99
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 99

```
Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Lys Gln Pro Pro Pro Ser
        35
```

<210> SEQ ID NO 100
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib -continued

```
<400> SEQUENCE: 100

Tyr Thr His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Lys Pro Pro Pro Ser
        35

<210> SEQ ID NO 101
<211> LENGTH: 38
<212> TYPE: PRT
<213> ORGANISM: Artificial Sequence
<220> FEATURE:
<223> OTHER INFORMATION: chemically synthesized

<400> SEQUENCE: 101

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Lys Pro Pro Pro Ser
        35

<210> SEQ ID NO 102
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 102

Tyr Thr His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 103
<211> LENGTH: 38
<212> TYPE: PRT
<213> ORGANISM: Artificial Sequence
<220> FEATURE:
<223> OTHER INFORMATION: chemically synthesized

<400> SEQUENCE: 103

Tyr Thr His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 104
<211> LENGTH: 38
```

```
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 104

Tyr Thr His Gly Thr Phe Thr Ser Asp Tyr Ser Lys Tyr Leu Asp Xaa
1               5                   10                  15

Ala Arg Ala Gln Glu Phe Val Xaa Trp Leu Glu Asp Glu Pro Ser Ser
            20                  25                  30

Gly Ala Pro Pro Pro Ser
        35

<210> SEQ ID NO 105
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (38)..(38)
<223> OTHER INFORMATION: AMIDATION

<400> SEQUENCE: 105

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Lys Ser
            20                  25                  30

Lys Glu Pro Pro Pro Ser
        35

<210> SEQ ID NO 106
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (38)..(38)
<223> OTHER INFORMATION: AMIDATION

<400> SEQUENCE: 106

Tyr Ser His Gly Thr Phe Thr Ser Asp Tyr Ser Lys Tyr Leu Asp Xaa
1               5                   10                  15
```

-continued

```
Lys Arg Ala Gln Glu Phe Val Xaa Trp Leu Glu Asp Glu Pro Lys Ser
            20                  25                  30

Lys Ser Pro Pro Pro Ser
        35

<210> SEQ ID NO 107
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (38)..(38)
<223> OTHER INFORMATION: AMIDATION

<400> SEQUENCE: 107

Tyr Ser His Gly Thr Phe Thr Ser Asp Tyr Ser Lys Tyr Leu Asp Xaa
1               5                   10                  15

Ala Arg Ala Gln Glu Phe Val Xaa Trp Leu Glu Asp Glu Pro Lys Ser
            20                  25                  30

Lys Ser Pro Pro Pro Ser
        35

<210> SEQ ID NO 108
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (38)..(38)
<223> OTHER INFORMATION: AMIDATION

<400> SEQUENCE: 108

Tyr Ser His Gly Thr Phe Thr Ser Asp Tyr Ser Lys Tyr Leu Asp Xaa
1               5                   10                  15

Ala Arg Ala Gln Glu Phe Val Xaa Trp Leu Glu Asp Glu Pro Lys Ser
            20                  25                  30

Lys Glu Pro Pro Pro Ser
        35

<210> SEQ ID NO 109
<211> LENGTH: 38
<212> TYPE: PRT
<213> ORGANISM: Artificial Sequence
<220> FEATURE:
<223> OTHER INFORMATION: chemically synthesized

<400> SEQUENCE: 109
```

-continued

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
                20                  25                  30

Lys Glu Pro Pro Pro Ser
        35

<210> SEQ ID NO 110
<211> LENGTH: 38
<212> TYPE: PRT
<213> ORGANISM: Artificial Sequence
<220> FEATURE:
<223> OTHER INFORMATION: chemically synthesized

<400> SEQUENCE: 110

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
                20                  25                  30

Lys Ser Pro Pro Pro Ser
        35

<210> SEQ ID NO 111
<211> LENGTH: 38
<212> TYPE: PRT
<213> ORGANISM: Artificial Sequence
<220> FEATURE:
<223> OTHER INFORMATION: chemically synthesized

<400> SEQUENCE: 111

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
                20                  25                  30

Lys Ala Pro Pro Pro Ser
        35

<210> SEQ ID NO 112
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (38)..(38)
<223> OTHER INFORMATION: AMIDATION

<400> SEQUENCE: 112

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
                20                  25                  30

Lys Glu Pro Pro Pro Ser
        35

<210> SEQ ID NO 113
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES

```
<222> LOCATION: (38)..(38)
<223> OTHER INFORMATION: AMIDATION

<400> SEQUENCE: 113

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 114
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (38)..(38)
<223> OTHER INFORMATION: AMIDATION

<400> SEQUENCE: 114

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
            20                  25                  30

Lys Ala Pro Pro Pro Ser
        35

<210> SEQ ID NO 115
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 115

Trp Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 116
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
```

-continued

<400> SEQUENCE: 116

Tyr Ser His Gly Thr Phe Thr Ser Asp Tyr Ser Lys Tyr Leu Asp Xaa
1               5                   10                  15

Lys Ala Ala Gln Glu Phe Val Xaa Trp Leu Glu Asp Glu Pro Ser Ser
            20                  25                  30

Gly Ala Pro Pro Pro Ser
        35

<210> SEQ ID NO 117
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 117

Tyr Ser His Gly Thr Phe Thr Ser Asp Tyr Ser Lys Tyr Leu Asp Xaa
1               5                   10                  15

Lys Thr Ala Gln Glu Phe Val Xaa Trp Leu Glu Asp Glu Pro Ser Ser
            20                  25                  30

Gly Ala Pro Pro Pro Ser
        35

<210> SEQ ID NO 118
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 118

Tyr Ser His Gly Thr Phe Thr Ser Asp Tyr Ser Lys Tyr Leu Asp Xaa
1               5                   10                  15

Lys Leu Ala Gln Glu Phe Val Xaa Trp Leu Glu Asp Glu Pro Ser Ser
            20                  25                  30

Gly Ala Pro Pro Pro Ser
        35

<210> SEQ ID NO 119
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES

```
<222> LOCATION: (24)..(24)
<223> OTHER INFORMATION: Aib

<400> SEQUENCE: 119

Tyr Ser His Gly Thr Phe Thr Ser Asp Tyr Ser Lys Tyr Leu Asp Xaa
1               5                   10                  15

Lys Glu Ala Gln Glu Phe Val Xaa Trp Leu Glu Asp Glu Pro Ser Ser
            20                  25                  30

Gly Ala Pro Pro Pro Ser
        35

<210> SEQ ID NO 120
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (38)..(38)
<223> OTHER INFORMATION: AMIDATION

<400> SEQUENCE: 120

Tyr Ser His Gly Thr Phe Thr Ser Asp Tyr Ser Lys Tyr Leu Asp Ala
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 121
<211> LENGTH: 38
<212> TYPE: PRT
<213> ORGANISM: Artificial Sequence
<220> FEATURE:
<223> OTHER INFORMATION: chemically synthesized

<400> SEQUENCE: 121

Tyr Ser Gln Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 122
<211> LENGTH: 38
<212> TYPE: PRT
<213> ORGANISM: Artificial Sequence
<220> FEATURE:
<223> OTHER INFORMATION: chemically synthesized

<400> SEQUENCE: 122

Tyr Ser Gln Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Lys Ser
            20                  25                  30

Lys Ala Pro Pro Pro Ser
        35

<210> SEQ ID NO 123
<211> LENGTH: 38
<212> TYPE: PRT
```

<213> ORGANISM: Artificial Sequence
<220> FEATURE:
<223> OTHER INFORMATION: chemically synthesized

<400> SEQUENCE: 123

Tyr Ser His Gly Thr Phe Thr Ser Asp Tyr Ser Lys Tyr Leu Asp Ser
1               5                   10                  15

Ala Arg Ala Gln Glu Phe Thr Lys Trp Leu Glu Asp Glu Pro Lys Ser
            20                  25                  30

Lys Ser Pro Pro Pro Ser
        35

<210> SEQ ID NO 124
<211> LENGTH: 38
<212> TYPE: PRT
<213> ORGANISM: Artificial Sequence
<220> FEATURE:
<223> OTHER INFORMATION: chemically synthesized

<400> SEQUENCE: 124

Tyr Ser His Gly Thr Phe Thr Ser Asp Tyr Ser Lys Tyr Leu Asp Ser
1               5                   10                  15

Ala Arg Ala Gln Glu Phe Val Lys His Leu Glu Asp Glu Pro Lys Ser
            20                  25                  30

Lys Ser Pro Pro Pro Ser
        35

<210> SEQ ID NO 125
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (38)..(38)
<223> OTHER INFORMATION: AMIDATION

<400> SEQUENCE: 125

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Lys Pro Pro Pro Ser
        35

<210> SEQ ID NO 126
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)

<223> OTHER INFORMATION: Aib

<400> SEQUENCE: 126

Tyr Ser Gln Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Lys Pro Pro Pro Ser
        35

<210> SEQ ID NO 127
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 127

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Lys Ser Ser
            20                  25                  30

Gly Lys Pro Pro Pro Ser
        35

<210> SEQ ID NO 128
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 128

Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Lys Lys Pro Pro Ser
        35

<210> SEQ ID NO 129
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:

```
<221> NAME/KEY: MOD_RES
<222> LOCATION: (24)..(24)
<223> OTHER INFORMATION: Aib

<400> SEQUENCE: 129

Tyr Ser His Gly Thr Phe Thr Ser Asp Tyr Ser Lys Tyr Leu Asp Xaa
1               5                   10                  15

Lys Arg Ala Gln Glu Phe Val Xaa His Leu Glu Asp Glu Pro Ser Ser
            20                  25                  30

Gly Lys Pro Pro Pro Ser
        35

<210> SEQ ID NO 130
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 130

Tyr Ser His Gly Thr Phe Thr Ser Asp Tyr Ser Lys Tyr Leu Asp Xaa
1               5                   10                  15

Lys Ala Ala Gln Glu Phe Val Xaa Trp Leu Glu Asp Glu Pro Ser Ser
            20                  25                  30

Gly Lys Pro Pro Pro Ser
        35

<210> SEQ ID NO 131
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 131

Trp Ser Gln Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Lys Pro Pro Pro Ser
        35

<210> SEQ ID NO 132
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
```

<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 132

Trp Ser Gln Gly Thr Phe Thr Ser Asp Tyr Ser Lys Tyr Leu Asp Xaa
1               5                   10                  15

Lys Ala Ala Gln Glu Phe Val Xaa Trp Leu Glu Asp Glu Pro Ser Ser
            20                  25                  30

Gly Ala Pro Pro Pro Ser
        35

<210> SEQ ID NO 133
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 133

Trp Ser Gln Gly Thr Phe Thr Ser Asp Tyr Ser Lys Tyr Leu Asp Xaa
1               5                   10                  15

Lys Ala Ala Gln Glu Phe Val Xaa Trp Leu Glu Asp Glu Pro Ser Ser
            20                  25                  30

Gly Lys Pro Pro Pro Ser
        35

<210> SEQ ID NO 134
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 134

Tyr Ser Gln Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 135
<211> LENGTH: 38
<212> TYPE: PRT
<213> ORGANISM: Artificial Sequence
<220> FEATURE:
<223> OTHER INFORMATION: chemically synthesized
<220> FEATURE:

```
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 135

Tyr Ser Gln Gly Thr Phe Thr Ser Asp Tyr Ser Lys Tyr Leu Asp Xaa
1               5                   10                  15

Lys Ala Ala Gln Glu Phe Val Xaa Trp Leu Glu Asp Glu Pro Ser Ser
            20                  25                  30

Gly Ala Pro Pro Pro Ser
        35

<210> SEQ ID NO 136
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 136

Tyr Ser Gln Gly Thr Phe Thr Ser Asp Tyr Ser Lys Tyr Leu Asp Xaa
1               5                   10                  15

Lys Ala Ala Gln Glu Phe Val Xaa Trp Leu Glu Asp Glu Pro Ser Ser
            20                  25                  30

Gly Lys Pro Pro Pro Ser
        35

<210> SEQ ID NO 137
<211> LENGTH: 29
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (17)..(17)
<223> OTHER INFORMATION: K at position 17 is in a lactam bridge with E
      at position 21
<220> FEATURE:
<221> NAME/KEY: MOD_RES
<222> LOCATION: (21)..(21)
<223> OTHER INFORMATION: E at position 21 is in a lactam bridge with K
      at position 17
<220> FEATURE:
<221> NAME/KEY: MOD_RES
<222> LOCATION: (24)..(24)
<223> OTHER INFORMATION: Xaa is K or K at position 17 is in a lactam
      bridge with E at position 28
<220> FEATURE:
<221> NAME/KEY: MOD_RES
<222> LOCATION: (27)..(27)
<223> OTHER INFORMATION: Xaa is Q or D
<220> FEATURE:
<221> NAME/KEY: MOD_RES
<222> LOCATION: (28)..(28)
<223> OTHER INFORMATION: Xaa is E or E at position 28 is in a lactam
      bridge with K at position 24

<400> SEQUENCE: 137
```

```
Tyr Ser Gln Gly Thr Phe Thr Ser Asp Tyr Ser Lys Tyr Leu Asp Ser
1               5                   10                  15

Lys Arg Ala Gln Glu Phe Val Xaa Trp Leu Xaa Xaa Thr
            20                  25
```

<210> SEQ ID NO 138
<211> LENGTH: 29
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (17)..(17)
<223> OTHER INFORMATION: K at position 17 is in a lactam bridge with E
      at position 21
<220> FEATURE:
<221> NAME/KEY: MOD_RES
<222> LOCATION: (21)..(21)
<223> OTHER INFORMATION: E at position 21 is in a lactam bridge with K
      at position 17
<220> FEATURE:
<221> NAME/KEY: MOD_RES
<222> LOCATION: (24)..(24)
<223> OTHER INFORMATION: K at position 24 is in a lactam bridge with E
      at position 28
<220> FEATURE:
<221> NAME/KEY: MOD_RES
<222> LOCATION: (28)..(28)
<223> OTHER INFORMATION: E at position 28 is in a lactam bridge with K
      at position 24

<400> SEQUENCE: 138

```
Tyr Ser Gln Gly Thr Phe Thr Ser Asp Tyr Ser Lys Tyr Leu Asp Ser
1               5                   10                  15

Lys Arg Ala Gln Glu Phe Val Lys Trp Leu Asp Glu Thr
            20                  25
```

<210> SEQ ID NO 139
<211> LENGTH: 29
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (17)..(17)
<223> OTHER INFORMATION: K at position 17 is in a lactam bridge with E
      at position 21
<220> FEATURE:
<221> NAME/KEY: MOD_RES
<222> LOCATION: (21)..(21)
<223> OTHER INFORMATION: E at position 21 is in a lactam bridge with K
      at position 17
<220> FEATURE:
<221> NAME/KEY: MOD_RES
<222> LOCATION: (24)..(24)
<223> OTHER INFORMATION: K at position 24 is in a lactam bridge with E
      at position 28
<220> FEATURE:
<221> NAME/KEY: MOD_RES
<222> LOCATION: (28)..(28)
<223> OTHER INFORMATION: E at position 28 is in a lactam bridge with K
      at position 24

<400> SEQUENCE: 139

```
Tyr Ser Gln Gly Thr Phe Thr Ser Asp Tyr Ser Lys Tyr Leu Asp Ser
1               5                   10                  15

Lys Arg Ala Gln Glu Phe Val Lys Trp Leu Gln Glu Thr
            20                  25
```

-continued

<210> SEQ ID NO 140
<211> LENGTH: 29
<212> TYPE: PRT
<213> ORGANISM: Homo sapiens

<400> SEQUENCE: 140

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 141
<211> LENGTH: 29
<212> TYPE: PRT
<213> ORGANISM: Homo sapiens

<400> SEQUENCE: 141

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 142
<211> LENGTH: 39
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (39)..(39)
<223> OTHER INFORMATION: AMIDATION

<400> SEQUENCE: 142

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 143
<211> LENGTH: 38
<212> TYPE: PRT
<213> ORGANISM: Artificial Sequence
<220> FEATURE:
<223> OTHER INFORMATION: chemically synthesized

<400> SEQUENCE: 143

Tyr Ser His Gly Thr Phe Thr Ser Asp Tyr Ser Lys Tyr Leu Asp Ala
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 144
<211> LENGTH: 38
<212> TYPE: PRT
<213> ORGANISM: Artificial Sequence
<220> FEATURE:
<223> OTHER INFORMATION: chemically synthesized

<400> SEQUENCE: 144

```
Tyr Ser His Gly Thr Phe Thr Ser Asp Tyr Thr Arg Leu Leu Glu Ser
1               5                   10                  15

Lys Arg Ala Gln Glu Phe Val Lys Trp Leu Glu Asp Glu Pro Ser Ser
            20                  25                  30

Gly Ala Pro Pro Pro Ser
        35
```

<210> SEQ ID NO 145
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 145

```
Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35
```

<210> SEQ ID NO 146
<211> LENGTH: 29
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 146

```
Tyr Ser His Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu
            20                  25
```

<210> SEQ ID NO 147
<211> LENGTH: 29
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib

<400> SEQUENCE: 147

```
Tyr Gly His Gly Thr Phe Thr Ser Asp His Ser Lys Tyr Leu Asp Xaa
1               5                   10                  15

Lys Arg Ala Gln Glu Phe Val Lys Trp Leu Glu Asp Glu
```

```
                    20                  25

<210> SEQ ID NO 148
<211> LENGTH: 29
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib

<400> SEQUENCE: 148

Tyr Ser His Gly Thr Phe Thr Ser Asp Tyr Ser Lys Trp Leu Asp Xaa
1               5                   10                  15

Lys Arg Ala Gln Glu Phe Val Lys Trp Leu Glu Asp Glu
            20                  25

<210> SEQ ID NO 149
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 149

Tyr Ser His Gly Thr Phe Thr Ser Asp Tyr Ser Lys Tyr Leu Asp Xaa
1               5                   10                  15

Ala Arg Ala Gln Glu Phe Val Xaa Trp Leu Glu Asp Glu Pro Ser Ser
            20                  25                  30

Gly Ala Pro Pro Pro Ser
        35

<210> SEQ ID NO 150
<211> LENGTH: 8
<212> TYPE: PRT
<213> ORGANISM: Artificial Sequence
<220> FEATURE:
<223> OTHER INFORMATION: chemically synthesized

<400> SEQUENCE: 150

Lys Arg Asn Lys Pro Pro Pro Ala
1               5

<210> SEQ ID NO 151
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is Y or W
<220> FEATURE:
<221> NAME/KEY: MISC_FEATURE
<222> LOCATION: (3)..(3)
<223> OTHER INFORMATION: Xaa is H or Q
<220> FEATURE:
<221> NAME/KEY: MISC_FEATURE
```

```
<222> LOCATION: (10)..(10)
<223> OTHER INFORMATION: Xaa is Y, K or K where the epsilon-amino group
      of the lysine sidechain is covalently joined to a lipophilic
      substituent, optionally via a spacer, as defined in the
      specification
<220> FEATURE:
<221> NAME/KEY: MISC_FEATURE
<222> LOCATION: (16)..(16)
<223> OTHER INFORMATION: Xaa is A, S, Aib, K or K where the epsilon-
      amino group of the lysine sidechain is covalently joined to a
      lipophilic substituent, optionally via a spacer, as defined in the
      specification
<220> FEATURE:
<221> NAME/KEY: MISC_FEATURE
<222> LOCATION: (17)..(17)
<223> OTHER INFORMATION: X is A, Aib, K or K where the epsilon-amino
      group of the lysine sidechain is covalently joined to a lipophilic
      substituent, optionally via a spacer, as defined in the
      specification
<220> FEATURE:
<221> NAME/KEY: MISC_FEATURE
<222> LOCATION: (18)..(18)
<223> OTHER INFORMATION: Xaa is Y, S, or R
<220> FEATURE:
<221> NAME/KEY: MISC_FEATURE
<222> LOCATION: (21)..(21)
<223> OTHER INFORMATION: Xaa is E, K, or K where the epsilon-amino group
      of the lysine sidechain is covalently joined to a lipophilic
      substituent, optionally via a spacer, as defined in the
      specification
<220> FEATURE:
<221> NAME/KEY: MISC_FEATURE
<222> LOCATION: (24)..(24)
<223> OTHER INFORMATION: Xaa is I, Aib, K, or K where the epsilon-amino
      group of the lysine sidechain is covalently joined to a lipophilic
      substituent, optionally via a spacer, as defined in the
      specification
<220> FEATURE:
<221> NAME/KEY: MISC_FEATURE
<222> LOCATION: (31)..(31)
<223> OTHER INFORMATION: Xaa is S, K, or K where the epsilon-amino group
      of the lysine sidechain is covalently joined to a lipophilic
      substituent, optionally via a spacer, as defined in the
      specification
<220> FEATURE:
<221> NAME/KEY: MISC_FEATURE
<222> LOCATION: (33)..(33)
<223> OTHER INFORMATION: Xaa is G, K, or K where the epsilon-amino group
      of the lysine sidechain is covalently joined to a lipophilic
      substituent, optionally via a spacer, as defined in the
      specification
<220> FEATURE:
<221> NAME/KEY: MISC_FEATURE
<222> LOCATION: (34)..(34)
<223> OTHER INFORMATION: Xaa is A or S

<400> SEQUENCE: 151

Xaa Ser Xaa Gly Thr Phe Thr Ser Asp Xaa Ser Lys Tyr Leu Asp Xaa
1               5                   10                  15

Xaa Xaa Ala Gln Xaa Phe Val Xaa Trp Leu Glu Asp Glu Pro Xaa Ser
            20                  25                  30

Xaa Xaa Pro Pro Pro Ser
        35

<210> SEQ ID NO 152
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
```

```
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula II to form an amide

<400> SEQUENCE: 152

Tyr Ser His Gly Thr Phe Thr Ser Asp Tyr Ser Lys Tyr Leu Asp Xaa
1               5                   10                  15

Lys Tyr Ala Gln Glu Phe Val Xaa Trp Leu Glu Asp Glu Pro Ser Ser
            20                  25                  30

Lys Ala Pro Pro Pro Ser
        35

<210> SEQ ID NO 153
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula II to form an amide

<400> SEQUENCE: 153

Tyr Ser His Gly Thr Phe Thr Ser Asp Tyr Ser Lys Tyr Leu Asp Xaa
1               5                   10                  15

Lys Tyr Ala Gln Glu Phe Val Lys Trp Leu Glu Asp Glu Pro Ser Ser
            20                  25                  30

Gly Ala Pro Pro Pro Ser
        35

<210> SEQ ID NO 154
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (24)..(24)
<223> OTHER INFORMATION: Aib

<400> SEQUENCE: 154

Tyr Ser His Gly Thr Phe Thr Ser Asp Tyr Ser Lys Tyr Leu Asp Lys
1               5                   10                  15

Lys Tyr Ala Gln Glu Phe Val Xaa Trp Leu Glu Asp Glu Pro Ser Ser
            20                  25                  30

Gly Ala Pro Pro Pro Ser
        35
```

<210> SEQ ID NO 155
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 155

Tyr Ser His Gly Thr Phe Thr Ser Asp Lys Ser Lys Tyr Leu Asp Xaa
1               5                   10                  15

Lys Tyr Ala Gln Glu Phe Val Xaa Trp Leu Glu Asp Glu Pro Ser Ser
            20                  25                  30

Gly Ala Pro Pro Pro Ser
            35

<210> SEQ ID NO 156
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula III to form an amide

<400> SEQUENCE: 156

Tyr Ser His Gly Thr Phe Thr Ser Asp Tyr Ser Lys Tyr Leu Asp Xaa
1               5                   10                  15

Lys Tyr Ala Gln Glu Phe Val Xaa Trp Leu Glu Asp Glu Pro Ser Ser
            20                  25                  30

Lys Ala Pro Pro Pro Ser
            35

<210> SEQ ID NO 157
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES

```
<222> LOCATION: (24)..(24)
<223> OTHER INFORMATION: K where the epsilon-amino group of the lysine
      sidechain is covalently bound to the indicated carbonyl of the
      structure of Formula III to form an amide

<400> SEQUENCE: 157

Tyr Ser His Gly Thr Phe Thr Ser Asp Tyr Ser Lys Tyr Leu Asp Xaa
1               5                   10                  15

Lys Tyr Ala Gln Glu Phe Val Lys Trp Leu Glu Asp Glu Pro Ser Ser
            20                  25                  30

Gly Ala Pro Pro Pro Ser
        35

<210> SEQ ID NO 158
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (24)..(24)
<223> OTHER INFORMATION: Aib

<400> SEQUENCE: 158

Tyr Ser His Gly Thr Phe Thr Ser Asp Tyr Ser Lys Tyr Leu Asp Lys
1               5                   10                  15

Lys Tyr Ala Gln Glu Phe Val Xaa Trp Leu Glu Asp Glu Pro Ser Ser
            20                  25                  30

Gly Ala Pro Pro Pro Ser
        35

<210> SEQ ID NO 159
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 159

Tyr Ser His Gly Thr Phe Thr Ser Asp Lys Ser Lys Tyr Leu Asp Xaa
1               5                   10                  15

Lys Tyr Ala Gln Glu Phe Val Xaa Trp Leu Glu Asp Glu Pro Ser Ser
            20                  25                  30

Gly Ala Pro Pro Pro Ser
        35
```

-continued

```
<210> SEQ ID NO 160
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula II to form an amide

<400> SEQUENCE: 160

Tyr Ser His Gly Thr Phe Thr Ser Asp Tyr Ser Lys Tyr Leu Asp Xaa
1               5                   10                  15

Lys Ser Ala Gln Glu Phe Val Xaa Trp Leu Glu Asp Glu Pro Ser Ser
            20                  25                  30

Lys Ala Pro Pro Pro Ser
        35

<210> SEQ ID NO 161
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula II to form an amide

<400> SEQUENCE: 161

Tyr Ser His Gly Thr Phe Thr Ser Asp Tyr Ser Lys Tyr Leu Asp Xaa
1               5                   10                  15

Lys Ser Ala Gln Glu Phe Val Lys Trp Leu Glu Asp Glu Pro Ser Ser
            20                  25                  30

Gly Ala Pro Pro Pro Ser
        35

<210> SEQ ID NO 162
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (24)..(24)
<223> OTHER INFORMATION: Aib
```

<400> SEQUENCE: 162

Tyr Ser His Gly Thr Phe Thr Ser Asp Tyr Ser Lys Tyr Leu Asp Lys
1               5                   10                  15

Lys Ser Ala Gln Glu Phe Val Xaa Trp Leu Glu Asp Glu Pro Ser Ser
            20                  25                  30

Gly Ala Pro Pro Pro Ser
        35

<210> SEQ ID NO 163
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 163

Tyr Ser His Gly Thr Phe Thr Ser Lys Ser Lys Tyr Leu Asp Xaa
1               5                   10                  15

Lys Ser Ala Gln Glu Phe Val Xaa Trp Leu Glu Asp Glu Pro Ser Ser
            20                  25                  30

Gly Ala Pro Pro Pro Ser
        35

<210> SEQ ID NO 164
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula III to form an amide

<400> SEQUENCE: 164

Tyr Ser His Gly Thr Phe Thr Ser Asp Tyr Ser Lys Tyr Leu Asp Xaa
1               5                   10                  15

Lys Ser Ala Gln Glu Phe Val Xaa Trp Leu Glu Asp Glu Pro Ser Ser
            20                  25                  30

Lys Ala Pro Pro Pro Ser
        35

<210> SEQ ID NO 165

```
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula III to form an amide

<400> SEQUENCE: 165

Tyr Ser His Gly Thr Phe Thr Ser Asp Tyr Ser Lys Tyr Leu Asp Xaa
1               5                   10                  15

Lys Ser Ala Gln Glu Phe Val Lys Trp Leu Glu Asp Glu Pro Ser Ser
            20                  25                  30

Gly Ala Pro Pro Pro Ser
        35

<210> SEQ ID NO 166
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (24)..(24)
<223> OTHER INFORMATION: Aib

<400> SEQUENCE: 166

Tyr Ser His Gly Thr Phe Thr Ser Asp Tyr Ser Lys Tyr Leu Asp Lys
1               5                   10                  15

Lys Ser Ala Gln Glu Phe Val Xaa Trp Leu Glu Asp Glu Pro Ser Ser
            20                  25                  30

Gly Ala Pro Pro Pro Ser
        35

<210> SEQ ID NO 167
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 167
```

Tyr Ser His Gly Thr Phe Thr Ser Asp Lys Ser Lys Tyr Leu Asp Xaa
1               5                   10                  15

Lys Ser Ala Gln Glu Phe Val Xaa Trp Leu Glu Asp Glu Pro Ser Ser
            20                  25                  30

Gly Ala Pro Pro Pro Ser
            35

<210> SEQ ID NO 168
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula II to form an amide

<400> SEQUENCE: 168

Trp Ser Gln Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Lys Ala Pro Pro Pro Ser
            35

<210> SEQ ID NO 169
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula II to form an amide

<400> SEQUENCE: 169

Trp Ser Gln Gly Thr Phe Thr Ser Asp Tyr Ser Lys Tyr Leu Asp Xaa
1               5                   10                  15

Lys Arg Ala Gln Glu Phe Val Lys Trp Leu Glu Asp Glu Pro Ser Ser
            20                  25                  30

Gly Ala Pro Pro Pro Ser
            35

<210> SEQ ID NO 170
<211> LENGTH: 38
<212> TYPE: PRT
<213> ORGANISM: Artificial Sequence
<220> FEATURE:
<223> OTHER INFORMATION: chemically synthesized -continued

```
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (24)..(24)
<223> OTHER INFORMATION: Aib

<400> SEQUENCE: 170

Trp Ser Gln Gly Thr Phe Thr Ser Asp Tyr Ser Lys Tyr Leu Asp Lys
1               5                  10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 171
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 171

Trp Ser Gln Gly Thr Phe Thr Ser Asp Lys Ser Lys Tyr Leu Asp Xaa
1               5                  10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 172
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula III to form an amide

<400> SEQUENCE: 172
```

```
Trp Ser Gln Gly Thr Phe Thr Ser Asp Tyr Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Lys Ala Pro Pro Pro Ser
        35

<210> SEQ ID NO 173
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula III to form an amide

<400> SEQUENCE: 173

Trp Ser Gln Gly Thr Phe Thr Ser Asp Tyr Ser Lys Tyr Leu Asp Xaa
1               5                   10                  15

Lys Arg Ala Gln Glu Phe Val Lys Trp Leu Glu Asp Glu Pro Ser Ser
            20                  25                  30

Gly Ala Pro Pro Pro Ser
        35

<210> SEQ ID NO 174
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (24)..(24)
<223> OTHER INFORMATION: Aib

<400> SEQUENCE: 174

Trp Ser Gln Gly Thr Phe Thr Ser Asp Tyr Ser Lys Tyr Leu Asp Lys
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 175
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
```

```
              structure of Formula III to form an amide
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 175

Trp Ser Gln Gly Thr Phe Thr Ser Asp Lys Ser Lys Tyr Leu Asp Xaa
1               5                   10                  15

Lys Arg Ala Gln Glu Phe Val Xaa Trp Leu Glu Asp Glu Pro Ser Ser
            20                  25                  30

Gly Ala Pro Pro Pro Ser
        35

<210> SEQ ID NO 176
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
              sidechain is covalently bound to the indicated carbonyl of the
              structure of Formula II to form an amide

<400> SEQUENCE: 176

Tyr Ser His Gly Thr Phe Thr Ser Asp Tyr Ser Lys Tyr Leu Asp Xaa
1               5                   10                  15

Lys Arg Ala Gln Glu Phe Val Ile Trp Leu Glu Asp Glu Pro Ser Ser
            20                  25                  30

Lys Ala Pro Pro Pro Ser
        35

<210> SEQ ID NO 177
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
              sidechain is covalently bound to the indicated carbonyl of the
              structure of Formula II to form an amide

<400> SEQUENCE: 177

Tyr Ser His Gly Thr Phe Thr Ser Asp Tyr Ser Lys Tyr Leu Asp Lys
1               5                   10                  15

Lys Arg Ala Gln Glu Phe Val Ile Trp Leu Glu Asp Glu Pro Ser Ser
            20                  25                  30

Gly Ala Pro Pro Pro Ser
        35

<210> SEQ ID NO 178
<211> LENGTH: 38
<212> TYPE: PRT
```

```
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (16)..(16)
<223> OTHER INFORMATION: Aib

<400> SEQUENCE: 178

Tyr Ser His Gly Thr Phe Thr Ser Asp Lys Ser Lys Tyr Leu Asp Xaa
1               5                   10                  15

Lys Arg Ala Gln Glu Phe Val Ile Trp Leu Glu Asp Glu Pro Ser Ser
            20                  25                  30

Gly Ala Pro Pro Pro Ser
        35

<210> SEQ ID NO 179
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (21)..(21)
<223> OTHER INFORMATION: K where the epsilon-amino group of the lysine
      sidechain is covalently bound to the indicated carbonyl of the
      structure of Formula II to form an amide

<400> SEQUENCE: 179

Tyr Ser His Gly Thr Phe Thr Ser Asp Tyr Ser Lys Tyr Leu Asp Xaa
1               5                   10                  15

Lys Arg Ala Gln Lys Phe Val Ile Trp Leu Glu Asp Glu Pro Ser Ser
            20                  25                  30

Gly Ala Pro Pro Pro Ser
        35

<210> SEQ ID NO 180
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula III to form an amide

<400> SEQUENCE: 180

Tyr Ser His Gly Thr Phe Thr Ser Asp Tyr Ser Lys Tyr Leu Asp Xaa
1               5                   10                  15

Lys Arg Ala Gln Glu Phe Val Ile Trp Leu Glu Asp Glu Pro Ser Ser
            20                  25                  30
```

```
Lys Ala Pro Pro Pro Ser
        35

<210> SEQ ID NO 181
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (21)..(21)
<223> OTHER INFORMATION: K where the epsilon-amino group of the lysine
      sidechain is covalently bound to the indicated carbonyl of the
      structure of Formula III to form an amide

<400> SEQUENCE: 181

Tyr Ser His Gly Thr Phe Thr Ser Asp Tyr Ser Lys Tyr Leu Asp Xaa
1               5                   10                  15

Lys Arg Ala Gln Lys Phe Val Ile Trp Leu Glu Asp Glu Pro Ser Ser
            20                  25                  30

Gly Ala Pro Pro Pro Ser
        35

<210> SEQ ID NO 182
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula III to form an amide

<400> SEQUENCE: 182

Tyr Ser His Gly Thr Phe Thr Ser Asp Tyr Ser Lys Tyr Leu Asp Lys
1               5                   10                  15

Lys Arg Ala Gln Glu Phe Val Ile Trp Leu Glu Asp Glu Pro Ser Ser
            20                  25                  30

Gly Ala Pro Pro Pro Ser
        35

<210> SEQ ID NO 183
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (16)..(16)
<223> OTHER INFORMATION: Aib

<400> SEQUENCE: 183

Tyr Ser His Gly Thr Phe Thr Ser Asp Lys Ser Lys Tyr Leu Asp Xaa
```

```
                1               5                  10                 15
Lys Arg Ala Gln Glu Phe Val Ile Trp Leu Glu Asp Glu Pro Ser Ser
                    20                  25                  30

Gly Ala Pro Pro Ser
        35
```

<210> SEQ ID NO 184
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (38)..(38)
<223> OTHER INFORMATION: AMIDATION

<400> SEQUENCE: 184

```
Tyr Ser Gln Gly Thr Phe Thr Ser Asp Tyr Ser Lys Tyr Leu Asp Ala
1               5                   10                  15

Ala Arg Ala Gln Glu Phe Val Lys Trp Leu Glu Asp Glu Pro Lys Ser
                    20                  25                  30

Lys Ser Pro Pro Pro Ser
        35
```

<210> SEQ ID NO 185
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (38)..(38)
<223> OTHER INFORMATION: AMIDATION

<400> SEQUENCE: 185

```
Tyr Ser Gln Gly Thr Phe Thr Ser Asp Tyr Ser Lys Tyr Leu Asp Ala
1               5                   10                  15

Ala Arg Ala Gln Glu Phe Val Lys Trp Leu Glu Asp Glu Pro Lys Ser
                    20                  25                  30

Lys Ser Pro Pro Pro Ser
        35
```

<210> SEQ ID NO 186
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula II to form an amide <220> FEATURE:
<221> NAME/KEY: MOD_RES
<222> LOCATION: (38)..(38)
<223> OTHER INFORMATION: AMIDATION

<400> SEQUENCE: 186

Tyr Ser Gln Gly Thr Phe Thr Ser Asp Tyr Ser Lys Tyr Leu Asp Lys
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 187
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (38)..(38)
<223> OTHER INFORMATION: AMIDATION

<400> SEQUENCE: 187

Tyr Ser Gln Gly Thr Phe Thr Ser Asp Lys Ser Lys Tyr Leu Asp Ala
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 188
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 188

Tyr Ser Gln Gly Thr Phe Thr Ser Asp Tyr Ser Lys Tyr Leu Asp Ala
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 189
<211> LENGTH: 38
<212> TYPE: PRT
<213> ORGANISM: Artificial Sequence

```
<220> FEATURE:
<223> OTHER INFORMATION: chemically synthesized
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 189

Tyr Ser Gln Gly Thr Phe Thr Ser Asp Tyr Ser Lys Tyr Leu Asp Ala
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 190
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 190

Tyr Ser Gln Gly Thr Phe Thr Ser Asp Tyr Ser Lys Tyr Leu Asp Lys
1               5                   10                  15

Ala Arg Ala Gln Glu Phe Val Lys Trp Leu Glu Asp Glu Pro Lys Ser
            20                  25                  30

Lys Ser Pro Pro Pro Ser
        35

<210> SEQ ID NO 191
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 191

Tyr Ser Gln Gly Thr Phe Thr Ser Asp Lys Ser Lys Tyr Leu Asp Ala
1               5                   10                  15

Ala Arg Ala Gln Glu Phe Val Lys Trp Leu Glu Asp Glu Pro Lys Ser
            20                  25                  30
```

Lys Ser Pro Pro Pro Ser
        35

<210> SEQ ID NO 192
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (38)..(38)
<223> OTHER INFORMATION: AMIDATION

<400> SEQUENCE: 192

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Lys Ala Pro Pro Pro Ser
        35

<210> SEQ ID NO 193
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (24)..(24)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (38)..(38)
<223> OTHER INFORMATION: AMIDATION

<400> SEQUENCE: 193

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 194
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (38)..(38)
<223> OTHER INFORMATION: AMIDATION

```
<400> SEQUENCE: 194

Tyr Ser His Gly Thr Phe Thr Ser Asp Tyr Ser Lys Tyr Leu Asp Lys
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 195
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula II to form an amide
<220> FEATURE:
<221> NAME/KEY: MOD_RES
<222> LOCATION: (38)..(38)
<223> OTHER INFORMATION: AMIDATION

<400> SEQUENCE: 195

Tyr Ser His Gly Thr Phe Thr Ser Asp Lys Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 196
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (33)..(33)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 196

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Lys Ala Pro Pro Pro Ser
        35

<210> SEQ ID NO 197
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (24)..(24)
```

```
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 197

Tyr Ser His Gly Thr Phe Thr Ser Asp Tyr Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 198
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (16)..(16)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 198

Tyr Ser His Gly Thr Phe Thr Ser Asp Tyr Ser Lys Tyr Leu Asp Lys
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 199
<211> LENGTH: 38
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: K where the epsilon-amino group of the lysine
      sidechain is covalently bound to the indicated carbonyl of the
      structure of Formula III to form an amide
<220> FEATURE:
<221> NAME/KEY: MOD_RES
<222> LOCATION: (38)..(38)
<223> OTHER INFORMATION: AMIDATION

<400> SEQUENCE: 199

Tyr Ser His Gly Thr Phe Thr Ser Asp Lys Ser Lys Tyr Leu Asp Ser
1               5                   10                  15

Ala Arg Ala Gln Glu Phe Val Lys Trp Leu Glu Asp Glu Pro Ser Ser
            20                  25                  30

Gly Ala Pro Pro Pro Ser
        35

<210> SEQ ID NO 200
```

```
<211> LENGTH: 33
<212> TYPE: PRT
<213> ORGANISM: Artificial Sequence
<220> FEATURE:
<223> OTHER INFORMATION: chemically synthesized

<400> SEQUENCE: 200

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

What is claimed is:

1. An isolated polypeptide comprising the amino acid sequence:

(SEQ ID NO: 151)
$X_1SX_3GTFTSDX_{10}SKYLDX_{16}X_{17}X_{18}AQX_{21}FVX_{24}WLEDEPX_{31}SX_{33}X_{34}PPPS$-OH, or a pharmaceutically acceptable salt thereof, wherein:
$X_1$=Y or W;
$X_3$=H or Q;
$X_{10}$=Y or K;
$X_{16}$=A, S, Aib, or K;
$X_{17}$=A, K, or Aib;
$X_{18}$=S or R;
$X_{21}$=E or K;
$X_{24}$=I, Aib, or K;
$X_{31}$=S or K;
$X_{33}$=G or K; and
$X_{34}$=A or S.

2. The isolated polypeptide of claim 1, or a pharmaceutically acceptable salt thereof, wherein $X_1$=Y.

3. The isolated polypeptide of claim 1, or a pharmaceutically acceptable salt thereof, wherein $X_3$=H.

4. The isolated polypeptide of claim 1, or a pharmaceutically acceptable salt thereof, wherein $X_{10}$=Y.

5. The isolated polypeptide of claim 1, or a pharmaceutically acceptable salt thereof, wherein $X_{16}$=Aib.

6. The isolated polypeptide of claim 1, or a pharmaceutically acceptable salt thereof, wherein $X_{17}$=K.

7. The isolated polypeptide of claim 1, or a pharmaceutically acceptable salt thereof, wherein $X_{18}$=R.

8. The isolated polypeptide of claim 1, or a pharmaceutically acceptable salt thereof, wherein $X_{21}$=E.

9. The isolated polypeptide of claim 1, or a pharmaceutically acceptable salt thereof, wherein $X_{24}$=Aib.

10. The isolated polypeptide of claim 1, or a pharmaceutically acceptable salt thereof, wherein $X_{31}$=S.

11. The isolated polypeptide of claim 1, or a pharmaceutically acceptable salt thereof, wherein $X_{33}$=G.

12. A pharmaceutical composition comprising the isolated polypeptide of claim 1, or a pharmaceutically acceptable salt thereof, and a suitable carrier.

13. A particle formulation comprising the isolated polypeptide of claim 1, or a pharmaceutically acceptable salt thereof, and at least one stabilizing component.

14. A suspension formulation comprising the particle formulation of claim 13 and a suspension vehicle.

15. An osmotic delivery device comprising the isolated polypeptide of claim 1, or a pharmaceutically acceptable salt thereof.

16. The osmotic delivery device of claim 15, further comprising:
an impermeable reservoir comprising interior and exterior surfaces and first and second open ends;
a semi-permeable membrane in sealing relationship with the first open end of the reservoir;
an osmotic engine within the reservoir and adjacent the semi-permeable membrane;
a piston adjacent the osmotic engine, wherein the piston forms a movable seal with the interior surface of the reservoir, the piston divides the reservoir into a first chamber and a second chamber, the first chamber comprising the osmotic engine;
a suspension formulation, wherein the second chamber comprises the suspension formulation and the suspension formulation is flowable and comprises the isolated polypeptide; and
a diffusion moderator inserted in the second open end of the reservoir, the diffusion moderator adjacent the suspension formulation.

17. A method of treating or alleviating a symptom of a disease or disorder associated with aberrant glucagon activity in a subject in need thereof, the method comprising administering to the subject the isolated polypeptide of claim 1, or a pharmaceutically acceptable salt thereof.

18. The method of claim 17, wherein the disease or disorder is type 2 diabetes mellitus.

19. The method of claim 17, wherein the isolated polypeptide is formulated for administration by a route selected from the group consisting of parenteral, oral, transdermal, rectal, intravenous, intradermal, subdermal, subcutaneous, and any combination thereof.

* * * * *